(12) United States Patent
Dragovich

(10) Patent No.: US 8,765,741 B2
(45) Date of Patent: Jul. 1, 2014

(54) 5,6-DIHYDRO-1H-PYRIDIN-2-ONE COMPOUNDS

(71) Applicant: Anadys Pharmaceuticals, Inc., San Diego, CA (US)

(72) Inventor: Peter Dragovich, San Mateo, CA (US)

(73) Assignee: Anadys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/041,376

(22) Filed: Sep. 30, 2013

(65) Prior Publication Data

US 2014/0031346 A1   Jan. 30, 2014

Related U.S. Application Data

(62) Division of application No. 13/567,667, filed on Aug. 6, 2012, now Pat. No. 8,546,602, which is a division of application No. 13/356,063, filed on Jan. 23, 2012, now Pat. No. 8,236,948, which is a division of application No. 13/043,167, filed on Mar. 8, 2011, now Pat. No. 8,101,800, which is a division of application No. 12/061,499, filed on Apr. 2, 2008, now Pat. No. 7,939,524.

(60) Provisional application No. 60/907,478, filed on Apr. 3, 2007.

(51) Int. Cl.
  *C07D 417/04* (2006.01)
  *C07D 513/04* (2006.01)
  *A61K 31/549* (2006.01)
  *A61K 31/5415* (2006.01)

(52) U.S. Cl.
  USPC .......................... 514/224.2; 544/51

(58) Field of Classification Search
  CPC .. C07D 417/04; C07D 513/04; A61K 31/549; A61K 31/5415
  USPC .......................... 544/51; 514/224.2
  See application file for complete search history.

(56) References Cited

U.S. PATENT DOCUMENTS

| | | | |
|---|---|---|---|
| 4,171,361 | A | 10/1979 | Dillard et al. |
| 7,425,552 | B2 | 9/2008 | Zhou et al. |
| 7,439,246 | B2 | 10/2008 | Borzilleri et al. |
| 7,479,489 | B2 | 1/2009 | Blake et al. |
| 7,582,626 | B2 | 9/2009 | Tran et al. |
| 7,582,754 | B2 | 9/2009 | Webber et al. |
| 7,601,709 | B2 | 10/2009 | Miao et al. |
| 7,674,810 | B2 | 3/2010 | Blake et al. |
| 7,834,009 | B2 | 11/2010 | Ellis et al. |
| 7,939,524 | B2 | 5/2011 | Tran et al. |
| 8,101,800 | B2 | 1/2012 | Tran et al. |
| 8,236,948 | B2 | 8/2012 | Tran et al. |
| 8,546,602 | B2 | 10/2013 | Tran et al. |
| 2005/0075331 | A1 | 4/2005 | Pratt et al. |
| 2008/0090814 | A1 | 4/2008 | Ellis et al. |
| 2008/0188466 | A1 | 8/2008 | Dragovich et al. |
| 2008/0214529 | A1 | 9/2008 | Ruebsam et al. |
| 2008/0227774 | A1 | 9/2008 | Ruebsam et al. |
| 2008/0275032 | A1 | 11/2008 | Zhou et al. |
| 2010/0034773 | A1 | 2/2010 | Tran et al. |

FOREIGN PATENT DOCUMENTS

| | | |
|---|---|---|
| JP | 2006-509042 | 3/2006 |
| WO | WO-01/85172 A1 | 11/2001 |
| WO | WO-02/098424 A1 | 12/2002 |
| WO | WO-03/059356 A2 | 7/2003 |
| WO | WO2004/041818 | 5/2004 |
| WO | WO2005/095353 | 10/2005 |
| WO | WO-2006115221 | 11/2006 |
| WO | WO-2008073982 A2 | 6/2008 |

OTHER PUBLICATIONS

Int'l Search Report of Int'l Appl. No. PCT/US05/45588, mailed Oct. 13, 2006.

(Continued)

*Primary Examiner* — Kahsay Habte
(74) *Attorney, Agent, or Firm* — Womble Caryle Sandridge & Rice, LLP

(57) ABSTRACT

The invention is directed to 5,6-dihydro-1H-pyridin-2-one compounds of Formula I

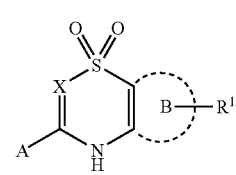

wherein
X is $CR^3$, and
A is

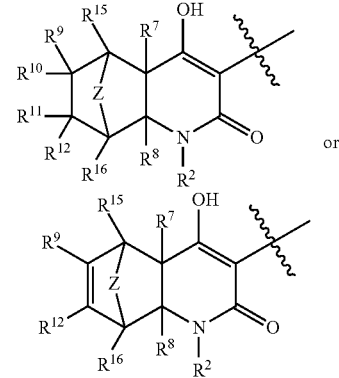

and pharmaceutical compositions containing such compounds that are useful in treating infections by hepatitis C virus.

22 Claims, 2 Drawing Sheets

(56) References Cited

OTHER PUBLICATIONS

Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).

Int'l Search Report and Written Opinion of Int'l Appl. No. PCT/US07/87272, mailed Apr. 16, 2008.

Int'l Search Report and Written Opinion of Int'l Appl. No. PCT/US07/87288, mailed Apr. 17, 2008.

Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1H)-ones by Intramolecular Wittig Reaction. Molecules, Feb. 28, 2002, vol. 7, pp. 124-128.

Pogam et al., Selection and Characterization of Replicon Variants Dually Resistant to Thumb- and Palm-Binding Nonnucleoside Polymerase Inhibitors of the Hepatitis C Virus, Journal of Virology, Jun. 2006, vol. 80, No. 12, pp. 6146-6154.

Int'l Search Report and Written Opinion of Int'l Appl No. PCT/US08/59164 dated Jun. 27, 2008.

Office Action dated Mar. 19, 2013, JP Application No. 2010-502271.

5,6-DIHYDRO-1H-PYRIDIN-2-ONE COMPOUNDS

This application is a divisional of U.S. application Ser. No. 13/567,667, filed Aug. 6, 2012, issuing as U.S. Pat. No. 8,546, 602 on Oct. 1, 2013, which is a divisional of U.S. application Ser. No. 13/356,063, filed Jan. 23, 2012, issued as U.S. Pat. No. 8,236,948 on Aug. 7, 2012, which is a divisional of U.S. application Ser. No. 13/043,167, filed Mar. 8, 2011, issued as U.S. Pat. No. 8,101,800 on Jan. 24, 2012, which is a divisional of U.S. application Ser. No. 12/061,499, filed Apr. 2, 2008, issued as U.S. Pat. No. 7,939,524 on May 10, 2011, which claims the benefit of U.S. Provisional Application No. 60/907,478, filed Apr. 3, 2007, the entire contents of which are incorporated herein.

FIELD OF THE INVENTION

The invention is directed to 5,6-dihydro-1H-pyridin-2-one compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $31,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of publications have described NS5B inhibitors useful in the treatment of hepatitis C infection. See, e.g., U.S. Patent Application Publication No. US 2008/0031852 (describing [1,2-b]pyridazinone compounds); U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 2002/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel 5,6-dihydro-1H-pyridin-2-one compounds and pharmaceutically acceptable salts thereof, which are useful in treating or preventing a hepatitis C virus infection in a patient in need thereof comprising administering to the patient a therapeutically or prophylactically effective amount of a 5,6-dihydro-1H-pyridin-2-one compound.

In a general aspect, the invention relates to compounds of Formula I

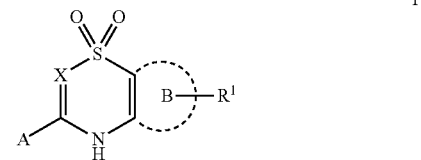

wherein
X is N or $CR^3$,
A is

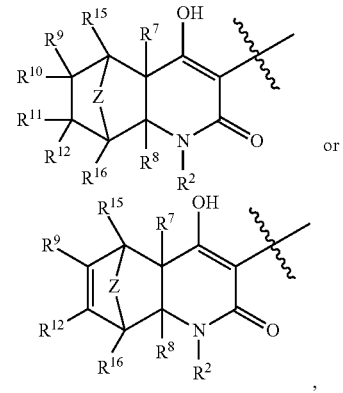

Ring B is 6-membered aryl or heterocyclyl, optionally substituted by 1-3 $R^1$ moieties, wherein is $R^1$ is H, halo, nitro, —$CHR^4$—$S(O)_2R^5$, —$C(S(O)_2R^5)$=$CHR^4$—, —$NR^5R^6$, —$NR^4S(O)_2R^5$, or —$NR^4S(O)_2NR^5R^6$, wherein $R^4$, $R^5$, and $R^6$ are independently H, $C_1$-$C_6$ alkyl, $C_3$-$C_8$ cycloalkyl, C(O)O—($C_1$-$C_6$ alkyl), aryl, or heterocyclyl, or $R^4$ and $R^5$ or $R^5$ and $R^6$ combine with the atom(s) to which they are attached to form a 5- or 6-membered heterocyclyl ring,
$R^2$ is H, $C_1$-$C_6$ alkyl, $C_3$-$C_8$ cycloalkyl, —$C_1$-$C_6$ alkylene($C_3$-$C_8$ cycloalkyl), —$C_1$-$C_6$ alkylene(aryl), —$C_1$-$C_6$ alkylene(heterocyclyl), aryl, or heterocyclyl, $R^3$ is H, halo, or $C_1$-$C_6$ alkyl,
Z is —$(CR^{13}R^{14})_n$—, or O,
n is 1 or 2,
$R^7$ and $R^8$ are independently H or $C_1$-$C_6$ alkyl,
$R^9, R^{10}, R^{11}, R^{12}, R^{13}, R^{14}, R^{15}$, and $R^{16}$ are independently H, $C_1$-$C_6$ alkyl, hydroxy, or halo,
wherein the above alkyl, alkylene, aryl, cycloalkyl, or heterocyclyl moieties provided in $R^1, R^2, R^3, R^4, R^5, R^6, R^7, R^8, R^9, R^{10}, R^{11}, R^{12}, R^{13}, R^{14}, R^{15}$, and $R^{16}$ are each optionally and independently substituted by 1-3 substituents selected from
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
keto,
nitro,
—C(O)OH, —C(O)NH$_2$, —C(O)($C_1$-$C_6$ alkylamine), —C(O)($C_1$-$C_6$ dialkylamine), —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl,
wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents,
or a pharmaceutically acceptable salt, hydrate, solvate, tautomer or stereoisomer thereof.

In one embodiment, the invention relates to compounds of Formula I wherein Ring B is selected from In another embodiment, Ring B is wherein $R^1$ is H, halo, nitro, —CHR$^4$—S(O)$_2$R$^5$, —C(S(O)$_2$R$^5$)=CHR$^4$—, —NR$^5$R$^6$, —NR$^4$S(O)$_2$R$^5$, or —NR$^4$S(O)$_2$NR$^5$R$^6$.

In one embodiment, the invention relates to compounds of Formula I wherein $R^1$ is —NR$^4$S(O)$_2$R$^5$, wherein $R^4$ and $R^5$ are independently H, $C_1$-$C_6$ alkyl or $C_3$-$C_8$ cycloalkyl.

In another embodiment, the invention relates to compounds of Formula I wherein $R^1$ is selected from In one embodiment, the invention relates to compounds of Formula I wherein $R^2$ is selected from -continued

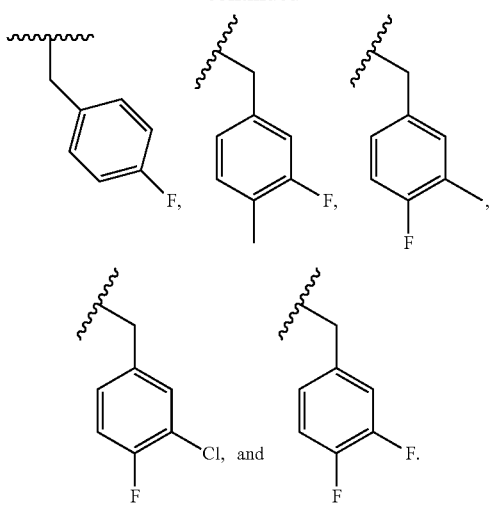

In another embodiment, the invention relates to compounds of Formula I wherein $R^2$ is selected from

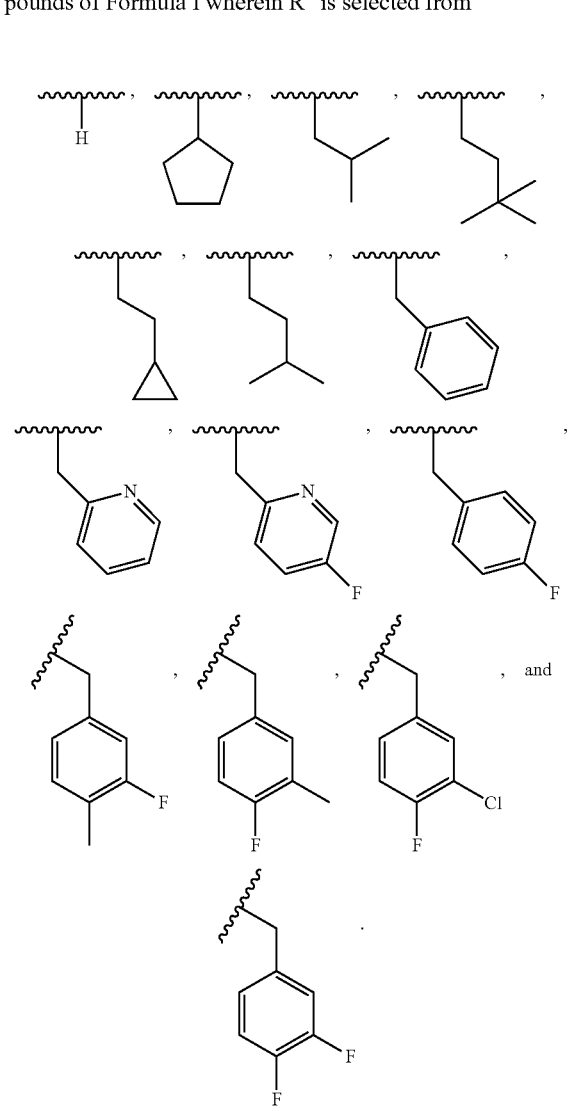

In yet another embodiment, the invention relates to compounds of Formula I wherein $R^2$ is selected from

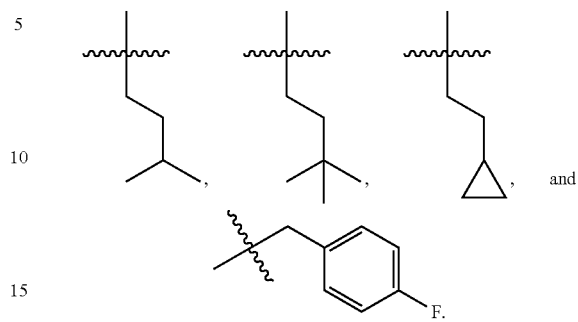

In one embodiment, the invention relates to compounds of Formula I wherein $R^3$ is selected from hydrogen or $C_1$-$C_6$ alkyl.

In another embodiment, the invention relates to compounds of Formula I wherein $R^3$ is selected from

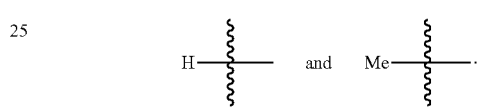

In one embodiment, the invention relates to compounds of Formula I wherein $R^7$ and $R^8$ are H.

In one embodiment, the invention relates to compounds of Formula I wherein $R^9$, $R^{10}$, $R^{11}$, $R^{12}$, $R^{13}$, $R^{14}$, $R^{15}$, and $R^{16}$ are independently selected from

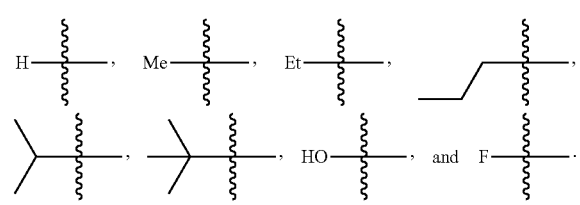

In a further embodiment, the invention relates to compounds of Formula I wherein $R^9$, $R^{10}$, $R^{11}$, $R^{12}$, $R^{13}$, $R^{14}$, $R^{15}$, and $R^{16}$ are independently selected from

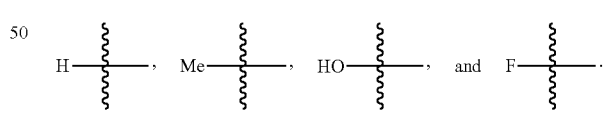

In another embodiment, the invention relates to compounds of Formula I wherein $R^9$, $R^{10}$, $R^{11}$, $R^{12}$, $R^{13}$, $R^{14}$, $R^{15}$, and $R^{16}$ are H or hydroxy.

In yet another embodiment, the invention relates to compounds of Formula I wherein $R^9$, $R^{10}$, $R^{11}$, $R^{12}$, $R^{13}$, $R^{14}$, $R^{15}$, and $R^{16}$ are H.

In one embodiment n is 1.

In another embodiment, the invention relates to compounds selected from
(rac-di-exo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, (rac-di-endo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-endo)-N-{3-[3-(5-Fluoro-pyridin-2-ylmethyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1S,2R,7S,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide, (rac-di-endo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide, N-{3-[(1S,2R,7S,8R)-3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[3-(3,3-Dimethyl-butyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1S,2R,7S,8R)-3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-N-methyl-methanesulfonamide, N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-N-methyl-methanesulfonamide, (1R,2S,7R,8S)-3-(4-Fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undec-5-en-4-one, (1R,2S,7R,8S)-5-[7-(1,1-Dioxo-4,5-dihydro-1H-1$\lambda^6$-thiophen-2-yl)-1,1-dioxo-1,4-dihydro-1$\lambda^6$-benzo[1,2,4]thiadiazin-3-yl]-3-(4-fluoro-benzyl)-6-hydroxy-3-aza-tricyclo[6.2.1.0$^{2,7}$]undec-5-en-4-one, (1R,2S,7R,8S)-5-[7-(1,1-Dioxo-tetrahydro-1$\lambda^6$-thiophen-2-yl)-1,1-dioxo-1,4-dihydro-1$\lambda^6$-benzo[1,2,4]thiadiazin-3-yl]-3-(4-fluoro-benzyl)-6-hydroxy-3-aza-tricyclo[6.2.1.0$^{2,7}$]undec-5-en-4-one, (1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[3-(2-Cyclopropyl-ethyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-N-methyl-methanesulfonamide, (rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (1R,2S,7R,8S)-5-[7-(1,1-Dioxo-1$\lambda^6$-isothiazolidin-2-yl)-1,1-dioxo-1,4-dihydro-1$\lambda^6$-benzo[1,2,4]thiadiazin-3-yl]-3-(4-fluoro-benzyl)-6-hydroxy-3-aza-tricyclo[6.2.1.0$^{2,7}$]undec-5-en-4-one, (1R,2S,7R,8S)-N-[3-(6-Hydroxy-4-oxo-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide, (1R,2S,7R,8S)-5-(1,1-Dioxo-1,4-dihydro-1$\lambda^6$-benzo[1,2,4]thiadiazin-3-yl)-3-(4-fluoro-benzyl)-6-hydroxy-3-aza-tricyclo[6.2.1.0$^{2,7}$]undec-5-en-4-one, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,4]thiazin-7-yl}-methanesulfonamide, (1R,2S,7R,8S)-5-(7-Amino-1,1-dioxo-1,4-dihydro-1$\lambda^6$-benzo[1,2,4]thiadiazin-3-yl)-3-(4-fluoro-benzyl)-6-hydroxy-3-aza-tricyclo[6.2.1.0$^{2,7}$]undec-5-en-4-one, (rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide, (rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide, (rac-di-exo)-6-Hydroxy-5-(7-iodo-1,1-dioxo-1,4-dihydro-1$\lambda^6$-benzo[1,2,4]thiadiazin-3-yl)-3-(3-methyl-butyl)-11-oxa-3-aza-tricyclo[6.2.1.0$^{2,7}$]undec-5-en-4-one, (1R,2S,7R,8S)-6-Hydroxy-5-(7-iodo-1,1-dioxo-1,4-dihydro-1$\lambda^6$-benzo[1,2,4]thiadiazin-3-yl)-3-(3-methyl-butyl)-3-aza-tricyclo[6.2.1.0$^{2,7}$]undec-5-en-4-one, Cyclopropanesulfonic acid {3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide, (rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide, (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide, (rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide, (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-N-methyl-methanesulfonamide, Cyclopropanesulfonic acid{3-(1R,2S,7R,8S)-[6-hydroxy-3-(3-methyl-butyl)-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide, (1R,2S,7R,8S)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-benzenesulfonamide, (rac-di-exo)-Cyclopropanesulfonic acid{3-[6-hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide, (rac-di-exo)-Cyclopropanesulfonic acid{3-[3-(3,3-dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-amide, N-[3-(1R,2S,7R,8S)-3-Cyclopentyl-6-hydroxy-4-oxo-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide, (rac-di-exo)-Cyclopropanesulfonic acid{3-[6-hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-amide, (rac-di-exo)-Cyclopropanesulfonic acid{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-amide, N-[3-(1R,2S,7R,8S)-(3-Cyclopentyl-6-hydroxy-4-oxo-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide-N-isopropyl carbamate, (rac-di-exo)-N-[3-(3-Cyclopentyl-6-hydroxy-4-oxo-11-oxa-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide, N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, cis-N-{3-[3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1$\lambda^6$-benzo[1,2,4]thiadiazin-7-yl}-methanesulfonamide, (2R,7S)-N-{3-[3-(4-Fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1$\lambda^6$-benzo[1,2,4]thiadiazin-7-yl}-methanesulfonamide, (2S,7R)-N-{3-[3-(4-Fluoro-benzyl)-6-hydroxy-4-oxo-3-aza-tetracyclo[6.3.2.0$^{2,7}$.0$^{9,11}$]tridec-5-en-5-yl]-1,1-dioxo-1,4-dihydro-1$\lambda^6$-benzo[1,2,4]thiadiazin-7-yl}-methanesulfonamide, (1R,2S,7R,8S)-5-(1,1-Dioxo-7-pyrrolidin-1-yl-1,4-dihydro-1$\lambda^6$-benzo[1,2,4]thiadiazin-3-yl)-6-hydroxy-3-(3-methyl-butyl)-3-aza-tricyclo[6.2.1.0$^{2,7}$]undec-5-en-4-one, Pyridine-3-sulfonic acid{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide, (1R,2S,7R,8S)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-sulfamide, (1R,2S,7R,8S)-N-[3-(3-Benzyl-6-hydroxy-4-oxo-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide, (1R,2S,7R,8S)-N-[3-(6-Hydroxy-3-isobutyl-4-oxo-3-aza-tricyclo[6.2.1.0$^{2,7}$]undec-5-en-5-yl)-1,1-dioxo-1,4-dihydro-1$\lambda^6$-benzo[1,2,4]thiadiazin-7-yl]-methanesulfonamide, (1R,2S,7R,8S)-N-{3-[3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-N-methyl-methane sulfonamide, N-{3-[(1R,2S,7R,8S)-3-(3-Fluoro-4-methyl-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, (1R,2S,7R,8S)-5-(7-Bromo-1,1-dioxo-1,4-dihydro-1$\lambda^6$-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-pyrido[2,3-e][1,2,4]thiadiazin-7-yl}-methanesulfonamide, (1R,2S,7R,8S)-5-(1,1-Dioxo-1,4-dihydro-1$\lambda^6$-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one, (1R,2S,7R,8S)-5-(1,1-Dioxo-1,4-dihydro-1$\lambda^6$-pyrido[4,3-e][1,2,4]thiadiazin-3-yl)-3-(4-fluoro-benzyl)-6-hydroxy-3-aza-tricyclo[6.2.1.0$^{2,7}$]undec-5-en-4-one, (1R,2S,7R,8S)-5-(1,1-Dioxo-1,4-dihydro-1$\lambda^6$-pyrido[3,2-e][1,2,4]thiadiazin-3-yl)-3-(4-fluoro-benzyl)-6-hydroxy-3-aza-tricyclo[6.2.1.0$^{2,7}$]undec-5-en-4-one, N-{3-[(1R,2S,7R,8S)-3-(2-Cyclopropyl-ethyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(4-Fluoro-benzyl)-6,9-dihydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, L-arginine salt, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, L-lysine salt, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, hemi magnesium salt, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, sodium salt, and N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, potassium salt.

The invention is also directed to pharmaceutically acceptable salts and pharmaceutically acceptable solvates of the compounds of Formula I. Advantageous methods of making the compounds of Formula I are also described.

In one aspect, the invention encompasses a method for treating or preventing hepatitis C virus infection in a mammal in need thereof, preferably in a human in need thereof, comprising administering to the patient a therapeutically or prophylactically effective amount of a Formula I compound. In one embodiment, the invention encompasses a method for treating or preventing hepatitis C virus infection by administering to a patient in need thereof a therapeutically or prophylactically effective amount of a Formula I compound that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent or an immunomodulatory agent.

DETAILED DESCRIPTION OF THE INVENTION

Figure 1:
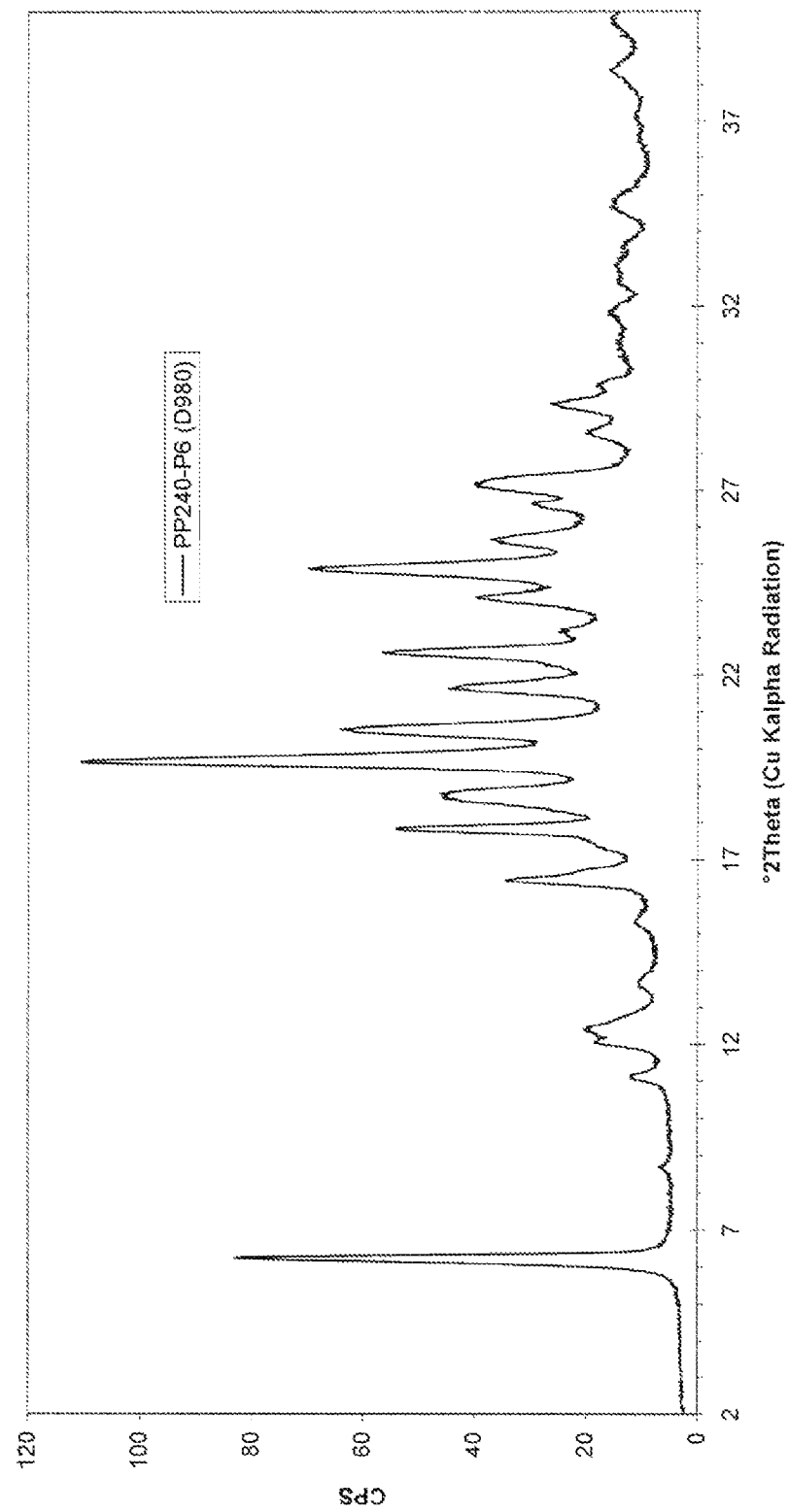
FIG. 1 shows a x-ray diffraction spectrum of N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (as prepared in Example 6 on a kg scale).

Where the following terms are used in this specification, they are used as defined below:

The terms "comprising," "having" and "including" are used herein in their open, non-limiting sense.

The term "alkyl", as used herein, unless otherwise indicated, includes $C_1$-$C_{12}$ saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkylene", as used herein, unless otherwise indicated, includes a $C_1$-$C_{12}$ divalent radical derived from alkyl, as exemplified by —$CH_2CH_2CH_2CH_2$—.

The term "alkenyl", as used herein, unless otherwise indicated, includes $C_1$-$C_{12}$ alkyl moieties having at least one carbon-carbon double bond wherein alkyl is as defined above and including E and Z isomers of said alkenyl moiety.

The term "alkynyl", as used herein, unless otherwise indicated, includes $C_1$-$C_{12}$ alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

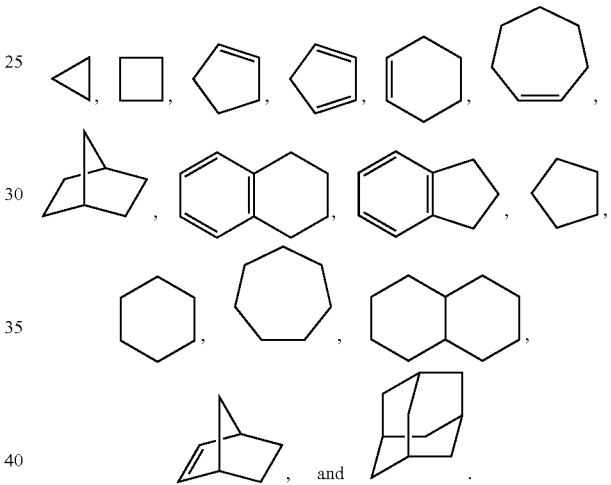

The term "aryl", as used herein, unless otherwise indicated, includes an organic radical derived from an aromatic hydrocarbon by removal of one hydrogen, such as phenyl or naphthyl, containing a total of from 6 to 10 carbon atoms.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-2-yl (C-attached) or pyrrol-3-yl (C-attached). Further, a group derived from imidazole may be imidazol-1-yl (N-attached) or imidazol-2-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

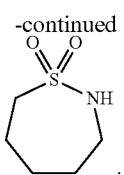

Unless defined otherwise, "alkyl," "alkylene," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The terms "endo" and "exo" are descriptors of the relative orientation of substituents attached to non-bridgehead atoms in a bicyclo[x.y.z]alkane (x≥y>z>0).

The terms "syn" and "anti" are descriptors of the relative orientation of substituents attached to bridgehead atoms in a bicyclo[x.y.z]alkane (x≥y>z>0).

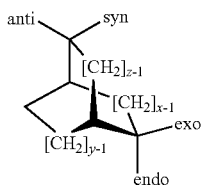

The term "exo" is given to a substituent (e.g., Br attached to C-2 in the example below) that is orientated towards the highest numbered bridge (z bridge, e.g., C-7 in example below); if the substituent is orientated away from the highest numbered bridge it is given the description "endo".

The term "syn" is given to a substituent attached to the highest numbered bridge (z bridge, e.g., F attached to C-7 in the example below) and is orientated towards the lowest numbered bridge (x bridge, e.g., C-2 and C-3 in example below); if the substituent is orientated away from the lowest numbered bridge it is given the description "anti."

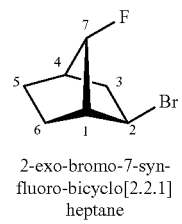 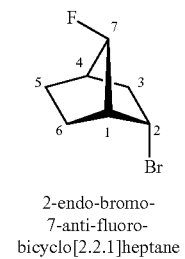

2-exo-bromo-7-syn-fluoro-bicyclo[2.2.1]heptane 2-endo-bromo-7-anti-fluoro-bicyclo[2.2.1]heptane The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring it is the mean plane of the ring(s).

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

When X = N:

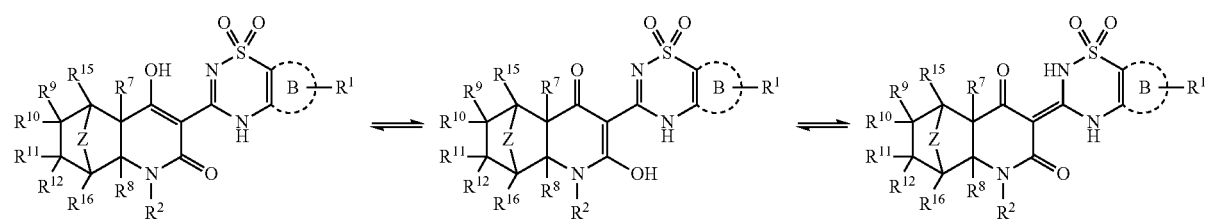

-continued

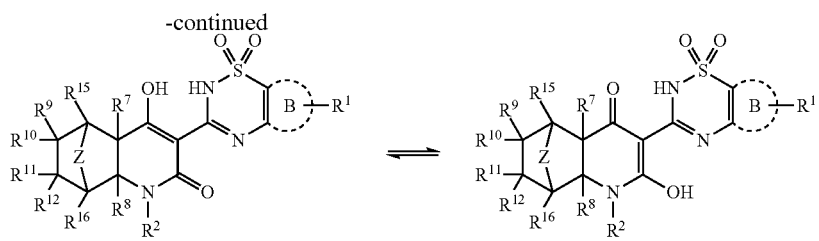

When X = CR³:

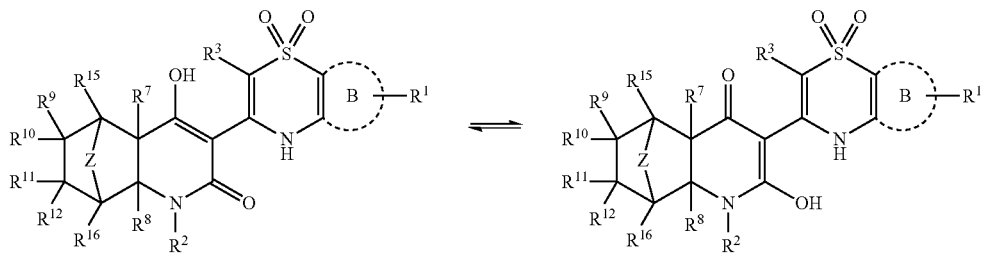

Or, the compounds of Formula I may exist as the following:

When X = N:

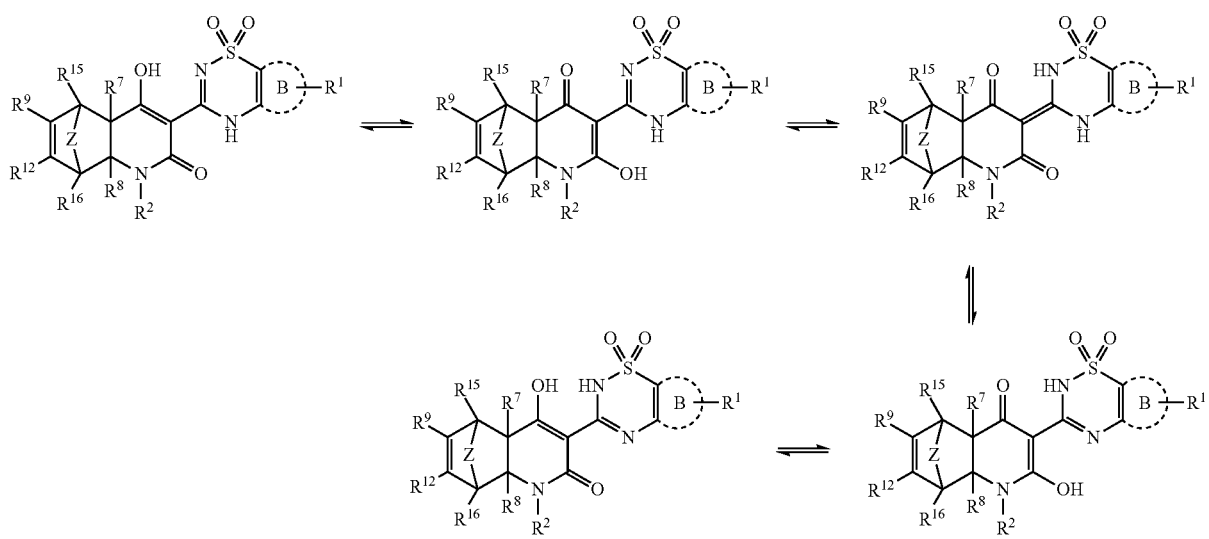

When X = CR³:

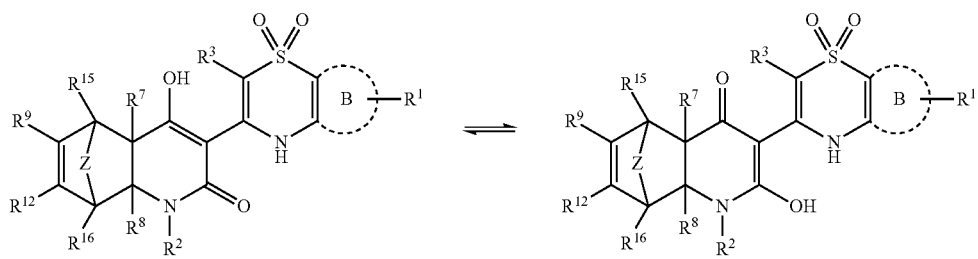

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, pentyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal, co-crystal, or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll-like receptor modulators. In one embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrochloride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the α-interferons, β-interferons, adefovir, clevadine, entecavir, pleconaril.

The Formula I compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll-like receptor (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061, SCH-503034, ITMN-191, or VX-950; and inhibitors of NS5B polymerase such as NM107 (and its prodrug NM283), R1626, R7078, BILN1941, GSK625433, GILD9128 or HCV-796.

The Formula I compounds of the invention can be administered or formulated in combination with an agent which inhibits HCV polymerase such as those described in Wu, *Curr Drug Targets Infect Disord.* 2003, 3(3), 207-19 or in combination with compounds that inhibit the helicase function of the virus such as those described in Bretner M, et al. *Nucleosides Nucleotides Nucleic Acids.* 2003, 22(5-8), 1531, or with inhibitors of other HCV specific targets such as those described in Zhang X., *IDrugs* 2002, 5(2), 154-8.

The Formula I compounds of the invention can be administered or formulated in combination with an agent which inhibits viral replication.

The Formula I compounds of the invention can be administered or formulated in combination with cytokines Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins The Formula I compounds of the invention can be administered or formulated in combination with β-interferons which include, but are not limited to, interferon β-1a, interferon β-1b.

The Formula I compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.,* 7, 1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with a cytochrome P450 monooxygenase inhibitor, such as, but not limited to, ritonavir or a pharmaceutically acceptable salt, ester, and prodrug thereof to improve the pharmacokinetics (e.g., increased half-life, increased time to peak plasma concentration, increased blood levels) of a Formula I compound that is metabolized by cytochrome P450 monooxygenase. Thus, the invention also encompasses a pharmaceutical composition comprising Formula I compounds of the invention and one or more cytochrome P450 monooxygenase inhibitors.

The Formula I compounds of the invention can be administered in combination with food to enhance absorption of the Formula I compounds in the gastrointestinal tract and to increase the bioavailability of the Formula I compounds.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingelheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a Formula I compound to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula I compounds to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference) A Formula I compound can also be formulated in rectal or vaginal compositions such as suppositories or retention enemas, e.g., containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.,* 1983, 23, 61; see also Levy et al., *Science,* 1985, 228, 190; During et al., *Ann. Neurol.,* 1989, 25, 351; Howard et al., *J. Neurosurg.,* 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS or HPLC and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO Flash-chromatography using prepacked RediSep silica gel columns, or Analogix flash column chromatography using prepacked SuperFlash silica gel columns. Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers ($cm^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

Enantiomeric excess (ee) values were determined by HPLC-analysis using the Chiralpak (Chiral Technologies Inc.) columns AS-RH, 2.1×150 mm, 5 micron, λ=312 nm or AS-RH, 4.6×250 mm, 5 micron, λ=310 nm.

AS-RH, 2.1×150 mm, 5 micron: Binary gradient HPLC separation. Solvent A: 0.1% Formic Acid in Water, Solvent B: 0.1% Formic Acid in Acetonitrile. Injected 10 μL of sample dissolved in 50% methanol-50% water [0.1 mg/mL].

| Time (min) | % B | Flow (mL/min) |
| --- | --- | --- |
| 0.0 | 55 | 0.3 |
| 5.0 | 95 | 0.3 |
| 5.5 | 95 | 0.3 |
| 6.0 | 55 | 0.3 |
| 12.0 | 55 | 0.3 |

AS-RH, 4.6×250 mm, 5 micron: Binary gradient HPLC separation. Solvent A: 0.05% TFA in Water, Solvent B: 0.05% TFA in Acetonitrile. Injected 3-5 μl of sample dissolved in acetonitrile [1 mg/mL].

| Time (min) | % B | Flow (mL/min) |
| --- | --- | --- |
| 0.0 | 50 | 0.8 |
| 8.0 | 95 | 0.8 |
| 10.0 | 95 | 0.8 |
| 11.0 | 50 | 0.8 |
| 13.0 | 50 | 0.8 |

The described synthetic pathways and experimental procedures utilize many common chemical abbreviations, 2,2-DMP (2,2-dimethoxypropane), Ac (acetyl), ACN (acetonitrile), Bn (benzyl), BnOH (benzyl alcohol), Boc (tert-butoxycarbonyl), Boc$_2$O (di-tert-butyl dicarbonate), Bz (benzoyl), CSI (chlorosulfonyl isocyanate), DBU (1,8-diazabicyclo[5.4.0]undec-7-ene), DCC (N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), KN(TMS)$_2$ (potassium bis(trimethylsilyl) amide), KO$^t$Bu (potassium tert-butoxide), LDA (lithium diisopropylamine), MCPBA (3-chloroperbenzoic acid), Me (methyl), MeCN (acetonitrile), MeOH (methanol), NaBH(OAc)$_3$ (sodium triacetoxyborohydride), NaCNBH$_3$ (sodium cyanoborohydride), NaH (sodium hydride), NaN(TMS)$_2$ (sodium bis(trimethylsilyl)amide), NaOAc (sodium acetate), NaOEt (sodium ethoxide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Scheme 1 provides a general procedure that can be used to prepare saturated 5,6-dihydro-1H-pyridin-2-one compounds of Formula I.

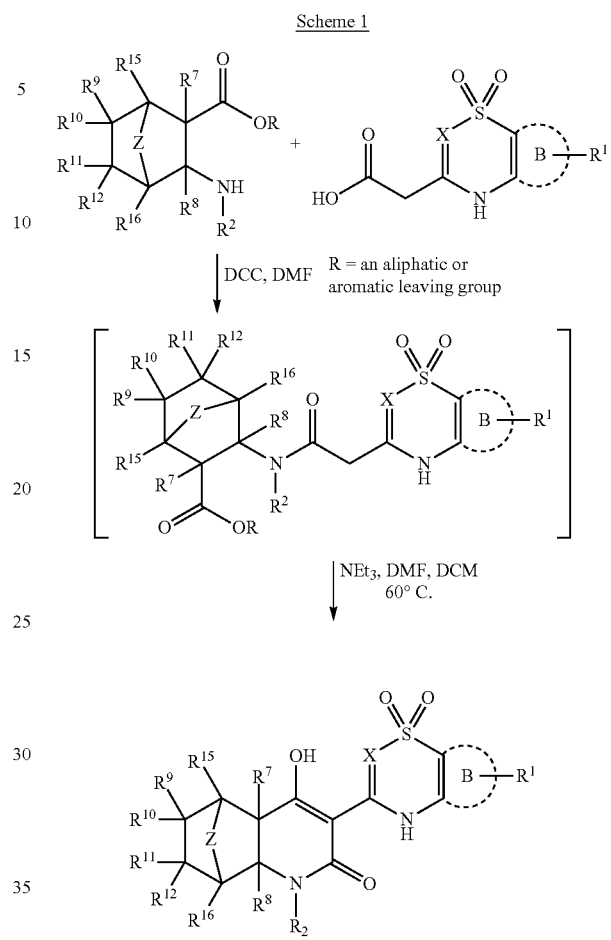

Scheme 1

The saturated cyclic N-substituted-β-amino acid ester intermediates, which can be obtained as described by one of the methods in schemes 3, 4, 6, 7 or 8 can be condensed with a carboxylic acid intermediate (or a salt thereof, e.g., sodium salt) using standard peptide coupling conditions used for the formation of amide bonds, such as DCC, to yield the shown amide. This intermediate can be cyclized with or without isolation in the presence of a base (e.g., triethylamine) to give the desired saturated 5,6-dihydro-1H-pyridin-2-one compounds.

Scheme 2 provides a general procedure that can be used to prepare unsaturated 5,6-dihydro-1H-pyridin-2-one compounds of Formula I.

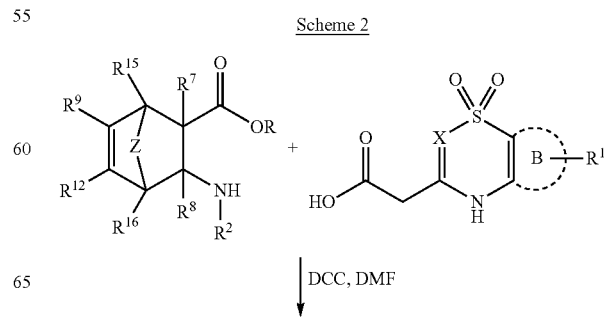

Scheme 2

-continued

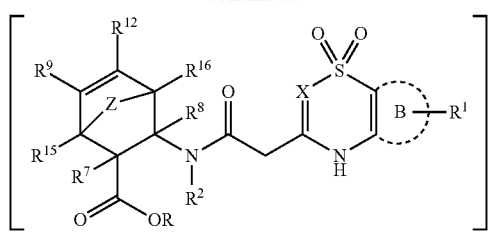

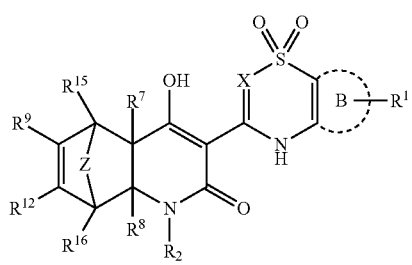

The unsaturated cyclic N-substituted-β-amino acid ester intermediates (with R as defined in scheme 1), which can be obtained as described by one of the methods in schemes 5 or 9, can be condensed with a carboxylic acid intermediate (or a salt thereof, e.g., sodium salt) using standard peptide coupling conditions used for the formation of amide bonds, such as DCC, to yield the shown amide. This intermediate can be cyclized with or without isolation in the presence of a base (e.g., triethylamine) to give the desired unsaturated 5,6-dihydro-1H-pyridin-2-one compounds.

Scheme 3 provides a general procedure that can be used to prepare saturated cyclic N-substituted-β-amino acid ester intermediates from saturated anhydrides.

Scheme 3

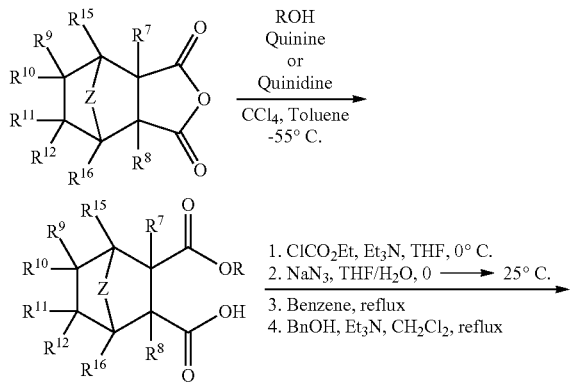

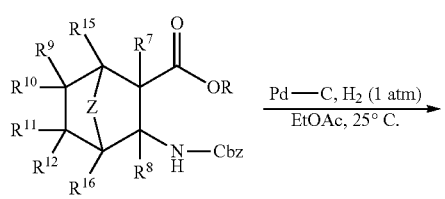

-continued

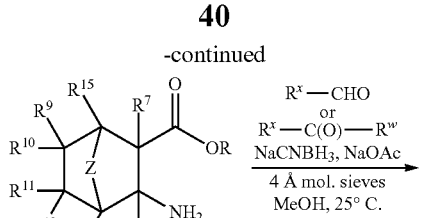

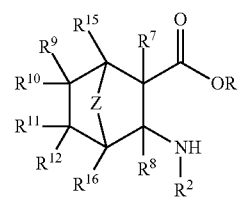

Commercially available saturated cyclic meso-anhydrides can be desymmetrized with the help of enzymes or chiral reagents, such as cinchona alkaloids (e.g., quinine or quinidine) as described in the literature to provide optically active saturated cyclic dicarboxylic acid monoesters (with R as defined in scheme 1). See *J. Org. Chem.*, 65, 6984-6991 (2000); *Synthesis*, 11, 1719-1730 (2001), and references cited therein.

These intermediates can be further elaborated into protected optically active saturated cyclic β-amino acid esters (e.g., Cbz-protected) via a rearrangement reaction, such as the Curtius rearrangement (shown) or a Hofmann degradation. Hydrogenation of the protected saturated cyclic β-amino acid esters under standard conditions can be used to remove the protecting group and furnish the optically active saturated cyclic β-amino acid esters, which can be isolated (and used) as either the free bases or their corresponding salts. The optically active saturated cyclic β-amino acid esters (or their salts) can then be treated with aldehydes or ketones, where $R^x$ and $R^w$ are independently $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene (aryl), —$C_1$-$C_5$ alkylene(heterocyclyl), aryl, or heterocyclyl, or $R^w$ can combine with $R^x$ to form a 3- to 8-membered ring, in the presence of a reducing agent (such as sodium cyanoborohydride) to afford the desired optically active saturated cyclic N-substituted-β-amino acid ester intermediates. Alternatively, the reaction sequence described above can be performed without enzymes or chiral reagents leading to the corresponding achiral intermediates and products.

Scheme 4 provides a general procedure that can be used to prepare saturated cyclic N-substituted-β-amino acid ester intermediates from unsaturated anhydrides.

Scheme 4

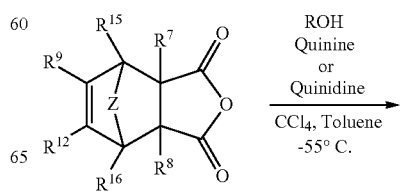

-continued

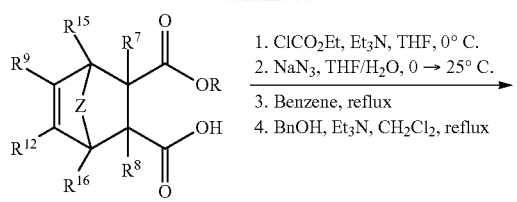

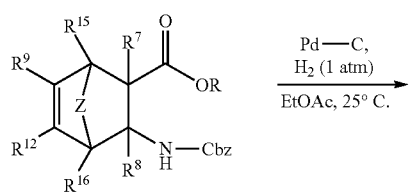

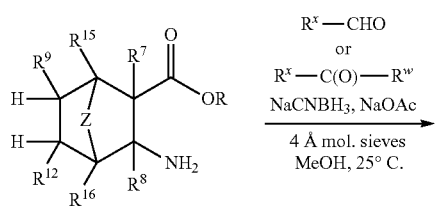

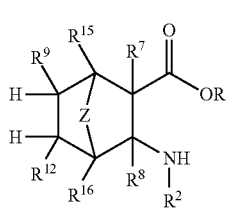

Scheme 5

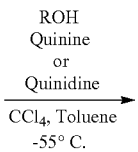

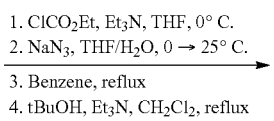

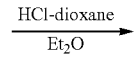

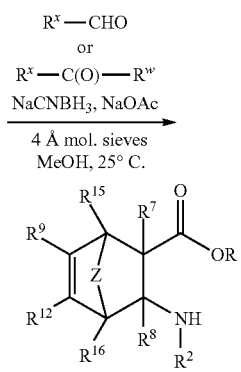

Commercially available unsaturated cyclic meso-anhydrides can be desymmetrized as described above (scheme 3) to provide optically active unsaturated cyclic dicarboxylic acid monoesters (with R as defined in scheme 1). These intermediates can be further elaborated into protected optically active unsaturated cyclic β-amino acid esters (e.g., Cbz-protected) via a rearrangement reaction, such as the Curtius rearrangement (shown) or a Hofmann degradation. Hydrogenation of the protected optically active unsaturated cyclic β-amino acid esters under standard conditions removes the protecting group and reduces the olefin to furnish the optically active saturated cyclic β-amino acid esters, which can be isolated (and used) as either the free bases or their corresponding salts.

The optically active saturated cyclic β-amino acid esters (or their salts) can then be treated with aldehydes or ketones (with $R^x$ and $R^w$ as defined in scheme 3) in the presence of a reducing agent (such as sodium cyanoborohydride) to afford the desired optically active saturated cyclic N-substituted-β-amino acid ester intermediates. Alternatively, the reaction sequence described above can be performed without enzymes or chiral reagents leading to the corresponding achiral intermediates and products.

Scheme 5 provides a general procedure that can be used to prepare unsaturated cyclic N-substituted-β-amino acid ester intermediates from unsaturated anhydrides.

Commercially available unsaturated cyclic meso-anhydrides can be desymmetrized as described above (scheme 4) to provide optically active unsaturated cyclic dicarboxylic acid monoesters (with R as defined in scheme 1). These intermediates can be further elaborated into protected optically active unsaturated cyclic β-amino acid esters (e.g., Boc-protected) via a rearrangement reaction, such as the Curtius rearrangement (shown) or a Hofmann degradation. The Boc protecting group can then be selectively removed in the presence of the olefin, thus leading to the optically active unsaturated cyclic β-amino acid ester intermediates, which can be isolated (and used) as either the salts or their corresponding free bases.

The optically active unsaturated cyclic β-amino acid esters (or their salts) can then be treated with aldehydes or ketones (with $R^x$ and $R^w$ as defined in scheme 3) in the presence of a reducing agent (such as sodium cyanoborohydride) to afford the desired optically active unsaturated cyclic N-substituted-β-amino acid ester intermediates. Alternatively, the reaction sequence described above can be performed without enzymes or chiral reagents leading to the corresponding achiral intermediates and products.

Scheme 6 provides an alternate general procedure that can be used to prepare saturated cyclic N-substituted-β-amino acid ester intermediates.

Scheme 6

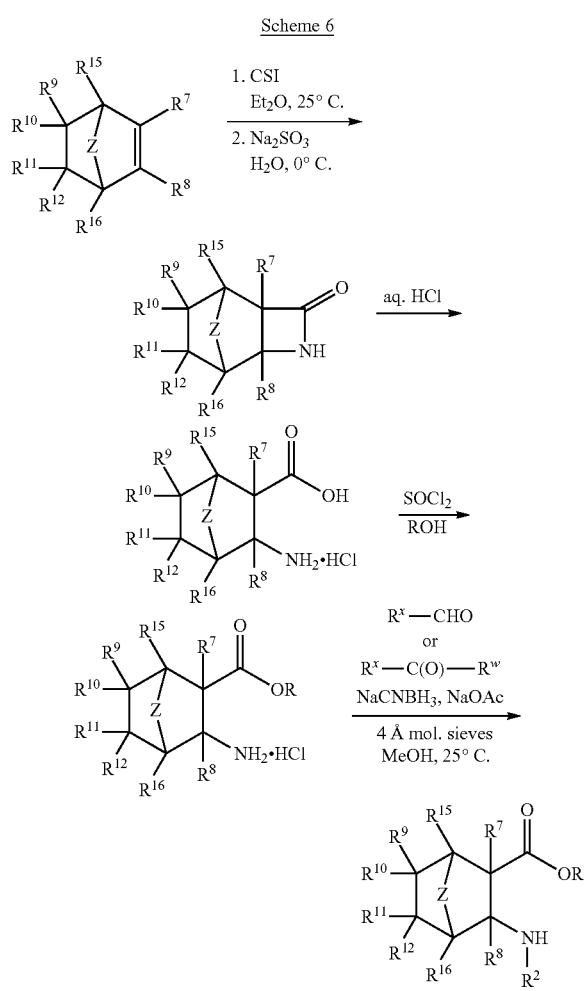

Bicyclic olefins, such as norbornene, can be reacted with chlorosulfonyl isocyanate to yield the β-lactams shown. These intermediates can be hydrolyzed in the presence of a strong acid (such as hydrochloric acid) to afford the saturated cyclic β-amino acids (or their salts), which can then be further elaborated into the corresponding esters using standard conditions (with R as defined in scheme 1). The saturated cyclic β-amino acid esters can then be treated with aldehydes or ketones (with $R^x$ and $R^w$ as defined in scheme 3) in the presence of a reducing agent, such as sodium cyanoborohydride, to afford the desired saturated cyclic N-substituted-β-amino acid ester intermediates.

Scheme 7 provides a general scheme describing a method that can be used to resolve the di-exo enantiomers by diastereomeric crystallization

Scheme 7

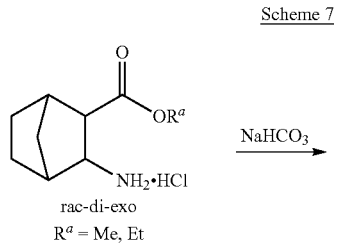

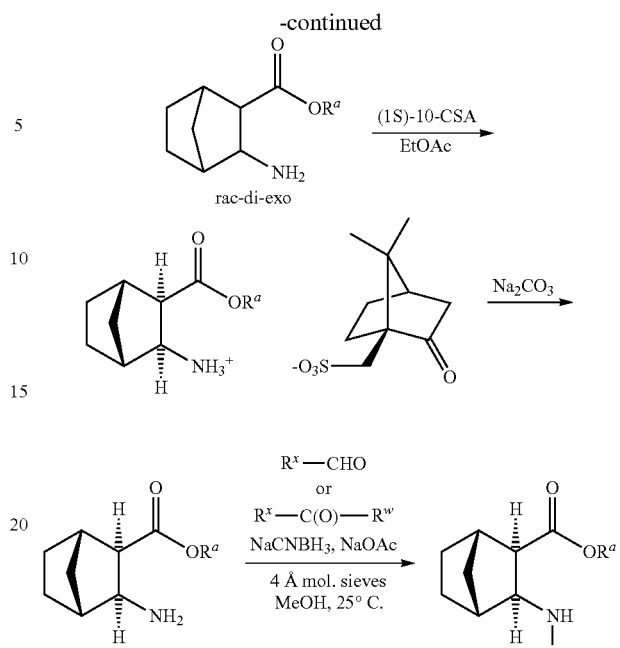

The racemic di-exo-β-amino acid ester derivatives obtained from norbornene as described above, can be resolved by forming diastereomeric salts with an optically pure acid, such as (1S)-(+)-10-camphorsulfonic acid. The (1R,2R,3S,4S)-β-amino acid ester derivatives form a crystalline salt with (1S)-(+)-10-camphorsulfonic acid that can be selectively isolated by filtration from an appropriate solvent (e.g., ethyl acetate) and treated with a base, such as sodium carbonate, to afford the free enantiomerically pure cyclic (1R,2R,3S,4S)-β-amino acid esters. The optically pure cyclic (1R,2R,3S,4S)-β-amino acid esters (or their salts) can then be treated with aldehydes or ketones (with $R^x$ and $R^w$ as defined in scheme 3) in the presence of a reducing agent, such as sodium cyanoborohydride, to afford the desired optically pure saturated cyclic N-substituted-(1R,2R,3S,4S)-β-amino acid ester intermediates.

Scheme 8 provides an alternative procedure that can be used to prepare enantiomerically pure saturated cyclic N-substituted-β-amino acid ester intermediates.

Scheme 8

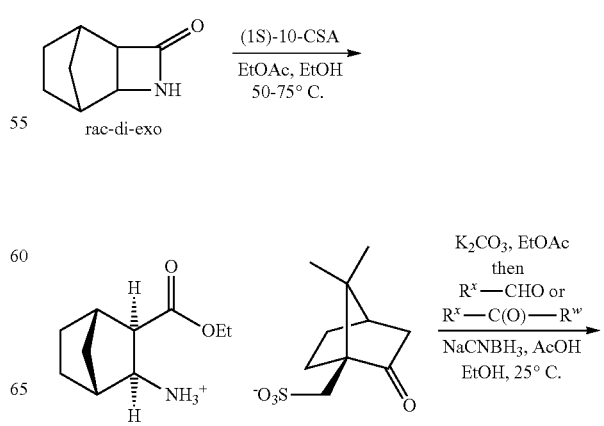

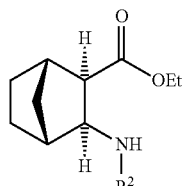

The β-lactam (prepared as described in scheme 6) can be opened and resolved by forming diastereomeric salts with an optically pure acid, such as (1S)-(+)-10-camphorsulfonic acid (as described in scheme 7) in the presence of an alcohol (e.g., ethanol) to directly afford the diastereomerically pure (1R,2R,3S,4S)-β-amino acid ester as a salt with (1S)-(+)-10-camphorsulfonic acid. Treatment with a base, such as potassium carbonate, followed by reductive alkylation with aldehydes or ketones (with $R^x$ and $R^w$ as defined in scheme 3) in the presence of a reducing agent, such as sodium cyanoborohydride, affords the desired enantiomerically pure saturated cyclic N-substituted-(1R,2R,3S,4S)-β-amino acid ester intermediates.

Scheme 9 provides a general procedure that can be used to prepare saturated cyclic N-substituted-β-amino acid ester intermediates.

Scheme 9

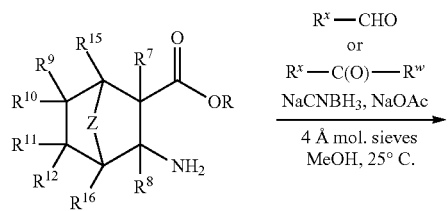

The saturated cyclic β-amino acid esters (or their salts, with R as defined in scheme 1) can be purchased, prepared from the corresponding commercially available saturated cyclic β-amino acids, or can be prepared by methods described in schemes 3, 4, 6 or 7. The saturated cyclic β-amino acid esters can then be treated with aldehydes or ketones (with $R^x$ and $R^w$ as defined in scheme 3) in the presence of a reducing agent, such as sodium cyanoborohydride, to afford the desired saturated cyclic N-substituted-β-amino acid ester intermediates. In each case the saturated cyclic β-amino acid esters or the desired saturated cyclic N-substituted-β-amino acid ester intermediates may be optically active.

Scheme 10 provides an alternative general procedure that can be used to prepare saturated cyclic N-substituted-β-amino acid ester intermediates.

Scheme 10

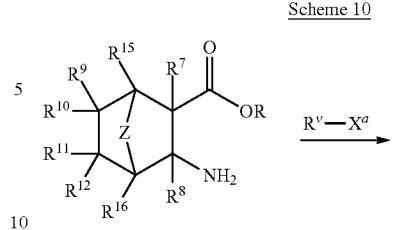

The saturated cyclic β-amino acid esters (or their salts, with R as defined in scheme 1) can be purchased, prepared from the corresponding commercially available saturated cyclic β-amino acids, or can be prepared by the method described in schemes 3, 4, 6 or 7. The saturated cyclic β-amino acid esters can then be treated with halides or pseudohalides $X^a$ (e.g., bromides, iodides or triflates), where $R^v$ is aryl or heterocyclyl, in the presence of metal catalyst such as copper (e.g., under Ullmann reaction conditions) or palladium (e.g., under Buchwald-Hartwig reaction conditions), to afford the desired saturated cyclic N-substituted-β-amino acid ester intermediates. In each case the saturated cyclic β-amino acid esters or the desired saturated cyclic N-substituted-β-amino acid ester intermediates may be optically active.

Scheme 11 provides a general procedure that can be used to prepare unsaturated cyclic N-substituted-β-amino acid ester intermediates.

Scheme 11

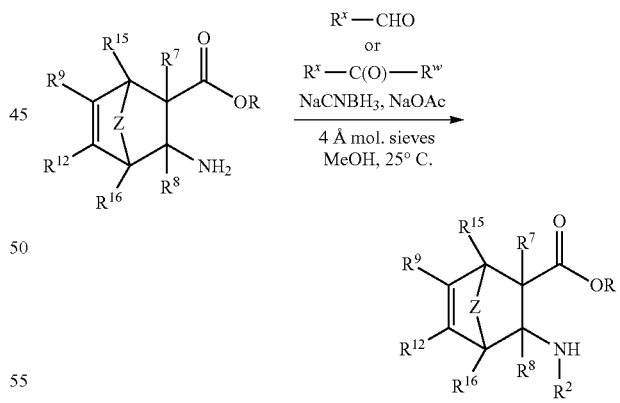

The unsaturated cyclic β-amino acid esters (or their salts, with R as defined in scheme 1) can be purchased, prepared from the corresponding commercially available unsaturated cyclic β-amino acids, or can be prepared by the method described in scheme 5. The unsaturated cyclic β-amino acid esters can then be treated with aldehydes or ketones (with $R^x$ and $R^w$ as defined in scheme 3) in the presence of a reducing agent, such as sodium cyanoborohydride, to afford the desired unsaturated cyclic N-substituted-β-amino acid ester intermediates. In each case the unsaturated cyclic β-amino acid esters or the desired unsaturated cyclic N-substituted-β-amino acid ester intermediates may be optically active.

Scheme 12 provides an alternative general procedure that can be used to prepare unsaturated cyclic N-substituted-β-amino acid ester intermediates.

Scheme 12

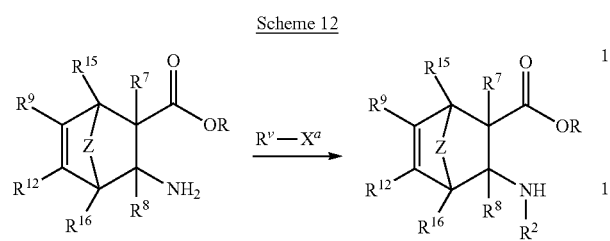

The unsaturated cyclic β-amino acid esters (or their salts, with R as defined in scheme 1) can be purchased, prepared from the corresponding commercially available unsaturated cyclic β-amino acids, or can be prepared by the method described in scheme 5. The unsaturated cyclic β-amino acid esters can then be treated with halides or pseudohalides $X^a$ (e.g., bromides, iodides or triflates), where $R^v$ is aryl or heterocyclyl, in the presence of metal catalyst such as copper (e.g., under Ullmann reaction conditions), to afford the desired unsaturated cyclic N-substituted-β-amino acid ester intermediates. In each case the unsaturated cyclic β-amino acid esters or the desired unsaturated cyclic N-substituted-β-amino acid ester intermediates may be optically active.

Scheme 13 provides a general procedure that can be used to prepare 7-substituted-1,1-dioxo-1,4-dihydro-1λ⁶-benzo[1,4]thiazin-3-yl-acetic acid intermediates.

Scheme 13

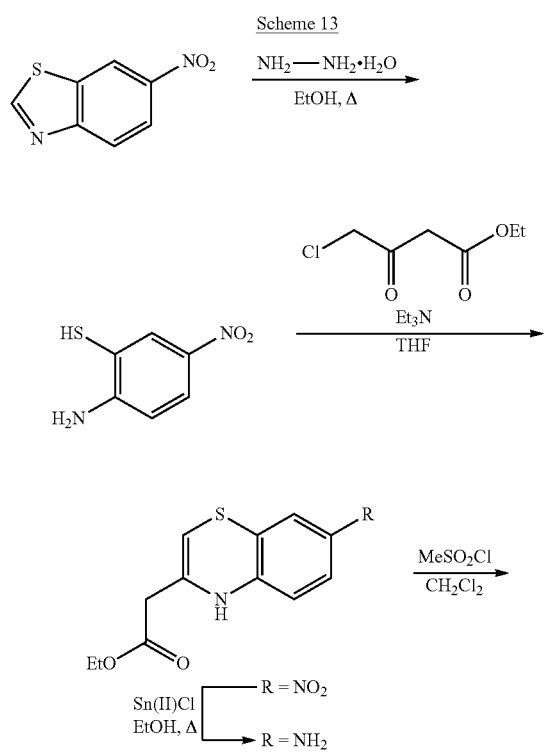

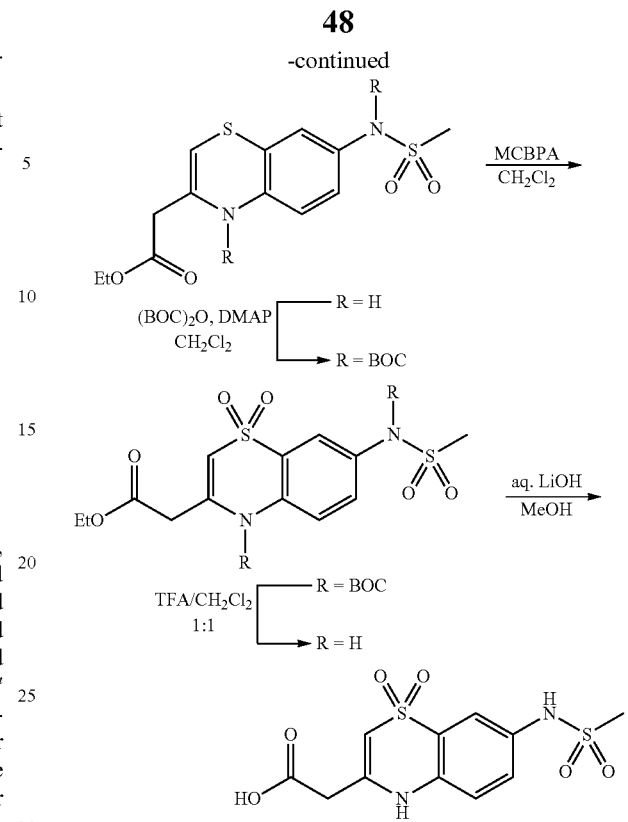

Commercially available 6-nitrobenzothiazole can be treated with hydrazine to obtain the 2-amino-5-nitro-benzenethiol, which can subsequently be reacted with chloroacetoacetate to give the (7-nitro-4H-benzo[1,4]thiazin-3-yl)-acetic acid ethyl ester. Reduction of the nitro group to the amino group can be accomplished by reaction with tin(II) chloride. Subsequent reaction with a sulfonyl chloride, such as methylsulfonyl chloride, can be used to obtain the corresponding sulfonamides. Protection of both nitrogens with a suitable protecting group such as a Boc group can be achieved by using standard methods for protecting amino groups. The sulfides can be oxidized using as suitable oxidizing reagent (e.g. MCPBA) to give the sulfones. Finally, deprotection of the amino groups using trifluoroacetic acid, followed by hydrolysis of the esters can be used to afford the desired acid intermediates.

Scheme 14 provides a general procedure that can be used to prepare 7-substituted-, 1-dioxo-1,4-dihydro-1λ⁶-benzo[1,2,4]thiadiazin-3-yl-acetic acid intermediates.

Scheme 14

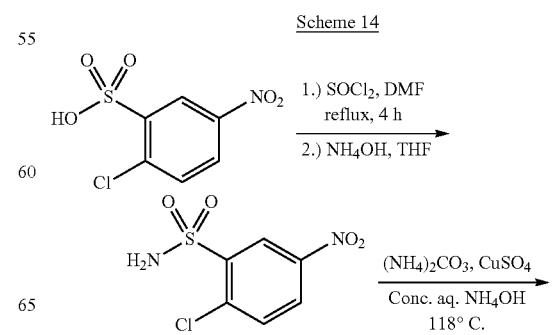

49

-continued

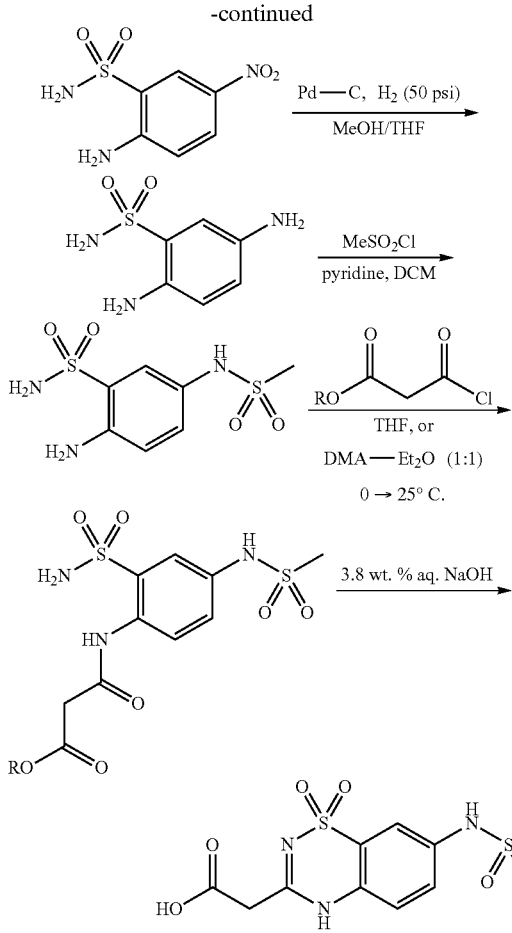

R = Me, Et

Commercially available 2-chloro-5-nitro-benzenesulfonic acid can be treated with thionyl chloride to give the sulfonyl-chloride, which can be further treated with ammonia to afford the sulfonamide intermediate. The chloride can be displaced with ammonia by treatment with ammonium hydroxide and ammonium carbonate in the presence of copper(II)sulfate. Reduction of the nitro group under standard hydrogenation conditions affords the aniline intermediate, which can be treated with a sulfonyl chloride, such as methylsulfonyl chloride, to yield the corresponding sulfonamide. Acylation of the 2-amino moiety with malonyl chlorides, e.g., ethyl 3-chloro-3-oxo-propionate, gives the corresponding amide, which can simultaneously be cyclized to the thiadiazine-dioxide and hydrolyzed to the desired acid intermediate.

Scheme 15 provides an alternative procedure that can be used to prepare the 2-amino-5-nitro-benzenesulfonamide intermediate.

Scheme 15

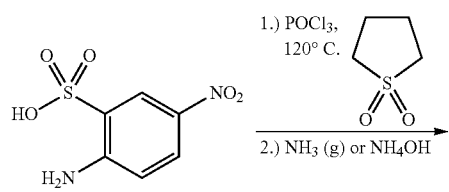

50

-continued

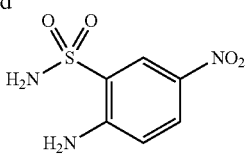

Commercially available 2-amino-5-nitro-benzenesulfonic acid can be converted to the corresponding sulfonyl chloride with phosphoryl chloride in the presence of a suitable co-solvent, such as sulfolane. Treatment with ammonia, e.g., aqueous ammonium hydroxide solution or ammonia gas, affords the desired 2-amino-5-nitro-benzenesulfonamide intermediate.

Scheme 16 provides an alternative procedure that can be used to prepare the 2-amino-5-methanesulfonylamino-benzenesulfonamide intermediate.

Scheme 16

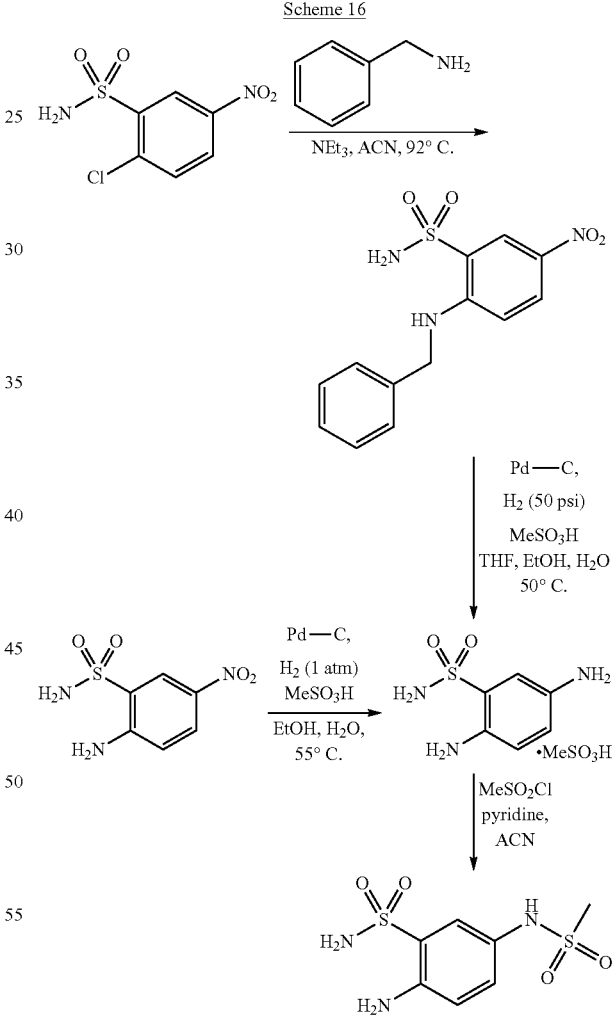

The 2-chloro-5-nitro-benzenesulfonamide intermediate (prepared as described in scheme 14) can be treated with a benzylic amine, such as benzylamine, to displace the chloro moiety. Hydrogenation under standard conditions in the presence of an acid (e.g., methanesulfonic acid) can be used to remove the benzylic group and to reduce the nitro group at the same time to afford the 2,5-diamino-benzenesulfonamide intermediate as a salt. Alternatively, the 2,5-diamino-benzenesulfonamide salt can be prepared by reduction of the 2-amino-5-nitro-benzenesulfonamide (prepared as described in schemes 14 and 15) under standard hydrogenation conditions in the presence of an acid (e.g., methanesulfonic acid). Subsequent reaction with methanesulfonyl chloride affords the desired 2-amino-5-methanesulfonylamino-benzenesulfonamide intermediate.

Scheme 17 provides a procedure that was used to prepare the (7-iodo-1,1-dioxo-1,4-dihydro-1λ⁶-benzo[1,2,4]thiadiazin-3-yl)-acetic acid intermediate.

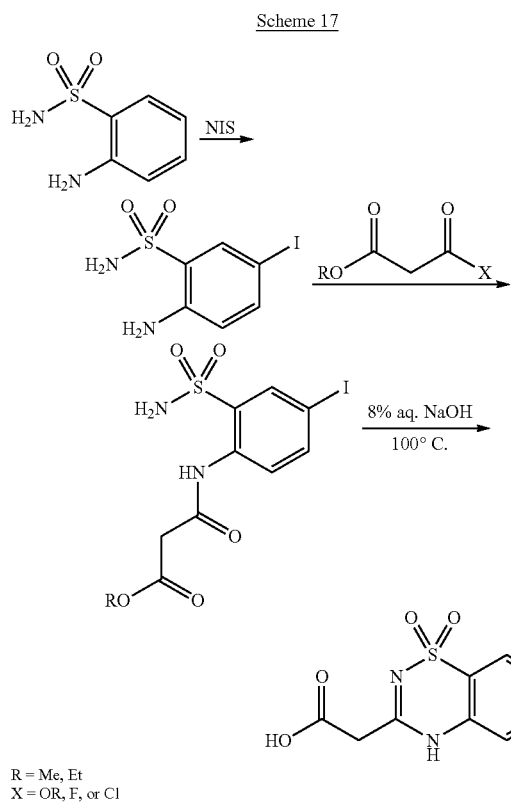

R = Me, Et
X = OR, F, or Cl

Commercially available 2-aminobenzenesulfonamide can be treated with N-iodosuccinimide (NIS) to afford 2-amino-5-iodo-benzenesulfonamide. Acylation with a malonyl halide monoester, such as ethyl 3-chloro-3-oxo-propionate, or with a dialkyl malonate, such as diethyl malonate, affords the corresponding amide, which can simultaneously be cyclized to the thiadiazine-dioxide and hydrolyzed to the desired acid intermediate (or a salt thereof, e.g., sodium salt).

Scheme 18 provides a procedure that was used to prepare the (1,1-dioxo-1,4-dihydro-1λ⁶-benzo[1,2,4]thiadiazin-3-yl)-acetic acid intermediate.

Scheme 18

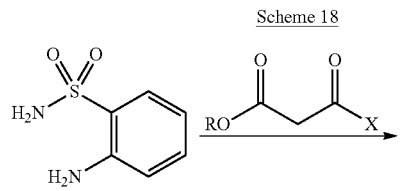

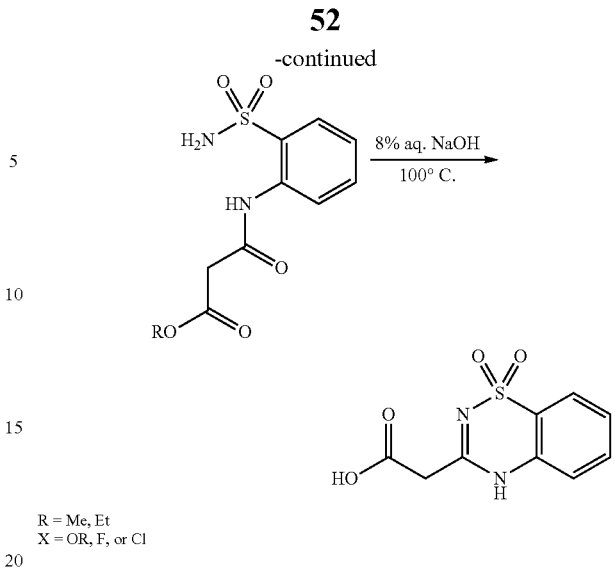

R = Me, Et
X = OR, F, or Cl

Commercially available 2-aminobenzenesulfonamide can be acylated with a malonyl halide monoester, such as ethyl 3-chloro-3-oxo-propionate, or with a dialkyl malonate, such as diethyl malonate, to afford the corresponding amide, which can simultaneously be cyclized to the thiadiazine-dioxide and hydrolyzed to the desired acid intermediate (or a salt thereof, e.g., sodium salt).

Scheme 19 provides a procedure that was used to prepare the 3-amino-pyridine-4-sulfonic acid amide intermediate.

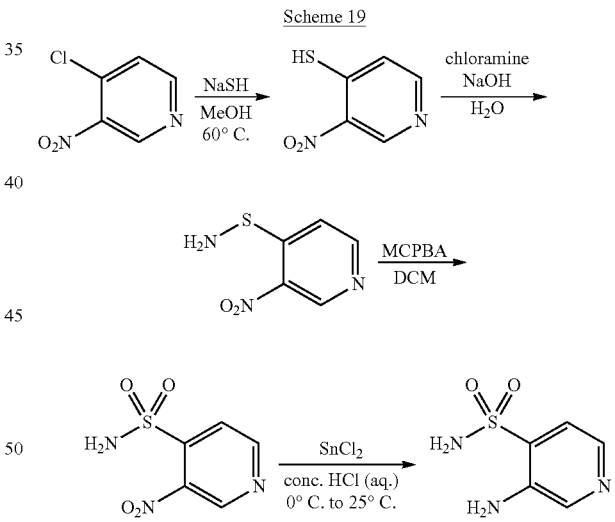

The 3-amino-pyridine-4-sulfonic acid amide intermediate can be prepared following procedures described in *Tetrahedron* 1998, 54, 13645-13654 (steps 2-4). Commercially available 4-chloro-3-nitro-pyridine can be treated with sodium sulfide hydrate to displace the chloro moiety. Treatment with chloramine followed by oxidation of the sulfur with an oxidizing agent, such as MCPBA, furnishes the nitro-sulfonamide intermediate. Reduction of the nitro group using standard conditions (e.g., tin(II)chloride) affords the desired 3-amino-pyridine-4-sulfonic acid amide intermediate.

Scheme 20 provides a procedure that was used to prepare the 4-amino-pyridine-3-sulfonic acid amide intermediate.

Scheme 20

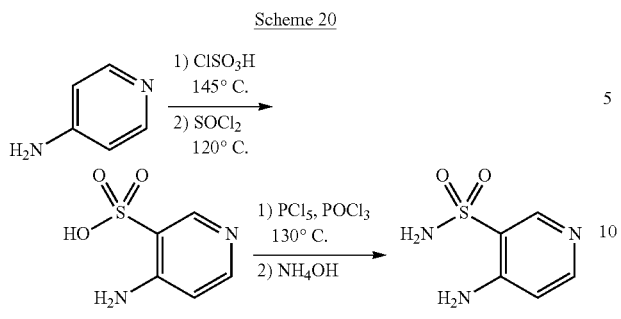

Commercially available pyridin-4-ylamine can be treated with chlorosulfonic acid in the presence of thionyl chloride to afford the sulfonyl chloride intermediate. Treatment with aqueous ammonium hydroxide solution affords the desired 4-amino-pyridine-3-sulfonic acid amide intermediate.

Scheme 21 provides a procedure that was used to prepare the 3-amino-pyridine-2-sulfonic acid amide intermediate.

Scheme 21

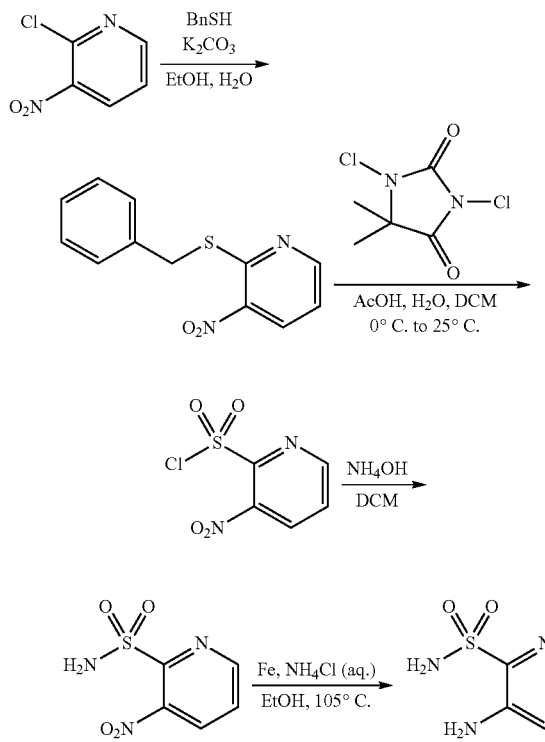

Commercially available 2-chloro-3-nitro-pyridine can be treated with benzyl mercaptan in the presence of a base (e.g., potassium carbonate) to afford the sulfide intermediate. Oxidation with 1,3-dichloro-5,5-dimethyl-hydantoin furnishes the sulfonyl chloride, which can be treated with aqueous ammonium hydroxide solution to yield the sulfonamide intermediate. Reduction of the nitro group under standard hydrogenation conditions affords the desired 3-amino-pyridine-2-sulfonic acid amide intermediate.

Scheme 22 provides a procedure that was used to prepare the 4-amino-pyridine-3-sulfonic acid amide intermediate.

Scheme 22

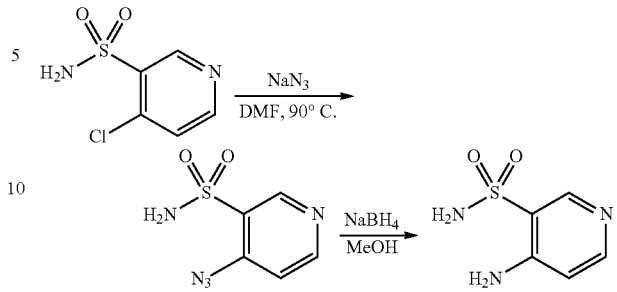

Commercially available 4-chloro-pyridine-3-sulfonic acid amide can be treated with sodium azide to furnish the azido intermediate, which can be reduced with a reducing agent (e.g., sodium borohydride) to afford the desired 4-amino-pyridine-3-sulfonic acid amide intermediate.

Scheme 23 provides a procedure that was used to prepare the acid intermediates derived from aminopyridine sulfonic acid amide intermediates.

Scheme 23

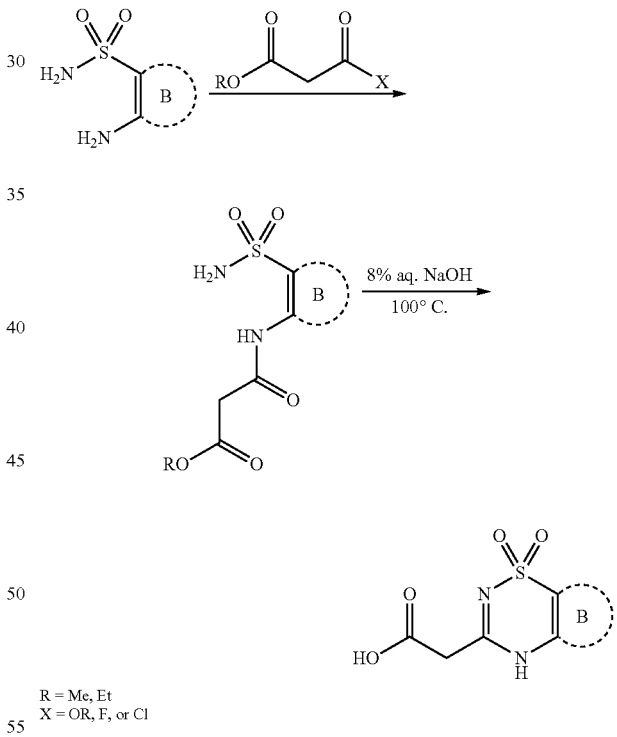

R = Me, Et
X = OR, F, or Cl

The aminopyridine sulfonic acid amide intermediates described in schemes 19-21 can be acylated with a malonyl halide monoester, such as ethyl 3-chloro-3-oxo-propionate, or with a dialkyl malonate, such as diethyl malonate, to afford the corresponding amide, which can simultaneously be cyclized to the thiadiazine-dioxide and hydrolyzed to the desired acid intermediate (or a salt thereof, e.g., sodium salt).

Scheme 24 provides a general procedure that was used to prepare 5,6-dihydro-1H-pyridin-2-one compounds of Formula I from the corresponding iodo precursors.

Scheme 24

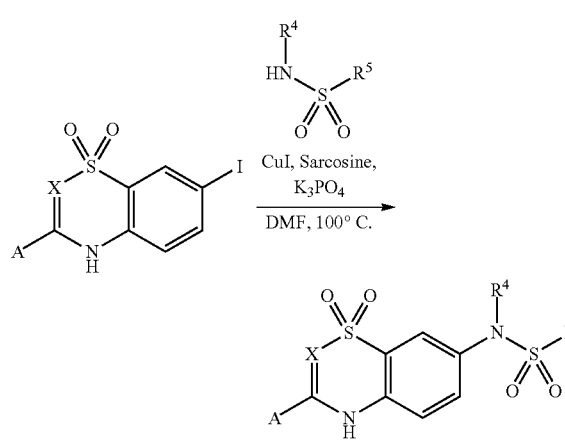

Optionally substituted 5,6-dihydro-1H-pyridin-2-ones can be treated with substituted sulfonamides in a copper-mediated displacement reaction to afford the desired 5,6-dihydro-1H-pyridin-2-one compounds of Formula I.

Scheme 25 provides a general procedure that was used to prepare 5,6-dihydro-1H-pyridin-2-one compounds of Formula I bearing a sulfamide moiety from the corresponding iodo precursors.

Scheme 25

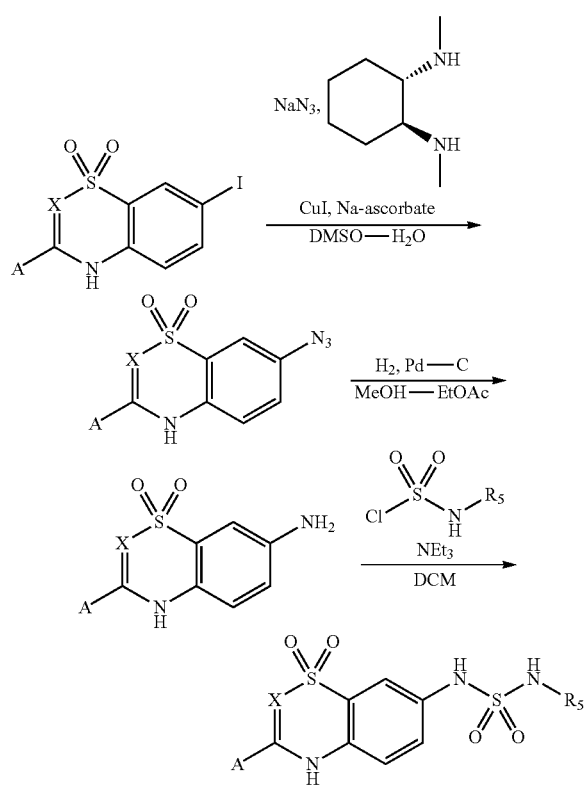

Optionally substituted 5,6-dihydro-1H-pyridin-2-ones can be treated with sodium azide to displace the iodo moiety. Reduction of the azido-intermediate using standard conditions, such as catalytic hydrogenation, affords the aniline intermediate. Further reaction with an optionally substituted sulfamoyl chloride in the presence of a base (e.g., triethylamine) affords the desired 5,6-dihydro-1H-pyridin-2-one compounds of Formula I.

Scheme 26 provides a general procedure that was used to prepare N-substituted 5,6-dihydro-1H-pyridin-2-one compounds of Formula I.

Scheme 26

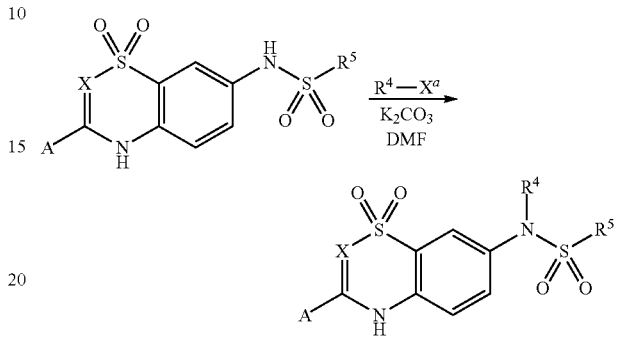

The sulfonamide moiety of optionally substituted 5,6-dihydro-1H-pyridin-2-ones can be N-alkylated by treatment with an alkylating agent, such as alkyl halides or pseudohalides $X^a$ (e.g., chlorides, bromides, iodides, mesylates, tosylates, triflates, or chloroformates), in the presence of a base (e.g., potassium carbonate) to afford the desired N-substituted 5,6-dihydro-1H-pyridin-2-one compounds of Formula I.

Scheme 27 provides a procedure that was used to prepare the 5,6-dihydro-1H-pyridin-2-one compounds of Formula I from the corresponding iodo precursors.

Scheme 27

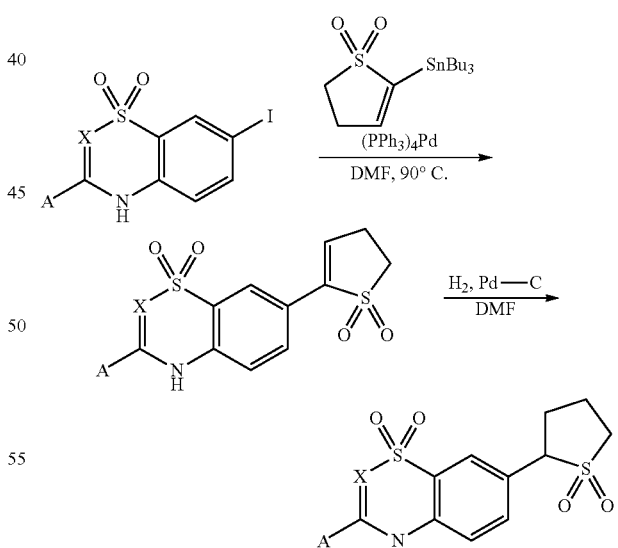

Optionally substituted 5,6-dihydro-1H-pyridin-2-ones can be treated with stannanes, such as the unsaturated cyclic sulfone shown above, in a Stille-type palladium-catalyzed reaction to afford the unsaturated intermediates shown. Reduction of the alkene using standard hydrogenation conditions affords the desired 5,6-dihydro-1H-pyridin-2-one compounds of Formula I.

Scheme 28 provides a general procedure that was used to prepare the 5,6-dihydro-1H-pyridin-2-one compounds of Formula I from the corresponding iodo precursors.

Scheme 28

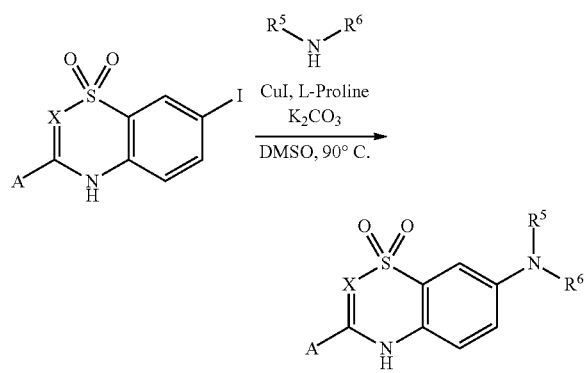

Optionally substituted 5,6-dihydro-1H-pyridin-2-ones can be treated with amines in a copper-mediated displacement reaction to afford the desired 5,6-dihydro-1H-pyridin-2-one compounds of Formula I.

Example 1

(rac-di-exo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

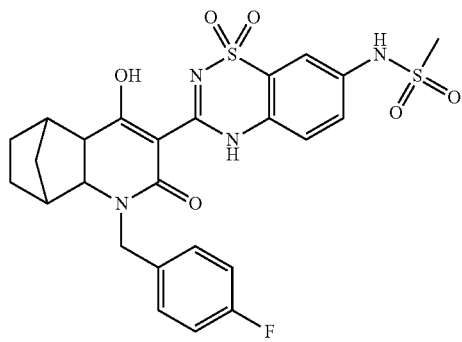 [SMILES: CS(=O)(=O)Nc1ccc2c(c1)S(=O)(=O)N=C(C1=C(O)C3C4CCC(C4)C3N(Cc3ccc(F)cc3)C1=O)N2]

a) 2-Chloro-5-nitrobenzenesulfonamide

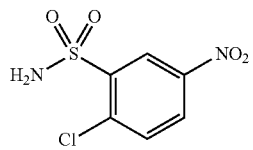 [SMILES: NS(=O)(=O)c1cc([N+](=O)[O-])ccc1Cl]

To a solution of thionyl chloride (11 mL) and 2-chloro-5-nitro-benzenesulfonic acid (4.78 g, 20.1 mmol) was added N,N-dimethylformamide (0.92 µL) and the reaction mixture was heated at reflux for 4 h. The reaction mixture was then carefully quenched by pouring it into water and the product was isolated by vacuum filtration. The sulfonyl chloride was dissolved in a minimal amount of toluene and then added to a mixture of concentrated aqueous ammonium hydroxide solution (25 mL) and tetrahydrofuran (25 mL) at −10° C. After stirring for 2 h the reaction was quenched by adding a 6.0 M aqueous hydrochloric acid solution until pH 4 was reached. The layers were separated and the organic layer was concentrated in vacuo to a slurry. Pentane was added and the product was isolated by vacuum filtration to afford 2-chloro-5-nitrobenzenesulfonamide (2.0 g, 8.48 mmol, 42.4%), as a solid. $^1$H NMR (400 MHz, DMSO-d$_6$) δ: 7.94 (d, 1H, J=8.8 Hz), 7.97 (bs, 2H), 8.40 (dd, 1H, J$_1$=8.6 Hz, J$_2$=3.1 Hz), 8.64 (d, 1H, J=3.1 Hz).

b) 2-Amino-5-nitrobenzenesulfonamide

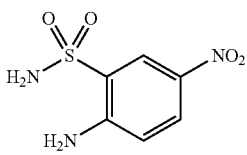 [SMILES: Nc1ccc([N+](=O)[O-])cc1S(N)(=O)=O]

2-Chloro-5-nitro-benzenesulfonamide (1.95 kg, 8.30 mol), ammonium carbonate (1.983 kg, 20.64 mol), and copper (II) sulfate (394 g, 2.47 mol) were charged to an autoclave and diluted with a 30% aqueous ammonium hydroxide solution (11.7 L, 330 mol). The mixture was heated at 118° C. for 3 days and was then cooled to 23° C. The mixture was filtered and the solids were then washed with water (20 L). This solid was dissolved in hot methanol (20 mL/g), and the mixture was filtered to remove undissolved solids. The filtrate was stored at 4° C. overnight, and the resulting solid product was then filtered. The filtrate was partially concentrated by vacuum distillation and, when the concentrate was cooled to 23° C., the solid product was then filtered off. The two crops of solid were combined and further dried in vacuo at 45° C. to afford the desired product, 2-amino-5-nitro-benzenesulfonamide (1.10 kg, 5.06 mol, 61%), as a solid. $^1$H NMR (400 MHz, DMSO-d$_6$) δ: 6.89 (d, J=9.3 Hz, 1H), 7.12 (bs, 2H), 7.57 (bs, 2H), 8.07 (dd, J$_1$=9.0 Hz, J$_2$=2.6 Hz, 1H), 8.43 (d, J=3.0 Hz, 1H).

Alternatively, 2-amino-5-nitrobenzenesulfonamide can be prepared as follows:

2-Amino-5-nitrobenzenesulfonic acid (200.00 g, 0.917 mol) was suspended in warm sulfolane (250 mL) and the suspension was heated to 80° C. Phosphorous oxychloride (126 mL, 1.375 mol) was added and resulting mixture was heated to 110-120° C. and stirred for 4 h. The resulting solution was cooled to 60° C. and added dropwise into concentrated aqueous ammonium hydroxide solution (800 mL, 11.9 mol) at <10° C. The flask was rinsed with warm sulfolane (50 mL) and the wash was added into the above reaction mixture. The resulting suspension was stirred at 25° C. for 1 h, heated to 95° C. and stirred for 1 hour. The mixture was cooled to 80° C. and the pH was adjusted to 6-8 with 3.0 M aqueous hydrochloric acid solution (~600 mL) and allowed to cool to 25° C. The dark green suspension was filtered, and the wet filter cake was washed with water (300 mL) and dried at 60° C. overnight to give the crude product (140 g) as a green-yellow solid. The crude product was dissolved in 0.5 M aqueous sodium hydroxide solution (1.4 L, 0.7 mol). Charcoal (14 g) was added and the mixture was heated to reflux and stirred for 15 min. The mixture was filtered through Celite and washed with 0.5 M aqueous sodium hydroxide solution (100 mL).

The pH of the filtrate was adjusted to 6-8 with concentrated aqueous hydrochloric acid solution (~60 mL) and the yellow suspension was allowed to cool to 25° C. The mixture was filtered and the wet filter cake was washed with water (200 mL) and dried at 60° C. overnight to afford the desired product, 2-amino-5-nitrobenzenesulfonamide (130 g, 0.599 mol, 65%) as a bright yellow powder.

c) 2,5-Diaminobenzenesulfonamide

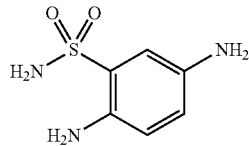

2-Amino-5-nitro-benzenesulfonamide (5.00 kg, 23.0 mol), methanol (65 L), tetrahydrofuran (65 L), and 10% palladium on carbon (250 g) were charged to an autoclave. The mixture was cycled with nitrogen and hydrogen purges (3×), and the mixture was then stirred under hydrogen (50 psi) at 23° C. overnight. The catalyst was removed by filtration and the filtrate was then concentrated in vacuo to give a brown solid. The solid was further dried in vacuo at 45° C. to afford the desired product, 2,5-diamino-benzenesulfonamide (4.21 kg, 22.4 mol, 98%), as a solid. $^1$H NMR (400 MHz, DMSO-$d_6$) δ: 4.54 (2H, bs), 4.98 (2H, bs), 6.55-6.60 (2H, m), 6.87 (1H, d, J=2.2 Hz), 6.99 (2H, bs). LC-MS (ESI) calcd for $C_6H_9N_3O_2S$ 187.04, found 188.3 [M+H$^+$].

d) 2-Amino-5-methanesulfonylamino-benzenesulfonamide

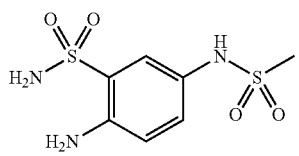 [SMILES: CS(=O)(=O)Nc1ccc(N)c(S(N)(=O)=O)c1]

2,5-Diamino-benzenesulfonamide (4.20 kg, 22.4 mol) was dissolved in dichloromethane (120 L) and pyridine (8.00 kg, 89.9 mol), and the resulting solution was cooled to 0° C. Methanesulfonyl chloride (2.80 kg, 24.4 mol) was added slowly, and the resulting mixture was allowed to warm to 23° C. and stirred for 2 days. The mixture was filtered and the resulting solid was washed with dichloromethane (2×20 L). The solid was diluted with water (100 L) and 1.0 M aqueous hydrochloric acid solution (25 L), and was then stirred at 23° C. for 1 h. The mixture was filtered and the resulting solid was washed with water (20 L) and then with methyl-tert-butyl ether (2×10 L). The solid was further dried in vacuo at 45° C. to afford the desired product, 2-amino-5-methanesulfonylamino-benzenesulfonamide (4.39 kg, 16.5 mol, 73%) as a pale pink solid. $^1$H NMR (400 MHz, CD$_3$OD) δ: 2.89 (3H, s), 6.82 (1H, d, J=8.5 Hz), 7.20 (1H, dd, $J_1$=8.5 Hz, $J_2$=2.5 Hz), 7.58 (1H, d, J=2.5 Hz). LC-MS (ESI) calcd for $C_7H_{11}N_3O_4S_2$ 265.02, found 266.0 [M+H$^+$].

Alternatively, 2-amino-5-methanesulfonylamino-benzenesulfonamide can be prepared as follows:

a') 2-Benzylamino-5-nitro-benzenesulfonamide

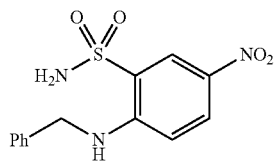 [SMILES: NS(=O)(=O)c1cc([N+](=O)[O-])ccc1NCc1ccccc1]

A mixture of 2-chloro-5-nitro-benzenesulfonamide (2.20 kg, 9.30 mol), benzylamine (1.5 L, 13.9 mol), triethylamine (2.5 L, 18.1 mol), and acetonitrile (22.0 L) were heated at 92° C. for 20 h. The mixture was then cooled to 40° C., and was then partially concentrated in vacuo. The residue was added to 0° C. water (22.0 L) and the resulting suspension was allowed to warm to 23° C. and stirred for 2 h. The suspension was filtered and the solid was then washed with water (5 L). The washed solid was suspended in absolute ethanol (11 L), and was then filtered and washed with absolute ethanol (5 L). The solid was further dried in vacuo at 45° C. to afford the desired product, 2-benzylamino-5-nitro-benzenesulfonamide (2.40 kg, 7.81 mol, 84%), as a yellow solid. $^1$H NMR (400 MHz, DMSO-$d_6$) δ: 4.64 (2H, d, J=4.6 Hz), 6.81 (1H, d, J=9.4 Hz), 7.23-7.44 (6H, m), 7.77 (2H, bs), 8.11 (1H, dd, $J_1$=9.4 Hz, $J_2$=2.3 Hz), 8.49 (1H, d, J=3.1 Hz). LC-MS (ESI) calcd for $C_{13}H_{13}N_3O_4S$ 307.06, found 308.2 [M+H$^+$] (100%), 615.2 [2M+H$^+$] (81%).

b') 2,5-Diamino-benzenesulfonamide methanesulfonate

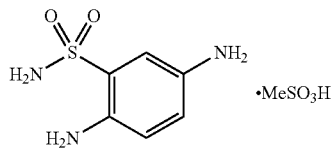

Methanesulfonic acid (465 mL, 7.16 mol) was added slowly to a solution of 2-benzylamino-5-nitro-benzenesulfonamide (2.20 kg, 7.16 mol) and tetrahydrofuran (11.0 L). The resulting solution was added to a mixture of 10% palladium on carbon (220 g of 50% water wet catalyst) and water (1.1 L) in a hydrogenation reactor. The mixture was further diluted with absolute ethanol (21.0 L) and was then hydrogenated with 55 psi hydrogen at 50° C. for 21 h. Additional 10% palladium on carbon (55 g of 50% water wet catalyst) was added, and hydrogenation at 55 psi and 50° C. was continued for 22 h. The resulting suspension was diluted with water (1.1 L) and the suspension was then filtered through a pad of Celite. The filtrate was partially concentrated in vacuo and was then diluted with acetonitrile (15.4 L). The solution was again partially concentrated in vacuo and diluted with acetonitrile (15.4 L). The resulting suspension was partially concentrated in vacuo and was allowed to stir at 23° C. for 2 h. The suspension was filtered and the solid was then washed with acetonitrile (3 L). The solid was further dried in vacuo at 45° C. to afford the desired product, 2,5-diamino-benzenesulfonamide methanesulfonate (1.88 kg, 6.64 mol, 93%), as a purple solid. $^1$H NMR (400 MHz, DMSO-$d_6$) δ:

2.34 (3H, s), 6.05 (2H, b), 6.87 (1H, d, J=8.6 Hz), 7.20 (1H, dd, J$_1$=8.6 Hz, J$_2$=2.3 Hz), 7.38 (2H, s), 7.53 (1H, d, J=2.3 Hz), 9.62 (3H, b). LC-MS (ESI) calcd for C$_6$H$_9$NO$_2$S 187.04, found 187.9 [M+H$^+$].

Alternatively, 2,5-diamino-benzenesulfonamide methanesulfonate can be prepared as follows:

2-Amino-5-nitrobenzenesulfonamide (prepared as described in Example 1b, 100.00 g, 0.460 mol) and 5% palladium on carbon (wet, 5.00 g) were suspended in ethanol (2 L) and water (100 mL). Methanesulfonic acid (33 mL, 0.51 mol) was added, and the resulting mixture was heated to 55° C. and stirred under atmospheric hydrogen for 8 h. The mixture was filtered and the filtrate was concentrated in vacuo to a volume of about 450 mL. To the concentrate was added acetonitrile (1 L) and resulting mixture was stirred at 25° C. overnight. The suspension was filtered to afford the desired product, 2,5-diamino-benzenesulfonamide methanesulfonate (122.36 g, 0.432 mol, 93.8%) as a purple solid.

c')
2-Amino-5-methanesulfonylamino-benzenesulfonamide

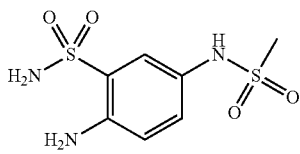 [SMILES: CS(=O)(=O)Nc1ccc(N)c(S(N)(=O)=O)c1]

2,5-Diamino-benzenesulfonamide methanesulfonate (1.80 kg, 6.35 mol) was suspended in acetonitrile (24 L). Pyridine (1.55 L, 19.1 mol) was added, followed by the careful slow addition of methanesulfonyl chloride (517 mL, 6.68 mol). After stirring at 23° C. for 20 h, the mixture was partially concentrated in vacuo at 55° C. Water (18 L) was added to the concentrate, and the resulting suspension was stirred at 23° C. for 2 h. The solid was filtered and was then washed with water (4 L) and air dried on the filter. The solid was suspended in absolute ethanol (9 L), stirred at 23° C. for 9 h, and was then filtered. The solid was washed with absolute ethanol (2×2 L), and was then further dried in vacuo at 50° C. to afford the desired product, 2-amino-5-methanesulfonylamino-benzenesulfonamide (1.45 kg, 5.48 mol, 86%), as a purple solid.

e) N-(4-Methanesulfonylamino-2-sulfamoyl-phenyl)-malonamic acid ethyl ester

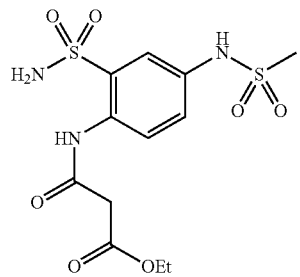 [SMILES: CCOC(=O)CC(=O)Nc1ccc(NS(C)(=O)=O)cc1S(N)(=O)=O]

2-Amino-5-methanesulfonylamino-benzenesulfonamide (23.27 g, 87.81 mmol) was dissolved in N,N-dimethylacetamide (100 mL) and diethyl ether (100 mL). Ethyl 3-chloro-3-oxo-propionate (13.88 g, 92.20 mmol) was added and the reaction mixture was stirred at 25° C. for 1 h. The reaction mixture was diluted with ethyl acetate (400 mL) and was extracted with water (400 mL). The aqueous layer was back-extracted with ethyl acetate (2×200 mL). The combined organic layers were dried over sodium sulfate, filtered, and most of the solvent was removed in vacuo to a volume of ~100 mL.

To the stirred solution was added hexanes (~100 mL) upon which a precipitate formed. The precipitate was collected by vacuum filtration, washed with hexanes and dried under high vacuum to afford the analytically pure product, N-(4-methanesulfonylamino-2-sulfamoyl-phenyl)-malonamic acid ethyl ester (31.22 g, 85.53 mmol, 97.4%), as a light-brown solid. $^1$H NMR (400 MHz, CD$_3$OD) δ: 1.31 (3H, t, J=7.0 Hz), 3.00 (3H, s), 3.59 (2H, s), 4.25 (2H, quartet, J=6.9 Hz), 7.42-7.45 (1H, m), 7.86 (1H, m), 7.92 (1H, d, J=8.8 Hz).

f) N-(4-Methanesulfonylamino-2-sulfamoylphenyl)-malonamic acid methyl ester

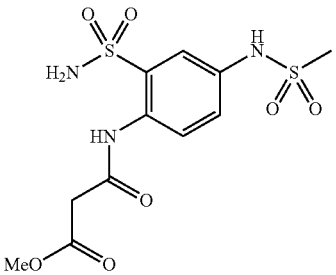 [SMILES: COC(=O)CC(=O)Nc1ccc(NS(C)(=O)=O)cc1S(N)(=O)=O]

2-Amino-5-methanesulfonylamino-benzenesulfonamide (prepared as described in Example 1d, 1.70 kg, 6.40 mol) was dissolved in tetrahydrofuran (35 L), and was then cooled to 0° C. Methyl 3-chloro-3-oxopropionate (792 mL, 7.40 mol) was added slowly, and the resulting mixture was then allowed to warm to 23° C. and stirred for 2 days. The solvent was removed in vacuo, and the residue was then diluted with water (4 L) and saturated aqueous sodium bicarbonate solution (2 L). The resulting solid was filtered, and was then washed with water (5 L). The solid was suspended in hot methanol (15 mL/g), and was then cooled to 23° C. and filtered to afford the desired product, N-(4-methanesulfonylamino-2-sulfamoyl-phenyl)-malonamic acid methyl ester (1.68 kg, 4.61 mol, 72%), as a brown solid. $^1$H NMR (400 MHz, DMSO-d$_6$) δ: 3.02 (3H, s), 3.60 (2H, s), 3.66 (3H, s), 7.38 (1H, dd, J$_1$=2.3 Hz, J$_2$=8.6 Hz), 7.53 (2H, bs), 7.73 (1H, d, J=2.4 Hz), 7.83 (1H, d, J=8.7 Hz), 9.43 (1H, s), 9.99 (1H, s).

g) (7-Methanesulfonylamino-1,1-dioxo-1,4-dihydro-1λ$^6$-benzo[1,2,4]thiadiazin-3-yl)-acetic acid

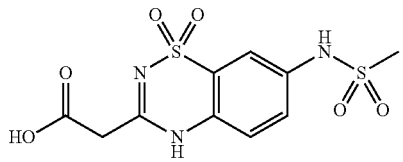

N-(4-Methanesulfonylamino-2-sulfamoyl-phenyl)-malonamic acid ethyl ester (prepared as described in Example 1e, 9.55 g, 26.16 mmol) was dissolved in 8% aqueous sodium hydroxide solution (262 mL) and heated at 100° C. for 1.5 h. The reaction mixture was cooled to 0° C. and the solution was acidified by slowly adding 12.0 M aqueous hydrochloric acid solution until pH 1-2 was reached. A precipitate started to form and the suspension was allowed to stir for 30 min at 0° C. The precipitate was collected by vacuum filtration, washed with cold water, and dried under high vacuum to afford the desired product, (7-methanesulfonylamino-1,1-dioxo-1,4-dihydro-1$\lambda^6$-benzo[1,2,4]thiadiazin-3-yl)-acetic acid (7.20 g, 21.621 mmol, 82.6%), as a pinkish solid. $^1$H NMR (400 MHz, DMSO-$d_6$) δ: 3.03 (3H, s), 3.56 (2H, s), 7.33 (1H, d, J=9.1 Hz), 7.52-7.54 (2H, m), 10.09 (1H, s), 12.24 (1H, s), 13.02 (1H, bs). LC-MS (ESI) calcd for $C_{10}H_{11}N_3O_6S_2$ 333.01, found 334.1 [M+H$^+$].

Alternatively, (7-methanesulfonylamino-1,1-dioxo-1,4-dihydro-1$\lambda^6$-benzo[1,2,4]thiadiazin-3-yl)-acetic acid can be prepared as follows:

N-(4-methanesulfonylamino-2-sulfamoyl-phenyl)-malonamic acid methyl ester (prepared as described in Example 1g, 1.35 kg, 3.69 mol) was added to 3.8 wt. % aqueous sodium hydroxide solution (14.0 kg). The resulting mixture was stirred at 23° C. for 30 h, and was then cooled to 0° C. A 2.0 M aqueous hydrochloric acid solution (9.72 L) was slowly added, stirring at 0° C. was continued for 30 min, and the mixture was then filtered. The solid was washed with water (1.4 L), and was then slurried in a mixture of methanol (1.4 L) and diethyl ether (2.7 L). After filtration, the solid was washed with diethyl ether (2×1.4 L) and was further dried in vacuo at 23° C. to afford the desired product, (7-methanesulfonylamino-1,1-dioxo-1,4-dihydro-1$\lambda^6$-benzo[1,2,4]thiadiazin-3-yl)-acetic acid (1.07 kg, 3.21 mol, 87%), as a light brown solid.

h) (rac-di-exo)-3-(4-Fluoro-benzylamino)-bicyclo[2.2.1]heptane-2-carboxylic acid ethyl ester

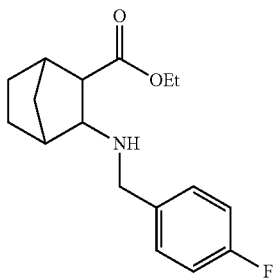 [SMILES: CCOC(=O)C1C2CCC(C2)C1NCc1ccc(F)cc1]

(rac-di-exo)-3-Amino-bicyclo[2.2.1]heptane-2-carboxylic acid ethyl ester hydrochloride (1 g, 4.6 mmol) was suspended in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a 1:1 mixture of saturated aqueous sodium bicarbonate solution (200 mL) and ethyl acetate (200 mL). After shaking, both layers were passed through a plug of Celite. The organic layer was further washed with saturated aqueous brine solution (50 mL), dried over magnesium sulfate, filtered, and concentrated in vacuo to afford the crude product, (rac-di-exo)-3-(4-fluoro-benzylamino)-bicyclo[2.2.1]heptane-2-carboxylic acid ethyl ester (0.993 g, 3.41 mmol, 74%), as a clear oil. LC-MS (ESI) calcd for $C_{17}H_{22}FNO_2$ 291.16, found 292.1 [M+H$^+$].

i) (rac-di-exo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

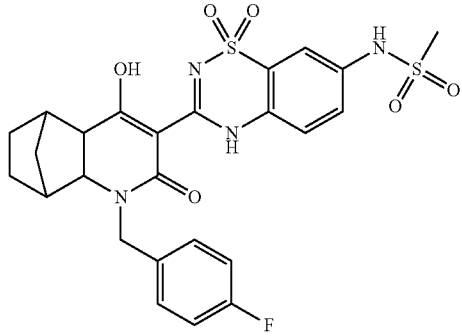 [SMILES: CS(=O)(=O)Nc1ccc2c(c1)S(=O)(=O)N=C(C1=C(O)C3C4CCC(C4)C3N(Cc3ccc(F)cc3)C1=O)N2]

(7-Methanesulfonylamino-1,1-dioxo-1,4-dihydro-1$\lambda^6$-benzo[1,2,4]thiadiazin-3-yl)-acetic acid (prepared as described in Example 1g, 0.1 g, 0.299 mmol) was dissolved in anhydrous N,N-dimethylformamide (1.5 mL). (rac-di-exo)-3-(4-Fluoro-benzylamino)-bicyclo[2.2.1]heptane-2-carboxylic acid ethyl ester (0.087 g, 0.3 mmol) was added followed by a 1.0 M solution of N,N-dicyclohexylcarbodiimide in dichloromethane (0.315 mL, 0.315 mmol). The mixture was stirred at 25° C. for 1.5 h. Triethylamine (0.124 mL, 0.9 mmol) was added and the mixture was stirred at 50° C. for 16 h. Upon cooling, the mixture was poured into 1.0 M aqueous hydrochloric acid solution (100 mL). The product was extracted into ethyl acetate (100 mL). The organic layer was washed with 1.0 M aqueous hydrochloric acid solution (50 mL), saturated aqueous brine solution (25 mL) and dried over magnesium sulfate. Purification by flash column chromatography (Merck silica gel 60, 40-63 nm, 0 to 1% methanol in dichloromethane) followed by crystallization from methanol afforded the desired product, (rac-di-exo)-N-{3-[3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (0.08 g, 0.141 mmol, 47%), as a white powder. $^1$H NMR (400 MHz, DMSO-$d_6$) δ: 1.18-1.21 (2H, m), 1.39-1.59 (5H, m), 2.61-2.64 (1H, m), 3.03 (1H, d, J=14.2 Hz), 3.05 (3H, s), 3.53 (1H, d, J=9.3 Hz), 4.41 (1H, d, J=14.8 Hz), 4.96 (1H, d, J=15.5 Hz), 7.14 (2H, t, J=9.0 Hz), 7.32 (2H, dd, $J_1$=8.7 Hz, $J_2$=6.2 Hz), 7.50 (1H, dd, $J_1$=9.3 Hz, $J_2$=2.4 Hz), 7.55-7.57 (2H, m), 10.17 (1H, s). LC-MS (ESI) calcd for $C_{25}H_{25}FN_4O_6S_2$ 560.12, found 561.3 [M+H$^+$]. HPLC-analysis: Chiralpak AS-RH 4.6×250 mm, 5 micron at r.t., Solvent A-Solvent B (see table for gradient), 0.8 mL/min, 310 nm, t1=7.72 min, t2=9.00 min.

Example 2

(rac-di-endo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

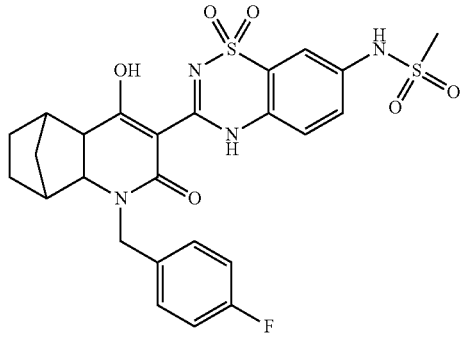 [SMILES: CS(=O)(=O)Nc1ccc2c(c1)S(=O)(=O)N=C(C1=C(O)C3C4CCC(C4)C3N(Cc3ccc(F)cc3)C1=O)N2]

a) (rac-di-endo)-3-(4-Fluoro-benzylamino)-bicyclo[2.2.1]heptane-2-carboxylic acid ethyl ester

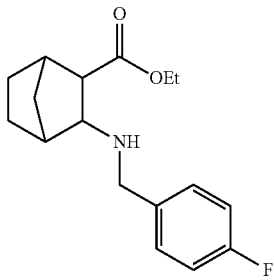 [SMILES: CCOC(=O)C1C2CCC(C2)C1NCc1ccc(F)cc1]

(rac-di-endo)-3-Amino-bicyclo[2.2.1]heptane-2-carboxylic acid ethyl ester hydrochloride (1 g, 4.6 mmol) was suspended in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a 1:1 mixture of saturated aqueous sodium bicarbonate solution (200 mL) and ethyl acetate (200 mL). After shaking, both layers were passed through a plug of Celite. The organic layer was further washed with saturated aqueous brine solution (50 mL), dried over magnesium sulfate, filtered, and concentrated in vacuo to afford the crude product, (di-endo)-3-(4-fluoro-benzylamino)-bicyclo[2.2.1]heptane-2-carboxylic acid ethyl ester (1.096 g, 3.77 mmol, 82%), as a clear oil. LC-MS (ESI) calcd for $C_{17}H_{22}FNO_2$ 291.16, found 292.1 [M+H$^+$].

b) (rac-di-endo)-N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

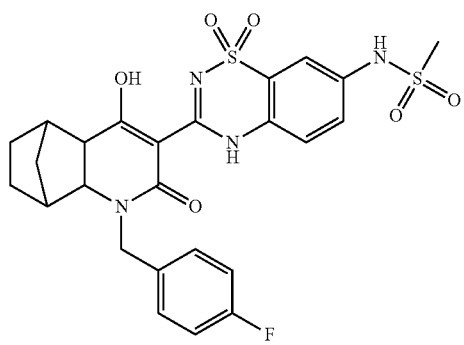 [SMILES: CS(=O)(=O)Nc1ccc2c(c1)S(=O)(=O)N=C(C1=C(O)C3C4CCC(C4)C3N(Cc3ccc(F)cc3)C1=O)N2]

(7-Methanesulfonylamino-1,1-dioxo-1,4-dihydro-1$\lambda^6$-benzo[1,2,4]thiadiazin-3-yl)-acetic acid (prepared as described in Example 1g, 0.1 g, 0.299 mmol) was dissolved in anhydrous N,N-dimethylformamide (1.5 mL). (rac-di-endo)-3-(4-Fluoro-benzylamino)-bicyclo[2.2.1]heptane-2-carboxylic acid ethyl ester (0.087 g, 0.3 mmol) was added followed by a 1.0 M solution of N,N-dicyclohexylcarbodiimide in dichloromethane (0.315 mL, 0.315 mmol). The mixture was stirred at 25° C. for 1.5 h. Triethylamine (0.124 mL, 0.9 mmol) was added and the mixture was stirred at 50° C. for 16 h. Upon cooling, the mixture was poured into 1.0 M aqueous hydrochloric acid solution (100 mL). The product was extracted into ethyl acetate (100 mL). The organic layer was washed with 1.0 M aqueous hydrochloric acid solution (50 mL), saturated aqueous brine solution (25 mL) and dried over magnesium sulfate. Purification by flash column chromatography (Merck silica gel 60, 40-63 nm, 0 to 1% methanol in dichloromethane) followed by crystallization from methanol afforded the desired product, (rac-di-endo)-N-{3-[3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (0.092 g, 0.164 mmol, 55%), as a white powder. $^1$H NMR (400 MHz, DMSO-$d_6$) δ: 1.25-1.48 (6H, m), 2.64-2.73 (2H, m), 3.06 (3H, s), 3.24 (1H, d, J=23.8 Hz), 3.72 (1H, d, J=11.6 Hz), 4.07 (1H, d, J=14.8 Hz), 5.12 (1H, d, J=15.3 Hz), 7.14 (2H, t, J=8.6 Hz), 7.39 (2H, dd, J$_1$=8.1 Hz, J$_2$=5.7 Hz), 7.51 (1H, dd, J$_1$=8.5 Hz, J$_2$=2.4 Hz), 7.57-7.60 (2H, m), 10.18 (1H, s). LC-MS (ESI) calcd for $C_{25}H_{25}FN_4O_6S_2$ 560.12, found 561.4 [M+H$^+$]. HPLC-analysis: Chiralpak AS-RH 4.6×250 mm, 5 micron at r.t., Solvent A-Solvent B (see table for gradient), 0.8 mL/min, 310 nm, t1=7.58 min, t2=10.08 min.

Example 3

(rac-di-endo)-N-{3-[3-(5-Fluoro-pyridin-2-ylmethyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

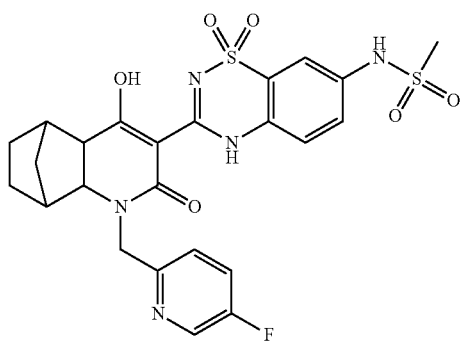 [SMILES: CS(=O)(=O)Nc1ccc2c(c1)S(=O)(=O)N=C(C1=C(O)C3C4CCC(C4)C3N(Cc3ccc(F)cn3)C1=O)N2]

a) (rac-di-endo)-3-[(5-Fluoro-pyridin-2-ylmethyl)-amino]-bicyclo[2.2.1]heptane-2-carboxylic acid ethyl ester

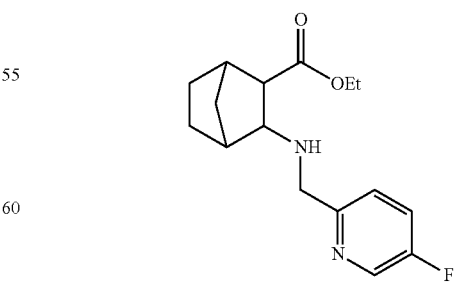

(rac-di-endo)-3-Amino-bicyclo[2.2.1]heptane-2-carboxylic acid ethyl ester hydrochloride (1 g, 4.6 mmol) was suspended in methanol (23 mL). Sodium acetate (0.755 g, 9.2 mmol) was added followed by 4 Å powdered molecular sieves (1 g) followed by 5-fluoro-pyridine-2-carbaldehyde (0.576 g, 4.6 mmol). Sodium cyanoborohydride (0.578 g, 9.2 mmol) was added and the mixture was stirred at 25° C. for 16 h. The mixture was poured into a 1:1 mixture of saturated aqueous sodium bicarbonate solution (200 mL) and ethyl acetate (200 mL). After shaking, both layers were passed through a plug of Celite. The organic layer was further washed with saturated aqueous brine solution (50 mL), dried over magnesium sulfate, filtered, and concentrated in vacuo to afford the crude product, (rac-di-endo)-3-[(5-fluoro-pyridin-2-ylmethyl)-amino]-bicyclo[2.2.1]heptane-2-carboxylic acid ethyl ester (1.247 g, 4.27 mmol, 93%), as a clear oil. LC-MS (ESI) calcd for $C_{16}H_{21}FN_2O_2$ 292.16, found 293.1 [M+H$^+$].

b) (rac-di-endo)-N-{3-[3-(5-Fluoro-pyridin-2-ylmethyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

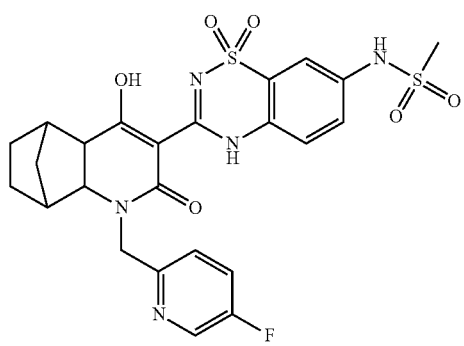 [SMILES: CS(=O)(=O)Nc1ccc2c(c1)S(=O)(=O)N=C(C1=C(O)C3C4CCC(C4)C3N(Cc3ccc(F)cn3)C1=O)N2]

(7-Methanesulfonylamino-1,1-dioxo-1,4-dihydro-1λ$^6$-benzo[1,2,4]thiadiazin-3-yl)-acetic acid (prepared as described in Example 1g, 0.1 g, 0.299 mmol) was dissolved in anhydrous N,N-dimethylformamide (1.5 mL). (rac-di-endo)-3-[(5-Fluoro-pyridin-2-ylmethyl)-amino]-bicyclo[2.2.1]heptane-2-carboxylic acid ethyl ester (0.088 g, 0.3 mmol) was added followed by a 1.0 M solution of N,N-dicyclohexylcarbodiimide in dichloromethane (0.315 mL, 0.315 mmol). The mixture was stirred at 25° C. for 1.5 h. Triethylamine (0.124 mL, 0.9 mmol) was added and the mixture was stirred at 50° C. for 16 h. Upon cooling, the mixture was poured into 1.0 M aqueous hydrochloric acid solution (100 mL). The product was extracted into ethyl acetate (100 mL). The organic layer was washed with 1.0 M aqueous hydrochloric acid solution (50 mL), saturated aqueous brine solution (25 mL), dried over magnesium sulfate, and concentrated in vacuo. Crystallization from methanol afforded the desired product, (rac-di-endo)-N-{3-[3-(5-fluoro-pyridin-2-ylmethyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.087 g, 0.156 mmol, 52%), as a light yellow powder. $^1$H NMR (400 MHz, DMSO-d$_6$) δ: 1.24-1.50 (6H, m), 2.64-2.73 (2H, m), 3.05 (3H, s), 3.28 (1H, d, J=12.2 Hz), 3.89 (1H, d, J=14.9 Hz), 4.25 (1H, d, J=15.7 Hz), 5.10 (1H, d, J=15.5 Hz), 7.46-7.51 (2H, m), 7.55-7.57 (2H, m), 7.66-7.71 (1H, m), 8.49 (1H, d, J=2.3 Hz), 10.17 (1H, s). LC-MS (ESI) calcd for $C_{24}H_{24}FN_5O_6S_2$ 561.12, found 562.4 [M+H$^+$].

Example 4

N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

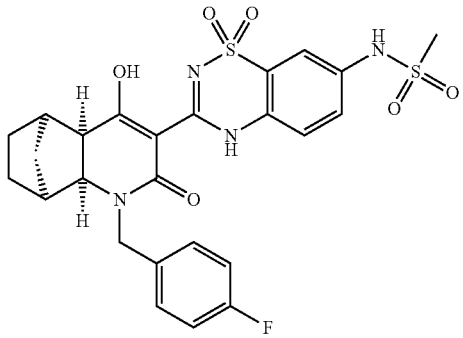

a) (1R,2S,3R,4S)-3-(Methoxycarbonyl)bicyclo[2.2.1]hept-5-ene-2-carboxylic acid

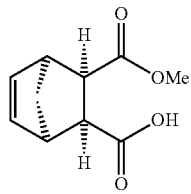

The starting material (a) was prepared as described in J. Org. Chem. 2000, 65, 6984-6991. cis-5-Norbornene-endo-2,3-dicarboxylic anhydride (4.104 g, 25 mmol) was suspended in a 1:1 mixture of toluene and carbon tetrachloride (500 mL). The mixture was stirred for 20 min. Quinine (8.92 g, 27.5 mmol) was added and the flask was degassed and backfilled with nitrogen. The solution was cooled to −55° C. While stirring, methanol (3.04 mL, 75 mmol) was added. The mixture was stirred at −55° C. for 20 h. Upon warming to 25° C., the mixture was concentrated in vacuo to a thick oil. The oil was dissolved in ethyl acetate (400 mL), washed with 1.0 M aqueous hydrochloric acid solution (2×400 mL), saturated aqueous brine solution (100 mL), dried over magnesium sulfate, filtered, and concentrated in vacuo to afford the desired product, (1R,2S,3R,4S)-3-(methoxycarbonyl)bicyclo[2.2.1]hept-5-ene-2-carboxylic acid (4.8 g, 24.5 mmol, 98%), as a clear waxy solid. $^1$H NMR (400 MHz, DMSO-d$_6$) δ: 1.26 (1H, d, J=8.5 Hz), 1.33 (1H, d, J=8.8 Hz), 3.00 (1H, s), 3.03 (1H, s), 3.21-3.30 (2H, m), 3.45 (3H, s), 6.02-6.04 (1H, m), 6.14-6.16 (1H, m), 11.86 (1H, s).

b) Methyl (1S,2R,3S,4R)-3-{[(benzyloxy)carbonyl]amino}bicyclo[2.2.1]hept-5-ene-2-carboxylate

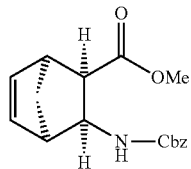

(1R,2S,3R,4S)-3-(Methoxycarbonyl)bicyclo[2.2.1]hept-5-ene-2-carboxylic acid (4.61 g, 23.5 mmol) was dissolved in anhydrous tetrahydrofuran (40 mL). The flask was degassed and backfilled with nitrogen and the mixture was cooled to 0° C. Triethylamine (9.9 mL, 70.5 mmol) was added followed by the dropwise addition of ethyl chloroformate (4.48 mL, 47 mmol) with vigorous stirring. Immediate precipitation was observed. Additional tetrahydrofuran (60 mL) was added. The mixture was stirred at 0° C. for 1 h. Sodium azide (4.58 g, 70.5 mmol) was dissolved in water (30 mL) and added to the reaction mixture at 0° C. The mixture was stirred at 0° C. for 5 min. The ice bath was removed. The mixture was warmed to 25° C. and was stirred for 2 h. The mixture was poured into water (300 mL) and the product extracted into ethyl acetate (300 mL). The organic layer was further washed with half-saturated aqueous sodium bicarbonate solution (2×100 mL), saturated aqueous brine solution (100 mL), dried over magnesium sulfate, filtered, and concentrated in vacuo to afford a clear oil. The oil was dissolved in anhydrous benzene (50 mL) and refluxed while stirring under nitrogen for 2 h. Upon cooling to 25° C. the solution was concentrated in vacuo to afford a slightly yellow oil. The oil was dissolved in dichloromethane (30 mL) and benzyl alcohol (2.68 mL, 25.9 mmol) was added followed by triethylamine (6.61 mL, 47 mmol). The mixture was refluxed under nitrogen for 16 h. Upon cooling to 25° C. the solution was concentrated in vacuo to afford a golden oil. Purification by flash column chromatography (Merck silica gel 60, 40-63 μm, 15% ethyl acetate in hexanes) afforded the desired product, methyl (1S,2R,3S,4R)-3-{[(benzyloxy)carbonyl]amino}bicyclo[2.2.1]hept-5-ene-2-carboxylate (5.51 g, 18.31 mmol, 78%), as a clear oil. $^1$H NMR (400 MHz, CDCl$_3$) δ: 1.38 (1H, d, J=9.1 Hz), 1.50 (1H, d, J=9.4 Hz), 3.10 (2H, s), 3.21 (1H, dd, J$_1$=9.2 Hz, J$_2$=2.3 Hz), 3.53 (3H, s), 4.62 (1H, dt, J$_1$=9.4 Hz, J$_2$=2.9 Hz), 5.07 (2H, q, J=13.0 Hz), 5.29 (1H, d, J=8.6 Hz), 6.15-6.17 (1H, m), 6.37-6.38 (1H, m), 7.29-7.35 (5H, m). LC-MS (ESI) calcd for C$_{17}$H$_{19}$NO$_4$ 301.13, found 258.1 (100%), 302.2 [M+H$^+$] (70%), 603.5 [2M+H$^+$] (20%).

c) Methyl (1R,2R,3S,4S)-3-aminobicyclo[2.2.1]heptane-2-carboxylate hydrochloride

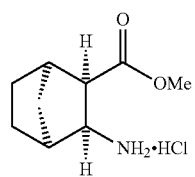

Methyl (1S,2R,3S,4R)-3-{[(benzyloxy)carbonyl]amino}bicyclo[2.2.1]hept-5-ene-2-carboxylate (5.5 g, 18.27 mmol) was dissolved in ethyl acetate (75 mL). 5% Palladium on carbon (650 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in ethyl acetate (15 mL) and added dropwise, with vigorous stirring, to a mixture of a 4.0 M solution of hydrochloric acid in 1,4-dioxane (10 mL, 40 mmol) in diethyl ether (90 mL). The desired product began to precipitate as a white solid. The mixture was stirred for 20 min. The precipitate was collected by vacuum filtration, and was washed with additional diethyl ether (15 mL). The solid was further dried in vacuo for 1 h to afford the desired product, methyl (1R,2R,3S,4S)-3-aminobicyclo[2.2.1]heptane-2-carboxylate hydrochloride (2.61 g, 12.69 mmol, 69%), as a white powder. $^1$H NMR (400 MHz, DMSO-d$_6$) δ: 1.34-1.43 (4H, m), 1.54 (1H, d, J=9.5 Hz), 1.68 (1H, d, J=11.4 Hz), 2.47-2.48 (2H, m), 3.03 (1H, dd, J$_1$=11.0 Hz, J$_2$=4.0 Hz), 3.49-3.53 (1H, m), 3.62 (3H, s), 8.07 (3H, bs). LC-MS (ESI) calcd for C$_9$H$_{15}$NO$_2$ (free amine) 169.11, found 170.1 [M+H$^+$] (100%), 339.2 [2M+H$^+$] (50%).

d) Methyl (1R,2R,3S,4S)-3-[(4-fluorobenzyl)amino]bicyclo[2.2.1]heptane-2-carboxylate

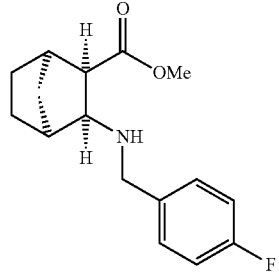

Methyl (1R,2R,3S,4S)-3-aminobicyclo[2.2.1]heptane-2-carboxylate hydrochloride (1 g, 4.86 mmol) was dissolved in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a mixture of saturated aqueous sodium bicarbonate solution (200 mL) and ethyl acetate (300 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1R,2R,3S,4S)-3-[(4-fluorobenzyl)amino]bicyclo[2.2.1]heptane-2-carboxylate (1.172 g, 4.23 mmol, 92%), as a clear oil. LC-MS (ESI) calcd for C$_{16}$H$_{20}$FNO$_2$ 277.15, found 278.2 [M+H$^+$].

e) N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

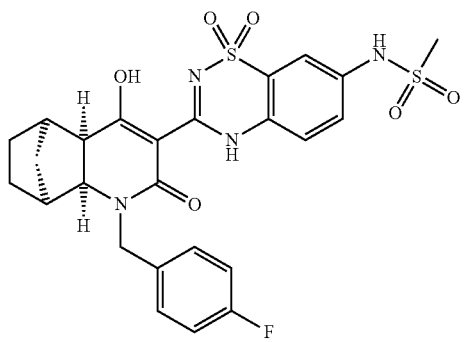

Methyl (1R,2R,3S,4S)-3-[(4-fluorobenzyl)amino]bicyclo[2.2.1]heptane-2-carboxylate (0.087 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in Example 1g, 0.1 g, 0.3 mmol) was added followed by N-methylmorpholine (0.07 mL, 0.63 mmol). The mixture was stirred until everything dissolved, approximately 5 min. 1-(3-Dimethylaminopropyl)-3-ethylcarbodiimide hydrochloride (0.061 g, 0.315 mmol) was added and the mixture was stirred at 25° C. for 4 h. Triethylamine (0.126 mL, 0.9 mmol) was added and the mixture was stirred at 50° C. for 16 h. Upon cooling to 25° C., the solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in methanol (4 mL) and the product was precipitated by the addition of 1.0 M aqueous hydrochloric acid solution (4 mL) while stirring. The solid was collected by vacuum filtration and further dried in vacuo to afford the desired product, N-{3-[(1S,2S,7R,8R)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.0805 g, 0.144 mmol, 48%), as a white powder. $^1$H NMR (400 MHz, DMSO-d$_6$) δ: 1.23-1.48 (6H, m), 2.67-2.68 (2H, m), 3.06 (3H, s), 3.24 (1H, d, J=15.0 Hz), 3.72 (1H, d, J=11.9 Hz), 4.07 (1H, d, J=15.6 Hz), 5.12 (1H, d, J=15.7 Hz), 7.14 (2H, t, J=8.4 Hz), 7.39 (2H, dd, J$_1$=8.2 Hz, J$_2$=5.8 Hz), 7.51 (1H, dd, J$_1$=8.4 Hz, J$_2$=2.3 Hz), 7.57-7.60 (2H, m), 10.18 (1H, s). LC-MS (ESI) calcd for C$_{25}$H$_{25}$FN$_4$O$_6$S$_2$ 560.12, found 561.3 [M+H$^+$]. ee=99% [HPLC-analysis: Chiralpak AS-RH 4.6×250 mm, 5 micron at r.t., Solvent A-Solvent B (see table for gradient), 0.8 mL/min, 310 nm, t1=7.58 min (major), t2=10.08 min].

Example 5

N-{3-[(1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

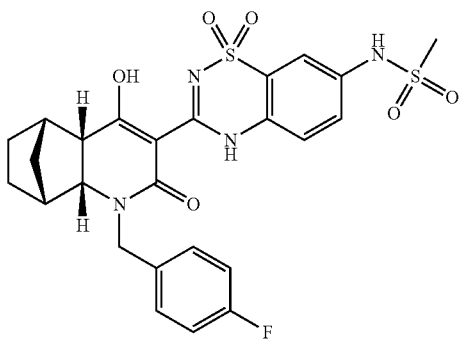 [SMILES: CS(=O)(=O)Nc1ccc2c(c1)S(=O)(=O)N=C(C1=C(O)[C@H]3[C@H]4CC[C@H](C4)[C@H]3N(Cc3ccc(F)cc3)C1=O)N2]

a) (1S,2R,3S,4R)-3-(Methoxycarbonyl)bicyclo[2.2.1]hept-5-ene-2-carboxylic acid

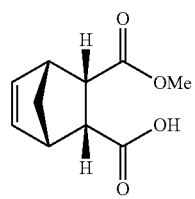 [SMILES: COC(=O)[C@@H]1[C@H](C(=O)O)[C@@H]2C=C[C@H]1C2]

The starting material (a) was prepared as described in *J. Org. Chem.* 2000, 65, 6984-6991. cis-5-Norbornene-endo-2,3-dicarboxylic anhydride (8.21 g, 50 mmol) was suspended in a 1:1 mixture of toluene and carbon tetrachloride (250 mL). The mixture was stirred for 10 min. Quinidine (17.84 g, 55 mmol) was added and the flask was degassed and backfilled with nitrogen. The solution was cooled to −55° C. While stirring, methanol (6.08 mL, 150 mmol) was added. The mixture was stirred at −55° C. for 18 h. Upon warming to 25° C., the mixture was concentrated in vacuo to a thick oil. The oil was dissolved in a mixture of ethyl acetate (400 mL) and 1.0 M aqueous hydrochloric acid solution (300 mL). After shaking, the layers were separated and the organic layer was further washed with 1.0 M aqueous hydrochloric acid solution (2×100 mL), saturated aqueous brine solution (100 mL), dried over magnesium sulfate, filtered, and concentrated in vacuo to afford the desired product, (1S,2R,3S,4R)-3-(methoxycarbonyl)bicyclo[2.2.1]hept-5-ene-2-carboxylic acid (9.15 g, 46.6 mmol, 94%), as a clear oil. $^1$H NMR (400 MHz, DMSO-d$_6$) δ: 1.26 (1H, d, J=8.4 Hz), 1.33 (1H, d, J=8.4 Hz), 3.00 (1H, s), 3.03 (1H, s), 3.21-3.29 (2H, m), 3.45 (3H, s), 6.02-6.04 (1H, m), 6.14-6.16 (1H, m), 11.86 (1H, s).

b) Methyl (1R,2S,3R,4S)-3-{[(benzyloxy)carbonyl]amino}bicyclo[2.2.1]hept-5-ene-2-carboxylate

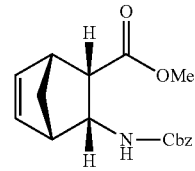 [SMILES: COC(=O)[C@@H]1[C@H](NC(=O)OCc2ccccc2)[C@@H]2C=C[C@H]1C2]

The intermediate (b) was prepared as described in *Synthesis* 2001, 11, 1719-1730. (1S,2R,3S,4R)-3-(Methoxycarbonyl)bicyclo[2.2.1]hept-5-ene-2-carboxylic acid (8.94 g, 45.57 mmol) was dissolved in anhydrous tetrahydrofuran (200 mL). The flask was degassed and backfilled with nitrogen and the mixture was cooled to 0° C. Triethylamine (19.2 mL, 136.7 mmol) was added followed by the dropwise addition of ethyl chloroformate (8.69 mL, 91.1 mmol) with vigorous stirring. Immediate precipitation was observed. The mixture was stirred at 0° C. for 1 h. Sodium azide (8.89 g, 136.7 mmol) was dissolved in water (60 mL) and added to the reaction mixture at 0° C. The mixture was stirred at 0° C. for 1 h. The ice bath was removed. The mixture was warmed to 25° C. and continued to stir for 2 h. The mixture was poured into water (400 mL) and the product extracted into ethyl acetate (400 mL). The organic layer was further washed with half-saturated aqueous sodium bicarbonate solution (2×200 mL), saturated aqueous brine solution (2×200 mL), dried over magnesium sulfate, filtered, and concentrated in vacuo to afford a slightly brown oil. The oil was dissolved in anhydrous benzene (100 mL) and refluxed while stirring under nitrogen for 2 h. Upon cooling to 25° C. the solution was concentrated in vacuo to afford a slightly brown oil. The oil was dissolved in dichloromethane (60 mL) and benzyl alcohol (5.19 mL, 50.13 mmol) was added followed by triethylamine (12.81 mL, 91.14 mmol). The mixture was refluxed under nitrogen for 16 h. Upon cooling to 25° C. the solution was concentrated in vacuo to afford a golden oil. Purification by flash column chromatography (Merck silica gel 60, 40-63 μm, 10% ethyl acetate in hexanes) afforded the desired product, methyl (1R,2S,3R,4S)-3-{[(benzyloxy)carbonyl]amino}bicyclo[2.2.1]hept-5-ene-2-carboxylate (10.1 g, 33.55 mmol, 74%), as a clear oil. $^1$H NMR (400 MHz, CDCl$_3$) δ: 1.38 (1H, d, J=8.7 Hz), 1.50 (1H, d, J=8.4 Hz), 3.10 (2H, s), 3.21 (1H, d, J=8.8 Hz), 3.53 (3H, s), 4.59-4.64 (1H, m), 5.07 (2H, q, J=13.0 Hz), 5.29 (1H, d, J=8.3 Hz), 6.15-6.17 (1H, m), 6.37-6.38 (1H, m), 7.27-7.36 (5H, m). LC-MS (ESI) calcd for C$_{17}$H$_{19}$NO$_4$ 301.13, found 258.1 (100%), 302.2 [M+H$^+$] (70%), 603.5 [2M+H$^+$] (20%).

c) Methyl (1S,2S,3R,4R)-3-aminobicyclo[2.2.1]heptane-2-carboxylate hydrochloride

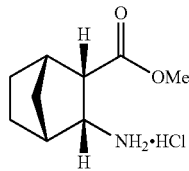

Methyl (1R,2S,3R,4S)-3-{[(benzyloxy)carbonyl]amino}bicyclo[2.2.1]hept-5-ene-2-carboxylate (10 g, 33.22 mmol) was dissolved in ethyl acetate (150 mL). 5% Palladium on carbon (1.5 mg) was added. The flask was degassed and backfilled with hydrogen gas via balloon. The mixture was stirred at 25° C. for 2 h. The mixture was passed through a plug of Celite and the filtrate was concentrated in vacuo to a volume of 50 mL. The solution was added dropwise, with vigorous stirring, to a mixture of 4.0 M hydrochloric acid solution in 1,4-dioxane (20 mL) in diethyl ether (200 mL). The desired product began to precipitate as a white solid. The mixture was stirred for 10 min. The precipitate was collected by vacuum filtration, washed with additional diethyl ether (15 mL). The solid was further dried in vacuo for 1 h to afford the desired product, methyl (1S,2S,3R,4R)-3-aminobicyclo[2.2.1]heptane-2-carboxylate hydrochloride (5.21 g, 25.33 mmol, 76.3%), as a white powder. $^1$H NMR (400 MHz, DMSO-d$_6$) δ: 1.33-1.42 (4H, m), 1.54 (1H, d, J=10.3 Hz), 1.69 (1H, d, J=11.5 Hz), 2.46-2.48 (2H, m), 3.03 (1H, dd, J$_1$=10.8 Hz, J$_2$=4.1 Hz), 3.46-3.55 (1H, m), 3.62 (3H, s), 8.09 (3H, bs). LC-MS (ESI) calcd for C$_9$H$_{15}$NO$_2$ (free amine) 169.11, found 170.1 [M+H$^+$] (100%), 339.2 [2M+H$^+$] (50%).

d) Methyl (1S,2S,3R,4R)-3-[(4-fluorobenzyl)amino]bicyclo[2.2.1]heptane-2-carboxylate

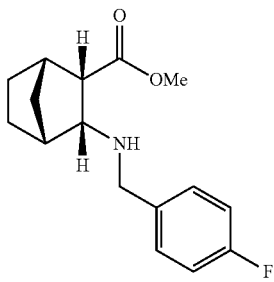 [SMILES: COC(=O)[C@H]1[C@H]2CC[C@H](C2)[C@H]1NCc1ccc(F)cc1]

Methyl (1S,2S,3R,4R)-3-aminobicyclo[2.2.1]heptane-2-carboxylate hydrochloride (1 g, 4.86 mmol) was dissolved in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a mixture of saturated aqueous sodium bicarbonate solution (200 mL) and ethyl acetate (300 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1S,2S,3R,4R)-3-[(4-fluorobenzyl)amino]bicyclo[2.2.1]heptane-2-carboxylate (1.11 g, 4.0 mmol, 87%), as a clear oil. LC-MS (ESI) calcd for C$_{16}$H$_{20}$FNO$_2$ 277.15, found 278.2 [M+H$^+$].

e) N-{3-[(1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

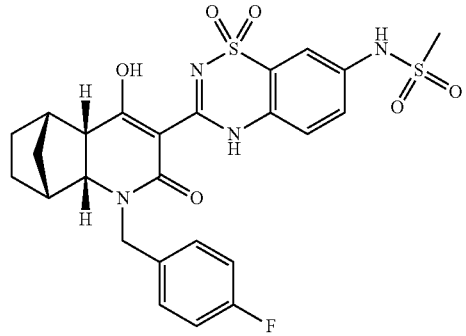 [SMILES: CS(=O)(=O)Nc1ccc2c(c1)S(=O)(=O)N=C(C1=C(O)[C@H]3[C@H]4CC[C@H](C4)[C@H]3N(Cc3ccc(F)cc3)C1=O)N2]

Methyl (1S,2S,3R,4R)-3-[(4-fluorobenzyl)amino]bicyclo[2.2.1]heptane-2-carboxylate (0.087 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in Example 1g, 0.1 g, 0.3 mmol) was added followed by N-methylmorpholine (0.07 mL, 0.63 mmol). The mixture was stirred until everything dissolved, approximately 5 min. 1-(3-Dimethylaminopropyl)-3-ethylcarbodiimide hydrochloride (0.061 g, 0.315 mmol) was added and the mixture was stirred at 25° C. for 4 h. Triethylamine (0.126 mL, 0.9 mmol) was added and the mixture was stirred at 50° C. for 16 h. Upon cooling to 25° C., the solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in methanol (4 mL) and the product was precipitated by the addition of 1.0 M aqueous hydrochloric acid solution (4 mL) while stirring. The solid was collected by vacuum filtration and further dried in vacuo to afford the desired product, N-{3-[(1R,2R,7S,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.0781 g, 0.139 mmol, 46%), as a white powder. $^1$H NMR (400 MHz, DMSO-d$_6$) δ: 1.23-1.48 (6H, m), 2.67-2.68 (2H, m), 3.06 (3H, s), 3.24 (1H, d, J=15.0 Hz), 3.72 (1H, d, J=11.9 Hz), 4.07 (1H, d, J=15.6 Hz), 5.12 (1H, d, J=15.7 Hz), 7.14 (2H, t, J=8.4 Hz), 7.39 (2H, dd, J$_1$=8.2 Hz, J$_2$=5.8 Hz), 7.51 (1H, dd, J$_1$=8.4 Hz, J$_2$=2.3 Hz), 7.57-7.60 (2H, m), 10.18 (1H, s). LC-MS (ESI) calcd for C$_{25}$H$_{25}$FN$_4$O$_6$S$_2$ 560.12, found 561.3 [M+H$^+$]. ee=99% [HPLC-analysis: Chiralpak AS-RH 4.6×250 mm, 5 micron at r.t., Solvent A-Solvent B (see table for gradient), 0.8 mL/min, 310 nm, t1=7.58 min, t2=10.08 min (major)].

Example 6

N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

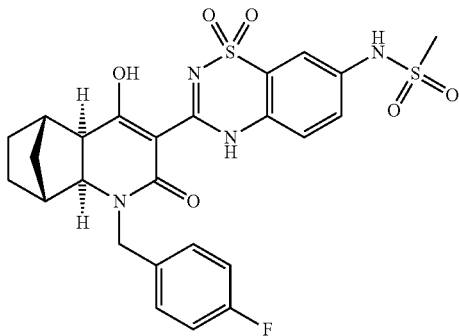

a) (1S,2S,3R,4R)-3-(Methoxycarbonyl)bicyclo[2.2.1]hept-5-ene-2-carboxylic acid

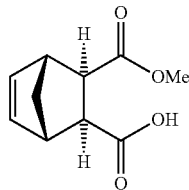

The starting material (a) was prepared as described in *J. Org. Chem.* 2000, 65, 6984-6991. cis-5-Norbornene-exo-2,3-dicarboxylic anhydride (5 g, 30.45 mmol) was suspended in a 1:1 mixture of toluene and carbon tetrachloride (610 mL). The mixture was stirred for 10 min. Quinine (10.87 g, 33.5 mmol) was added and the flask was degassed and backfilled with nitrogen. The solution was cooled to −55° C. While stirring, methanol (3.7 mL, 91.35 mmol) was added. The mixture was stirred at −55° C. for 16 h. Upon warming to 25° C., the mixture was concentrated in vacuo to a foam. The foam was dissolved in a mixture of ethyl acetate (400 mL) and 1.0 M aqueous hydrochloric acid solution (400 mL). The layers were separated and the organic layer was further washed with 1.0 M aqueous hydrochloric acid solution (2×200 mL), saturated aqueous brine solution (100 mL) and dried over magnesium sulfate, filtered, and concentrated in vacuo to afford the desired product, (1S,2S,3R,4R)-3-(methoxycarbonyl)bicyclo[2.2.1]hept-5-ene-2-carboxylic acid (5.95 g, 30.3 mmol, 99%), as a clear oil. ¹H NMR (400 MHz, DMSO-d₆) δ: 1.31 (1H, d, J=8.5 Hz), 1.98 (1H, d, J=8.6 Hz), 2.51 (2H, d, J=1.6 Hz), 2.95 (2H, bs), 3.52 (3H, s), 6.17-6.21 (2H, m), 12.16 (1H, s).

b) Methyl (1R,2R,3S,4S)-3-{[(benzyloxy)carbonyl]amino}bicyclo[2.2.1]hept-5-ene-2-carboxylate

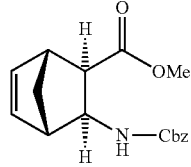

(1S,2S,3R,4R)-3-(Methoxycarbonyl)bicyclo[2.2.1]hept-5-ene-2-carboxylic acid (5.9 g, 30 mmol) was dissolved in anhydrous tetrahydrofuran (133 mL). The flask was degassed and backfilled with nitrogen and the mixture was cooled to 0° C. Triethylamine (12.64 mL, 90 mmol) was added followed by the dropwise addition of ethyl chloroformate (5.72 mL, 60 mmol) with vigorous stirring. Immediate precipitation was observed. The mixture was stirred at 0° C. for 1 h. Sodium azide (5.86 g, 90 mmol) was dissolved in water (40 mL) and added to the reaction mixture at 0° C. The mixture was stirred at 0° C. for 5 min. The ice bath was removed. The mixture was warmed to 25° C. and continued to stir for 2 h. The mixture was poured into water (300 mL) and the product extracted into ethyl acetate (300 mL). The organic layer was further washed with half-saturated aqueous sodium bicarbonate solution (2×100 mL), saturated aqueous brine solution (100 mL), dried over magnesium sulfate, filtered, and concentrated in vacuo to afford a light brown oil. The oil was dissolved in anhydrous benzene (66 mL) and refluxed while stirring under nitrogen for 2 h. Upon cooling to 25° C. the solution was concentrated in vacuo to afford a light brown oil. The oil was dissolved in dichloromethane (40 mL) and benzyl alcohol (3.41 mL, 33 mmol) was added followed by triethylamine (8.44 mL, 60 mmol). The mixture was refluxed under nitrogen for 16 h. Upon cooling to 25° C. the solution was concentrated in vacuo to afford a thick oil. Purification by flash column chromatography (Merck silica gel 60, 40-63 μm; 1$^{st}$ column: 3:1 hexanes/ethyl acetate; 2$^{nd}$ column: 2:4:1 dichloromethane/pentane/diethyl ether) afforded the desired product, methyl (1R,2R,3S,4S)-3-{[(benzyloxy)carbonyl]amino}bicyclo[2.2.1]hept-5-ene-2-carboxylate (6.95 g, 23.09 mmol, 77%), as a pale yellow oil. ¹H NMR (400 MHz, CDCl₃) δ: 1.59 (1H, d, J=9.3 Hz), 1.96 (1H, d, J=9.3 Hz), 2.66 (1H, d, J=7.9 Hz), 2.75 (1H, s), 2.96 (1H, s), 3.59 (3H, s), 4.01 (1H, t, J=8.5 Hz), 5.09 (2H, q, J=10.4 Hz), 5.46 (1H, d, J=9.4 Hz), 6.17-6.22 (2H, m), 7.29-7.36 (5H, m). LC-MS (ESI) calcd for C₁₇H₁₉NO₄ 301.13, found 258.1 (100%), 302.2 [M+H⁺] (70%), 603.5 [2M+H⁺] (20%).

c) Methyl (1S,2R,3S,4R)-3-aminobicyclo[2.2.1]heptane-2-carboxylate hydrochloride

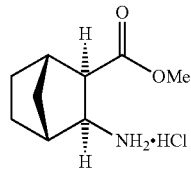

Methyl (1R,2R,3S,4S)-3-{[(benzyloxy)carbonyl]amino}bicyclo[2.2.1]hept-5-ene-2-carboxylate (1 g, 3.32 mmol) was dissolved in ethyl acetate (15 mL). 5% Palladium on carbon (120 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (10 mL) and added dropwise, with vigorous stirring, to a mixture of 4.0 M hydrochloric acid solution in 1,4-dioxane (1.8 mL) in diethyl ether (18 mL). The desired product began to precipitate as a white solid. Additional diethyl ether (10 mL) was added and the mixture was stirred for 10 min. The precipitate was collected by vacuum filtration, washed with additional diethyl ether (2×8 mL). The solid was further dried in vacuo for 1 h to afford the desired product, methyl (1S,2R, 3S,4R)-3-aminobicyclo[2.2.1]heptane-2-carboxylate hydrochloride (0.64 g, 3.11 mmol, 94%), as a white powder. $^1$H NMR (400 MHz, DMSO-$d_6$) δ: 1.17-1.27 (3H, m), 1.40-1.61 (2H, m), 1.91 (1H, d, J=10.7 Hz), 2.36 (1H, d, J=4.1 Hz), 2.44 (1H, d, J=3.1 Hz), 2.75 (1H, d, J=7.8 Hz), 3.30-3.38 (1H, m), 3.61 (3H, s), 8.05 (3H, bs). LC-MS (ESI) calcd for $C_9H_{15}NO_2$ (free amine) 169.11, found 170.3 [M+H$^+$] (100%), 339.3 [2M+H$^+$] (50%).

d) Methyl (1S,2R,3S,4R)-3-[(4-fluorobenzyl)amino]bicyclo[2.2.1]heptane-2-carboxylate

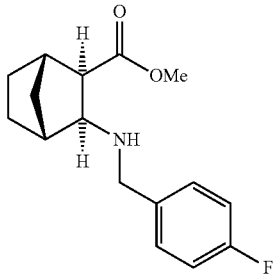

Methyl (1S,2R,3S,4R)-3-aminobicyclo[2.2.1]heptane-2-carboxylate hydrochloride (prepared as described in Example 6c, 0.5 g, 2.43 mmol) was dissolved in methanol (12 mL). Sodium acetate (0.4 g, 4.86 mmol) was added followed by 4 Å powdered molecular sieves (0.5 g) and 4-fluoro-benzaldehyde (0.302 g, 2.43 mmol). Sodium cyanoborohydride (0.305 g, 4.86 mmol) was added and the mixture was stirred at 25° C. for 16 h. The mixture was poured into a mixture of saturated aqueous sodium bicarbonate solution (200 mL) and ethyl acetate (300 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1S,2R,3S,4R)-3-[(4-fluorobenzyl)amino]bicyclo[2.2.1]heptane-2-carboxylate (0.663 g, 2.39 mmol, 98%), as a clear oil. LC-MS (ESI) calcd for $C_{16}H_{20}FNO_2$ 277.15, found 278.2 [M+H$^+$].

e) N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

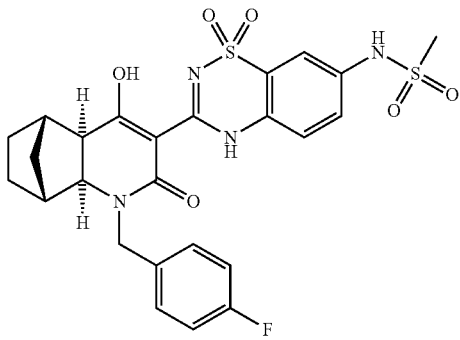

Methyl (1S,2R,3S,4R)-3-[(4-fluorobenzyl)amino]bicyclo[2.2.1]heptane-2-carboxylate (0.6 g, 2.16 mmol) was dissolved in anhydrous N,N-dimethylformamide (20 mL). (7-Methanesulfonylamino-1,1-dioxo-1,4-dihydro-1λ$^6$-benzo[1,2,4]thiadiazin-3-yl)-acetic acid (prepared as described in Example 1g, 0.72 g, 2.16 mmol) was added followed by N-methylmorpholine (0.5 mL, 4.54 mmol). The mixture was stirred until everything dissolved, approximately 5 min. 1-(3-Dimethylaminopropyl)-3-ethylcarbodiimide hydrochloride (0.435 g, 2.27 mmol) was added and the mixture was stirred at 25° C. for 45 min. Triethylamine (0.91 mL, 6.48 mmol) was added and the mixture was stirred at 50° C. for 16 h.

Upon cooling to 25° C., the solution was diluted with ethyl acetate (300 mL) and washed with 1.0 M aqueous hydrochloric acid solution (3×300 mL), saturated aqueous brine solution (100 mL), dried over magnesium sulfate, filtered, and concentrated in vacuo to afford a golden oil. Purification by flash column chromatography (Merck silica gel 60, 40-63 µm, 0 to 0.75% methanol in dichloromethane) afforded the product as white foam. The foam was dissolved in methanol (10 mL) and the product was precipitated by the addition of a 1.0 M aqueous hydrochloric acid solution (20 mL) while stirring. The solid was collected by vacuum filtration and further dried in vacuo to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.573 g, 1.02 mmol, 47%), as a white powder. $^1$H NMR (400 MHz, DMSO-$d_6$) δ: 1.16-1.22 (2H, m), 1.37-1.65 (4H, m), 2.49-2.53 (1H, m), 2.63 (1H, d, J=2.3 Hz), 3.02 (1H, d, J=8.5 Hz), 3.05 (3H, s), 3.52 (1H, d, J=9.4 Hz), 4.41 (1H, d, J=15.6 Hz), 4.95 (1H, d, J=15.6 Hz), 7.14 (2H, t, J=9.0 Hz), 7.32 (2H, dd, J$_1$=8.1 Hz, J$_2$=5.7 Hz), 7.50 (1H, dd, J$_1$=9.5 Hz, J$_2$=2.3 Hz), 7.55-7.57 (2H, m), 10.17 (1H, s). LC-MS (ESI) calcd for $C_{25}H_{25}FN_4O_6S_2$ 560.12, found 561.3 [M+H$^+$]. ee=90% [HPLC-analysis: Chiralpak AS-RH 2.1×150 mm, 5 micron at r.t., Solvent A-Solvent B (see table for gradient), 0.3 mL/min, 312 nm, t1=4.3 min (major), t2=6.0 min].

Alternatively, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide can be prepared as follows:

f) (rac-di-exo)-3-Aza-tricyclo[4.2.1.0$^{2,5}$]nonan-4-one

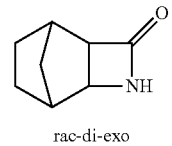

rac-di-exo

Bicyclo[2.2.1]hept-2-ene (1000 g, 10.6 mol) was dissolved in ethyl acetate (1.7 L) and the resulting solution was cooled to 0° C. Chlorosulfonyl isocyanate (969 mL, 11.1 mol) was added at 0-20° C. over 30 min. The mixture was allowed to warm to 25° C. and stirred for 4 h, then cooled to 0° C. A mixture of sodium sulfite (1500 g, 11.9 mol) in water (6 L) was added at 0-20° C. The milky suspension was stirred at 25° C. for 30 min and cooled to 0° C. A 50% aqueous sodium hydroxide solution (1.6 L, 30.3 mol) was added at 0-15° C. to adjust to pH 7. A saturated aqueous sodium carbonate solution (300 mL) was added to adjust the pH to 7.5-8.0. The mixture was filtered and the solid was washed with ethyl acetate (3×2 L) and the solid was discarded. The combined ethyl acetate extracts were washed with saturated aqueous brine solution (2 L), dried over magnesium sulfate and filtered. The solution was concentrated in vacuo to dryness to afford the desired product, (rac-di-exo)-3-aza-tricyclo[4.2.1.0$^{2,5}$]nonan-4-one (1220 g, 8.9 mol, 84%), as a white glassy solid. $^1$H NMR (400 MHz, CDCl$_3$) δ 1.02-1.11 (2H, m), 1.24 (1H, dt, J$_1$=10.9 Hz, J$_2$=1.6 Hz), 1.51-1.72 (3H, m), 2.37-2.37 (1H, m), 2.43-2.44 (1H, m), 2.99-3.00 (1H, m), 3.40 (1H, d, J=3.4 Hz), 5.73 (1H, bs).

g) (rac-di-exo)-3-Amino-bicyclo[2.2.1]heptane-2-carboxylic acid hydrochloride

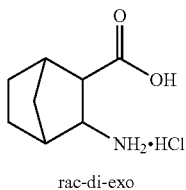

rac-di-exo

To (rac-di-exo)-3-aza-tricyclo[4.2.1.0$^{2,5}$]nonan-4-one (23.37 g, 170.4 mmol) was added a 12.0 M aqueous hydrochloric acid solution (150 mL). The mixture was stirred at 25° C. for 12 h. The solvent was evaporated in vacuo and the crude compound was dried under high vacuum for 0.5 h. The crude compound was triturated with acetone and filtered to afford (rac-di-exo)-3-amino-bicyclo[2.2.1]heptane-2-carboxylic acid hydrochloride (28.43 g, 148.3 mmol, 87%), as a white solid. $^1$H NMR (400 MHz, DMSO-d$_6$) δ 1.15-1.26 (3H, m), 1.42-1.59 (2H, m), 1.87 (1H, d, J=10.3 Hz), 2.33 (1H, d, J=3.4 Hz), 2.45 (1H, d, J=2.3 Hz), 2.67 (1H, d, J=7.6 Hz), 3.23-3.26 (1H, m), 7.93 (3H, bs), 12.73 (1H, bs).

h) (rac-di-exo)-3-Amino-bicyclo[2.2.1]heptane-2-carboxylic acid ethyl ester hydrochloride

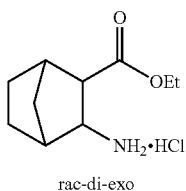

rac-di-exo

To absolute ethanol (75 mL) at −10° C. was added thionyl chloride (4.1 mL, 54.5 mmol) dropwise followed by (rac-di-exo)-3-amino-bicyclo[2.2.1]heptane-2-carboxylic acid hydrochloride (9.60 g, 50.1 mmol). The mixture was stirred at 0° C. for 1 h, at 25° C. for 4 h, and heated at reflux for 0.5 h. The solution was concentrated in vacuo and dried under high vacuum to afford the crude (rac-di-exo)-3-amino-bicyclo[2.2.1]heptane-2-carboxylic acid ethyl ester hydrochloride (11.01 g, 50.1 mmol, 100%), as an off-white solid. $^1$H NMR (400 MHz, DMSO-d$_6$) δ 1.17-1.27 (3H, m), 1.21 (3H, t, J=7.0 Hz), 1.43-1.57 (2H, m), 1.91 (1H, d, J=10.0 Hz), 2.36 (1H, d, J=3.9 Hz), 2.42 (1H, d, J=3.0 Hz), 2.72 (1H, d, J=7.6 Hz), 3.28 (1H, d, J=8.3 Hz), 4.00-4.13 (2H, m), 8.06 (3H, bs).

i) (rac-di-exo)-3-Amino-bicyclo[2.2.1]heptane-2-carboxylic acid ethyl ester

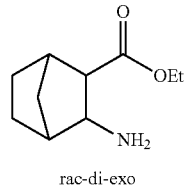 [SMILES: CCOC(=O)C1C2CCC(C2)C1N]

rac-di-exo

To (rac-di-exo)-3-amino-bicyclo[2.2.1]heptane-2-carboxylic acid ethyl ester hydrochloride (11.01 g, 50.1 mmol) was added saturated aqueous sodium bicarbonate solution (50 mL) and the mixture was stirred at 25° C. for 0.5 h. The crude product was extracted with ethyl acetate (3×100 mL). The solution was dried over magnesium sulfate, filtered, and concentrated in vacuo and dried under high vacuum for 2 h to afford the crude (rac-di-exo)-3-amino-bicyclo[2.2.1]heptane-2-carboxylic acid ethyl ester (8.17 g, 44.6 mmol, 89%), as a brown oil. $^1$H NMR (400 MHz, CDCl$_3$) δ 1.10-1.26 (3H, m), 1.29 (3H, t, J=7.0 Hz), 1.45-1.62 (2H, m), 1.86 (2H, bs), 1.95 (1H, dt, J$_1$=10.3 Hz, J$_2$=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

j) (1R,2S,3R,4S)-3-Ethoxycarbonyl-bicyclo[2.2.1]hept-2-yl-aminium (1'S)-(+)-10-camphorsulfonate

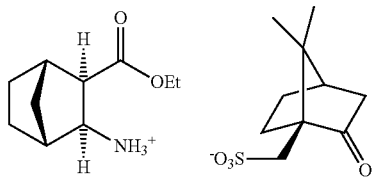

To a solution of (rac-di-exo)-3-amino-bicyclo[2.2.1]heptane-2-carboxylic acid ethyl ester (408.47 g, 2.98 mol) in ethyl acetate (500 mL) was added a solution of (1S)-(+)-10-camphorsulfonic acid (691.70 g, 2.98 mol) in ethanol (800 mL) at 50-75° C. over 30 min. The resulting solution was stirred at 70° C. for 1 h. More ethyl acetate (2.7 L) was added at >55° C. The solution was allowed to cool to 50° C. and seeded with (1R,2S,3R,4S)-3-ethoxycarbonyl-bicyclo[2.2.1]hept-2-yl-aminium (1'S)-(+)-10-camphorsulfonate (ca. 20 mg). The mixture was allowed to cool to 25° C. and stirred for 16 h. The suspension was filtered and the wet filter cake was washed with ethyl acetate (2×500 mL). The crude salt was recrystallized from ethanol (600 mL) and ethyl acetate (3 L) to afford the desired product, (1R,2S,3R,4S)-3-ethoxycarbonyl-bicyclo[2.2.1]hept-2-yl-aminium (1'S)-(+)-10-camphorsulfonate (334.84 g, 0.806 mol, 27%, >99.5% de), as a white solid. $^1$H NMR (400 MHz, CDCl$_3$) δ 0.84 (3H, s), 1.08 (3H, s), 1.30 (3H, t, J=6.9 Hz), 1.32-1.43 (4H, m), 1.58-1.75 (3H, m), 1.89 (1H, d, J=17.7 Hz), 1.95-2.07 (3H, m), 2.33 (1H, dt, J$_1$=18.4 Hz, J$_2$=3.9 Hz), 2.53 (1H, s), 2.58-2.65 (1H, m), 2.69 (1H, d, J=2.9 Hz), 2.76-2.79 (2H, m), 3.26 (1H, d, J=14.1 Hz), 3.60 (1H, d, J=7.4 Hz), 4.14-4.27 (2H, m), 7.80 (3H, bs).

Alternatively, (1R,2S,3R,4S)-3-ethoxycarbonyl-bicyclo[2.2.1]hept-2-yl-aminium (1'S)-(+)-10-camphorsulfonate can be prepared as follows:

(rac-di-exo)-3-Aza-tricyclo[4.2.1.0$^{2,5}$]nonan-4-one (prepared as described in Example 6f, 1220 g, 8.9 mol) was dissolved in ethyl acetate (1.7 L). The solution was heated to 50° C. and a solution of (1S)-(+)-10-camphorsulfonic acid (2066 g, 8.9 mol) in ethanol (2.5 L) at 50-75° C. over 30 min. The resulting solution was stirred at 70° C. for 2 h. More ethyl acetate (8 L) was added causing the temperature to drop to >55° C. and the solution was seeded with (1R,2S,3R,4S)-3-ethoxycarbonyl-bicyclo[2.2.1]hept-2-yl-aminium (1'S)-(+)-10-camphorsulfonate (ca. 100 mg). The mixture was allowed to cool to 25° C. and stirred for 16 h. The precipitate was collected by filtration and the wet filter cake was washed with ethyl acetate (2×2 L). The crude salt was dried at 25° C. for 48 h and then was recrystallized from ethanol (2 L) and ethyl acetate (2.5 L) to afford the desired product, (1R,2S,3R,4S)-3-ethoxycarbonyl-bicyclo[2.2.1]hept-2-yl-aminium (1'S)-(+)-10-camphorsulfonate (920 g, 2.21 mol, 25%, >99.9% de), as a white solid.

k) (1S,2R,3S,4R)-3-Amino-bicyclo[2.2.1]heptane-2-carboxylic acid ethyl ester

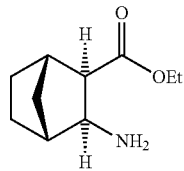

To (1R,2S,3R,4S)-3-ethoxycarbonyl-bicyclo[2.2.1]hept-2-yl-aminium (1'S)-(+)-10-camphorsulfonate (2.76 g, 6.64 mmol) was added ethyl acetate (28 mL) and saturated aqueous sodium carbonate solution (28 mL) and the mixture was stirred at 25° C. for 0.5 h. The organic layer was separated and the aqueous layer was extracted with ethyl acetate (2×50 mL). The solution was dried over magnesium sulfate, filtered, and concentrated in vacuo and dried under high vacuum for 1 h to afford (1S,2R,3S,4R)-3-amino-bicyclo[2.2.1]heptane-2-carboxylic acid ethyl ester (1.15 g, 6.28 mmol, 95%), as a colorless oil. $^1$H NMR (400 MHz, CDCl$_3$) δ 1.10-1.26 (3H, m), 1.29 (3H, t, J=7.0 Hz), 1.45-1.62 (2H, m), 1.86 (2H, bs), 1.95 (1H, dt, J$_1$=10.3 Hz, J$_2$=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

In order to determine the enantiomeric excess, (1S,2R,3S,4R)-3-amino-bicyclo[2.2.1]heptane-2-carboxylic acid ethyl ester was derivatized to the (S)-mandelate salt as follows: To a solution of (1S,2R,3S,4R)-3-amino-bicyclo[2.2.1]heptane-2-carboxylic acid ethyl ester (34.2 mg, 0.187 mmol) in ethyl acetate (1 mL) was added (S)-α-hydroxyphenylacetic acid (28.7 mg, 0.187 mmol) and the mixture was stirred at 25° C. for 0.5 h. The solid was filtered and dried under high vacuum to afford (1R,2S,3R,4S)-3-ethoxycarbonyl-bicyclo[2.2.1]hept-2-yl-aminium (S)-α-hydroxyphenylacetate (11.4 mg, 0.034 mmol, 18%, de=97%), as a white solid. $^1$H NMR (400 MHz, CDCl$_3$) δ 1.08-1.20 (3H, m), 1.28 (3H, t, J=7.1 Hz), 1.50-1.59 (2H, m), 1.79 (1H, d, J=10.9 Hz), 2.23 (1H, s), 2.46-2.48 (2H, m), 3.04 (1H, d, J=7.8 Hz), 4.05-4.18 (2H, m), 4.89 (1H, s), 5.49 (3H, bs), 7.22-7.31 (3H, m), 7.43 (2H, d, J=6.9 Hz).

l) (1S,2R,3S,4R)-3-(4-Fluorobenzylamino)-bicyclo[2.2.1]heptane-2-carboxylic acid ethyl ester

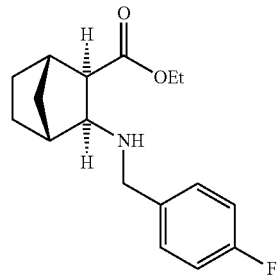

To a solution of (1S,2R,3S,4R)-3-amino-bicyclo[2.2.1]heptane-2-carboxylic acid ethyl ester (1.15 g, 6.28 mmol) in ethanol (30 mL) was added 4-fluorobenzaldehyde (0.68 mL, 6.31 mmol), glacial acetic acid (0.4 mL, 6.99 mmol), and sodium cyanoborohydride (1.04 g, 15.7 mmol) at 25° C. After stirring for 3 h, the mixture was diluted with ethyl acetate (50 mL) and quenched with saturated aqueous sodium bicarbonate solution (50 mL) for 0.5 h. The mixture was filtered through Celite. The organic layer was separated and the aqueous layer was extracted with ethyl acetate (2×50 mL). When all solvent was removed, a solid was formed. The solid was filtered, washed with water, and dried in vacuo to afford the desired product, (1S,2R,3S,4R)-3-(4-fluorobenzylamino)-bicyclo[2.2.1]heptane-2-carboxylic acid ethyl ester (1.74 g, 5.97 mmol, 95%), as a white solid. $^1$H NMR (400 MHz, CDCl$_3$) δ 1.05-1.16 (2H, m), 1.21 (1H, dt, J$_1$=8.0 Hz, J$_2$=1.6 Hz), 1.27 (3H, t, J=7.4 Hz), 1.45-1.61 (2H, m), 1.94 (1H, dt, J$_1$=10.1 Hz, J$_2$=1.9 Hz), 2.28 (1H, d, J=3.9 Hz), 2.43 (1H, d, J=3.3 Hz), 2.60 (1H, dd, J$_1$=8.8 Hz, J$_2$=1.5 Hz), 2.94 (1H, d, J=7.8 Hz), 3.66 (1H, d, J=13.2 Hz), 3.80 (1H, d, J=13.5 Hz), 4.13 (2H, q, J=7.0 Hz), 6.97 (2H, t, J=8.5 Hz), 7.26 (2H, t, J=7.1 Hz).

Alternatively, (1S,2R,3S,4R)-3-(4-Fluorobenzylamino)-bicyclo[2.2.1]heptane-2-carboxylic acid ethyl ester can be prepared as follows:

(1R,2S,3R,4S)-3-ethoxycarbonyl-bicyclo[2.2.1]hept-2-yl-aminium (1'S)-(+)-10-camphorsulfonate (prepared as described in Example 6j, 2000 g, 4.81 mol) and powdered potassium carbonate (1320 g, 9.62 mol) were suspended in ethyl acetate (20 L). The suspension was stirred at 25° C. for 16 h and filtered. The ethyl acetate filtrate was concentrated in vacuo to afford the free amine (1050 g) as a liquid. The liquid was dissolved in ethanol (10 L), and 4-fluorobenzaldehyde (558 mL, 5.3 mol) and acetic acid (362 mL, 6.3 mol) were added, causing the temperature to rise to 28-30° C. The solution was allowed to cool to 25° C. and stirred for 30 min. A cloudy solution of sodium cyanoborohydride (756 g, 12.03 mol) in ethanol (5 L) was added in 20 min, causing the temperature to rise to 45-50° C. The mixture was allowed to cool to 25° C. and stirred for 16 h. The mixture was concentrated in vacuo to a volume of about 13-14 L. Water (1-2 L) was added, and the resulting mixture was further concentrated in vacuo. A saturated aqueous sodium bicarbonate solution (4 L) and water (4 L) were added with stirring. The pH was adjusted to 8.0-8.5 by adding additional saturated aqueous sodium bicarbonate solution (~500 mL). The mixture was stirred for 1 h before the solids were collected by filtration and the wet filter cake was washed with water (2 L). The solid was dried in vacuo at 35° C. for 64 h to afford the desired product, (1S,2R,3S,4R)-3-(4-fluoro-benzylamino)-bicyclo[2.2.1]heptane-2-carboxylic acid ethyl ester (1350 g, 4.63 mol, 96%), as a white solid.

m) (1S,2R,3S,4R)-3-{(4-Fluorobenzyl)-[2-(7-methanesulfonylamino-1,1-dioxo-1,4-dihydro-1$\lambda^6$-benzo[1,2,4]thiadiazin-3-yl)-acetyl]-amino}-bicyclo[2.2.1]heptane-2-carboxylic acid ethyl ester

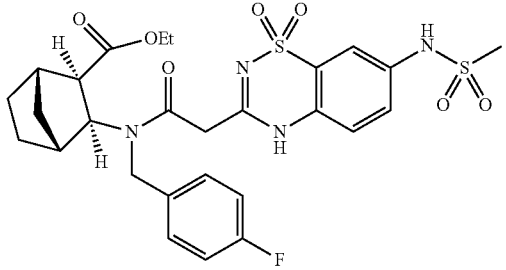 [SMILES: CCOC(=O)[C@@H]1[C@H]2CC[C@H](C2)[C@@H]1N(Cc1ccc(F)cc1)C(=O)CC1=NS(=O)(=O)c2cc(NS(C)(=O)=O)ccc2N1]

To a solution of (1S,2R,3S,4R)-3-(4-fluorobenzylamino)-bicyclo[2.2.1]heptane-2-carboxylic acid ethyl ester (100.6 mg, 0.345 mmol) in N,N-dimethylformamide (3.0 mL) was added (7-methanesulfonylamino-1,1-dioxo-1,4-dihydro-1$\lambda^6$-benzo[1,2,4]thiadiazin-3-yl)-acetic acid (prepared as described in Example 1g, 120.8 mg, 0.362 mmol), 4-dimethylaminopyridine (10.6 mg, 0.086 mmol), and 1-[3-(dimethylamino)propyl]-3-ethylcarbodiimide hydrochloride (70.9 mg, 0.362 mmol). After stirring at 25° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layer was dried over magnesium sulfate, filtered, and concentrated in vacuo, and dried under high vacuum to afford the crude product, (1S,2R,3S,4R)-3-{(4-fluorobenzyl)-[2-(7-methanesulfonylamino-1,1-dioxo-1,4-dihydro-1$\lambda^6$-benzo[1,2,4]thiadiazin-3-yl)-acetyl]-amino}-bicyclo[2.2.1]heptane-2-carboxylic acid ethyl ester, as a faintly yellow oil. The crude product was used in the next step without further purification. LC-MS (ESI) calcd for $C_{27}H_{31}FN_4O_7S_2$ 606.16, found 607.2 [M+H$^+$].

n) N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

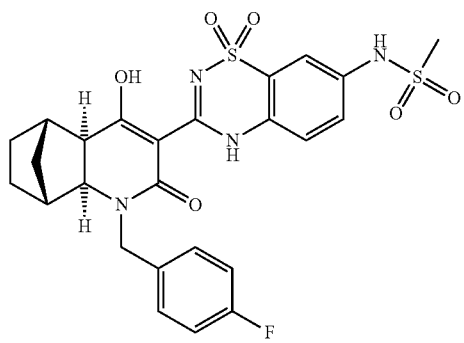

To a solution of the crude (1S,2R,3S,4R)-3-{(4-fluorobenzyl)-[2-(7-methanesulfonylamino-1,1-dioxo-1,4-dihydro-1$\lambda^6$-benzo[1,2,4]thiadiazin-3-yl)-acetyl]-amino}-bicyclo[2.2.1]heptane-2-carboxylic acid ethyl ester in absolute ethanol (3 mL) was added a 21 wt. % solution of sodium ethoxide in ethanol (0.51 mL, 1.37 mmol). After stirring at 60° C. for 2 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layer was dried over magnesium sulfate, filtered, and concentrated in vacuo. The crude mixture was purified by flash column chromatography (Teledyne Isco RediSep column; 0 to 100% ethyl acetate in hexanes) to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (131.5 mg, 0.235 mmol, 68% over two steps), as an off-white solid. $^1$H NMR (400 MHz, CD$_3$OD) δ 1.28 (2H, d, J=11.0 Hz), 1.47 (1H, t, J=10.8 Hz), 1.57-1.74 (3H, m), 2.56 (1H, d, J=3.2 Hz), 2.75 (1H, d, J=2.3 Hz), 2.96 (1H, d, J=9.2 Hz), 3.02 (3H, s), 3.58 (1H, d, J=9.2 Hz), 4.42 (1H, d, J=15.5 Hz), 5.03 (1H, d, J=15.7 Hz), 7.04 (2H, t, J=8.5 Hz), 7.31 (2H, dd, J$_1$=7.9 Hz, J$_2$=5.5 Hz), 7.37 (1H, d, J=8.8 Hz), 7.54 (1H, dd, J$_1$=8.3 Hz, J$_2$=2.3 Hz), 7.69 (1H, d, J=2.3 Hz). LC-MS (ESI) calcd for $C_{25}H_{25}FN_4O_6S_2$ 560.12, found 561.4 [M+H$^+$]. ee=98.5% [HPLC-analysis: Chiralpak AS-RH 2.1×150 mm, 5 micron at r.t., Solvent A-Solvent B (see table for gradient), 0.3 mL/min, 312 nm, t1=7.58 min (major), t2=8.95 min].

Alternatively, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide can be prepared as follows:

(7-Methanesulfonylamino-1,1-dioxo-1,4-dihydro-1$\lambda^6$-benzo[1,2,4]thiadiazin-3-yl)-acetic acid (prepared as described in Example 1g, 1.88 kg, 5.63 mol) and (1S,2R,3S,4R)-3-(4-fluoro-benzylamino)-bicyclo[2.2.1]heptane-2-carboxylic acid ethyl ester (prepared as described in Example 6l, 1.72 kg, 5.91 mol) were dissolved in acetonitrile (18.8 L) at 23° C. N-Methylmorpholine (1.25 kg, 12.4 mol) was added and the resulting suspension was stirred at 23° C. for 1 h. The suspension was cooled to 0° C. and 1-[3-(dimethylamino)propyl]-3-ethylcarbodiimide hydrochloride (1.19 kg, 6.20 mol) was added in one portion. The mixture was stirred at 0° C. for 3 h, and was then allowed to warm to 23° C. and stirred overnight. Triethylamine (1.88 kg, 18.6 mol) was added and the mixture was then heated at 50° C. for 3 h. The mixture was partially concentrated in vacuo at 45° C., and was then diluted with ethyl acetate (22.5 L) and washed with 2.0 M aqueous hydrochloric acid solution (22.6 L). The resulting aqueous fraction was extracted with ethyl acetate (2×9.4 L). The combined organic extracts were washed with 1.0 M aqueous hydrochloric acid solution (10.4 L) and then with water (18.8 L). The resulting organic fraction was filtered through Celite (600 g), and the filtrate was then partially concentrated in vacuo at 45° C. Absolute ethanol (5.6 L) was added to the residue, and the mixture was then heated at 50° C. with stirring. Dichloromethane (400 mL) was added in portions until crystallization initiated. Absolute ethanol (20.7 L) was added in portions over 1 h, and the resulting mixture was stirred at 23° C. overnight. The mixture was filtered and the solid was then washed with absolute ethanol (1.9 L). The solid was further dried in vacuo at 45° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1- dioxo-1,4-dihydro-1λ⁶-benzo[1,2,4]thiadiazin-7-yl}-methanesulfonamide (2.46 kg, 4.39 mol, 78%), as an off-white crystalline solid.

X-ray data—FIG. 1 shows a x-ray diffraction of N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide (as prepared in Example 6 on a kg scale). In the x-ray graph, the angle of diffraction 2 theta is plotted on the x-axis and the peak intensity is plotted on the y-axis. The strongest lines in the x-ray diffraction graph are observed at angles of 6.2°, 17.9°, 19.7°, 20.5°, 22.6°, and 24.8°±0.3°, with lesser intensity lines at 12.4°, 16.5°, 18.7°, 21.6°, 23.2°, 24.1°, 25.6°, 26.6°, 27.1°, 28.5°, and 29.3°.

Figure 2:
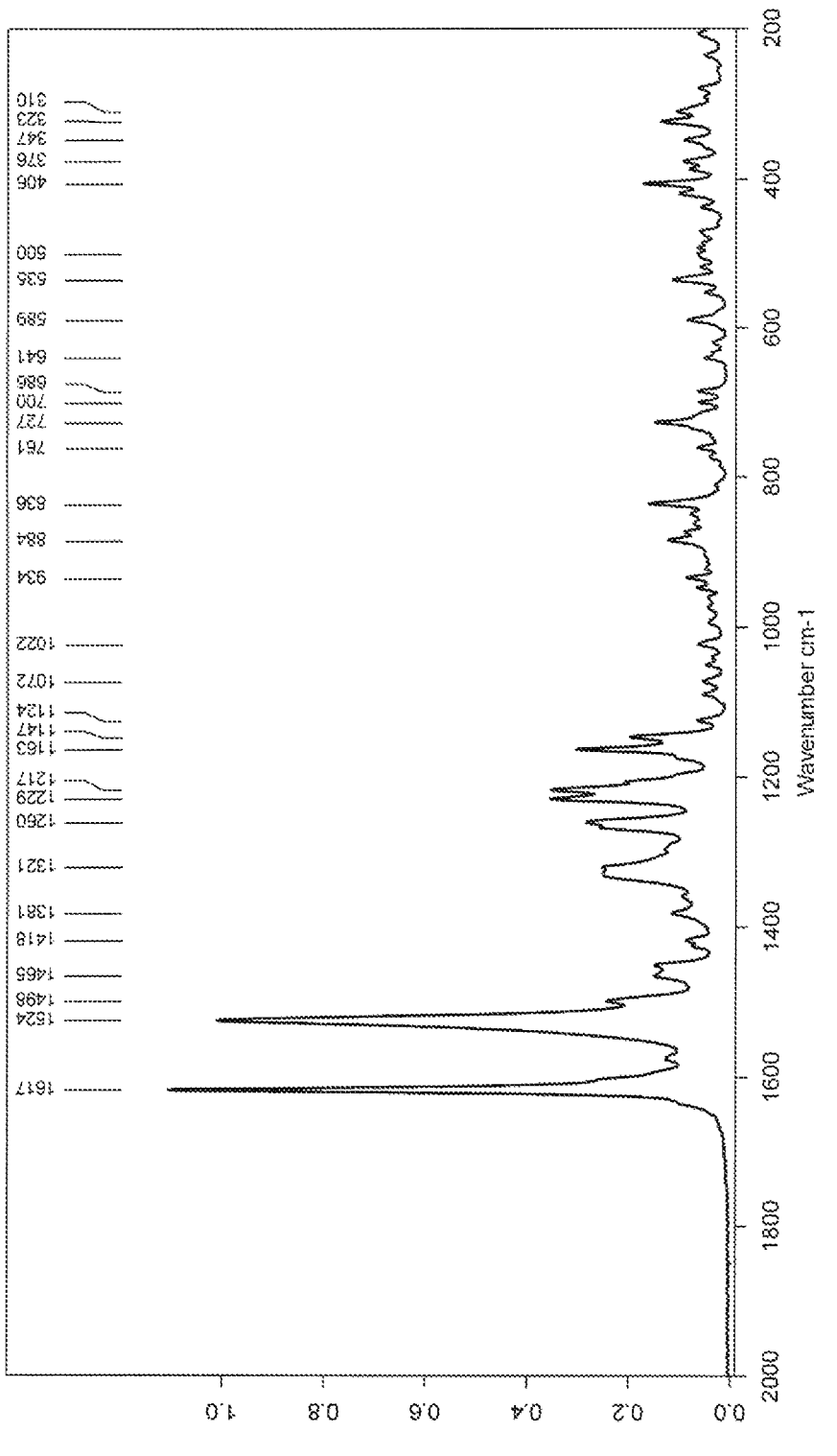
FIG. 2 shows a FT-Raman spectrum of N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (as prepared in Example 6 on a kg scale).

IR data—FIG. 2 shows a FT-Raman spectrum of N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide (as prepared in Example 6 on a kg scale), which is characterized by the following major IR bands at 1617, 1524, 1321, 1260, 1229, 1217, and 1163 cm⁻¹, with minor bands at 1498, 1465, 1147, 836, 727, and 406 cm⁻¹.

Example 7

N-{3-[(1S,2R,7S,8R)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

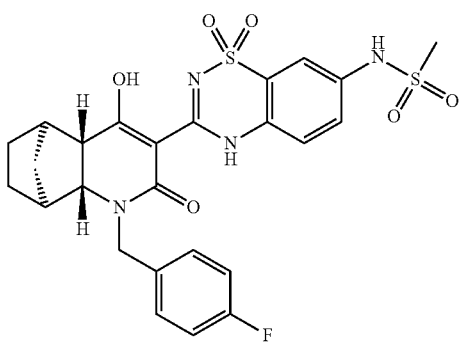

a) (1R,2R,3S,4S)-3-(Methoxycarbonyl)bicyclo[2.2.1]hept-5-ene-2-carboxylic acid

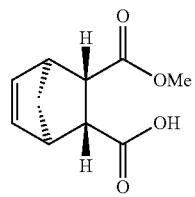

The starting material (a) was prepared as described in *J. Org. Chem.* 2000, 65, 6984-6991. cis-5-Norbornene-exo-2,3-dicarboxylic anhydride (5 g, 30.45 mmol) was suspended in a 1:1 mixture of toluene and carbon tetrachloride (150 mL). The mixture was stirred for 10 min. Quinidine (10.9 g, 33.5 mmol) was added and the flask was degassed and backfilled with nitrogen. The solution was cooled to −55° C. While stirring, methanol (3.7 mL, 91.35 mmol) was added. The mixture was stirred at −55° C. for 16 h. Upon warming to 25° C., the mixture was concentrated in vacuo to a foam. The foam was dissolved in a mixture of ethyl acetate (400 mL) and 1.0 M aqueous hydrochloric acid solution (400 mL). The layers were separated and the organic layer was further washed with 1.0 M aqueous hydrochloric acid solution (2×100 mL), saturated aqueous brine solution (100 mL) and dried over magnesium sulfate, filtered, and concentrated in vacuo to afford the desired product, (1R,2R,3S,4S)-3-(methoxycarbonyl)bicyclo[2.2.1]hept-5-ene-2-carboxylic acid (5.92 g, 30.2 mmol, 99%), as a clear oil. ¹H NMR (400 MHz, DMSO-d₆) δ: 1.29 (1H, d, J=10.2 Hz), 1.96 (1H, d, J=8.6 Hz), 2.47-2.49 (2H, m), 2.93-2.94 (2H, m), 3.51 (3H, s), 6.15-6.20 (2H, m), 12.15 (1H, s).

b) Methyl (1S,2S,3R,4R)-3-{[(benzyloxy)carbonyl]amino}bicyclo[2.2.1]hept-5-ene-2-carboxylate

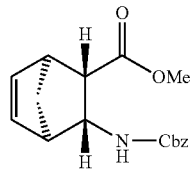

The intermediate (b) was prepared as described in *Synthesis* 2001, 11, 1719-1730. (1R,2R,3S,4S)-3-(Methoxycarbonyl)bicyclo[2.2.1]hept-5-ene-2-carboxylic acid (5.9 g, 30 mmol) was dissolved in anhydrous tetrahydrofuran (133 mL). The flask was degassed and backfilled with nitrogen and the mixture was cooled to 0° C. Triethylamine (12.64 mL, 90 mmol) was added followed by the dropwise addition of ethyl chloroformate (5.72 mL, 60 mmol) with vigorous stirring. Immediate precipitation was observed. The mixture was stirred at 0° C. for 1 h. Sodium azide (5.86 g, 90 mmol) was dissolved in water (40 mL) and added to the reaction mixture at 0° C. The mixture was stirred at 0° C. for 5 min. The ice bath was removed. The mixture was warmed to 25° C. and continued to stir for 2 h. The mixture was poured into water (300 mL) and the product extracted into ethyl acetate (350 mL). The organic layer was further washed with half-saturated aqueous sodium bicarbonate solution (2×100 mL), saturated aqueous brine solution (100 mL), dried over magnesium sulfate, filtered, and concentrated in vacuo to afford a light brown oil.

The oil was dissolved in anhydrous benzene (66 mL) and refluxed while stirring under nitrogen for 2 h. Upon cooling to 25° C. the solution was concentrated in vacuo to afford a light yellow oil. The oil was dissolved in dichloromethane (40 mL) and benzyl alcohol (3.41 mL, 33 mmol) was added followed by triethylamine (8.44 mL, 60 mmol). The mixture was refluxed under nitrogen for 16 h. Upon cooling to 25° C. the solution was concentrated in vacuo to afford a thick oil. Purification by flash column chromatography (Merck silica gel 60, 40-63 μm; 1ˢᵗ column: 3:1 hexanes/ethyl acetate; 2ⁿᵈ column: 2:4:1 dichloromethane/pentane/diethyl ether) afforded the desired product, methyl (1S,2S,3R,4R)-3-{[(benzyloxy)carbonyl]amino}bicyclo[2.2.1]hept-5-ene-2-carboxylate (6.195 g, 20.58 mmol, 69%), as a faintly yellow oil. ¹H NMR (400 MHz, CDCl₃) δ: 1.60 (1H, d, J=9.4 Hz), 1.97 (1H, d, J=9.3 Hz), 2.66 (1H, d, J=7.5 Hz), 2.75 (1H, s), 2.96 (1H, s), 3.60 (3H, s), 4.02 (1H, t, J=8.9 Hz), 5.09 (2H, q, J=10.5 Hz), 5.47 (1H, d, J=8.8 Hz), 6.18-6.23 (2H, m), 7.29-7.37 (5H, m). LC-MS (ESI) calcd for $C_{17}H_{19}NO_4$ 301.13, found 258.1 (100%), 302.2 [M+H$^+$] (70%), 603.4 [2M+H$^+$] (20%).

c) Methyl (1R,2S,3R,4S)-3-aminobicyclo[2.2.1]heptane-2-carboxylate hydrochloride

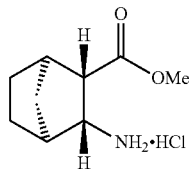

Methyl (1S,2S,3R,4R)-3-{[(benzyloxy)carbonyl]amino}bicyclo[2.2.1]hept-5-ene-2-carboxylate (1 g, 3.32 mmol) was dissolved in ethyl acetate (15 mL). 5% Palladium on carbon (120 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (10 mL) and added dropwise, with vigorous stirring, to a mixture of 4.0 M hydrochloric acid solution in 1,4-dioxane (1.8 mL, 7.2 mmol) in diethyl ether (18 mL). The desired product began to precipitate as a white solid. Additional diethyl ether (10 mL) was added and the mixture was stirred for 10 min. The precipitate was collected by vacuum filtration and washed with additional diethyl ether (2×8 mL). The solid was further dried in vacuo for 1 h to afford the desired product, methyl (1R,2S,3R,4S)-3-aminobicyclo[2.2.1]heptane-2-carboxylate hydrochloride (0.554 g, 2.7 mmol, 81%), as a white powder. $^1$H NMR (400 MHz, DMSO-$d_6$) δ: 1.18-1.27 (3H, m), 1.37-1.61 (2H, m), 1.90 (1H, d, J=11.0 Hz), 2.35 (1H, d, J=3.8 Hz), 2.44 (1H, d, J=3.1 Hz), 2.75 (1H, d, J=8.7 Hz), 3.29-3.34 (1H, m), 3.61 (3H, s), 8.03 (3H, bs). LC-MS (ESI) calcd for $C_9H_{15}NO_2$ (free amine) 169.11, found 170.3 [M+H$^+$] (100%), 339.3 [2M+H$^+$] (50%).

d) Methyl (1R,2S,3R,4S)-3-[(4-fluorobenzyl)amino]bicyclo[2.2.1]heptane-2-carboxylate

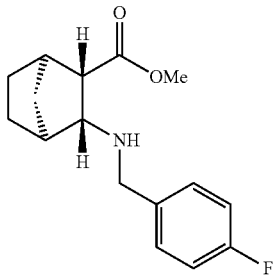

Methyl (1R,2S,3R,4S)-3-aminobicyclo[2.2.1]heptane-2-carboxylate hydrochloride (0.5 g, 2.43 mmol) was dissolved in methanol (12 mL). Sodium acetate (0.4 g, 4.86 mmol) was added followed by 4 Å powdered molecular sieves (0.5 g) and 4-fluoro-benzaldehyde (0.302 g, 2.43 mmol). Sodium cyanoborohydride (0.305 g, 4.86 mmol) was added and the mixture was stirred at 25° C. for 3 h. The mixture was poured into ethyl acetate (300 mL) and shaken with saturated aqueous sodium bicarbonate solution (200 mL). Both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1R,2S,3R,4S)-3-[(4-fluorobenzyl)amino]bicyclo[2.2.1]heptane-2-carboxylate (0.675 g, 2.43 mmol, 99%), as a clear oil. LC-MS (ESI) calcd for $C_{16}H_{20}FNO_2$ 277.15, found 278.2 [M+H$^+$].

e) N-{3-[(1S,2R,7S,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

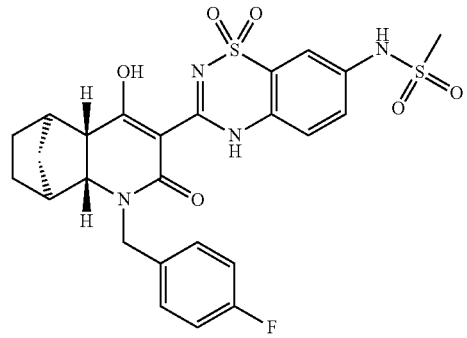

Methyl (1R,2S,3R,4S)-3-[(4-fluorobenzyl)amino]bicyclo[2.2.1]heptane-2-carboxylate (0.6 g, 2.16 mmol) was dissolved in anhydrous N,N-dimethylformamide (20 mL). (7-Methanesulfonylamino-1,1-dioxo-1,4-dihydro-1λ$^6$-benzo[1,2,4]thiadiazin-3-yl)-acetic acid (prepared as described in Example 1g, 0.72 g, 2.16 mmol) was added followed by N-methylmorpholine (0.5 mL, 4.54 mmol). The mixture was stirred until everything dissolved, approximately 5 min. 1-(3-Dimethylaminopropyl)-3-ethylcarbodiimide hydrochloride (0.435 g, 2.27 mmol) was added and the mixture was stirred at 25° C. for 45 min. Triethylamine (0.91 mL, 6.48 mmol) was added and the mixture was stirred at 50° C. for 16 h. Upon cooling to 25° C., the solution was diluted with ethyl acetate (300 mL) and washed with 1.0 M aqueous hydrochloric acid solution (3×300 mL), saturated aqueous brine solution (100 mL), dried over magnesium sulfate, filtered, and concentrated in vacuo to afford a golden oil. Purification by flash column chromatography (Merck silica gel 60, 40-63 μm, 0 to 0.75% methanol in dichloromethane) afforded the product as white foam. The foam was dissolved in methanol (10 mL) and the product was precipitated by the addition of 1.0 M aqueous hydrochloric acid solution (20 mL) while stirring. The solid was collected by vacuum filtration and further dried in vacuo to afford the desired product, N-{3-[(1S,2R,7S,8R)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.592 g, 1.06 mmol, 49%), as a white powder. $^1$H NMR (400 MHz, DMSO-$d_6$) δ: 1.15-1.22 (2H, m), 1.39-1.61 (4H, m), 2.49-2.55 (1H, m), 2.62-2.63 (1H, m), 3.02 (1H, d, J=9.8 Hz), 3.05 (3H, s), 3.52 (1H, d, J=9.3 Hz), 4.41 (1H, d, J=15.5 Hz), 4.95 (1H, d, J=15.5 Hz), 7.14 (2H, t, J=8.7 Hz), 7.32 (2H, dd, $J_1$=8.2 Hz, $J_2$=5.7 Hz), 7.50 (1H, dd, $J_1$=8.4 Hz, $J_2$=2.4 Hz), 7.55-7.57 (2H, m), 10.17 (1H, s). LC-MS (ESI) calcd for $C_{25}H_{25}FN_4O_6S_2$ 560.12, found 561.3 [M+H$^+$]. ee=96% [HPLC-analysis: Chiralpak AS-RH 2.1×150 mm, 5 micron at r.t., Solvent A-Solvent B (see table for gradient), 0.3 mL/min, 312 nm, t1=4.3 min, t2=6.0 min (major)].

Example 8

(rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

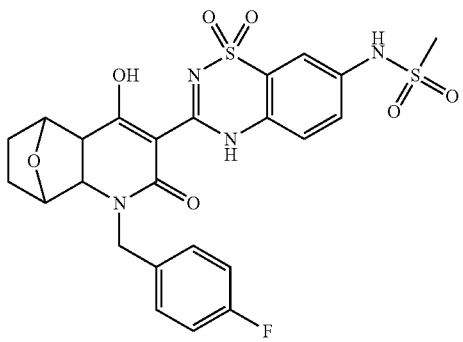

a) (rac-di-exo)-3-Amino-7-oxa-bicyclo[2.2.1]heptane-2-carboxylic acid methyl ester

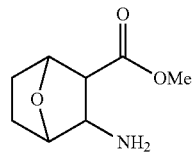 [SMILES: COC(=O)C1C2CCC(O2)C1N]

To a stirred solution of (rac-di-exo)-3-amino-7-oxa-bicyclo[2.2.1]heptane-2-carboxylic acid (1.0 g, 6.37 mmol) in anhydrous methanol and benzene (1:1, 20 mL), a 2.0 M solution of (trimethylsilyl)diazomethane in diethyl ether (6.37 mL, 12.7 mmol) was added dropwise. The resulting mixture was stirred for 1 h, and concentrated in vacuo to afford the desired product, (rac-di-exo)-3-amino-7-oxa-bicyclo[2.2.1]heptane-2-carboxylic acid methyl ester (1.02 g, 5.85 mmol, 94%), as a colorless oil. $^1$H NMR (400 MHz, CDCl$_3$) δ: 1.53 (2H, m), 1.62 (2H, m), 2.68 (1H, d, J=7.6 Hz), 3.27 (1H, d, J=7.6 Hz), 3.59 (3H, s), 4.14 (1H, d, J=6.0 Hz), 4.67 (1H, d, J=4.8 Hz).

b) (rac-di-exo)-3-(4-Fluoro-benzylamino)-7-oxa-bicyclo[2.2.1]heptane-2-carboxylic acid methyl ester

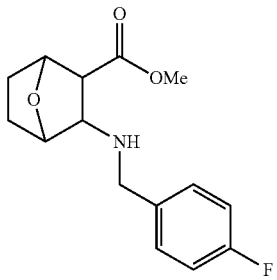 [SMILES: COC(=O)C1C2CCC(O2)C1NCc1ccc(F)cc1]

4-Fluoro-benzaldehyde (0.62 mL, 5.85 mmol) was added to a solution of (rac-di-exo)-3-amino-7-oxa-bicyclo[2.2.1]heptane-2-carboxylic acid methyl ester (1.02 g, 5.85 mmol) in anhydrous methanol (20 mL) at 25° C. under a nitrogen atmosphere. After stirring for 10 min, glacial acetic acid (0.8 mL) and sodium cyanoborohydride (920 mg, 14.6 mmol) were added sequentially, and the resulting mixture was stirred at 25° C. for 18 h. The reaction mixture was poured into saturated aqueous sodium bicarbonate solution and extracted with ethyl acetate. The combined organic layers were washed with saturated aqueous brine solution, dried over sodium sulfate, filtered, and concentrated in vacuo. The residue was dried under high vacuum to afford the desired product, (rac-di-exo)-3-(4-fluoro-benzylamino)-7-oxa-bicyclo[2.2.1]heptane-2-carboxylic acid methyl ester (1.40 g, 5.02 mmol, 86%), as a colorless oil. $^1$H NMR (400 MHz, CDCl$_3$) δ: 1.73 (4H, m), 2.86 (1H, d, J=8.0 Hz), 3.15 (1H, d, J=8.0 Hz), 3.68 (1H, d, J=13.6 Hz), 3.73 (3H, s), 3.84 (1H, d, J=13.6 Hz), 4.46 (1H, d, J=5.2 Hz), 4.73 (1H, d, J=4.8 Hz), 6.99 (2H, m), 7.26 (2H, m).

c) (rac-di-exo)-3-{(4-Fluoro-benzyl)-[2-(7-methanesulfonylamino-1,1-dioxo-1,4-dihydro-1λ$^6$-benzo[1,2,4]thiadiazin-3-yl)-acetyl]-amino}-7-oxa-bicyclo[2.2.1]heptane-2-carboxylic acid methyl ester

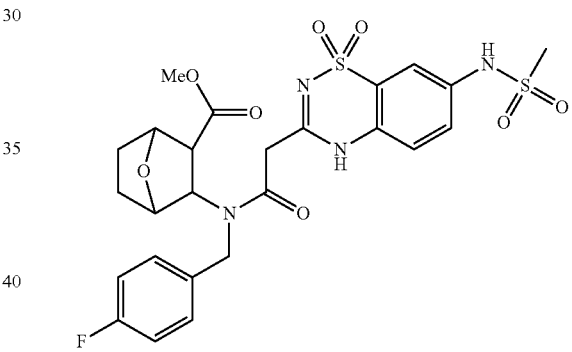

To a stirred solution of (rac-di-exo)-3-(4-fluoro-benzylamino)-7-oxa-bicyclo[2.2.1]heptane-2-carboxylic acid methyl ester (190 mg, 0.68 mmol) in anhydrous N,N-dimethylformamide (4 mL) under a nitrogen atmosphere, (7-methanesulfonylamino-1,1-dioxo-1,4-dihydro-1λ$^6$-benzo[1,2,4]thiadiazin-3-yl)-acetic acid (prepared as described in Example 1g, 185 mg, 0.55 mmol), N-methylmorpholine (149 μL, 1.36 mmol) and 1-(3-dimethylaminopropyl)-3-ethylcarbodiimide hydrochloride (130 mg, 0.68 mmol) were added sequentially. After stirring at 25° C. for 3 h, the reaction mixture was poured into 1.0 M aqueous hydrochloric acid solution, and extracted with ethyl acetate. The combined organic layers were washed with saturated aqueous brine solution, dried over sodium sulfate, filtered, and concentrated in vacuo. The crude product, (rac-di-exo)-3-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-7-oxa-bicyclo[2.2.1]heptane-2-carboxylic acid methyl ester, was used in the next step without further purification. LC-MS (ESI) calcd for $C_{25}H_{27}FN_4O_8S_2$ 594.13, found 595.2 [M+H$^+$].

d) (rac-di-exo)-N-{3-[3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

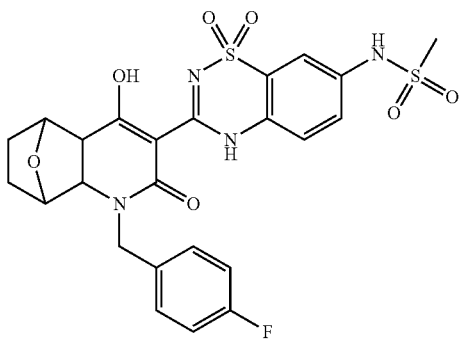

To a stirred solution of the crude (rac-di-exo)-3-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-7-oxa-bicyclo[2.2.1]heptane-2-carboxylic acid methyl ester in absolute ethanol (8 mL) under a nitrogen atmosphere, a 21 wt % solution of sodium ethoxide in ethanol (0.81 mL, 1.10 mmol) was added. The mixture was stirred at 60° C. for 30 min, and then cooled to 25° C. 1.0 M aqueous hydrochloric acid solution (4 mL, 4 mmol) was added slowly to the mixture, upon which a white solid precipitated. The suspension was stirred for 15 min, filtered through a filter funnel, and washed with water. The solid was collected, dried under high vacuum to afford analytically pure (rac-di-exo)-N-{3-[3-(4-fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (165 mg, 0.29 mmol, 53% over two steps), as an off-white solid. $^1$H NMR (400 MHz, DMSO-d$_6$) δ: 1.67 (4H, m), 3.05 (3H, s), 3.32 (1H, m), 3.79 (1H, d, J=9.2 Hz), 4.39 (1H, d, J=15.6 Hz), 4.69 (1H, d, J=4.4 Hz), 4.76 (1H, d, J=3.6 Hz), 5.04 (1H, d, J=15.6 Hz), 7.16 (2H, m), 7.33 (2H, m), 7.49 (1H, dd, J=9.2 Hz), 7.56 (2H, m), 10.17 (1H, s), 13.89 (1H, s). LC-MS (ESI) calcd for C$_{24}$H$_{23}$FN$_4$O$_7$S$_2$ 562.10, found 563.4 [M+H$^+$].

Example 9

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

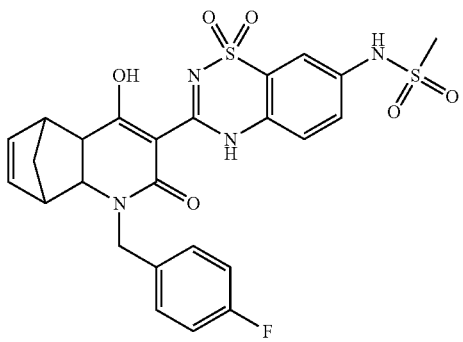

a) (rac-di-exo)-3-Amino-bicyclo[2.2.1]hept-5-ene-2-carboxylic acid methyl ester hydrochloride

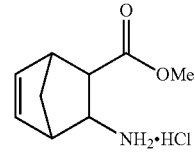

(rac-di-exo)-3-Amino-bicyclo[2.2.1]hept-5-ene-2-carboxylic acid hydrochloride (1 g, 5.27 mmol) was dissolved in methanol (7 mL). Benzene (10 mL) was added followed by the dropwise addition of a 2.0 M solution of (trimethylsilyl)diazomethane in dichloromethane (5 mL, 10 mmol). The yellow solution was stirred at 25° C. for 10 min. Additional 2.0 M solution of (trimethylsilyl)diazomethane in dichloromethane (2 mL, 4 mmol) was added. The yellow solution was stirred at 25° C. for 10 min. The solution was concentrated in vacuo to afford a yellow oil. The oil was dissolved in methanol (15 mL) and concentrated in vacuo to afford the desired product, (rac-di-exo)-3-amino-bicyclo[2.2.1]hept-5-ene-2-carboxylic acid methyl ester hydrochloride (1.07 g, 5.25 mmol, 99%), as a yellow oil. LC-MS (ESI) calcd for C$_9$H$_{13}$NO$_2$ (free amine) 167.09, found 168.2 [M+H$^+$] (100%), 335.4 [2M+H$^+$] (25%).

b) (rac-di-exo)-3-(4-Fluoro-benzylamino)-bicyclo[2.2.1]hept-5-ene-2-carboxylic acid methyl ester

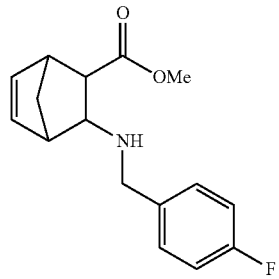 [SMILES: COC(=O)C1C2C=CC(C2)C1NCc1ccc(F)cc1]

(rac-di-exo)-3-Amino-bicyclo[2.2.1]hept-5-ene-2-carboxylic acid methyl ester hydrochloride (1.07 g, 5.25 mmol) was suspended in methanol (23 mL). Sodium acetate (0.865 g, 10.54 mmol) was added followed by 4 Å powdered molecular sieves (1 g) and 4-fluoro-benzaldehyde (0.621 g, 5 mmol). Sodium cyanoborohydride (0.662 g, 10.54 mmol) was added and the mixture was stirred at 25° C. for 16 h. The mixture was poured into a 1:1 mixture of saturated aqueous sodium bicarbonate solution (200 mL) and ethyl acetate (200 mL). The mixture was shaken and the layers separated. The organic layer was further washed with saturated aqueous brine solution (50 mL), dried over magnesium sulfate, filtered, and concentrated in vacuo to afford the crude product, (rac-di-exo)-3-(4-fluoro-benzylamino)-bicyclo[2.2.1]hept-5-ene-2-carboxylic acid methyl ester (1.044 g, 3.79 mmol, 76%), as a clear oil. LC-MS (ESI) calcd for C$_{16}$H$_{18}$FNO$_2$ 275.13, found 276.2 [M+H$^+$].

c) (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

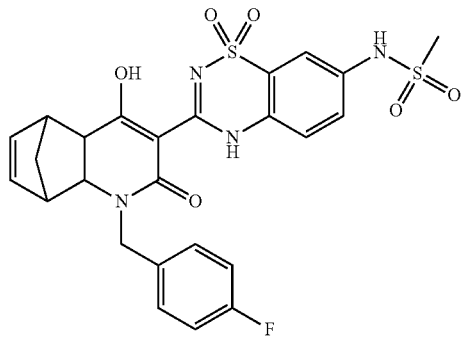

(rac-di-exo)-3-(4-Fluoro-benzylamino)-bicyclo[2.2.1]hept-5-ene-2-carboxylic acid methyl ester (0.083 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in Example 1g, 0.1 g, 0.3 mmol) was added followed by N-methylmorpholine (0.07 mL, 0.63 mmol). The mixture was stirred until everything dissolved, approximately 5 min. 1-(3-Dimethylaminopropyl)-3-ethylcarbodiimide hydrochloride (0.061 g, 0.315 mmol) was added and the mixture was stirred at 25° C. for 45 min. Triethylamine (0.126 mL, 0.9 mmol) was added and the mixture was stirred at 50° C. for 16 h. After cooling to 25° C., the solution was diluted with a 1.0 M aqueous hydrochloric acid solution (8 mL). The resulting precipitate was collected by vacuum filtration, dissolved in methanol and concentrated in vacuo to afford the crude product as a beige powder. Purification by flash column chromatography (Merck silica gel 60, 40-63 μm, 0 to 0.75% methanol in dichloromethane) afforded the product as a white foam. The foam was triturated with a 1:1 mixture of diethyl ether and hexanes (6 mL) and the resulting solid was collected by vacuum filtration. The solid was dried in vacuo for 16 h to afford the desired product, (rac-di-exo)-N-{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide (40.3 mg, 0.072 mmol, 24%), as a white powder. $^1$H NMR (400 MHz, DMSO-d$_6$) δ: 1.37 (1H, d, J=9.5 Hz), 1.62 (1H, d, J=9.4 Hz), 2.81-2.89 (1H, m), 3.05 (3H, s), 3.19-3.40 (4H, m), 4.52 (1H, d, J=15.5 Hz), 5.04 (1H, d, J=14.8 Hz), 6.13 (1H, dd, J$_1$=5.5 Hz, J$_2$=3.1 Hz), 6.35 (1H, dd, J$_1$=5.9 Hz, J$_2$=2.5 Hz), 7.14 (2H, t, J=9.1 Hz), 7.34 (2H, dd, J$_1$=7.8 Hz, J$_2$=5.6 Hz), 7.49 (1H, dd, J$_1$=8.8 Hz, J$_2$=2.0 Hz), 7.54-7.59 (2H, m), 10.16 (1H, s). LC-MS (ESI) calcd for C$_{25}$H$_{23}$FN$_4$O$_6$S$_2$ 558.10, found 559.1 [M+H$^+$].

Example 10

(rac-di-endo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

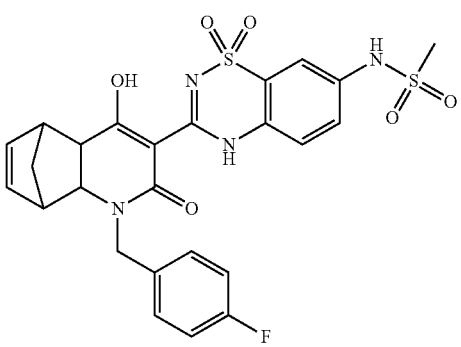 [SMILES: CS(=O)(=O)Nc1ccc2c(c1)S(=O)(=O)N=C(C1=C(O)C3C4C=CC(C4)C3N(Cc3ccc(F)cc3)C1=O)N2]

a) (rac-di-endo)-3-(4-Fluoro-benzylamino)-bicyclo[2.2.1]hept-5-ene-2-carboxylic acid ethyl ester

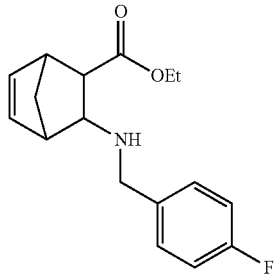 [SMILES: CCOC(=O)C1C2C=CC(C2)C1NCc1ccc(F)cc1]

(rac-di-endo)-3-Amino-bicyclo[2.2.1]hept-5-ene-2-carboxylic acid ethyl ester hydrochloride (1 g, 4.6 mmol) was suspended in methanol (23 mL). Sodium acetate (0.753 g, 9.18 mmol) was added followed by 4 Å powdered molecular sieves (1 g) and 4-fluoro-benzaldehyde (0.57 g, 4.59 mmol). Sodium cyanoborohydride (0.577 g, 9.18 mmol) was added and the mixture was stirred at 25° C. for 16 h. The mixture was poured into a 1:1 mixture of saturated aqueous sodium bicarbonate solution (200 mL) and ethyl acetate (200 mL). The mixture was shaken and the layers separated. The organic layer was further washed with saturated aqueous brine solution (50 mL), dried over magnesium sulfate, filtered, and concentrated in vacuo to afford the crude product, (rac-di-endo)-3-(4-fluoro-benzylamino)-bicyclo[2.2.1]hept-5-ene-2-carboxylic acid methyl ester (1.18 g, 4.08 mmol, 88%), as a clear oil. LC-MS (ESI) calcd for C$_{17}$H$_{20}$FNO$_2$ 289.15, found 290.2 [M+H$^+$].

b) (rac-di-endo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

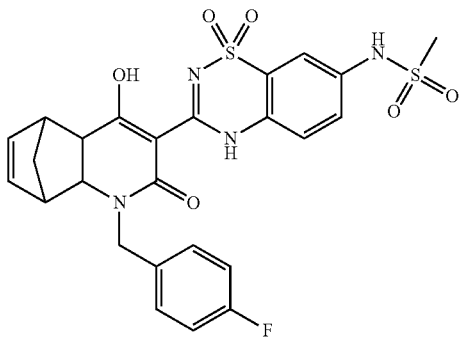 [SMILES: CS(=O)(=O)Nc1ccc2c(c1)S(=O)(=O)N=C(C1=C(O)C3C4C=CC(C4)C3N(Cc3ccc(F)cc3)C1=O)N2]

(rac-di-endo)-3-(4-Fluoro-benzylamino)-bicyclo[2.2.1]hept-5-ene-2-carboxylic acid methyl ester (0.087 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in Example 1g, 0.1 g, 0.3 mmol) was added followed by N-methylmorpholine (0.07 mL, 0.63 mmol). The mixture was stirred until everything dissolved, approximately 5 min. 1-(3-Dimethylaminopropyl)-3-ethylcarbodiimide hydrochloride (0.061 g, 0.315 mmol) was added and the mixture was stirred at 25° C. for 45 min. Triethylamine (0.126 mL, 0.9 mmol) was added and the mixture was stirred at 50° C. for 16 h. After cooling to 25° C., the solution was diluted with a 1.0 M aqueous hydrochloric acid solution (8 mL, 8 mmol). The resulting precipitate was collected by vacuum filtration, dissolved in methanol and concentrated in vacuo to afford the crude product as a beige powder. Purification by flash column chromatography (Merck silica gel 60, 40-63 µm, 0 to 0.75% methanol in dichloromethane) afforded the product as white foam. The foam was triturated with a 1:1 mixture of diethyl ether and hexanes (6 mL) and the resulting solid was collected by vacuum filtration. The solid was dried in vacuo for 16 h to afford the desired product, (rac-di-endo)-N-{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide (69.3 mg, 0.124 mmol, 41%), as a white powder. $^1$H NMR (400 MHz, DMSO-d$_6$) δ: 1.28-1.28 (2H, m), 3.33-3.41 (3H, m), 3.92-4.00 (1H, m), 4.33 (1H, d, J=14.7 Hz), 4.96 (1H, d, J=15.6 Hz), 5.89-5.92 (1H, m), 6.11-6.13 (1H, m), 7.10 (2H, t, J=9.1 Hz), 7.35 (2H, dd, J$_1$=8.2 Hz, J$_2$=5.9 Hz), 7.43 (1H, dd, J$_1$=8.4 Hz, J$_2$=2.4 Hz), 7.48-7.50 (2H, m), 10.10 (1H, s). LC-MS (ESI) calcd for C$_{25}$H$_{23}$FN$_4$O$_6$S$_2$ 558.10, found 559.0 [M+H$^+$].

Example 11

N-{3-[(1S,2R,7S,8R)-3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

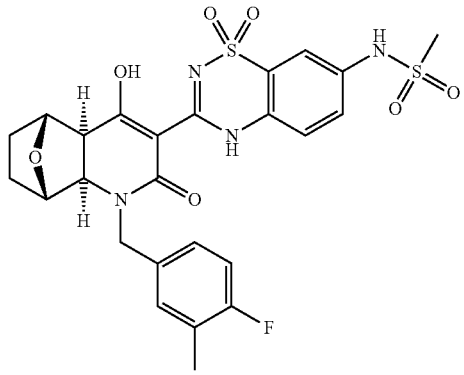

a) (1S,2R,3S,4R)-3-(Methoxycarbonyl)-7-oxabicyclo[2.2.1]heptane-2-carboxylic acid

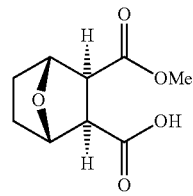

exo-4,10-Dioxa-tricyclo[5.2.1.0$^{2,6}$]decane-3,5-dione (5.10 g, 30.3 mmol) was dissolved in a 1:1 mixture of toluene and carbon tetrachloride (600 mL). The mixture was cooled to −55° C. under a nitrogen atmosphere, and then quinine (10.54 g, 32.5 mmol) was added. Methanol (3.59 mL, 90 mmol) in a 1:1 mixture of toluene and carbon tetrachloride (30 mL) was slowly added via an addition funnel. The suspension was stirred at −55° C. for 60 h, and then allowed to warm to 25° C. The mixture was concentrated in vacuo and the residue was dissolved in ethyl acetate (400 mL), washed with a 1.0 M aqueous hydrochloric acid solution (2×300 mL) and saturated aqueous brine solution, dried over magnesium sulfate and filtered. The filtrate was concentrated in vacuo to afford the desired product, (1S,2R,3S,4R)-3-(methoxycarbonyl)-7-oxabicyclo[2.2.1]heptane-2-carboxylic acid (2.46 g, 12.3 mmol, 41%), as a clear oil. $^1$H NMR (400 MHz, DMSO-d$_6$) δ: 1.49-1.53 (4H, m), 2.99 (2H, s), 3.50 (3H, s), 4.66 (2H, m), 12.15 (1H, s).

b) Methyl (1R,2S,3R,4S)-3-{[(benzyloxy)carbonyl]amino}-7-oxabicyclo[2.2.1]heptane-2-carboxylate

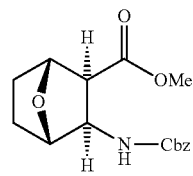

(1S,2R,3S,4R)-3-(Methoxycarbonyl)-7-oxabicyclo[2.2.1]heptane-2-carboxylic acid (2.46 g, 12.3 mmol) was dissolved in anhydrous tetrahydrofuran (35 mL) and cooled to −10° C. under a nitrogen atmosphere. Triethylamine (5.13 mL, 36.9 mmol) was added followed by the dropwise addition of ethyl chloroformate (2.35 mL, 24.6 mmol) with vigorous stirring. Immediate precipitation was observed. The mixture was stirred at −10° C. for 1 h. Sodium azide (2.40 g, 36.9 mmol) was dissolved in water (17 mL) and added to the reaction mixture at −10° C. The mixture was stirred at −10° C. for 15 min, and then was allowed to warm to 25° C. and stirred for 2 h. The mixture was poured into water (100 mL) and extracted with ethyl acetate. The combined organic layers were washed with saturated aqueous sodium bicarbonate solution and saturated aqueous brine solution, dried over magnesium sulfate and filtered. The filtrate was concentrated in vacuo to afford the acyl azide intermediate as a clear oil. The oil was dissolved in anhydrous benzene (80 mL) and refluxed for 2 h under a nitrogen atmosphere. The solution was allowed to cool to 25° C., and concentrated in vacuo to afford a yellow oil. The oil was dissolved in dichloromethane (45 mL), triethylamine (3.46 mL, 24.6 mmol) and benzyl alcohol (1.27 mL, 12.3 mmol) were added sequentially. The resulting mixture was refluxed for 16 h under a nitrogen atmosphere. The mixture was allowed to cool to 25° C., concentrated in vacuo and the residue was purified by flash column chromatography (Teledyne Isco RediSep column; 0 to 50% ethyl acetate in hexanes) to afford the desired product, methyl (1R,2S,3R,4S)-3-{[(benzyloxy)carbonyl]amino}-7-oxabicyclo[2.2.1]heptane-2-carboxylate (2.23 g, 7.30 mmol, 59%), as a clear oil. $^1$H NMR (400 MHz, CDCl$_3$) δ: 1.51 (2H, m), 1.72 (1H, m), 1.79 (1H, m), 2.97 (1H, d, J=8.4 Hz), 3.56 (3H, s), 4.33 (1H, m), 4.37 (d, 1H, J=5.6 Hz), 4.78 (1H, d, J=4.4 Hz), 5.10 (2H, m), 5.42 (1H, d, J=10.0 Hz), 7.35 (5H, m). LC-MS (ESI) calcd for C$_{16}$H$_{19}$NO$_5$ 305.1, found 306.5 [M+H$^+$].

c) Methyl (1R,2S,3R,4S)-3-amino-7-oxabicyclo[2.2.1]heptane-2-carboxylate

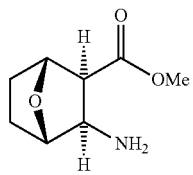

To a solution of methyl (1R,2S,3R,4S)-3-{[(benzyloxy)carbonyl]amino}-7-oxabicyclo[2.2.1]heptane-2-carboxylate (2.23 g, 7.30 mmol) in ethyl acetate (60 mL), 5% palladium on carbon (0.5 g, 22% by weight) was added. The flask was degassed and backfilled with hydrogen gas via balloon. The mixture was stirred at 25° C. for 16 h, passed through a plug of Celite and rinsed with ethyl acetate. The filtrate was concentrated in vacuo to afford the desired product, methyl (1R,2S,3R,4S)-3-amino-7-oxabicyclo[2.2.1]heptane-2-carboxylate (1.0 g, 5.84 mmol, 80%), as a clear oil. $^1$H NMR (400 MHz, CDCl$_3$) δ: 1.43 (2H, m), 1.67 (1H, m), 1.76 (1H, m), 2.82 (1H, d, J=7.6 Hz), 3.41 (1H, d, J=7.6 Hz), 3.73 (3H, s), 4.28 (1H, d, J=6.0 Hz), 4.81 (1H, d, J=4.8 Hz).

d) Methyl (1R,2S,3R,4S)-3-[(4-fluoro-3-methylbenzyl)amino]-7-oxabicyclo[2.2.1]heptane-2-carboxylate

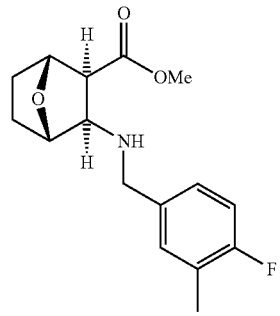

To a stirred solution of methyl (1R,2S,3R,4S)-3-amino-7-oxabicyclo[2.2.1]heptane-2-carboxylate (400 mg, 2.34 mmol) in methanol (8 mL) under a nitrogen atmosphere, 4-fluoro-3-methyl-benzaldehyde (0.29 mL, 2.34 mmol) was added. The mixture was stirred for 10 min, and then acetic acid (0.4 mL) was added followed by sodium cyanoborohydride (368 mg, 5.85 mmol). The resulting mixture was stirred at 25° C. for 16 h, and then poured into a mixture of saturated aqueous sodium bicarbonate solution (50 mL) and ethyl acetate (100 mL). The layers were separated and the aqueous layer was extracted with ethyl acetate. The combined organic layers were washed with saturated aqueous brine solution, dried over magnesium sulfate and filtered. The filtrate was concentrated in vacuo to afford the desired product, methyl (1R,2S,3R,4S)-3-[(4-fluoro-3-methylbenzyl)amino]-7-oxabicyclo[2.2.1]heptane-2-carboxylate (610 mg, 2.08 mmol, 80%), as a clear oil. $^1$H NMR (400 MHz, CDCl$_3$) δ: 1.40 (2H, m), 1.76 (2H, m), 2.27 (3H, d, J=2.0 Hz), 2.86 (1H, d, J=7.6 Hz), 3.16 (1H, d, J=8.4 Hz), 3.64 (1H, d, J=13.2 Hz), 3.74 (3H, s), 3.79 (1H, d, J=13.6 Hz), 4.46 (1H, d, J=5.2 Hz), 4.73 (1H, d, J=4.8 Hz), 6.92 (2H, m), 7.07 (2H, m).

e) N-{3-[(1S,2R,7S,8R)-3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

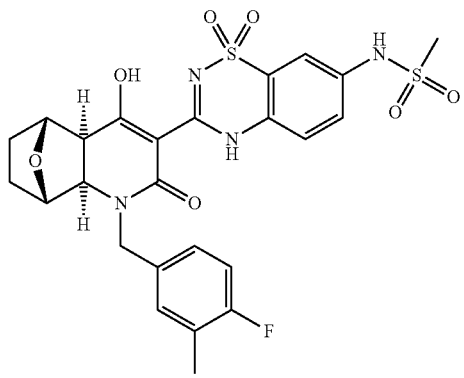

To a stirred solution of methyl (1R,2S,3R,4S)-3-[(4-fluoro-3-methylbenzyl)amino]-7-oxabicyclo[2.2.1]heptane-2-carboxylate (100 mg, 0.34 mmol) and (7-methanesulfonylamino-1,1-dioxo-1,4-dihydro-1λ$^6$-benzo[1,2,4]thiadiazin-3-yl)-acetic acid (prepared as described in Example 1g, 114 mg, 0.34 mmol) in anhydrous N,N-dimethylformamide (4 mL) under a nitrogen atmosphere, N-methylmorpholine (0.075 mL, 0.68 mmol) and 1-(3-dimethylaminopropyl)-3-ethylcarbodiimide hydrochloride (72 mg, 0.37 mmol) were added sequentially. The mixture was stirred at 25° C. for 2.5 h, poured into 1.0 M aqueous hydrochloric acid solution, and then was extracted with ethyl acetate. The combined organic layers were washed with saturated aqueous brine solution, dried over magnesium sulfate and filtered. The filtrate was concentrated in vacuo to afford the amide intermediate which was used in the next step without further purification.

The above intermediate was dissolved in ethanol (5 mL), a 21 wt. % solution of sodium ethoxide in ethanol (0.5 mL, 1.36 mmol) was added and the mixture was stirred at 60° C. for 30 min. The reaction mixture was cooled to 0° C., and then 0.3 M aqueous hydrochloric acid solution (10 mL) was slowly added. The product precipitated upon stirring. The solid was collected by filtration, rinsed with water, and further purified by prep-HPLC [Column Luna 5μ C18 (2) 100 Å AXIA 150× 21.2 mm, micron, 30%-95% in 7 min @ 30 mL/min flow rate, 0.05% trifluoroacetic acid in acetonitrile/0.05% trifluoroacetic acid in water] to afford the desired product, N-{3-[(1S,2R,7S,8R)-3-(4-fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (60 mg, 0.10 mmol, 31%), as an off-white solid. $^1$H NMR (400 MHz, DMSO-d$_6$) δ: 1.50-1.71 (4H, m), 2.21 (3H, d, J=2.0 Hz), 3.05 (3H, s), 3.40 (1H, m), 3.78 (1H, d, J=9.2 Hz), 4.34 (1H, d, J=15.2 Hz), 4.71 (1H, d, J=4.8 Hz), 4.76 (1H, d, J=3.6 Hz), 5.02 (1H, d, J=15.6 Hz), 7.06-7.21 (3H, m), 7.49 (1H, dd, J=8.4, 2.4 Hz), 7.56 (2H, m). LC-MS (ESI) calcd for C$_{25}$H$_{25}$FN$_4$O$_7$S$_2$ 576.1, found 577.5 [M+H$^+$]. Anal. calcd for C$_{25}$H$_{25}$FN$_4$O$_7$S$_2$: C, 52.07; H, 4.37; N, 9.72. found: C, 51.75; H, 4.63; N, 9.77.

Example 12

(rac-di-exo)-N-{3-[3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

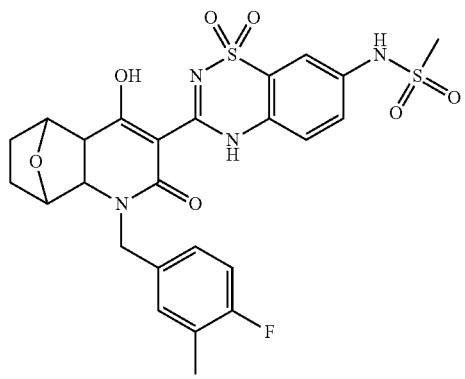 [SMILES: Cc1cc(CN2C(=O)C(C3=NS(=O)(=O)c4cc(NS(C)(=O)=O)ccc4N3)=C(O)C3C4CCC(O4)C32)ccc1F]

a) (rac-di-exo)-3-(4-Fluoro-3-methyl-benzylamino)-7-oxa-bicyclo[2.2.1]heptane-2-carboxylic acid methyl ester

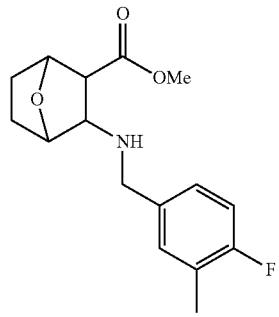 [SMILES: COC(=O)C1C2CCC(O2)C1NCc1ccc(F)c(C)c1]

4-Fluoro-3-methyl-benzaldehyde (0.14 mL, 1.10 mmol) was added to a solution of (rac-di-exo)-3-amino-7-oxa-bicyclo[2.2.1]heptane-2-carboxylic acid methyl ester (prepared as described in Example 8a, 200 mg, 1.17 mmol) in anhydrous methanol (10 mL) at 25° C. under a nitrogen atmosphere. After stirring for 20 min, glacial acetic acid (0.3 mL) and sodium cyanoborohydride (184 mg, 2.93 mmol) were added sequentially, and the resulting mixture was stirred at 25° C. for 18 h. The reaction mixture was poured into saturated aqueous sodium bicarbonate solution and extracted with ethyl acetate. The combined organic layers were washed with saturated aqueous brine solution, dried over sodium sulfate and filtered. The filtrate was concentrated in vacuo to afford the desired product, (rac-di-exo)-3-(4-fluoro-3-methyl-benzylamino)-7-oxa-bicyclo[2.2.1]heptane-2-carboxylic acid methyl ester (167 mg, 0.57 mmol, 49%), as a yellow oil. $^1$H NMR (400 MHz, CDCl$_3$) δ: 1.38-1.48 (2H, m), 1.65-1.82 (2H, m), 2.27 (3H, s), 2.89 (1H, d, J=7.6 Hz), 3.26 (1H, d, J=8.0 Hz), 3.67 (1H, d, J=13.2 Hz), 3.75 (3H, s), 3.86 (1H, d, J=13.2 Hz), 4.66 (1H, d, J=5.2 Hz), 4.71 (1H, d, J=4.4 Hz), 6.93 (1H, t, J=9.6 Hz), 7.13 (1H, m), 7.19 (1H, m). LC-MS (ESI) calcd for C$_{16}$H$_{20}$FNO$_3$ 293.14, found 294.3 [M+H$^+$].

b) (rac-di-exo)-N-{3-[3-(4-Fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

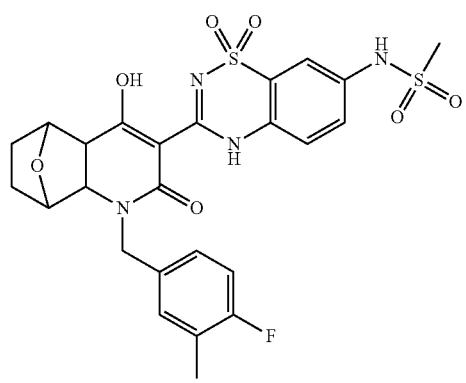 [SMILES: Cc1cc(CN2C(=O)C(C3=NS(=O)(=O)c4cc(NS(C)(=O)=O)ccc4N3)=C(O)C3C4CCC(O4)C32)ccc1F]

To a stirred solution of (rac-di-exo)-3-(4-fluoro-3-methyl-benzylamino)-7-oxa-bicyclo[2.2.1]heptane-2-carboxylic acid methyl ester (26 mg, 0.08 mmol) in anhydrous N,N-dimethylformamide (2 mL) under a nitrogen atmosphere, (7-methanesulfonylamino-1,1-dioxo-1,4-dihydro-1λ$^6$-benzo[1,2,4]thiadiazin-3-yl)-acetic acid (prepared as described in Example 1g, 30 mg, 0.09 mmol), N-methylmorpholine (22 μL, 0.2 mmol) and 1-(3-dimethylaminopropyl)-3-ethylcarbodiimide hydrochloride (19 mg, 0.10 mmol) were added sequentially. After stirring at 25° C. for 1.5 h, the reaction mixture was diluted with ethyl acetate, washed with 1.0 M aqueous hydrochloric acid solution and saturated aqueous brine solution, dried over sodium sulfate and filtered. The filtrate was concentrated in vacuo to afford the crude intermediate. The crude amide intermediate was dissolved in absolute ethanol (5 mL), and a 21 wt. % solution of sodium ethoxide in ethanol (0.13 mL, 0.35 mmol) was added. The mixture was stirred at 60° C. for 1 h, and then was allowed to cool to 25° C. A 1.0 M aqueous hydrochloric acid solution (4 mL) was added slowly to the mixture, and a white solid precipitated upon stirring. The solid was collected by filtration, rinsed with water and dried in vacuo to afford the desired product, (rac-di-exo)-N-{3-[3-(4-fluoro-3-methyl-benzyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (20 mg, 0.034 mmol, 43%), as an off-white solid. $^1$H NMR (400 MHz, DMSO-d$_6$) δ: 1.50-1.70 (4H, m), 2.21 (3H, s), 3.05 (3H, s), 3.78 (1H, d, J=8.8 Hz), 4.33 (1H, d, J=15.2 Hz), 4.70 (1H, d, J=4.4 Hz), 4.76 (1H, d, J=4.0 Hz), 5.03 (1H, d, J=14.8 Hz), 7.04-7.20 (3H, m), 7.49 (1H, m), 7.56 (2H, m), 10.17 (1H, s). LC-MS (ESI) calcd for C$_{25}$H$_{25}$FN$_4$O$_7$S$_2$ 576.11, found 577.3 [M+H$^+$].

Example 13

(rac-di-exo)-N-{3-[3-(3,3-Dimethyl-butyl)-6-hydroxy-4-oxo-11-oxa-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

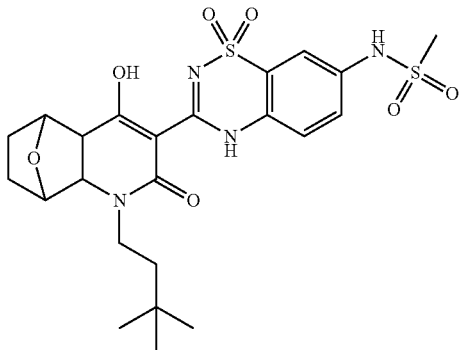 [SMILES: CC(C)(C)CCN1C(=O)C(C2=NS(=O)(=O)c3cc(NS(C)(=O)=O)ccc3N2)=C(O)C2C3CCC(O3)C21]

a) (rac-di-exo)-3-(3,3-Dimethyl-butylamino)-7-oxa-bicyclo[2.2.1]heptane-2-carboxylic acid methyl ester

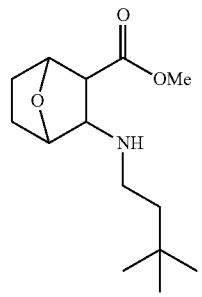 [SMILES: COC(=O)C1C2CCC(O2)C1NCCC(C)(C)C]

3,3-Dimethyl-butyraldehyde (120 mg, 1.20 mmol) was added to a solution of (rac-di-exo)-3-amino-7-oxa-bicyclo[2.2.1]heptane-2-carboxylic acid methyl ester (prepared as described in Example 8a, 200 mg, 1.17 mmol) in anhydrous methanol (10 mL) at 25° C. under a nitrogen atmosphere. After stirring for 20 min, glacial acetic acid (0.3 mL) and sodium cyanoborohydride (150 mg, 2.38 mmol) were added sequentially, and the resulting mixture was stirred at 25° C. for 18 h. The reaction mixture was poured into saturated aqueous sodium bicarbonate solution and was extracted with ethyl acetate. The combined organic layers were washed with saturated aqueous brine solution, dried over sodium sulfate and filtered. The filtrate was concentrated in vacuo to afford the desired product, (rac-di-exo)-3-(3,3-dimethyl-butylamino)-7-oxa-bicyclo[2.2.1]heptane-2-carboxylic acid methyl ester (300 mg, 1.17 mmol, 100%), as a yellow oil. $^1$H NMR (400 MHz, CDCl$_3$) δ: 0.91 (9H, s), 1.42 (4H, m), 1.70-1.80 (2H, m), 2.46 (1H, m), 2.74 (1H, m), 2.89 (1H, d, J=8.4 Hz), 3.26 (1H, d, J=8.0 Hz), 3.71 (3H, s), 4.61 (1H, s), 4.70 (1H, m). LC-MS (ESI) calcd for C$_{14}$H$_{25}$NO$_3$ 255.18, found 256.2 [M+H$^+$].

b) (rac-di-exo)-3-(3,3-Dimethyl-butyl)-6-hydroxy-5-(7-iodo-1,1-dioxo-1,4-dihydro-1$\lambda^6$-benzo[1,2,4]thiadiazin-3-yl)-11-oxa-3-aza-tricyclo[6.2.1.0$^{2,7}$]undec-5-en-4-one

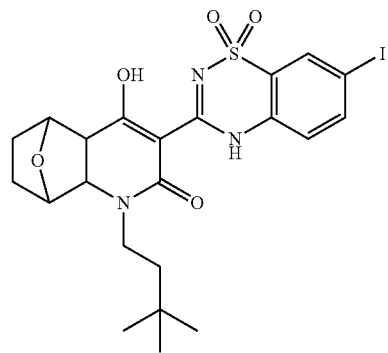 [SMILES: CC(C)(C)CCN1C(=O)C(C2=NS(=O)(=O)c3cc(I)ccc3N2)=C(O)C2C3CCC(O3)C21]

To a stirred solution of (rac-di-exo)-3-(3,3-dimethyl-butylamino)-7-oxa-bicyclo[2.2.1]heptane-2-carboxylic acid methyl ester (200 mg, 0.78 mmol) in anhydrous N,N-dimethylformamide (4 mL) under a nitrogen atmosphere, (7-iodo-1,1-dioxo-1,4-dihydro-1$\lambda^6$-benzo[1,2,4]thiadiazin-3-yl)-acetic acid (prepared as described in US patent application US 2008/0031852, 287 mg, 0.78 mmol), N-methylmorpholine (0.2 mL, 1.72 mmol) and 1-(3-dimethylaminopropyl)-3-ethylcarbodiimide hydrochloride (165 mg, 0.86 mmol) were added sequentially. After stirring at 25° C. for 2.5 h, the reaction mixture was diluted with ethyl acetate, washed with 1.0 M aqueous hydrochloric acid solution and saturated aqueous brine solution, dried over sodium sulfate and filtered. The filtrate was concentrated in vacuo to afford the crude amide intermediate. The above intermediate was dissolved in absolute ethanol (10 mL), and a 21 wt. % solution of sodium ethoxide in ethanol (1.17 mL, 3.16 mmol) was added. The mixture was stirred at 60° C. for 1 h, and then was allowed to cool to 25° C. A 1.0 M aqueous hydrochloric acid solution (4 mL) was added slowly to the mixture, and white solid precipitated upon stirring. The solid was collected by filtration, rinsed with water and dried in vacuo to afford the desired product, (rac-di-exo)-3-(3,3-dimethyl-butyl)-6-hydroxy-5-

(7-iodo-1,1-dioxo-1,4-dihydro-1λ⁶-benzo[1,2,4]thiadiazin-3-yl)-11-oxa-3-aza-tricyclo[6.2.1.0²,⁷]undec-5-en-4-one (200 mg, 0.35 mmol, 45%), as a yellow solid. ¹H NMR (400 MHz, DMSO-d₆) δ: 0.93 (9H, s), 1.45 (2H, m), 1.63 (2H, m), 1.71 (2H, m), 1.95 (1H, m), 3.30 (1H, m), 3.84 (1H, m), 3.89 (1H, m), 4.74 (2H, bs), 7.35 (1H, d, J=8.4 Hz), 7.98 (1H, dd, J=8.4, 1.6 Hz), 8.07 (1H, d, J=1.6 Hz). LC-MS (ESI) calcd for C₂₂H₂₆IN₃O₅S 571.06, found 572.3 [M+H⁺].

c) (rac-di-exo)-N-{3-[3-(3,3-Dimethyl-butyl)-6-hydroxy-4-oxo-11-oxa-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

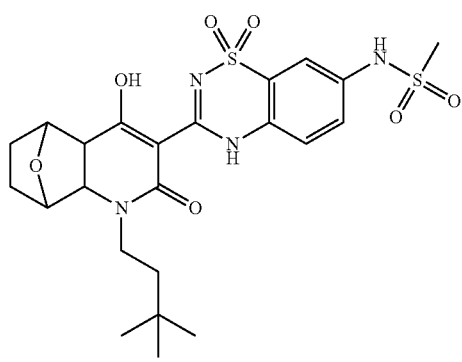 [SMILES: CC(C)(C)CCN1C(=O)C(C2=NS(=O)(=O)c3cc(NS(C)(=O)=O)ccc3N2)=C(O)C2C3CCC(O3)C21]

A reaction flask was charged with copper (I) iodide (20 mg, 0.11 mmol), sarcosine (N-methyl glycine) (10 mg, 0.11 mmol), methanesulfonamide (83 mg, 0.87 mmol), (rac-di-exo)-3-(3,3-dimethyl-butyl)-6-hydroxy-5-(7-iodo-1,1-dioxo-1,4-dihydro-1λ⁶-benzo[1,2,4]thiadiazin-3-yl)-11-oxa-3-aza-tricyclo[6.2.1.0²,⁷]undec-5-en-4-one (100 mg, 0.17 mmol) and potassium phosphate (111 mg, 0.52 mmol). The flask was degassed and backfilled with nitrogen, and then anhydrous N,N-dimethylformamide (3 mL) was added. The resulting suspension was vigorously stirred at 100° C. for 16 h, and then allowed to cool to 25° C. The mixture was passed through a plug of Celite and rinsed with 10% methanol/dichloromethane. The filtrate was concentrated in vacuo, and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (rac-di-exo)-N-{3-[3-(3,3-dimethyl-butyl)-6-hydroxy-4-oxo-11-oxa-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide (25 mg, 0.046 mmol, 27%), as an off-white solid. ¹H NMR (400 MHz, DMSO-d₆) δ: 0.94 (9H, s), 1.48 (2H, m), 1.63 (2H, m), 1.70 (2H, m), 2.97 (1H, m), 3.30 (1H, m), 3.80-3.90 (2H, m), 4.75 (2H, s), 7.49 (1H, dd, J=8.4, 2.4 Hz), 7.56 (2H, m), 10.17 (1H, s). LC-MS (ESI) calcd for C₂₃H₃₀N₄O₇S₂ 538.16, found 539.4 [M+H⁺].

Example 14

N-{3-[(1S,2R,7S,8R)-3-(4-Fluoro-benzyl)-6-hydroxy-4-oxo-11-oxa-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

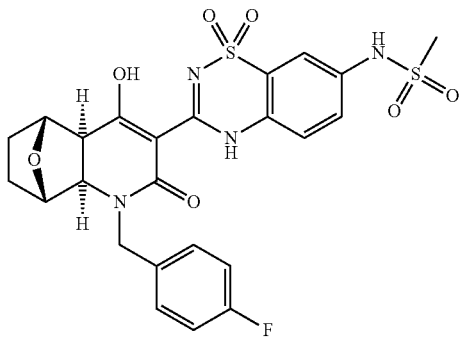

a) (rac-di-exo)-Methyl 3-amino-7-oxabicyclo[2.2.1]heptane-2-carboxylate

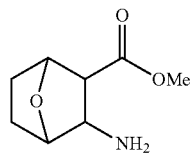 [SMILES: COC(=O)C1C2CCC(O2)C1N]

To a stirred solution of (rac-di-exo)-3-amino-7-oxa-bicyclo[2.2.1]heptane-2-carboxylic acid (1.0 g, 6.37 mmol) in a 1:1 mixture of anhydrous methanol and benzene (20 mL), a 2.0 M solution of (trimethylsilyl)diazomethane in hexanes (6.37 mL, 12.7 mmol) was added dropwise. The resulting mixture was stirred for 1 h, and concentrated in vacuo to afford the desired product, (rac-di-exo)-methyl 3-amino-7-oxabicyclo[2.2.1]heptane-2-carboxylate (1.02 g, 5.96 mmol, 94%), as a colorless oil. ¹H NMR (400 MHz, CDCl₃) δ: 1.53 (2H, m), 1.62 (2H, m), 2.68 (1H, d, J=7.6 Hz), 3.27 (1H, d, J=7.6 Hz), 3.59 (3H, s), 4.14 (1H, d, J=6.0 Hz), 4.67 (1H, d, J=4.8 Hz).

b) (rac-di-exo)-Methyl 3-[(4-fluorobenzyl)amino]-7-oxabicyclo[2.2.1]heptane-2-carboxylate

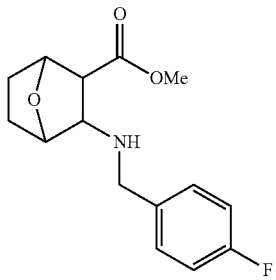 [SMILES: COC(=O)C1C2CCC(O2)C1NCc1ccc(F)cc1]

4-Fluoro-benzaldehyde (0.62 mL, 5.85 mmol) was added to a solution of (rac-di-exo)-methyl 3-amino-7-oxabicyclo[2.2.1]heptane-2-carboxylate (1.02 g, 5.85 mmol) in anhydrous methanol (20 mL) at 25° C. under a nitrogen atmosphere. After stirring for 10 min, glacial acetic acid (0.8 mL) and sodium cyanoborohydride (920 mg, 14.6 mmol) were added sequentially, and the resulting mixture was stirred at 25° C. for 18 h. The reaction mixture was poured into saturated sodium bicarbonate solution and extracted with ethyl acetate. The combined organic layers were washed with saturated aqueous brine solution, dried over sodium sulfate and filtered. The filtrate was concentrated in vacuo, and the residue was dried under high vacuum to afford the desired product, (rac-di-exo)-methyl 3-[(4-fluorobenzyl)amino]-7-oxabicyclo[2.2.1]heptane-2-carboxylate (1.40 g, 5.01 mmol, 86%), as a colorless oil. $^1$H NMR (400 MHz, CDCl$_3$) δ: 1.30-1.42 (2H, m), 1.73 (2H, m), 2.86 (1H, d, J=8.0 Hz), 3.15 (1H, d, J=8.0 Hz), 3.68 (1H, d, J=13.6 Hz), 3.73 (3H, s), 3.84 (1H, d, J=13.6 Hz), 4.46 (1H, d, J=5.2 Hz), 4.73 (1H, d, J=4.8 Hz), 6.99 (2H, m), 7.26 (2H, m).

c) Methyl (1R,2S,3R,4S)-3-[(4-fluorobenzyl)amino]-7-oxabicyclo[2.2.1]heptane-2-carboxylate

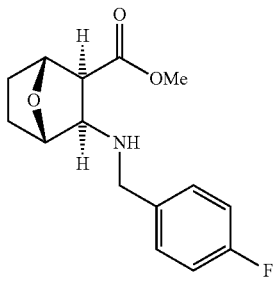

To a stirred solution of (rac-di-exo)-methyl 3-[(4-fluorobenzyl)amino]-7-oxabicyclo[2.2.1]heptane-2-carboxylate (210 mg, 0.75 mmol) in ethyl acetate (6 mL), a solution of (S)-(+)-mandelic acid (57.2 mg, 0.38 mmol) in ethyl acetate (3 mL) was added dropwise. The clear solution became cloudy and turned into a suspension upon stirring for 15 min, and stirring was continued for 20 min. The solid was collected by filtration, rinsed with ethyl acetate and dried in vacuo to afford the desired product in a mandelic acid salt form (90 mg, 0.21 mmol, 56%) (>96% de, based on $^1$H NMR analysis), as a white solid. $^1$H NMR (400 MHz, CDCl$_3$) δ: 1.37-1.49 (2H, m), 1.75 (2H, m), 2.88 (1H, d, J=8.0 Hz), 3.78 (1H, d, J=7.6 Hz), 3.65 (1H, d, J=12.8 Hz), 3.72 (3H, s), 3.91 (1H, d, J=13.2 Hz), 4.62 (1H, d, J=5.2 Hz), 4.70 (1H, d, J=4.8 Hz), 5.12 (1H, s), 6.94 (2H, m), 7.19 (2H, m), 7.34 (3H, m), 7.46 (2H, m).

The above obtained intermediate (90 mg, 0.21 mmol) was suspended in a 1:1 mixture of saturated aqueous sodium bicarbonate solution (5 mL) and ethyl acetate (5 mL), and stirred for 30 min at 25° C. The layers were separated and the aqueous layer was extracted with ethyl acetate. The combined organic layers were washed with saturated aqueous brine solution, dried over magnesium sulfate and filtered. The filtrate was concentrated in vacuo to afford the free amine, methyl (1R,2S,3R,4S)-3-[(4-fluorobenzyl)amino]-7-oxabicyclo[2.2.1]heptane-2-carboxylate (56 mg, 0.21 mmol, 95%), as a clear oil. $^1$H NMR (400 MHz, CDCl$_3$) δ: 1.25-1.44 (2H, m), 1.64-1.82 (2H, m), 2.86 (1H, d, J=8.0 Hz), 3.15 (1H, d, J=8.0 Hz), 3.67 (1H, d, J=13.6 Hz), 3.73 (3H, s), 3.84 (1H, d, J=13.6 Hz), 4.46 (1H, d, J=5.2 Hz), 4.72 (1H, d, J=4.8 Hz), 6.99 (2H, m), 7.26 (2H, m).

d) N-{3-[(1S,2R,7S,8R)-3-(4-Fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

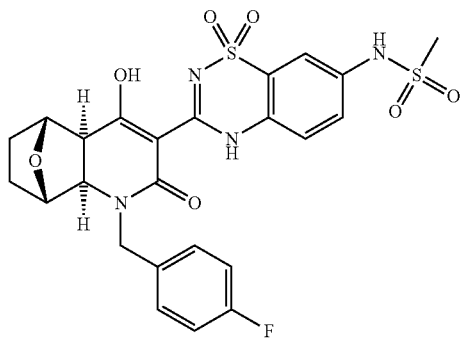

To a stirred solution of methyl (1R,2S,3R,4S)-3-[(4-fluorobenzyl)amino]-7-oxabicyclo[2.2.1]heptane-2-carboxylate (0.056 g, 0.21 mmol) in anhydrous N,N-dimethylformamide (3 mL) under a nitrogen atmosphere, (7-methanesulfonylamino-1,1-dioxo-1,4-dihydro-1λ$^6$-benzo[1,2,4]thiadiazin-3-yl)-acetic acid (prepared as described in Example 1g, 0.070 g, 0.21 mmol) was added followed by N-methylmorpholine (0.046 mL, 0.42 mmol) and 1-(3-dimethylaminopropyl)-3-ethylcarbodiimide hydrochloride (40 mg, 0.21 mmol). The mixture was stirred at 25° C. for 1 h, triethylamine (0.88 mL, 0.63 mmol) was added and the resulting mixture was stirred at 50° C. for 16 h. The reaction mixture was allowed to cool to 25° C., diluted with ethyl acetate, washed with 1.0 M aqueous hydrochloric acid solution and saturated aqueous brine solution, dried over magnesium sulfate and filtered. The filtrate was concentrated in vacuo and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, N-{3-[(1S,2R,7S,8R)-3-(4-fluoro-benzyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (48 mg, 0.085 mmol, 41%), as an off-white solid. $^1$H NMR (400 MHz, DMSO-d$_6$) δ: 1.51-1.71 (4H, m), 3.05 (3H, s), 3.30 (1H, m), 3.79 (1H, d, J=8.4 Hz), 4.40 (1H, d, J=15.6 Hz), 4.70 (1H, d, J=4.8 Hz), 4.76 (1H, d, J=4.8 Hz), 5.04 (1H, d, J=14.8 Hz), 7.15 (2H, t, J=8.4 Hz), 7.33 (2H, m), 7.49 (1H, dd, J=8.4, 2.4 Hz), 7.55 (2H, m). LC-MS (ESI) calcd for C$_{24}$H$_{23}$FN$_4$O$_7$S$_2$ 562.1, found 563.5 [M+H$^+$]. Anal. calcd for C$_{24}$H$_{23}$FN$_4$O$_7$S$_2$: C, 51.24; H, 4.12; N, 9.96. found: C, 51.10; H, 4.51; N, 9.98. ee>98% [HPLC-analysis: Chiralpak AS-RH 4.6×250 mm, 5 micron, 0.8 mL/min, 310 nm].

Example 15

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

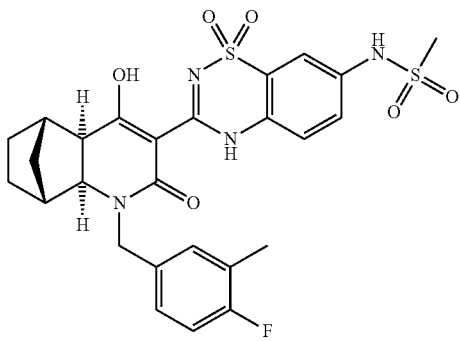

a) Methyl (1S,2R,3S,4R)-3-(4-fluoro-3-methyl-benzylamino)-bicyclo[2.2.1]heptane-2-carboxylate

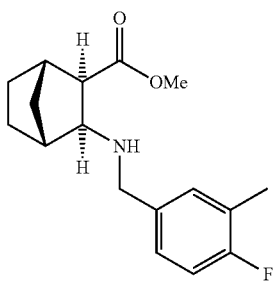

Methyl (1S,2R,3S,4R)-3-aminobicyclo[2.2.1]heptane-2-carboxylate hydrochloride (prepared as described in Example 6c, 0.32 g, 1.56 mmol) was dissolved in methanol (8 mL). Sodium acetate (0.26 g, 3.12 mmol) was added followed by 4 Å powdered molecular sieves (0.32 g) and 4-fluoro-3-methyl benzaldehyde (0.19 mL, 1.56 mmol). Sodium cyanoborohydride (0.24 g, 3.12 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, methyl (1S,2R,3S,4R)-3-(4-fluoro-3-methyl-benzylamino)-bicyclo[2.2.1]heptane-2-carboxylate (0.35 g, 1.20 mmol, 77%), as a clear oil. LC-MS (ESI) calcd for $C_{17}H_{22}FNO_2$ 291.36, found 292.5 [M+H$^+$].

b) N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

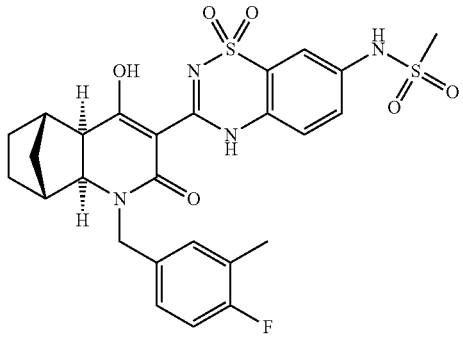

Methyl (1S,2R,3S,4R)-3-(4-fluoro-3-methyl-benzylamino)-bicyclo[2.2.1]heptane-2-carboxylate (0.090 g, 0.31 mmol) was dissolved in anhydrous N,N-dimethylformamide (3 mL). (7-Methanesulfonylamino-1,1-dioxo-1,4-dihydro-1λ$^6$-benzo[1,2,4]thiadiazin-3-yl)-acetic acid (prepared as described in Example 1g, 0.10 g, 0.31 mmol) was added followed by N-methylmorpholine (0.071 mL, 0.65 mmol). The mixture was stirred until everything dissolved, approximately 5 min. 1-(3-Dimethylaminopropyl)-3-ethylcarbodiimide hydrochloride (0.062 g, 0.32 mmol) was added and the mixture was stirred at 25° C. for 4 h. Triethylamine (0.13 mL, 0.92 mmol) was added and the mixture was stirred at 50° C. for 16 h. Upon cooling to 25° C., the solution was diluted with ethyl acetate (50 mL) and washed with 1.0 M aqueous hydrochloric acid solution (2×50 mL), saturated aqueous brine solution (20 mL), dried over magnesium sulfate, filtered, and concentrated in vacuo to afford a golden oil. Purification by flash column chromatography (Teledyne Isco RediSep column; 50 to 100% ethyl acetate in hexanes) afforded the desired product, N-{3-[(1R,2S,7R,8S)-3-(4-fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.12 g, 0.21 mmol, 68%), as a white powder. $^1$H NMR (400 MHz, CDCl$_3$) δ: 1.43-2.85 (9H, m), 2.29 (3H, s), 3.07 (3H, s), 3.45-3.47 (1H, m), 5.17-5.21 (2H, m), 6.95-7.05 (3H, m), 7.59-7.66 (3H, m). LC-MS (ESI) calcd for $C_{26}H_{27}FN_4O_6S_2$ 574.64, found 575.3 [M+H$^+$].

Example 16

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

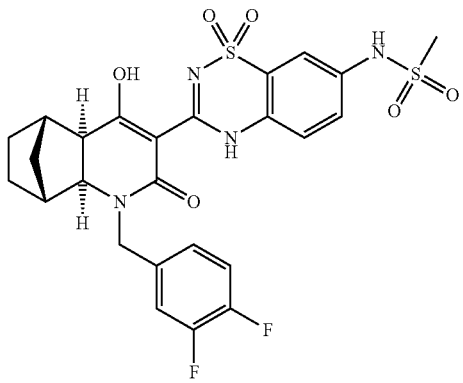

a) Methyl (1S,2R,3S,4R)-3-(3,4-difluoro-benzylamino)-bicyclo[2.2.1]heptane-2-carboxylate

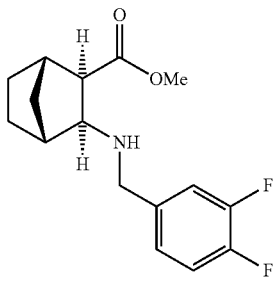

Methyl (1S,2R,3S,4R)-3-aminobicyclo[2.2.1]heptane-2-carboxylate hydrochloride (prepared as described in Example 6c, 0.32 g, 1.58 mmol) was dissolved in methanol (8 mL). Sodium acetate (0.26 g, 3.16 mmol) was added followed by 4 Å powdered molecular sieves (0.33 g) and 3,4-difluoro benzaldehyde (0.17 mL, 1.58 mmol). Sodium cyanoborohydride (0.22 g, 3.16 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, methyl (1S,2R,3S,4R)-3-(3,4-difluoro-benzylamino)-bicyclo[2.2.1]heptane-2-carboxylate (0.36 g, 1.22 mmol, 78%), as a clear oil. LC-MS (ESI) calcd for $C_{16}H_{19}F_2NO_2$ 295.32, found 296.3 [M+H$^+$].

b) N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

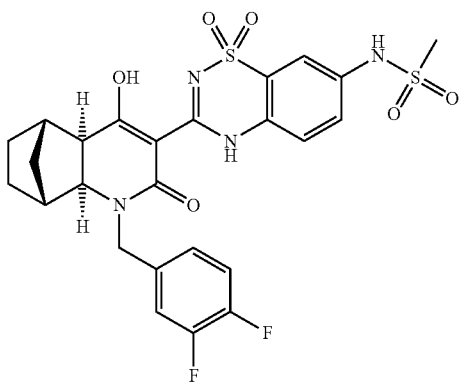

Methyl (1S,2R,3S,4R)-3-(4-fluoro-3-methyl-benzylamino)-bicyclo[2.2.1]heptane-2-carboxylate (0.088 g, 0.30 mmol) was dissolved in anhydrous N,N-dimethylformamide (3 mL). (7-Methanesulfonylamino-1,1-dioxo-1,4-dihydro-1λ$^6$-benzo[1,2,4]thiadiazin-3-yl)-acetic acid (prepared as described in Example 1g, 0.10 g, 0.30 mmol) was added followed by N-methylmorpholine (0.069 mL, 0.63 mmol). The mixture was stirred until everything dissolved, approximately 5 min. 1-(3-Dimethylaminopropyl)-3-ethylcarbodiimide hydrochloride (0.060 g, 0.32 mmol) was added and the mixture was stirred at 25° C. for 4 h. Triethylamine (0.12 mL, 0.90 mmol) was added and the mixture was stirred at 50° C. for 16 h. Upon cooling to 25° C., the solution was diluted with ethyl acetate (40 mL) and washed with 1.0 M aqueous hydrochloric acid solution (2×20 mL), saturated aqueous brine solution (20 mL), dried over magnesium sulfate, filtered, and concentrated in vacuo to afford a golden oil. Purification by flash column chromatography (Teledyne Isco RediSep column; 50 to 100% ethyl acetate in hexanes) afforded the desired product, N-{3-[(1R,2S,7R,8S)-3-(3,4-difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.082 g, 0.14 mmol, 47%), as a white powder. $^1$H NMR (400 MHz, CDCl$_3$) δ: 1.42-1.79 (6H, m), 2.51-2.54 (1H, m), 2.84-2.88 (2H, m), 3.07 (3H, s), 3.47-3.49 (1H, m), 5.06-5.10 (2H, m), 6.95-7.18 (3H, m), 7.60-7.66 (3H, m). LC-MS (ESI) calcd for $C_{25}H_{24}F_2N_4O_6S_2$ 578.61, found 579.2 [M+H$^+$].

Example 17

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide

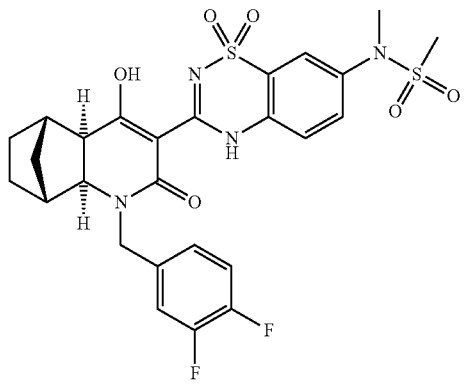

N-{3-[(1R,2S,7R,8S)-3-(3,4-Difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 16, 114 mg, 0.20 mmol) was dissolved in N,N-dimethylformamide (7 mL). Potassium carbonate (55 mg, 0.40 mmol) and iodomethane (0.014 mL, 0.22 mmol) were added sequentially. The reaction was stirred at 25° C. for 18 h. The reaction was quenched via the addition of 1.0 M aqueous hydrochloric acid solution (20 mL). The mixture was extracted with ethyl acetate (3×30 mL). The combined organic layers were washed with saturated aqueous brine solution (20 mL), dried over magnesium sulfate, filtered, and concentrated in vacuo to afford a golden oil. Purification by flash column chromatography (Teledyne Isco RediSep column; 0 to 20% ethyl acetate in dichloromethane) afforded the desired product, N-{3-[(1R,2S,7R,8S)-3-(3,4-difluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide (94 mg, 0.06 mmol, 77%) as a white powder. $^1$H NMR (400 MHz, CDCl$_3$) δ: 1.42-1.76 (6H, m), 2.51-2.54 (1H, m), 2.84-2.88 (2H, m), 3.07 (3H, s), 3.38 (3H, s), 3.47-3.49 (1H, m), 5.07-5.10 (2H, m), 6.96-7.16 (3H, m), 7.72-8.01 (3H, m). LC-MS (ESI) calcd for $C_{26}H_{26}F_2N_4O_6S_2$ 592.63, found 593.4 [M+H$^+$].

Example 18

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide

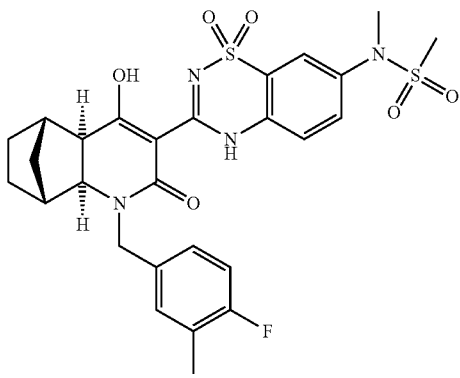

N-{3-[(1R,2S,7R,8S)-3-(4-Fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 15, 92 mg, 0.16 mmol) was dissolved in N,N-dimethylformamide (6 mL). Potassium carbonate (44 mg, 0.32 mmol) and iodomethane (0.011 mL, 0.18 mmol) were added sequentially. The reaction was stirred at 25° C. for 18 h. The reaction was quenched via the addition of 1.0 M aqueous hydrochloric acid solution (20 mL). The mixture was extracted with ethyl acetate (3×30 mL). The combined organic layers were washed with saturated aqueous brine solution (20 mL), dried over magnesium sulfate, filtered, and concentrated in vacuo to afford a golden oil. Purification by flash column chromatography (Teledyne Isco RediSep column; 0 to 20% ethyl acetate in dichloromethane) afforded the desired product, N-{3-[(1R,2S,7R,8S)-3-(4-fluoro-3-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide (91 mg, 0.15 mmol, 96%), as a white powder. $^1$H NMR (400 MHz, CDCl$_3$) δ: 1.18-2.85 (9H, m), 2.90 (3H, s), 2.97 (3H, s), 3.38 (3H, s), 3.45-3.47 (1H, m), 5.17-5.21 (2H, m), 6.96-7.08 (3H, m), 7.72-8.02 (3H, m). LC-MS (ESI) calcd for C$_{27}$H$_{29}$FN$_4$O$_6$S$_2$ 588.67, found 589.2 [M+H$^+$].

Example 19

(1R,2S,7R,8S)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one

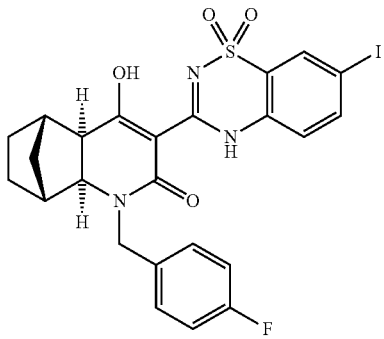

N,N-diisopropylethylamine (1.79 mL, 10.3 mmol) and (benzotriazol-1yloxy)-tris(dimethylamino)-phosphonium-hexafluorophosphate (1.52 g, 3.44 mmol) were added sequentially to a solution of (1S,2R,3S,4R)-3-(4-fluoro-benzylamino)-bicyclo[2.2.1]heptane-2-carboxylic acid ethyl ester (prepared as described in Example 61, 1.0 g, 3.43 mmol) and (7-iodo-1,1-dioxo-1,4-dihydro-1λ$^6$-benzo[1,2,4]thiadiazin-3-yl)-acetic acid (prepared as described in US patent application US 2008/0031852, 1.26 g, 3.44 mmol) in N,N-dimethylformamide (25 mL) at 25° C. The resulting solution was stirred at 25° C. for 19 h, and then was concentrated in vacuo. The residue was partitioned between 1.0 M aqueous hydrochloric acid solution (150 mL) and ethyl acetate (2×150 mL). The organic layers were dried over sodium sulfate, filtered and concentrated in vacuo. The resulting orange oil was dissolved in ethanol (50 mL) at 25° C. A 21 wt. % solution of sodium ethoxide in ethanol (3.33 mL, 10.3 mmol) was added and the reaction mixture was heated at 60° C. for 3 h. After cooling to 25° C., the reaction mixture was concentrated in vacuo to approximately 5 mL volume and was then partitioned between 1.0 M aqueous hydrochloric acid solution (150 mL) and ethyl acetate (2×150 mL). The organic layers were dried over sodium sulfate, filtered and concentrated in vacuo. The residue was purified by flash column chromatography (Teledyne Isco RediSep column; 0 to 60% ethyl acetate in hexanes) to afford the desired product, (1R,2S,7R,8S)-3-(4-fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (1.0 g, 1.69 mmol, 49%), as a pale yellow foam. $^1$H NMR (400 MHz, DMSO-d$_6$) δ: 1.15-1.21 (3H, m), 1.38-1.41 (1H, m), 1.46-1.61 (3H, m), 2.62 (1H, d, J=2.4 Hz), 2.98 (1H, d, J=9.4 Hz), 3.52 (1H, d, J=9.3 Hz), 4.40 (1H, d, J=15.7 Hz), 4.95 (1H, d, J=15.6 Hz), 7.14 (2H, d, J=17.9 Hz), 7.11-7.16 (2H, m), 7.30-7.34 (3H, m), 7.97 (1H, dd, J$_1$=2.3 Hz, J$_2$=8.6 Hz), 8.07 (1H, d, J=1.5 Hz). LC-MS (ESI) calcd for C$_{24}$H$_{21}$FIN$_3$O$_4$S 593.03, found 594.2 [M+H$^+$].

Example 20

(1R,2S,7R,8S)-5-[7-(1,1-Dioxo-4,5-dihydro-1H-1λ$^6$-thiophen-2-yl)-1,1-dioxo-1,4-dihydro-1λ$^6$-benzo[1,2,4]thiadiazin-3-yl]-3-(4-fluoro-benzyl)-6-hydroxy-3-aza-tricyclo[6.2.1.0$^{2,7}$]undec-5-en-4-one

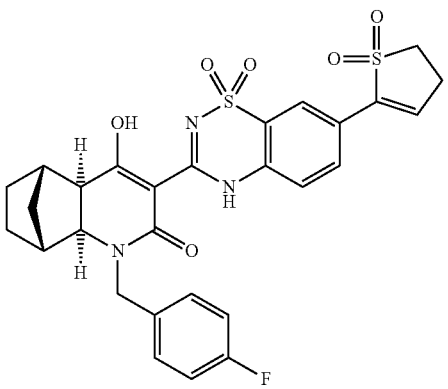

To a solution of (1R,2S,7R,8S)-3-(4-fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (prepared as described in Example 19, 200 mg, 0.34 mmol) and tributyl-(1,1-dioxo-4,5-dihydro-1H-1λ$^6$-thiophen-2-yl)-stannane (prepared as described in US patent application US 2008/0031852, 180 mg, 0.44 mmol) in anhydrous N,N-dimethylformamide (7 mL) under a nitrogen atmosphere, Pd(PPh$_3$)$_4$ (20 mg, 0.017 mmol) was added. The resulting mixture was stirred at 90° C. for 22 h, and then allowed to cool to 25° C. The reaction mixture was concentrated in vacuo and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (1R,2S,7R,8S)-5-[7-(1,1-dioxo-4,5-dihydro-1H-1λ$^6$-thiophen-2-yl)-1,1-dioxo-1,4-dihydro-1λ$^6$-benzo[1,2,4]thiadiazin-3-yl]-3-(4-fluoro-benzyl)-6-hydroxy-3-aza-tricyclo[6.2.1.0$^{2,7}$]undec-5-en-4-one (38 mg, 0.065 mmol, 20%), as an off-white solid. $^1$H NMR (400 MHz, DMSO-d$_6$) δ: 1.19 (2H, m), 1.42-1.61 (4H, m), 2.50 (1H, m), 2.65 (1H, m), 2.97 (2H, m), 3.05 (1H, m), 3.53 (3H, m), 4.43 (1H, d, J=14.4 Hz), 4.96 (1H, d, J=15.6 Hz), 7.15 (2H, m), 7.33 (2H, m), 7.41 (1H, t, J=3.6 Hz), 7.66 (1H, d, J=9.2 Hz), 7.96 (1H, dd, J=8.8, 2.4 Hz), 8.10 (1H, d, J=2.4 Hz). LC-MS (ESI) calcd for C$_{28}$H$_{26}$FN$_3$O$_6$S$_2$ 583.12, found 584.2 [M+H$^+$].

Example 21

(1R,2S,7R,8S)-5-[7-(1,1-Dioxo-tetrahydro-1λ$^6$-thiophen-2-yl)-1,1-dioxo-1,4-dihydro-1λ$^6$-benzo[1,2,4]thiadiazin-3-yl]-3-(4-fluoro-benzyl)-6-hydroxy-3-aza-tricyclo[6.2.1.0$^{2,7}$]undec-5-en-4-one

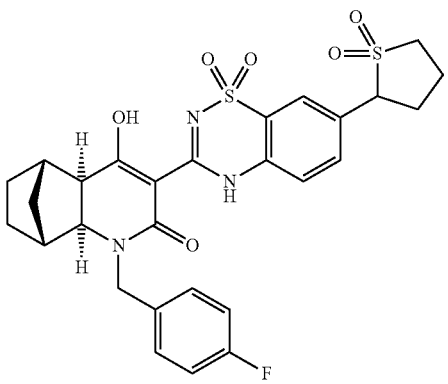

(1R,2S,7R,8S)-5-[7-(1,1-Dioxo-4,5-dihydro-1H-1λ$^6$-thiophen-2-yl)-1,1-dioxo-1,4-dihydro-1λ$^6$-benzo[1,2,4]thiadiazin-3-yl]-3-(4-fluoro-benzyl)-6-hydroxy-3-aza-tricyclo[6.2.1.0$^{2,7}$]undec-5-en-4-one (prepared as described in Example 20, 30 mg, 0.05 mmol) was dissolved in methanol (15 mL) and 5% palladium on charcoal (100 mg) was added. The flask was degassed and backfilled with hydrogen gas via balloon. The mixture was stirred at 25° C. for 16 h. The mixture was passed through a plug of Celite, rinsed with 10% methanol/dichloromethane, and the filtrate was concentrated in vacuo. The residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (1R,2S,7R,8S)-[7-(1,1-dioxo-tetrahydro-1λ$^6$-thiophen-2-yl)-1,1-dioxo-1,4-dihydro-1λ$^6$-benzo[1,2,4]thiadiazin-3-yl]-3-(4-fluoro-benzyl)-6-hydroxy-3-aza-tricyclo[6.2.1.0$^{2,7}$]undec-5-en-4-one (26 mg, 0.044 mmol, 86%), as a white powder. $^1$H NMR (400 MHz, DMSO-d$_6$) δ: 1.19 (2H, m), 1.40-1.60 (4H, m), 2.12 (1H, m), 2.67 (1H, m), 2.36 (1H, m), 2.50 (1H, m), 2.65 (1H, m), 3.03 (1H, m), 3.23 (1H, m), 3.32 (1H, m), 3.53 (1H, d, J=10.0 Hz), 4.42 (1H, d, J=15.2 Hz), 4.56 (1H, dd, J=11.6, 6.8 Hz), 4.97 (1H, d, J=15.6 Hz), 7.14 (2H, m), 7.33 (2H, m), 7.58 (1H, d, J=8.8 Hz), 7.69 (1H, dd, J=8.8, 2.4 Hz), 7.82 (1H, d, J=2.4 Hz); LC-MS (ESI) calcd for C$_{28}$H$_{28}$FN$_3$O$_6$S$_2$ 585.14, found 586.3 [M+H$^+$].

Example 22

(1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

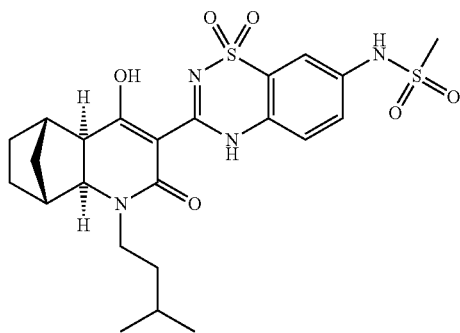

a) (1S,2R,3S,4R)-3-(3-Methyl-butylamino)-bicyclo[2.2.1]heptane-2-carboxylic acid ethyl ester

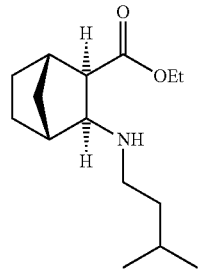

(1S,2R,3S,4R)-3-Amino-bicyclo[2.2.1]heptane-2-carboxylic acid ethyl ester (prepared as described in Example 6k, 0.5 g, 2.7 mmol) was dissolved in methanol (25 mL). Isovaleraldehyde (0.233 g, 2.7 mmol) was added followed by acetic acid (1 mL). The solution continued to stir at 25° C. for 10 min. Sodium cyanoborohydride (0.424 g, 6.75 mmol) was added and the mixture was stirred at 25° C. for 5 h. The mixture was poured into aqueous half-saturated aqueous sodium bicarbonate solution (100 mL). The aqueous layer was extracted with ethyl acetate (2×100 mL). The organic layer was dried over sodium sulfate, filtered, and concentrated in vacuo to afford the crude product, (1S,2R,3S,4R)-3-(3-methyl-butylamino)-bicyclo[2.2.1]heptane-2-carboxylic acid ethyl ester (0.43 g, 1.7 mmol, 63%), as a light yellow oil, which was used in the next step without any further purification. LC-MS (ESI) calcd for $C_{15}H_{27}NO_2$ 253.2, found 254.1 [M+H$^+$].

b) (1S,2R,3S,4R)-3-[[2-(7-Methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]heptane-2-carboxylic acid ethyl ester

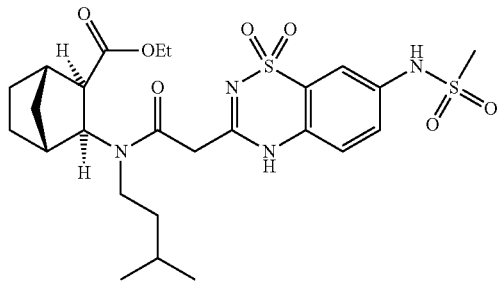

(7-Methanesulfonylamino-1,1-dioxo-1,4-dihydro-1λ$^6$-benzo[1,2,4]thiadiazin-3-yl)-acetic acid (prepared as described in Example 1g, 0.216 g, 0.649 mmol) was dissolved in anhydrous N,N-dimethylformamide (5 mL). (1S,2R,3S,4R)-3-(3-Methyl-butylamino)-bicyclo[2.2.1]heptane-2-carboxylic acid ethyl ester (0.164 g, 0.649 mmol) was added followed by 1-(3-dimethylaminopropyl)-3-ethylcarbodiimide hydrochloride (0.13 g, 0.681 mmol). Then N-methylmorpholine (0.138 g, 1.36 mmol) was added into the above reaction mixture. The mixture was stirred at 25° C. for 4 h. The solution was poured into 1.0 M aqueous hydrochloric acid solution (100 mL). The aqueous layer was extracted with ethyl acetate (2×100 mL). The organic layer was dried over magnesium sulfate, filtered, and concentrated in vacuo to afford the crude product, (1S,2R,3S,4R)-3-[[2-(7-methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]heptane-2-carboxylic acid ethyl ester, as a light yellow oil, which was used in the next step without any further purification. LC-MS (ESI) calcd for $C_{25}H_{36}N_4O_7S_2$ 568.2, found 569.5 [M+H$^+$].

c) (1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

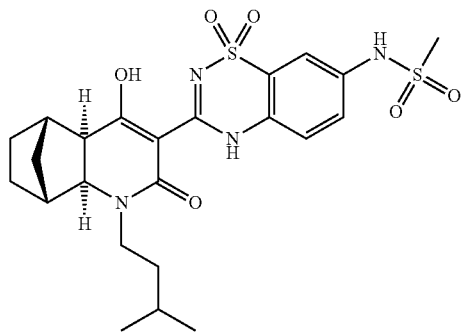

The crude (1S,2R,3S,4R)-3-[[2-(7-methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]heptane-2-carboxylic acid ethyl ester was dissolved in ethanol (7 mL) and a 21 wt. % solution of sodium ethoxide in ethanol (1.15 mL, 3.25 mmol) was added into the above solution. The mixture was stirred at 60° C. for 4 h and cooled down to 25° C. The mixture was poured into 0.5 M aqueous hydrochloric acid solution (100 mL). The aqueous layer was extracted with ethyl acetate (2×100 mL). The organic layer was dried over sodium sulfate, filtered, and concentrated in vacuo to afford the crude product, which was purified by flash column chromatography (Teledyne Isco RediSep column; 100% ethyl acetate) to afford the desired product, (1R,2S,7R,8S)-N-{3-[6-hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.19 g, 0.364 mmol, 56.1% over two steps), as an off-white solid. $^1$H NMR (400 MHz, DMSO-d$_6$) δ: 0.89-0.93 (6H, m), 1.16-1.23 (2H, m), 1.28-1.32 (1H, m), 1.35-1.62 (7H, m), 1.99-1.99 (1H, m), 2.52-2.54 (1H, m), 2.63 (1H, bs), 3.06 (3H, s), 3.62-3.72 (2H, m), 7.50 (1H, dd, J$_1$=8.9 Hz, J$_2$=2.2 Hz), 7.57-7.59 (2H, m), 10.17 (1H, s). LC-MS (ESI) calcd for $C_{23}H_{30}N_4O_6S_2$ 522.16, found 523.6 [M+H$^+$].

Example 23

(rac-di-exo)-N-{3-[3-(2-Cyclopropyl-ethyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

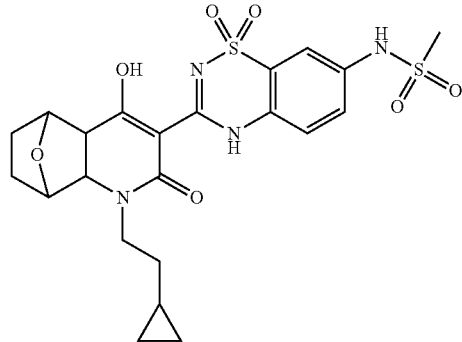 [SMILES: CS(=O)(=O)Nc1ccc2c(c1)S(=O)(=O)N=C(C1=C(O)C3C4CCC(O4)C3N(CCC3CC3)C1=O)N2]

a) Cyclopropylacetaldehyde

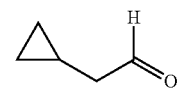

To a 2.0 M solution of oxalyl chloride in dichloromethane (9.8 mL, 19.6 mmol) at −78° C. was added dimethyl sulfoxide dropwise. After stirring for 15 min at −78° C., a solution of cyclopropylethyl alcohol (1.5 g, 17.4 mmol) in dichloromethane (3.5 mL) was added. After stirring for an additional 1 h, triethylamine (13.8 mL, 98.3 mmol) was added. The reaction mixture was allowed to warm to 25° C. and diluted with water. The organic layer was separated and the aqueous layer was extracted with dichloromethane (3×50 mL). The combined organic layers were dried over anhydrous magnesium sulfate and concentrated in vacuo at 0° C. to afford the crude cyclopropylacetaldehyde, which was used in the next step without further purification. $^1$H NMR (400 MHz, CDCl$_3$) δ 0.19 (2H, dd, J$_1$=10.3 Hz, J$_2$=5.2 Hz), 0.62 (2H, dd, J$_1$=13.2 Hz, J$_2$=5.3 Hz), 1.03-0.97 (1H, m), 2.30 (2H, d, J=5.1 Hz), 9.79 (1H, d, J=1.7 Hz).

b) (rac-di-exo)-3-(2-Cyclopropyl-ethylamino)-7-oxa-bicyclo[2.2.1]heptane-2-carboxylic acid methyl ester

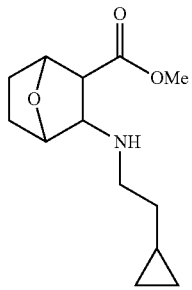 [SMILES: COC(=O)C1C2CCC(O2)C1NCCC1CC1]

Cyclopropylacetaldehyde (148 mg, 1.75 mmol) was added to a solution of (rac-di-exo)-3-amino-7-oxa-bicyclo[2.2.1]heptane-2-carboxylic acid methyl ester (prepared as described in Example 8a, 300 mg, 1.75 mmol) in anhydrous methanol (10 mL) at 25° C. under a nitrogen atmosphere. After stirring for 20 min, glacial acetic acid (0.3 mL) and sodium cyanoborohydride (150 mg, 2.38 mmol) were added sequentially, and the resulting mixture was stirred at 25° C. for 18 h. The reaction mixture was poured into saturated aqueous sodium bicarbonate solution and was extracted with ethyl acetate. The combined organic layers were washed with saturated aqueous brine solution, dried over sodium sulfate and filtered. The filtrate was concentrated in vacuo to afford the desired product, (rac-di-exo)-3-(2-cyclopropyl-ethylamino)-7-oxa-bicyclo[2.2.1]heptane-2-carboxylic acid methyl ester (220 mg, 0.92 mmol, 53%), as a yellow oil. $^1$H NMR (400 MHz, CDCl$_3$) δ: 0.19 (2H, m), 0.52 (2H, m), 0.70 (1H, m), 1.65-2.00 (6H, m), 3.10 (1H, d, J=8.4 Hz), 3.23 (2H, m), 3.82 (3H, s), 3.93 (1H, m), 4.90 (1H, d, J=4.8 Hz), 5.17 (1H, d, J=5.2 Hz).

c) (rac-di-exo)-N-{3-[3-(2-Cyclopropyl-ethyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

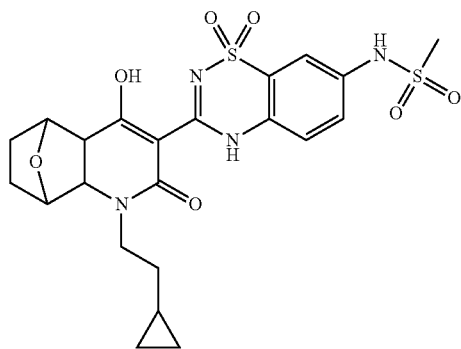 [SMILES: CS(=O)(=O)Nc1ccc2c(c1)S(=O)(=O)N=C(C1=C(O)C3C4CCC(O4)C3N(CCC3CC3)C1=O)N2]

To a stirred solution of (rac-di-exo)-3-(2-cyclopropyl-ethylamino)-7-oxa-bicyclo[2.2.1]heptane-2-carboxylic acid methyl ester (120 mg, 0.50 mmol) in anhydrous N,N-dimethylformamide (2 mL) under a nitrogen atmosphere, (7-methanesulfonylamino-1,1-dioxo-1,4-dihydro-1λ$^6$-benzo[1,2,4]thiadiazin-3-yl)-acetic acid (prepared as described in Example 1g, 107 mg, 0.32 mmol), N-methylmorpholine (0.12 mL, 1.09 mmol) and 1-(3-dimethylaminopropyl)-3-ethylcarbodiimide hydrochloride (105 mg, 0.55 mmol) were added sequentially. After stirring at 25° C. for 2 h, the reaction mixture was diluted with ethyl acetate, washed with 1.0 M aqueous hydrochloric acid solution and saturated aqueous brine solution, dried over sodium sulfate and filtered. The filtrate was concentrated in vacuo to afford the crude intermediate. The crude amide intermediate was dissolved in absolute ethanol (5 mL), and a 21 wt. % solution of sodium ethoxide in ethanol (0.8 mL, 2.16 mmol) was added. The mixture was stirred at 60° C. for 2 h, and then was allowed to cool to 25° C. A 0.5 M aqueous hydrochloric acid solution (10 mL) was added, and then the mixture was extracted with ethyl acetate, washed with saturated aqueous brine solution, dried over sodium sulfate and filtered. The filtrate was concentrated in vacuo and the residue was purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (rac-di-exo)-N-{3-[3-(2-cyclopropyl-ethyl)-6-hydroxy-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (25 mg, 0.048 mmol, 15%), as a yellow solid. $^1$H NMR (400 MHz, DMSO-d$_6$) δ: 0.07 (2H, m), 0.41 (2H, m), 0.70 (1H, m), 1.37-1.72 (6H, m), 3.05 (3H, s), 3.07 (1H, m), 3.30 (m, 1H), 3.92 (2H, m), 4.74 (2H, m), 7.49 (1H, m), 7.55 (2H, m), 10.16 (1H, s). LC-MS (ESI) calcd for C$_{22}$H$_{26}$N$_4$O$_7$S$_2$ 522.12, found 523.4 [M+H$^+$].

Example 24

(1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide

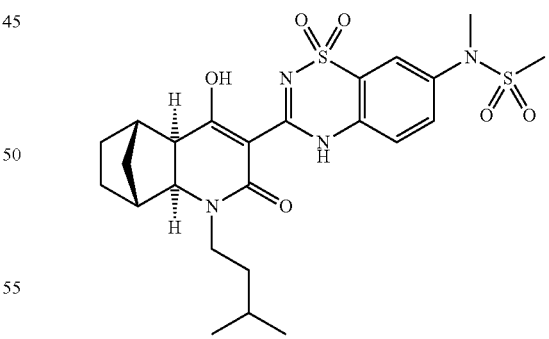

(1R,2S,7R,8S)-N-{3-[6-Hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 22, 90 mg, 0.172 mmol) was dissolved in anhydrous N,N-dimethylformamide (2 mL). Potassium carbonate (0.04 g, 0.344 mmol) was added followed by iodomethane (0.027 g, 0.189 mmol). The mixture was stirred at 25° C. for 5 h. The reaction mixture was extracted with ethyl acetate (2×100 mL) and water (100 mL). The organic layer was washed with saturated aqueous brine solution (50 mL), dried over sodium sulfate and filtered. The filtrate was concentrated in vacuo to afford the crude product, which was purified by flash column chromatography (Teledyne Isco RediSep column; 40% ethyl acetate in hexanes) to afford the desired product, (1R,2S,7R,8S)-N-{3-[6-hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide (0.052 g, 0.097 mmol, 56.4%), as a white solid. $^1$H NMR (400 MHz, DMSO-d$_6$) δ: 0.92 (6H, d, J=6.4 Hz), 1.21-1.26 (1H, m), 1.28-1.33 (1H, m), 1.39-1.63 (7H, m), 2.54 (1H, bs), 2.63-2.67 (1H, m), 3.00 (3H, s), 3.06-3.17 (1H, m), 3.29 (3H, s), 3.63-3.72 (2H, m), 7.62 (1H, d, J=8.5 Hz), 7.70-7.73 (1H, m), 7.85 (1H, s). LC-MS (ESI) calcd for C$_{24}$H$_{32}$N$_4$O$_6$S$_2$ 536.18, found 537.6.6 [M+H$^+$].

Example 25

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

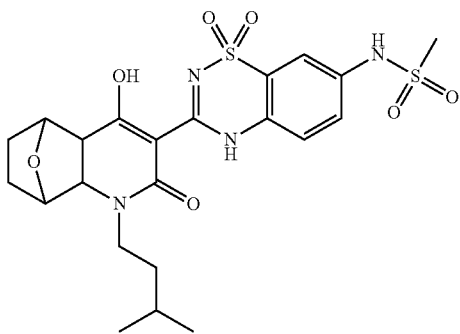 [SMILES: CC(C)CCN1C(=O)C(C2=NS(=O)(=O)c3cc(NS(C)(=O)=O)ccc3N2)=C(O)C2C3CCC(O3)C21]

a) (rac-di-exo)-3-(3-Methyl-butylamino)-7-oxa-bicyclo[2.2.1]heptane-2-carboxylic acid methyl ester

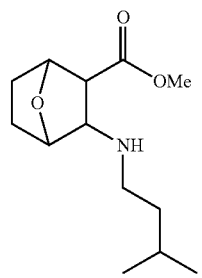 [SMILES: COC(=O)C1C2CCC(O2)C1NCCC(C)C]

(rac-di-exo)-3-amino-7-oxa-bicyclo[2.2.1]heptane-2-carboxylic acid methyl ester (prepared as described in Example 8a, 0.4 g, 2.34 mmol) was dissolved in methanol (20 mL). Isovaleraldehyde (0.202 g, 2.34 mmol) was added followed by acetic acid (1 mL). The solution continued to stir at 25° C. for 10 min. Sodium cyanoborohydride (0.37 g, 5.85 mmol) was added and the mixture was stirred at 25° C. for 16 h. The mixture was poured into a half-saturated aqueous sodium bicarbonate solution (150 mL). The aqueous layer was extracted with ethyl acetate (2×150 mL). The organic layer was dried over sodium sulfate, filtered, and concentrated in vacuo to afford the crude product, (rac-di-exo)-3-(3-methyl-butylamino)-7-oxa-bicyclo[2.2.1]heptane-2-carboxylic acid methyl ester (0.3 g, 2.34 mmol, 53.1%), as a clear oil. LC-MS (ESI) calcd for C$_{13}$H$_{23}$NO$_3$ 241.17, found 242.4 [M+H$^+$].

b) (rac-di-exo)-3-[[2-(7-Methanesulfonylamino-1,1-dioxo-1,4-dihydro-1λ$^6$-benzo[1,2,4]thiadiazin-3-yl)-acetyl]-(3-methyl-butyl)-amino]-7-oxa-bicyclo[2.2.1]heptane-2-carboxylic acid methyl ester

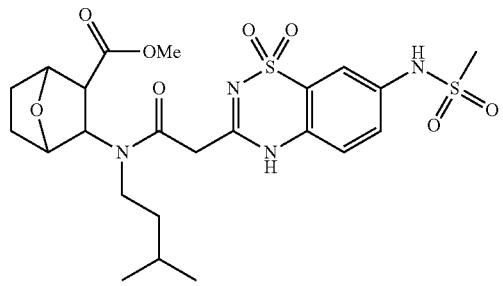 [SMILES: COC(=O)C1C2CCC(O2)C1N(CCC(C)C)C(=O)CC1=NS(=O)(=O)c2cc(NS(C)(=O)=O)ccc2N1]

(7-Methanesulfonylamino-1,1-dioxo-1,4-dihydro-1λ$^6$-benzo[1,2,4]thiadiazin-3-yl)-acetic acid (prepared as described in Example 1g, 0.211 g, 0.696 mmol) was dissolved in anhydrous N,N-dimethylformamide (6 mL). (rac-di-exo)-3-(3-Methyl-butylamino)-7-oxa-bicyclo[2.2.1]heptane-2-carboxylic acid methyl ester (0.168 g, 0.696 mmol) was added followed by 1-(3-dimethylaminopropyl)-3-ethylcarbodiimide hydrochloride (0.14 g, 0.731 mmol). Then N-methylmorpholine (0.148 g, 1.46 mmol) was added into the above reaction mixture. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate, filtered, and concentrated in vacuo to afford the crude product, (rac-di-exo)-3-[[2-(7-methanesulfonylamino-1,1-dioxo-1,4-dihydro-1λ$^6$-benzo[1,2,4]thiadiazin-3-yl)-acetyl]-(3-methyl-butyl)-amino]-7-oxa-bicyclo[2.2.1]heptane-2-carboxylic acid methyl ester, as a light yellow oil, which was used in the next step without any further purification. LC-MS (ESI) calcd for C$_{23}$H$_{32}$N$_4$O$_8$S$_2$ 556.17, found 557.4 [M+H$^+$].

c) (rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

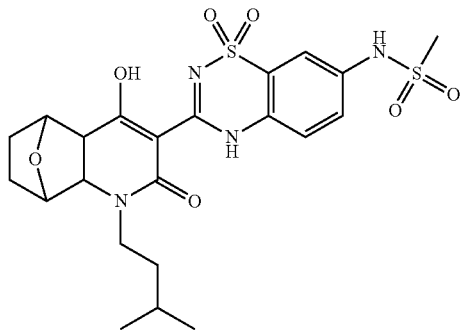 [SMILES: CC(C)CCN1C(=O)C(C2=NS(=O)(=O)c3cc(NS(C)(=O)=O)ccc3N2)=C(O)C2C3CCC(O3)C21]

The crude (rac-di-exo)-3-[[2-(7-methanesulfonylamino-1,1-dioxo-1,4-dihydro-1λ⁶-benzo[1,2,4]thiadiazin-3-yl)-acetyl]-(3-methyl-butyl)-amino]-7-oxa-bicyclo[2.2.1]heptane-2-carboxylic acid methyl ester was dissolved in ethanol (7 mL), and a 21 wt. % solution of sodium ethoxide in ethanol (1.3 mL, 3.48 mmol) was added into the above solution. The mixture was stirred at 60° C. for 4 h and cooled down to 25° C. The mixture was poured into 0.5 M aqueous hydrochloric acid solution (100 mL). The aqueous layer was extracted with ethyl acetate (2×100 mL). The organic layer was dried over sodium sulfate, filtered, and concentrated in vacuo to afford the crude product, which was purified by flash column chromatography (Teledyne Isco RediSep column; 100% ethyl acetate) to afford the desired product, (rac-di-exo)-N-{3-[6-hydroxy-3-(3-methyl-butyl)-4-oxo-11-oxa-3-aza-tricyclo[6.2.1.0²,⁷]undec-5-en-5-yl]-1,1-dioxo-1,4-dihydro-1λ⁶ benzo[1,2,4]thiadiazin-7-yl}-methanesulfonamide (0.07 g, 0.133 mmol, 19.2% over two steps), as a light yellow solid. $^1$H NMR (400 MHz, DMSO-$d_6$) δ: 0.92 (6H, d, J=5.5 Hz), 1.06-1.31 (2H, m), 1.40-1.72 (6H, m), 3.05 (3H, s), 3.17-3.22 (1H, m), 3.80-3.87 (2H, m), 4.72-4.73 (2H, m), 7.47-7.55 (3H, m), 10.12 (1H, bs). LC-MS (ESI) calcd for $C_{22}H_{28}N_4O_7S_2$ 524.14, found 525.4 [M+H$^+$].

Example 26

(1R,2S,7R,8S)-5-[7-(1,1-Dioxo-1λ⁶-isothiazolidin-2-yl)-1,1-dioxo-1,4-dihydro-1λ⁶-benzo[1,2,4]thiadiazin-3-yl]-3-(4-fluoro-benzyl)-6-hydroxy-3-aza-tricyclo[6.2.1.0²,⁷]undec-5-en-4-one

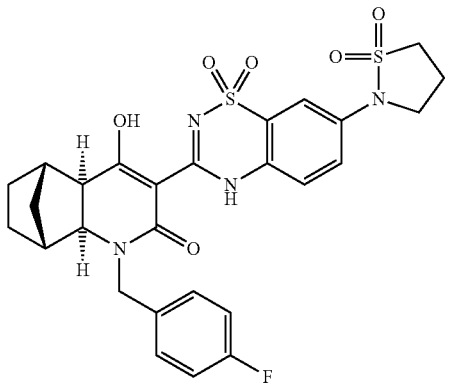

A reaction flask was charged with copper (I) iodide (8 mg, 0.042 mmol), sarcosine (N-methyl glycine) (9 mg, 0.1 mmol), isothiazolidine 1,1-dioxide (204 mg, 1.685 mmol), (1R,2S,7R,8S)-3-(4-fluoro-benzyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undec-5-en-4-one (prepared as described in Example 19, 100 mg, 0.168 mmol) and potassium phosphate (179 mg, 0.842 mmol). The flask was degassed and backfilled with nitrogen, and then anhydrous N,N-dimethylformamide (3 mL) was added. The resulting suspension was vigorously stirred at 100° C. for 17 h, and then allowed to cool to 25° C. The mixture was diluted with ethyl acetate (30 mL) and washed with 1.0 M aqueous hydrochloric acid solution (2×20 mL) and saturated aqueous brine solution (40 mL). The organic layer was dried over magnesium sulfate, filtered, and concentrated in vacuo. Purification by flash column chromatography (Teledyne Isco RediSep column; 1$^{st}$ column: 100% dichloromethane, 2$^{nd}$ column: 5% hexanes in dichloromethane) to afford the desired product. The crude product was triturated with absolute ethanol (3×) and dried in vacuo at 60° C. to afford the desired product, (1R,2S,7R,8S)-5-[7-(1,1-dioxo-1λ⁶-isothiazolidin-2-yl)-1,1-dioxo-1,4-dihydro-1λ⁶-benzo[1,2,4]thiadiazin-3-yl]-3-(4-fluoro-benzyl)-6-hydroxy-3-aza-tricyclo[6.2.1.0²,⁷]undec-5-en-4-one (70 mg, 0.119 mmol, 71%), as a solid. $^1$H NMR (400 MHz, DMSO-$d_6$) δ: 1.17-1.24 (2H, m), 1.40-1.61 (4H, m), 2.39-2.46 (2H, m), 2.51-2.54 (1H, m), 2.64-2.65 (1H, m), 3.03-3.05 (1H, m), 3.53-3.60 (3H, m), 3.83 (2H, t, J=6.3 Hz), 4.43 (1H, d, J=15.4 Hz), 4.97 (1H, d, J=15.6 Hz), 7.15 (2H, t, J=9.0 Hz), 7.32-7.35 (2H, m), 7.51-7.54 (2H, m), 7.62 (1H, d, J=8.5 Hz). LC-MS (ESI) calcd for $C_{27}H_{27}FN_4O_6S_2$ 586.14, found 587.4 [M+H$^+$].

Example 27

(1R,2S,7R,8S)-N-[3-(6-Hydroxy-4-oxo-3-aza-tricyclo[6.2.1.0²,⁷]undec-5-en-5-yl)-1,1-dioxo-1,4-dihydro-1λ⁶-benzo[1,2,4]thiadiazin-7-yl]-methanesulfonamide

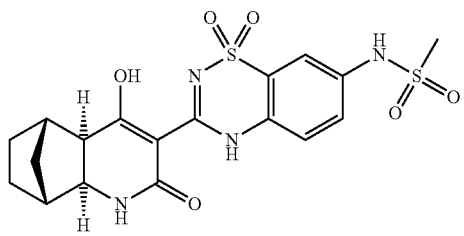

A suspension of (1R,2S,3R,4S)-3-ethoxycarbonyl-bicyclo[2.2.1]hept-2-yl-aminium (1'S)-(+)-10-camphorsulfonate (prepared as described in Example 6j, 5.00 g, 12.0 mmol) and potassium carbonate (4.16 g, 30.1 mmol) in ethyl acetate (80 mL) was stirred at 25° C. for 5 h, then was filtered through a medium frit. The filtrate was concentrated in vacuo to afford the crude (1S,2R,3S,4R)-3-amino-bicyclo[2.2.1]heptane-2-carboxylic acid ethyl ester (2.14 g). A portion of this material (1.00 g, 5.52 mmol) and (7-methanesulfonylamino-1,1-dioxo-1,4-dihydro-1λ⁶-benzo[1,2,4]thiadiazin-3-yl)-acetic acid (prepared as described in Example 1g, 1.84 g, 5.52 mmol) were dissolved in N,N-dimethylformamide at 25° C. and 1-(3-dimethylaminopropyl)-3-ethylcarbodiimide hydrochloride (1.11 g, 5.79 mmol) and N-methylmorpholine (1.27 mL, 11.6 mmol) were added sequentially. The resulting solution was stirred at 25° C. for 22 h, and then was concentrated in vacuo. The residue was partitioned between 1.0 M aqueous hydrochloric acid solution (200 mL) and ethyl acetate (2×150 mL). The organic layers were dried over sodium sulfate, filtered and concentrated in vacuo. The resulting orange oil was dissolved in ethanol (70 mL) at 25° C. A 21 wt. % solution of sodium ethoxide in ethanol (10.7 mL, 33.0 mmol) was added and the reaction mixture was heated at 90° C. for 3 d. After cooling to 25° C., the reaction mixture was concentrated in vacuo to a volume of approximately 5 mL and was then partitioned between 1.0 M aqueous hydrochloric acid solution (200 mL) and ethyl acetate (2×150 mL). The organic layers were dried over sodium sulfate, filtered and concentrated in vacuo. The residue was purified by flash column chromatography (Teledyne Isco RediSep column; 0 to 7% methanol in dichloromethane) to afford the desired product, (1R,2S,7R,8S)-N-[3-(6-hydroxy-4-oxo-3-aza-tricyclo[6.2.1.0²,⁷]undec-5-en-5-yl)-1,1-dioxo-1,4-dihydro-1λ⁶-benzo[1,2,4]thiadiazin-7-yl]-methanesulfonamide (0.25 g, 0.552 mmol, 10%), as a white solid. $^1$H NMR (400 MHz, DMSO-$d_6$) δ: 1.17-1.22 (2H, m), 1.39-1.58 (3H, m), 2.24 (1H, bs), 2.32 (1H, bs), 2.64-2.66 (1H, m), 2.84-2.87 (1H, m), 3.04 (3H, s), 3.54 (1H, bs), 3.63 (1H, bs), 7.49 (2H, bs), 7.55 (1H, bs), 8.11 (1H, bs), 9.52 (1H, bs), 10.12 (1H, bs). LC-MS (ESI) calcd for $C_{18}H_{20}N_4O_6S_2$ 452.08, found 453.2 [M+H$^+$].

Example 28

(1R,2S,7R,8S)-5-(1,1-Dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one

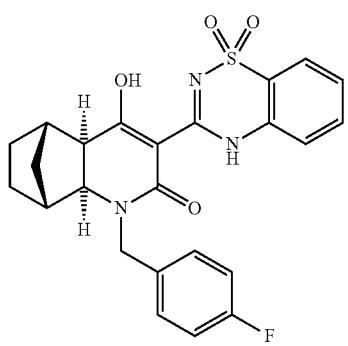

a) N-(2-Sulfamoyl-phenyl)-malonamic acid ethyl ester

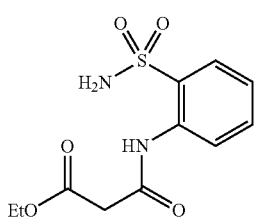 [SMILES: CCOC(=O)CC(=O)Nc1ccccc1S(N)(=O)=O]

2-Amino-benzenesulfonamide (5 g, 29 mmol) was dissolved in N,N-dimethylacetamide (25 mL) and diethyl ether (25 mL). Ethyl-3-chloro-3-oxo-propionate (4.6 g, 30.45 mmol) was added into the above reaction solution. The reaction mixture was stirred at 25° C. for 3 h. The product started to precipitate and was collected by vacuum filtration. The solid was dissolved in ethyl acetate (200 mL) and extracted with water (200 mL). The aqueous layer was back-extracted with ethyl acetate (200 mL). The combined organic layers were dried over sodium sulfate, filtered, and concentrated in vacuo to afford the crude product, N-(2-sulfamoyl-phenyl)-malonamic acid ethyl ester, as a white solid, which was used in the next step without further purification. $^1$H NMR (400 MHz, DMSO-$d_6$) δ: 1.23 (3H, t, J=7.0 Hz), 3.61 (2H, s), 4.14 (2H, quartet, J=7.0 Hz), 7.29-7.33 (1H, m), 7.53 (2H, bs), 7.56-7.60 (1H, m), 7.84-7.86 (1H, m), 7.97-7.99 (1H, m), 9.54 (1H, bs). LC-MS (ESI) calcd for $C_{11}H_{14}N_2O_5S$ 286.06, found 287.1 [M+H$^+$].

b) (1,1-Dioxo-1,4-dihydro-1λ⁶-benzo[1,2,4]thiadiazin-3-yl)-acetic acid

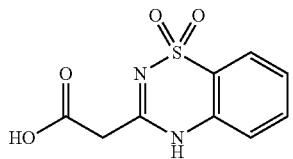 [SMILES: O=C(O)CC1=NS(=O)(=O)c2ccccc2N1]

Solid sodium hydroxide (3.48 g, 87 mmol) was dissolved in water to make a saturated solution. The crude N-(2-sulfamoyl-phenyl)-malonamic acid ethyl ester was added into the sodium hydroxide solution. The reaction mixture was heated at 110° C. for 2.5 h, and then was cooled down to 25° C. The reaction mixture was acidified by slowly adding a 12.0 M aqueous hydrochloric acid solution (9.67 g, 116 mmol) while cooling in an ice-water bath. The product precipitated and was collected by vacuum filtration. The solid was washed with cold water and dried under high vacuum to afford the crude product, (1,1-dioxo-1,4-dihydro-1λ⁶-benzo[1,2,4]thiadiazin-3-yl)-acetic acid (5 g, 20.8 mmol, 71.7% over two steps), as a white solid. $^1$H NMR (400 MHz, DMSO-$d_6$) δ: 3.58 (2H, s), 7.31 (1H, d, J=8.0 Hz), 7.44 (1H, dd, $J_1$=7.8 Hz, $J_2$=7.8 Hz), 7.67 (1H, dd, $J_1$=7.8 Hz, $J_2$=7.8 Hz), 7.79 (1H, d, J=7.9 Hz), 12.18 (1H, bs), 13.03 (1H, bs). LC-MS (ESI) calcd for $C_9H_8N_2O_4S$ 240.02, found 241.1 [M+H$^+$].

c) (1S,2R,3S,4R)-3-[[2-(1,1-Dioxo-1,4-dihydro-1λ⁶-benzo[1,2,4]thiadiazin-3-yl)-acetyl]-(4-fluoro-benzyl)-amino]-bicyclo[2.2.1]heptane-2-carboxylic acid ethyl ester

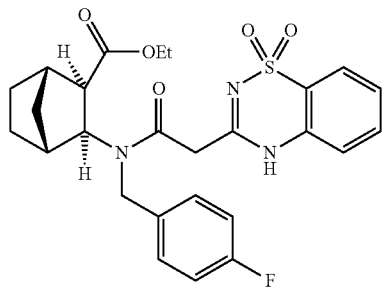

(1,1-Dioxo-1,4-dihydro-1□6-benzo[1,2,4]thiadiazin-3-yl)-acetic acid (0.2 g, 0.833 mmol) was dissolved in anhydrous N,N-dimethylformamide (8 mL). (1S,2R,3S,4R)-3-(4-Fluoro-benzylamino)-bicyclo[2.2.1]heptane-2-carboxylic acid ethyl ester (prepared as described in Example 6l, 0.244 g, 0.833 mmol) was added followed by 1-(3-dimethylaminopropyl)-3-ethylcarbodiimide hydrochloride (0.168 g, 0.875 mmol). Then N-methylmorpholine (0.177 g, 1.75 mmol) was added into the above reaction mixture. The mixture was stirred at 25° C. for 16 h. The solution was poured into 1.0 M aqueous hydrochloric acid solution (100 mL). The aqueous layer was extracted with ethyl acetate (2×100 mL). The organic layer was dried over sodium sulfate, filtered, and concentrated in vacuo to afford the crude product, (1S,2R,3S,4R)-3-[[2-(1,1-dioxo-1,4-dihydro-1□6-benzo[1,2,4]thiadiazin-3-yl)-acetyl]-(4-fluoro-benzyl)-amino]-bicyclo[2.2.1]heptane-2-carboxylic acid ethyl ester, as an orange oil, which was used in the next step without any further purification. LC-MS (ESI) calcd for C26H28FN3O5S 513.58, found 514.4 [M+H+].

d) (1R,2S,7R,8S)-5-(1,1-Dioxo-1,2-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one

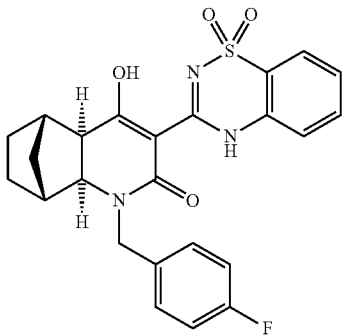

The crude (1S,2R,3S,4R)-3-[[2-(1,1-dioxo-1,4-dihydro-1λ⁶-benzo[1,2,4]thiadiazin-3-yl)-acetyl]-(4-fluoro-benzyl)-amino]-bicyclo[2.2.1]heptane-2-carboxylic acid ethyl ester was dissolved in ethanol (8 mL), and a 21 wt. % solution of sodium ethoxide in ethanol (1.6 mL, 4.2 mmol) was added into the above solution. The mixture was stirred at 60° C. for 4 h and allowed to cool down to 25° C. The mixture was poured into 0.5 M aqueous hydrochloric acid solution (100 mL). The product started to precipitate and was collected by vacuum filtration. The precipitate was purified by flash column chromatography (Teledyne Isco RediSep column; 100% ethyl acetate) to afford the desired product, (1R,2S,7R,8S)-5-(1,1-dioxo-1,2-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (0.242 g, 0.517 mmol, 62.1% over two steps), as a white solid. ¹H NMR (400 MHz, DMSO-d₆) δ: 1.16-1.22 (2H, m), 1.40-1.60 (4H, m), 2.51 (1H, bs), 2.64 (1H, d, J=2.1 Hz), 3.03 (1H, d, J=8.0 Hz), 3.54 (1H, d, J=9.3 Hz), 4.42 (1H, d, J=15.6 Hz), 4.97 (1H, d, J=15.7 Hz), 7.15 (2H, t, J=8.8 Hz), 7.33 (2H, dd, J₁=8.0 Hz, J₂=5.9 Hz), 7.45-7.53 (2H, m), 7.67-7.71 (1H, m), 7.85 (1H, d, J=7.9 Hz). LC-MS (ESI) calcd for C₂₄H₂₂FN₃O₄S 467.13, found 468.2 [M+H⁺]. Anal. calcd for C₂₄H₂₂FN₃O₄S: C, 61.66; H, 4.74; N, 8.99. found C, 61.96; H, 4.88; N, 8.99.

Example 29

N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,4]thiazin-7-yl}-methanesulfonamide

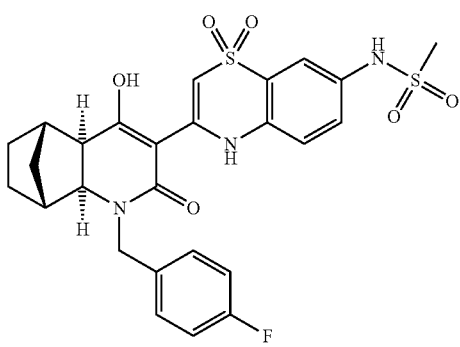

a) (7-Methanesulfonylamino-1,1-dioxo-1,4-dihydro-1λ⁶-benzo[1,4]thiazin-3-yl)-acetic acid

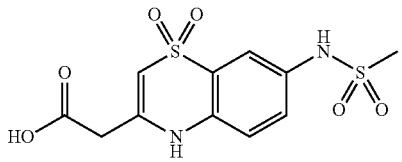

A solution of (7-methanesulfonylamino-1,1-dioxo-1,4-dihydro-1λ⁶-benzo[1,4]thiazin-3-yl)-acetic acid ethyl ester (prepared as described in US patent application US 2008/0031852, 600 mg, 1.666 mmol) in methanol (30 mL) was cooled to 0° C. in an ice-water bath and treated with 2.0 M aqueous lithium hydroxide solution (4.17 mL, 8.332 mmol). The reaction mixture was allowed to warm to 25° C. and stirred for 1 h. The methanol was removed in vacuo and the reaction mixture was poured into 0.5 M aqueous hydrochloric acid solution (20 mL) on ice, extracted with ethyl acetate (3×50 mL), dried over sodium sulfate, filtered, and concentrated in vacuo to afford an orange solid. The crude solid was triturated with diethyl ether to afford the desired product, (7-methanesulfonylamino-1,1-dioxo-1,4-dihydro-1λ⁶-benzo[1,4]thiazin-3-yl)-acetic acid (409 mg, 1.232 mmol, 73.9%), as a yellow solid. LC-MS calcd for C₁₁H₁₂N₂O₆S₂ 332.4, found 333.0 [M+H⁺].

b) N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,4]thiazin-7-yl}-methanesulfonamide

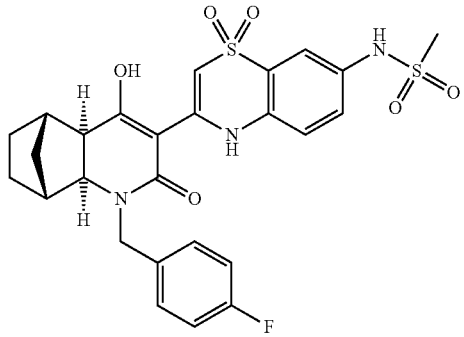

Methyl (1S,2R,3S,4R)-3-[(4-fluorobenzyl)amino]bicyclo[2.2.1]heptane-2-carboxylate (prepared as described in Example 6d, 0.20 g, 0.69 mmol) was dissolved in anhydrous N,N-dimethylformamide (7 mL). (7-Methanesulfonylamino-1,1-dioxo-1,4-dihydro-1λ⁶-benzo[1,4]thiazin-3-yl)-acetic acid (0.23 g, 0.69 mmol) was added followed by N-methylmorpholine (0.17 mL, 1.52 mmol). The mixture was stirred until everything dissolved, approximately 5 min. 1-(3-Dimethylaminopropyl)-3-ethylcarbodiimide hydrochloride (0.15 g, 0.76 mmol) was added and the mixture was stirred at 25° C. for 16 h. The reaction was quenched via addition of saturated aqueous sodium bicarbonate solution (20 mL). The mixture was extracted with ethyl acetate (3×30 mL). The organic layers were combined and washed with saturated aqueous brine solution (20 mL). The resulting solution was dried over magnesium sulfate, filtered, and concentrated in vacuo to afford a golden oil. The oil was dissolved in ethanol (10 mL). A 21 wt. % solution of sodium ethoxide in ethanol (0.65 mL, 1.74 mmol) was added. The reaction was stirred at 60° C. for 16 h. The reaction was quenched via the addition of 1.0 M aqueous hydrochloric acid solution (10 mL). The mixture was extracted with ethyl acetate (3×20 mL). The organic layer was further washed with saturated aqueous sodium bicarbonate solution (2×20 mL), saturated aqueous brine solution (20 mL), dried over magnesium sulfate, filtered, and concentrated in vacuo to afford a clear oil. Purification by flash column chromatography (Teledyne Isco RediSep column; 22 to 75% ethyl acetate in hexanes) afforded the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,4]thiazin-7-yl}-methanesulfonamide (0.020 g, 0.04 mmol, 5.3%), as a yellow powder. $^1$H NMR (400 MHz, CDCl$_3$) δ: 1.21-1.64 (6H, m), 2.52-2.71 (3H, m), 3.07 (3H, s), 3.39-3.52 (1H, m), 5.15-5.28 (2H, m), 6.60 (1H, s), 7.02-7.06 (2H, m), 7.22-7.26 (2H, m), 7.54-7.66 (3H, m). LC-MS (ESI) calcd for C$_{26}$H$_{26}$FN$_3$O$_6$S$_2$ 559.63, found 560.5 [M+H$^+$].

Example 30

(1R,2S,7R,8S)-5-(7-Amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one

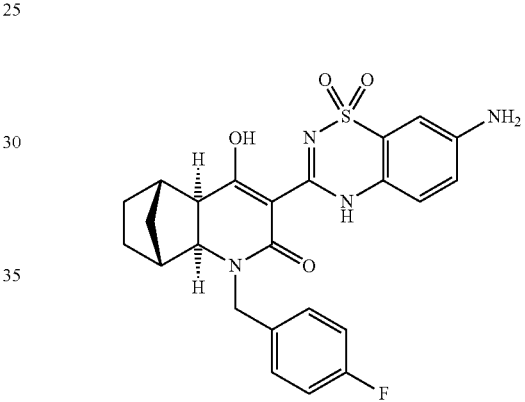

b) (1R,2S,7R,8S)-5-(7-Amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one

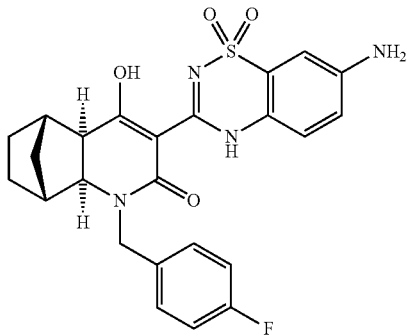

a) (1R,2S,7R,8S)-5-(7-Azido-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one

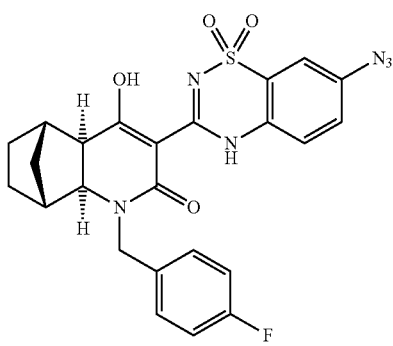

(1R,2S,7R,8S)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (prepared as described in Example 19, 0.513 g, 0.864 mmol), sodium azide (1.12 g, 17.2 mmol), sodium ascorbate (0.086 g, 0.43 mmol), copper (I) iodide (0.16 g, 0.84 mmol), and trans-N,N'-dimethylcyclohexane-1,2-diamine (0.20 mL, 1.27 mmol) were dissolved in a 5:1 mixture of dimethyl sulfoxide and water (10 mL) at 25° C. The reaction flask was degassed and backfilled with nitrogen (5×). After stirring at 25° C. for 14 h, the reaction mixture was partitioned between water (150 mL) and ethyl acetate (2×150 mL). The organic layer was dried over sodium sulfate, filtered and concentrated in vacuo. The residue was purified by flash column chromatography (Teledyne Isco RediSep column; 0 to 60% ethyl acetate in hexanes) to afford the desired product, (1R,2S,7R,8S)-5-(7-azido-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one (0.348 g, 0.684 mmol, 79%), as a dark brown foam, which was used in the next step without any further purification.

(1R,2S,7R,8S)-5-(7-Azido-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one (0.348 g, 0.684 mmol) was dissolved in a 1:1 mixture if methanol and ethyl acetate (15 mL) at 25° C. Palladium on carbon (0.40 g, 5%, "wet") was added, resulting in a black suspension. The reaction was maintained under a hydrogen atmosphere (balloon) at 25° C. for 6 h, and then was filtered through Celite. The Celite was washed with ethyl acetate (2×30 mL) and the filtrate was concentrated in vacuo. The residue was purified by flash column chromatography (Teledyne Isco RediSep column; 50 to 100% ethyl acetate in hexanes) to afford the desired product, (1R,2S,7R,8S)-5-(7-amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one (0.159 g, 0.330 mmol, 48%), as a pale yellow solid. $^1$H NMR (400 MHz, CDCl$_3$) δ: 1.08-1.19 (3H, m), 1.40-1.57 (3H, m), 2.99 (1H, d, J=7.2 Hz), 3.31 (3H, s), 3.36-3.37 (1H, m), 3.50 (1H, d, J=7.8 Hz), 4.39 (1H, d, J=14.6 Hz), 4.93 (1H, d, J=14.5 Hz), 6.86-6.91 (3H, m), 7.13-7.15 (2H, m), 7.21 (1H, d, J=8.8 Hz), 7.30 (2H, bs), 13.79 (1H, s). LC-MS (ESI) calcd for C$_{24}$H$_{23}$FN$_4$O$_4$S 482.14, found 483.4 [M+H$^+$].

Example 31

(rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

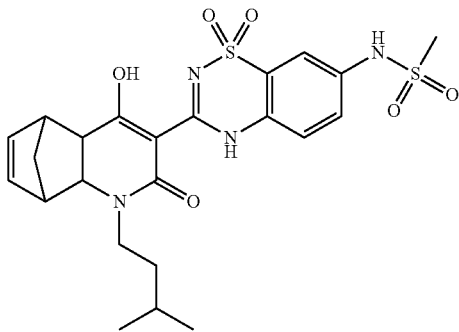

a) (rac-di-exo)-3-Amino-bicyclo[2.2.1]hept-5-ene-2-carboxylic acid methyl ester hydrochloride

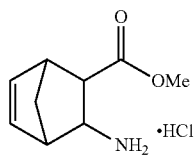 [SMILES: COC(=O)C1C2C=CC(C2)C1N ; Cl]

(rac-di-exo)-3-Amino-bicyclo[2.2.1]hept-5-ene-2-carboxylic acid hydrochloride (1.0 g, 5.27 mmol) was dissolved in methanol (7 mL). Benzene (10 mL) was added followed by the dropwise addition of a 2.0 M solution of (trimethylsilyl)diazomethane in diethyl ether (5 mL, 10 mmol). After stirring for 10 min, additional 2.0 M solution of (trimethylsilyl)diazomethane in diethyl ether (3 mL, 6 mmol) was added and the reaction mixture was stirred for an additional 20 min after which time the solution remained yellow in color. The solvents were removed in vacuo, the residue was taken up in methanol (15 mL) and the solvent was removed in vacuo to afford the crude product, (rac-di-exo)-3-amino-bicyclo[2.2.1]hept-5-ene-2-carboxylic acid methyl ester hydrochloride (0.98 g, 4.83 mmol, 91.6%), as a yellow oil, which was used in the next step without any further purification.

b) (rac-di-exo)-3-(3-Methyl-butylamino)-bicyclo[2.2.1]hept-5-ene-2-carboxylic acid methyl ester

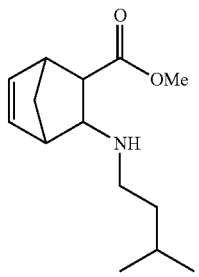 [SMILES: COC(=O)C1C2C=CC(C2)C1NCCC(C)C]

(rac-di-exo)-3-Amino-bicyclo[2.2.1]hept-5-ene-2-carboxylic acid methyl ester hydrochloride (0.955 g, 4.703 mmol) was suspended in methanol (10 mL). Sodium acetate (0.791 g, 9.652 mmol) was added followed by 4 Å powdered molecular sieves (1.0 g) and 3-methyl-butyraldehyde (0.385 g, 4.468 mmol). Sodium cyanoborohydride (0.593 g, 9.406 mmol) was added and the mixture was stirred at 25° C. for 18 h. The mixture was poured into a saturated aqueous sodium bicarbonate solution (100 mL) and extracted with ethyl acetate (100 mL). The layers were separated and the organic layer was washed with saturated aqueous brine solution, dried over sodium sulfate, filtered, and concentrated in vacuo. Further purification by flash column chromatography (Teledyne Isco RediSep column; 0 to 10% methanol in dichloromethane) afforded the desired product, (rac-di-exo)-3-(3-methyl-butylamino)-bicyclo[2.2.1]hept-5-ene-2-carboxylic acid methyl ester (0.774 g, 3.14 mmol, 66.7%), as a yellow oil. $^1$H NMR (400 MHz, CDCl$_3$) δ: 0.89 (3H, d, J=1.6 Hz), 0.90 (3H, d, J=2.1 Hz), 1.27-1.39 (2H, m), 1.54-1.64 (2H, m), 2.07 (1H, d, J=9.4 Hz), 2.42-2.56 (2H, m), 2.66-2.73 (1H, m), 2.84 (1H, bs), 2.92 (1H, bs), 2.98 (1H, d, J=7.7 Hz), 3.69 (3H, s), 6.14 (2H, s). LC-MS calcd for C$_{14}$H$_{23}$NO$_2$ 237.17, found 238.2 [M+H$^+$].

c) (rac-di-exo)-3-[[2-(7-Methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester

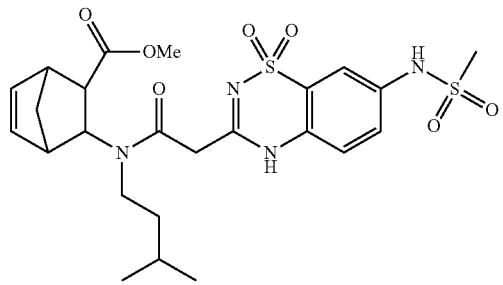 [SMILES: COC(=O)C1C2C=CC(C2)C1N(CCC(C)C)C(=O)CC1=NS(=O)(=O)c2cc(NS(C)(=O)=O)ccc2N1]

To a solution of (rac-di-exo)-3-(3-methyl-butylamino)-bicyclo[2.2.1]hept-5-ene-2-carboxylic acid methyl ester (208.7 mg, 0.880 mmol) in N,N-dimethylformamide (3 mL) was added (7-methanesulfonylamino-1,1-dioxo-1,4-dihydro-1λ$^6$-benzo[1,2,4]thiadiazin-3-yl)-acetic acid (prepared as described in Example 1g, 351.7 mg, 1.056 mmol) and the mixture was vortexed until all material had completely dissolved. A 1.0 M solution of N,N-dicyclohexylcarbodiimide in dichloromethane (1.144 mL, 1.144 mmol) was added to the above solution and the mixture was stirred at 25° C. for 18 h under a nitrogen atmosphere. The precipitated N,N-dicyclohexylurea was removed by filtration over Celite, the filter cake was washed with dichloromethane (3×5 mL), and the solvent was removed in vacuo. The residue was dissolved in a 1:1 mixture of ethyl acetate and hexanes (20 mL), washed with saturated aqueous brine solution, saturated aqueous sodium bicarbonate solution and water. The layers were separated and the aqueous layers were back-extracted with a 1:1 mixture of ethyl acetate and hexanes (20 mL). The combined organic layers were dried over sodium sulfate, filtered, and concentrated in vacuo to afford the crude product, (rac-di-exo)-3-[[2-(7-methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester, as a yellow oil, which was used in the next step without any further purification. LC-MS calcd for C$_{24}$H$_{32}$N$_4$O$_7$S$_2$ 552.17, found 553.3 [M+H$^+$].

d) (rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

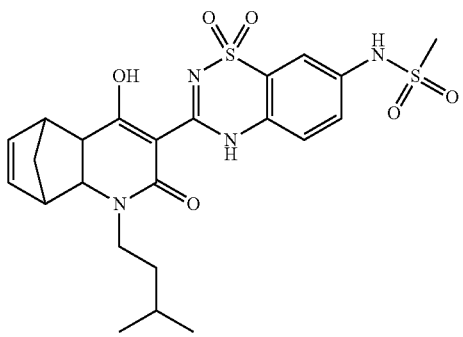

The crude (rac-di-exo)-3-[[2-(7-methanesulfonylamino-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester was dissolved in ethanol (20 mL). To this solution was added a 21 wt. % solution of sodium ethoxide in ethanol (1.141 g, 3.52 mmol) and the reaction mixture was stirred at 25° C. for 2 h. Upon addition of a 1.0 M aqueous hydrochloric acid solution the product precipitated and was collected by vacuum filtration. Further purification by trituration with dichloromethane and ethyl acetate gave a tan solid, which was further washed with ethyl acetate, and then dried in vacuo, to afford the desired product, (rac-di-exo)-N-{3-[6-hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide (116.6 mg, 0.224 mmol, 25.5%), as an off-white solid. $^1$H NMR (400 MHz, DMSO-d$_6$) δ: 0.93 (6H, d, J=5.3 Hz), 1.35-1.70 (5H, m), 2.85 (1H, d, J=8.7 Hz), 3.06 (3H, s), 3.13-3.31 (5H, m), 3.49 (1H, d, J=8.6 Hz), 3.75-3.83 (1H, m), 6.23 (1H, s), 6.39 (1H, s), 7.50-7.58 (3H, m), 10.18 (1H, s). LC-MS calcd for C$_{23}$H$_{28}$N$_4$O$_6$S$_2$ 520.15, found 521.4 [M+H$^+$].

Example 32

(rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-methanesulfonamide

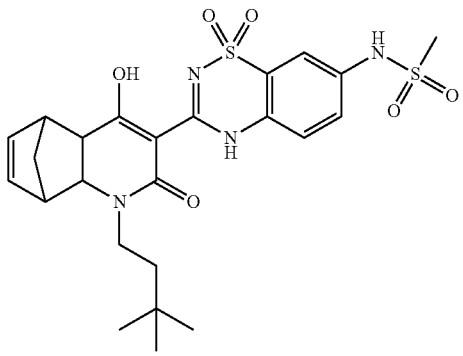

a) (rac-di-exo)-3-(3,3-Dimethyl-butylamino)-bicyclo[2.2.1]hept-5-ene-2-carboxylic acid methyl ester

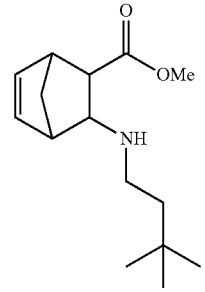 [SMILES: COC(=O)C1C2C=CC(C2)C1NCCC(C)(C)C]

(rac-di-exo)-3-Amino-bicyclo[2.2.1]hept-5-ene-2-carboxylic acid methyl ester hydrochloride (0.984 g, 4.846 mmol) was suspended in methanol (10 mL). Sodium acetate (0.795 g, 9.692 mmol) was added followed by 4 Å powdered molecular sieves (1.0 g) and 3,3-dimethylbutyraldehyde (0.461 g, 4.604 mmol). Sodium cyanoborohydride (0.610 g, 9.692 mmol) was added and the mixture was stirred at 25° C. for 18 h. The mixture was poured into a saturated aqueous sodium bicarbonate solution (100 mL) and extracted with ethyl acetate (100 mL). The layers were separated and the organic layer was washed with saturated aqueous brine solution, dried over sodium sulfate, filtered, and concentrated in vacuo. Further purification by flash column chromatography (Teledyne Isco RediSep column; 0 to 10% methanol in dichloromethane) afforded the desired product, (rac-di-exo)-3-(3,3-dimethyl-butylamino)-bicyclo[2.2.1]hept-5-ene-2-carboxylic acid methyl ester (0.773 g, 3.08 mmol, 63.5%), as a yellow oil. $^1$H NMR (400 MHz, CDCl$_3$) δ: 0.91 (9H, s), 1.31-1.40 (2H, m), 1.55 (1H, d, J=9.5 Hz), 2.08 (1H, d, J=8.8 Hz), 2.43-2.49 (1H, m), 2.55 (1H, d, J=7.8 Hz), 2.64-2.74 (1H, m), 2.85 (1H, bs), 2.93 (1H, bs), 2.99 (1H, d, J=7.7 Hz), 3.69 (3H, s), 6.15 (2H, s). LC-MS calcd for C$_{15}$H$_{25}$NO$_2$ 251.19, found 252.2 [M+H$^+$].

b) (rac-di-exo)-3-{(3,3-Dimethyl-butyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]hept-5-ene-2-carboxylic acid methyl ester

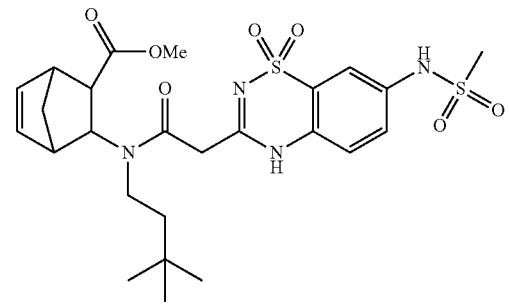 [SMILES: COC(=O)C1C2C=CC(C2)C1N(CCC(C)(C)C)C(=O)CC1=NS(=O)(=O)c2cc(NS(C)(=O)=O)ccc2N1]

To a solution of (rac-di-exo)-3-(3,3-dimethyl-butylamino)-bicyclo[2.2.1]hept-5-ene-2-carboxylic acid methyl ester (233.3 mg, 0.929 mmol) in N,N-dimethylformamide (3 mL) was added (7-methanesulfonylamino-1,1-dioxo-1,4-dihydro-1λ$^6$-benzo[1,2,4]thiadiazin-3-yl)-acetic acid (prepared as described in Example 1g, 371.2 mg, 1.115 mmol)

and the mixture was vortexed until all material had completely dissolved. A 1.0 M solution of N,N-dicyclohexylcarbodiimide in dichloromethane (1.208 mL, 1.208 mmol) was added to the above solution and the mixture was stirred at 25° C. for 18 h under a nitrogen atmosphere. The precipitated N,N-dicyclohexylurea was removed by filtration over Celite, the filter cake was washed with dichloromethane (3×5 mL), and the solvent was removed in vacuo. The residue was dissolved in a 1:1 mixture of ethyl acetate and hexanes (20 mL), washed with saturated aqueous brine solution, saturated aqueous sodium bicarbonate solution and water. The layers were separated and the aqueous layers were back-extracted with a 1:1 mixture of ethyl acetate and hexanes (20 mL). The combined organic layers were dried over sodium sulfate, filtered, and concentrated in vacuo to afford the crude product, (rac-di-exo)-3-{(3,3-dimethyl-butyl)-[2-(7-methanesulfonylamino-1,1-dioxo-1,4-dihydro-1$\lambda^6$-benzo[1,2,4]thiadiazin-3-yl)-acetyl]-amino}-bicyclo[2.2.1]hept-5-ene-2-carboxylic acid methyl ester, as a yellow oil, which was used in the next step without any further purification. LC-MS calcd for $C_{25}H_{34}N_4O_7S_2$ 566.19, found 567.4 [M+H$^+$].

c) (rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide

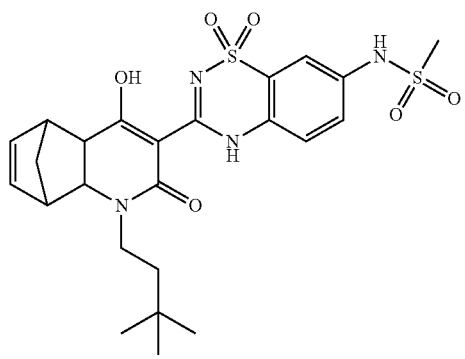

The crude (rac-di-exo)-3-{(3,3-dimethyl-butyl)-[2-(7-methanesulfonylamino-1,1-dioxo-1,4-dihydro-1$\lambda^6$-benzo[1,2,4]thiadiazin-3-yl)-acetyl]-amino}-bicyclo[2.2.1]hept-5-ene-2-carboxylic acid methyl ester (710.8 mg, 0.929 mmol) was dissolved in ethanol. To this solution was added a 21 wt. % solution of sodium ethoxide in ethanol (1.204 g, 3.716 mmol) and the reaction mixture was stirred at 25° C. for 2 h. Upon addition of a 1.0 M aqueous hydrochloric acid solution the product precipitated and was collected by vacuum filtration. Further purification by trituration with dichloromethane and ethyl acetate gave a tan solid, which was further washed with ethyl acetate, and then dried in vacuo, to afford the desired product, (rac-di-exo)-N-{3-[3-(3,3-dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-methanesulfonamide (210.7 mg, 0.394 mmol, 42.5% over two steps), as an off-white solid. $^1$H NMR (400 MHz, DMSO-d$_6$) δ: 0.96 (9H, s), 1.39-1.56 (4H, m), 2.85 (1H, d, J=9.3 Hz), 3.06 (3H, s), 3.12-3.30 (5H, m), 3.49 (1H, d, J=9.1 Hz), 3.74-3.81 (1H, m), 6.23 (1H, s), 6.40 (1H, s), 7.50-7.60 (3H, m), 10.18 (1H, s). LC-MS calcd for $C_{24}H_{30}N_4O_6S_2$ 534.16, found 535.4 [M+H$^+$].

Example 33

(rac-di-exo)-6-Hydroxy-5-(7-iodo-1,1-dioxo-1,4-dihydro-1$\lambda^6$-benzo[1,2,4]thiadiazin-3-yl)-3-(3-methyl-butyl)-11-oxa-3-aza-tricyclo[6.2.1.0$^{2,7}$]undec-5-en-4-one

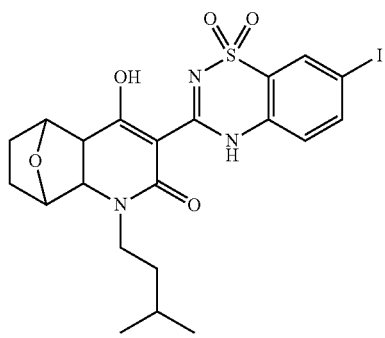 [SMILES: CC(C)CCN1C(=O)C(C2=NS(=O)(=O)c3cc(I)ccc3N2)=C(O)C2C3CCC(O3)C21]

a) (rac-di-exo)-3-[[2-(7-Iodo-1,1-dioxo-1,4-dihydro-1$\lambda^6$-benzo[1,2,4]thiadiazin-3-yl)-acetyl]-(3-methyl-butyl)-amino]-7-oxa-bicyclo[2.2.1]heptane-2-carboxylic acid methyl ester

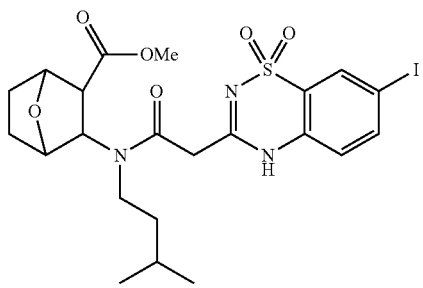 [SMILES: COC(=O)C1C2CCC(O2)C1N(CCC(C)C)C(=O)CC1=NS(=O)(=O)c2cc(I)ccc2N1]

(7-Iodo-1,1-dioxo-1,4-dihydro-1$\lambda^6$-benzo[1,2,4]thiadiazin-3-yl)-acetic acid (prepared as described in US patent application US 2008/0031852, 0.2 g, 0.546 mmol) was dissolved in anhydrous N,N-dimethylformamide (5 mL). (rac-di-exo)-3-(3-Methyl-butylamino)-7-oxa-bicyclo[2.2.1]heptane-2-carboxylic acid methyl ester (prepared as described in Example 25a, 0.132 g, 0.546 mmol) was added followed by 1-(3-dimethylaminopropyl)-3-ethylcarbodiimide hydrochloride (0.11 g, 0.573 mmol). Then N-methylmorpholine (0.116 g, 1.15 mmol) was added into the above reaction mixture. The mixture was stirred at 25° C. for 16 h. The solution was poured into 1.0 M aqueous hydrochloric acid solution (100 mL). The aqueous layer was extracted with ethyl acetate (2×100 mL). The organic layer was dried over sodium sulfate, filtered, and concentrated in vacuo to afford the crude product, (rac-di-exo)-3-[[2-(7-iodo-1,1-dioxo-1,4-dihydro-1$\lambda^6$-benzo[1,2,4]thiadiazin-3-yl)-acetyl]-(3-methyl-butyl)-amino]-7-oxa-bicyclo[2.2.1]heptane-2-carboxylic acid methyl ester, as a light yellow oil, which was used in the next step without any further purification. LC-MS (ESI) calcd for $C_{22}H_{28}IN_3O_6S$ 589.07, found 590.5 [M+H$^+$].

b) (rac-di-exo)-6-Hydroxy-5-(7-iodo-1,1-dioxo-1,4-dihydro-1λ⁶-benzo[1,2,4]thiadiazin-3-yl)-3-(3-methyl-butyl)-11-oxa-3-aza-tricyclo[6.2.1.0$^{2,7}$]undec-5-en-4-one

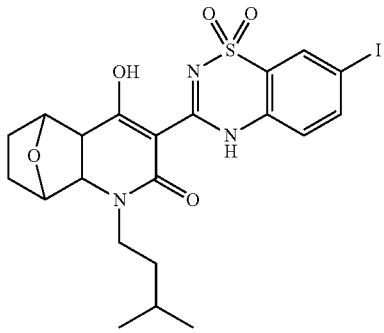 [SMILES: CC(C)CCN1C(=O)C(C2=NS(=O)(=O)c3cc(I)ccc3N2)=C(O)C2C3CCC(O3)C21]

The crude (rac-di-exo)-3-[[2-(7-iodo-1,1-dihydro-1λ⁶-benzo[1,2,4]thiadiazin-3-yl)-acetyl]-(3-methyl-butyl)-amino]-7-oxa-bicyclo[2.2.1]heptane-2-carboxylic acid methyl ester was dissolved in ethanol (5 mL), and a 21 wt. % solution of sodium ethoxide in ethanol (1 mL, 2.73 mmol) was added into the above solution. The mixture was stirred at 60° C. for 6 h and allowed to cool to 25° C. The mixture was poured into 0.5 M aqueous hydrochloric acid solution (100 mL). The product started to precipitate and was collected by vacuum filtration. The precipitate was purified by flash column chromatography (Teledyne Isco RediSep column; 100% ethyl acetate) to afford the desired product, (rac-di-exo)-6-hydroxy-5-(7-iodo-1,1-dioxo-1,4-dihydro-1λ⁶-benzo[1,2,4]thiadiazin-3-yl)-3-(3-methyl-butyl)-11-oxa-3-aza-tricyclo[6.2.1.0$^{2,7}$]undec-5-en-4-one (0.066 g, 0.118 mmol, 21.7% over two steps), as a white solid. ¹H NMR (400 MHz, DMSO-d₆) δ: 0.92 (6H, d, J=6.2 Hz), 1.41-1.73 (7H, m), 2.52-2.52 (1H, m), 2.94-3.07 (1H, m), 3.81-3.92 (2H, m), 4.75 (2H, d, J=2.2 Hz), 7.37 (1H, d, J=8.5 Hz), 8.00 (1H, dd, J₁=8.6 Hz, J₂=2.2 Hz), 8.08 (1H, s). LC-MS (ESI) calcd for $C_{21}H_{24}IN_3O_5S$ 557.05, found 558.2 [M+H⁺]. Anal. calcd for $C_{21}H_{24}IN_3O_5S \cdot 0.5H_2O$: C, 44.53; H, 4.45; N, 7.45. found C, 44.69; H, 4.15; N, 7.45.

Example 34

(1R,2S,7R,8S)-6-Hydroxy-5-(7-iodo-1,1-dioxo-1,4-dihydro-1λ⁶-benzo[1,2,4]thiadiazin-3-yl)-3-(3-methyl-butyl)-3-aza-tricyclo[6.2.1.0$^{2,7}$]undec-5-en-4-one

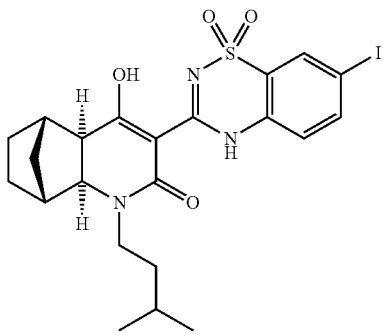

a) (1S,2R,3S,4R)-3-[[2-(7-Iodo-1,1-dioxo-1,4-dihydro-1λ⁶-benzo[1,2,4]thiadiazin-3-yl)-acetyl]-(3-methyl-butyl)-amino]-bicyclo[2.2.1]heptane-2-carboxylic acid ethyl ester

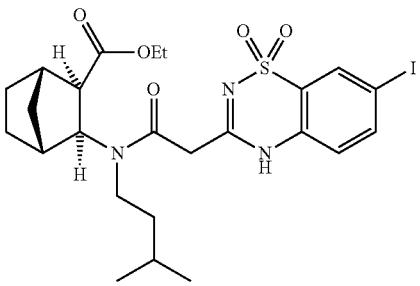

(7-Iodo-1,1-dioxo-1,4-dihydro-1λ⁶-benzo[1,2,4]thiadiazin-3-yl)-acetic acid (prepared as described in US patent application US 2008/0031852, 0.2 g, 0.546 mmol) was dissolved in anhydrous N,N-dimethylformamide (5 mL). (1S,2R,3S,4R)-3-(3-Methyl-butylamino)-bicyclo[2.2.1]heptane-2-carboxylic acid ethyl ester (prepared as described in Example 22a, 0.138 g, 0.546 mmol) was added followed by 1-(3-dimethylaminopropyl)-3-ethylcarbodiimide hydrochloride (0.11 g, 0.573 mmol). Then N-methylmorpholine (0.116 g, 1.15 mmol) was added into the above reaction mixture. The mixture was stirred at 25° C. for 16 h. The solution was poured into 1.0 M aqueous hydrochloric acid solution (100 mL). The aqueous layer was extracted with ethyl acetate (2×100 mL). The organic layer was dried over sodium sulfate, filtered, and concentrated in vacuo to afford the crude product, (1S,2R,3S,4R)-3-[[2-(7-iodo-1,1-dioxo-1,4-dihydro-1λ⁶-benzo[1,2,4]thiadiazin-3-yl)-acetyl]-(3-methyl-butyl)-amino]-bicyclo[2.2.1]heptane-2-carboxylic acid ethyl ester, as a light yellow oil, which was used in the next step without any further purification. LC-MS (ESI) calcd for $C_{24}H_{32}IN_3O_5S$ 601.11, found 602.6 [M+H⁺].

b) (1R,2S,7R,8S)-6-Hydroxy-5-(7-iodo-1,1-dioxo-1,4-dihydro-1λ⁶-benzo[1,2,4]thiadiazin-3-yl)-3-(3-methyl-butyl)-3-aza-tricyclo[6.2.1.0$^{2,7}$]undec-5-en-4-one

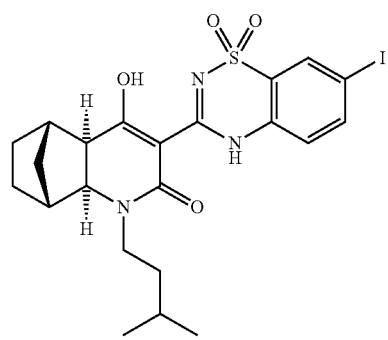

The crude (1S,2R,3S,4R)-3-[[2-(7-iodo-1,1-dioxo-1,4-dihydro-1λ⁶-benzo[1,2,4]thiadiazin-3-yl)-acetyl]-(3-methyl-butyl)-amino]-bicyclo[2.2.1]heptane-2-carboxylic acid ethyl ester (0.546 mmol) was dissolved in ethanol (5 mL), and a 21 wt. % solution of sodium ethoxide in ethanol (1 mL, 2.73 mmol) was added into the above solution. The mixture was stirred at 60° C. for 6 h and allowed to cool to 25° C. The mixture was poured into 0.5 M aqueous hydrochloric acid solution (100 mL). The product started to precipitate and was collected by vacuum filtration. The precipitate was purified by flash column chromatography (Teledyne Isco RediSep column; 40% ethyl acetate in hexanes) to afford the desired product, (1R,2S,7R,8S)-6-hydroxy-5-(7-iodo-1,1-dioxo-1,4-dihydro-1$\lambda^6$-benzo[1,2,4]thiadiazin-3-yl)-3-(3-methyl-butyl)-3-aza-tricyclo[6.2.1.0$^{2,7}$]undec-5-en-4-one (0.122 g, 0.2 mmol, 40.3% over two steps), as a light yellow solid. $^1$H NMR (400 MHz, DMSO-d$_6$) δ: 0.92 (6H, d, J=5.4 Hz), 1.16-1.63 (9H, m), 2.99-3.12 (2H, m), 3.62-3.71 (2H, m), 7.37 (1H, d, J=8.3 Hz), 7.99 (1H, dd, J$_1$=8.6 Hz, J$_2$=1.6 Hz), 8.08 (1H, s). LC-MS (ESI) calcd for $C_{22}H_{26}IN_3O_4S$ 555.07, found 556.3 [M+H$^+$].

Example 35

Cyclopropane sulfonic acid{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide

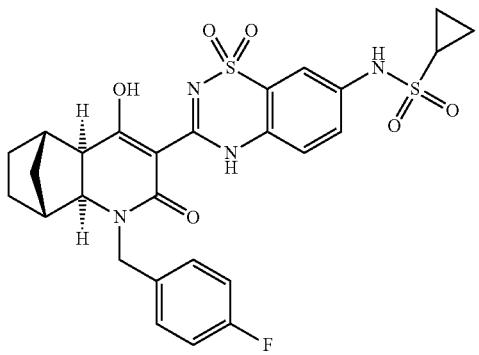

(1R,2S,7R,8S)-3-(4-Fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undec-5-en-4-one (prepared as described in Example 19, 81 mg, 0.14 mmol), cyclopropane sulfonic acid amide (132 mg, 1.09 mmol), sarcosine (N-methyl glycine) (18 mg, 0.20 mmol), copper (I) iodide (26 mg, 0.14 mmol), and potassium phosphate (173 mg, 0.82 mmol) were combined and dissolved in N,N-dimethylformamide (4 mL). The flask was degassed and backfilled with nitrogen (3×). The reaction was stirred at 100° C. for 4 h. The mixture was allowed to cool to 25° C., diluted with ethyl acetate (20 mL), and extracted with saturated aqueous sodium bicarbonate solution (2×20 mL). The combined organic layers were dried over magnesium sulfate, filtered and concentrated in vacuo. Purification by flash column chromatography (Teledyne Isco RediSep column; 0 to 8% methanol in dichloromethane) afforded the desired product, cyclopropane sulfonic acid {3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide (76 mg, 0.13 mmol, 96%), as a white powder. $^1$H NMR (400 MHz, DMSO-d$_6$) δ: 0.85-1.68 (8H, m), 2.50-2.62 (2H, m), 2.83-2.97 (3H, m), 3.45-3.47 (1H, m), 4.56 (1H, bs), 5.17-5.20 (1H, m), 7.03-7.07 (2H, m), 7.20-7.23 (2H, m), 7.63-7.69 (2H, m), 8.01 (1H, s). LC-MS (ESI) calcd for $C_{27}H_{27}FN_4O_6S_2$ 586.14, found 587.4 [M+H$^+$].

Example 36

(rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide

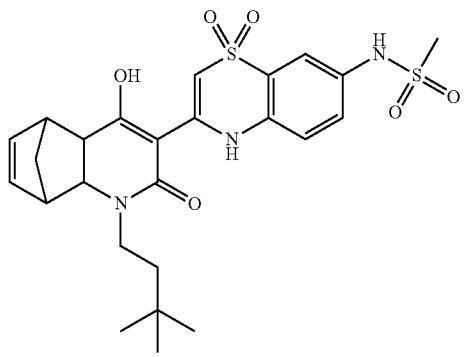

a) (rac-di-exo)-3-{(3,3-Dimethyl-butyl)-[2-(7-methanesulfonylamino-1,1-dioxo-1,4-dihydro-1$\lambda^6$-benzo[1,4]thiazin-3-yl)-acetyl]-amino}-bicyclo[2.2.1]hept-5-ene-2-carboxylic acid methyl ester

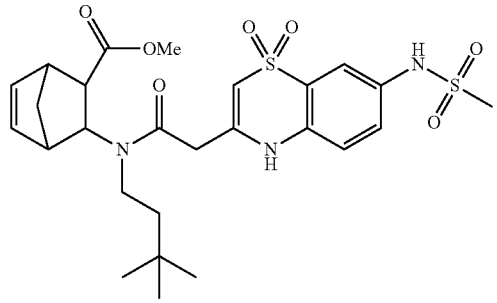 [SMILES: COC(=O)C1C2C=CC(C2)C1N(CCC(C)(C)C)C(=O)CC1=CS(=O)(=O)c2cc(NS(C)(=O)=O)ccc2N1]

To a stirred solution of (rac-di-exo)-3-(3,3-dimethyl-butylamino)-bicyclo[2.2.1]hept-5-ene-2-carboxylic acid methyl ester (prepared as described in Example 32a, 103 mg, 0.410 mmol) in anhydrous N,N-dimethylformamide (3 mL) under a nitrogen atmosphere, (7-methanesulfonylamino-1,1-dioxo-1,4-dihydro-1$\lambda^6$-benzo[1,4]thiazin-3-yl)-acetic acid (prepared as described in Example 29a, 136 mg, 0.410 mmol), N-methylmorpholine (87.1 mg, 0.861 mmol) and 1-(3-dimethylaminopropyl)-3-ethylcarbodiimide hydrochloride (82.3 mg, 0.431 mmol) were added sequentially. After stirring at 25° C. for 90 min, 1.0 M aqueous hydrochloric acid solution (10 mL) and saturated aqueous brine solution were added to the reaction mixture. The mixture was extracted with ethyl acetate (3×10 mL) and the combined organic layers were dried over sodium sulfate, filtered, and concentrated in vacuo. The crude product, (rac-di-exo)-3-{(3,3-dimethyl-butyl)-[2-(7-methanesulfonylamino-1,1-dioxo-1,4-dihydro-1$\lambda^6$-benzo[1,4]thiazin-3-yl)-acetyl]-amino}-bicyclo[2.2.1]hept-5-ene-2-carboxylic acid methyl ester, was directly used in the next step without further purification. LC-MS calcd for $C_{26}H_{35}N_3O_7S_2$ 565.19, found 566.5 [M+H$^+$].

b) (rac-di-exo)-N-{3-[3-(3,3-Dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,4]thiazin-7-yl}-methanesulfonamide

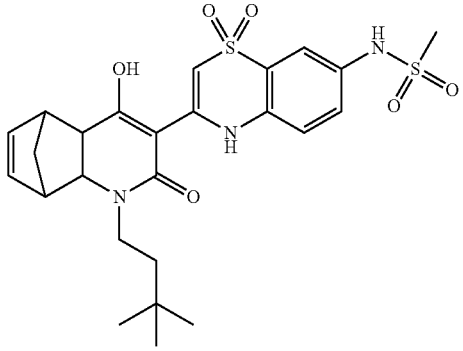 [SMILES: CC(C)(C)CCN1C(=O)C(C2=CS(=O)(=O)c3cc(NS(C)(=O)=O)ccc3N2)=C(O)C2C3C=CC(C3)C21]

The crude (rac-di-exo)-3-{(3,3-dimethyl-butyl)-[2-(7-methanesulfonylamino-1,1-dioxo-1,4-dihydro-1λ$^6$-benzo[1,4]thiazin-3-yl)-acetyl]-amino}-bicyclo[2.2.1]hept-5-ene-2-carboxylic acid methyl ester was dissolved in ethanol (10 mL). To this solution was added a 21 wt. % solution of sodium ethoxide in ethanol (0.399 g, 1.23 mmol) and the reaction mixture was stirred at 25° C. for 2.5 h. A 1.0 M aqueous hydrochloric acid solution (10 mL) was added and, after stirring for another 30 min, additional 1.0 M aqueous hydrochloric acid solution (5 mL) was added upon which the product precipitated. The solid was collected by vacuum filtration, washed with 1.0 M aqueous hydrochloric acid solution (5 mL), and then dried in vacuo, to afford the desired product, (rac-di-exo)-N-{3-[3-(3,3-dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,4]thiazin-7-yl}-methanesulfonamide (59 mg, 0.111 mmol, 27.1% over two steps), as a yellow-tan solid. $^1$H NMR (400 MHz, CDCl$_3$) δ: 1.00-1.01 (9H, m), 1.26-1.29 (2H, m), 1.51-1.70 (4H, m), 2.57-2.63 (1H, m), 3.07 (3H, s), 3.10-3.17 (2H, m), 3.24-3.26 (1H, m), 3.35-3.39 (1H, m), 3.39-3.99 (1H, m), 4.90 (0.7H, d, J=16.7 Hz), 5.20 (0.3H, d, J=16.2 Hz), 5.27 (0.7H, d, J=16.9 Hz), 5.73 (0.3H, d, J=16.1 Hz), 6.17-6.22 (1H, m), 6.36-6.39 (1H, m), 7.17 (1H, s), 7.22-7.25 (2H, m), 7.56-7.61 (1H, m), 7.67-7.69 (1H, m). LC-MS calcd for C$_{25}$H$_{31}$N$_3$O$_6$S$_2$ 533.17, found 534.4 [M+H$^+$].

Example 37

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,4]thiazin-7-yl}-methanesulfonamide

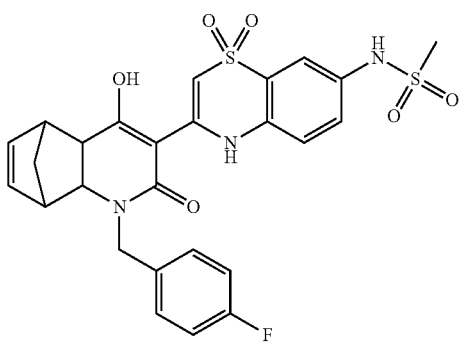 [SMILES: CS(=O)(=O)Nc1ccc2c(c1)S(=O)(=O)C=C(C1=C(O)C3C4C=CC(C4)C3N(Cc3ccc(F)cc3)C1=O)N2]

a) (rac-di-exo)-3-{(4-Fluoro-benzyl)-[2-(7-methanesulfonylamino-1,1-dioxo-1,4-dihydro-1λ$^6$-benzo[1,4]thiazin-3-yl)-acetyl]-amino}-bicyclo[2.2.1]hept-5-ene-2-carboxylic acid methyl ester

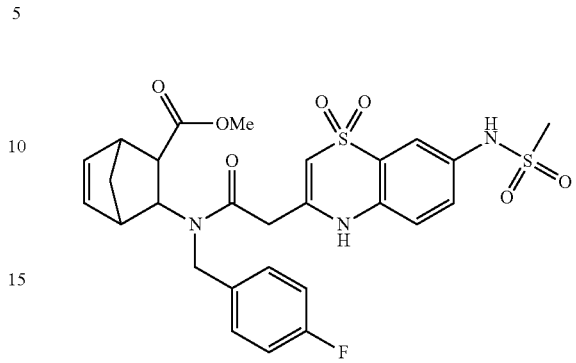

To a stirred solution of (rac-di-exo)-3-(4-fluoro-benzylamino)-bicyclo[2.2.1]hept-5-ene-2-carboxylic acid methyl ester (prepared as described in Example 9b, 112.7 mg, 0.410 mmol) in anhydrous N,N-dimethylformamide (3 mL) under a nitrogen atmosphere, (7-methanesulfonylamino-1,1-dioxo-1,4-dihydro-1λ$^6$-benzo[1,4]thiazin-3-yl)-acetic acid (prepared as described in Example 29a, 136 mg, 0.410 mmol), N-methylmorpholine (87.1 mg, 0.861 mmol) and 1-(3-dimethylaminopropyl)-3-ethylcarbodiimide hydrochloride (82.3 mg, 0.431 mmol) were added sequentially. After stirring at 25° C. for 90 min, 1.0 M aqueous hydrochloric acid solution (10 mL) and saturated aqueous brine solution (10 mL) were added to the reaction mixture. The mixture was extracted with ethyl acetate (3×10 mL) and the combined organic layers were dried over sodium sulfate, filtered, and concentrated in vacuo. The crude product, (rac-di-exo)-3-{(4-fluoro-benzyl)-[2-(7-methanesulfonylamino-1,1-dioxo-1,4-dihydro-1λ$^6$-benzo[1,4]thiazin-3-yl)-acetyl]-amino}-bicyclo[2.2.1]hept-5-ene-2-carboxylic acid methyl ester, was used in the next step without any further purification. LC-MS calcd for C$_{27}$H$_{28}$FN$_3$O$_7$S$_2$ 589.14, found 590.5 [M+H$^+$].

c) (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,4]thiazin-7-yl}-methanesulfonamide

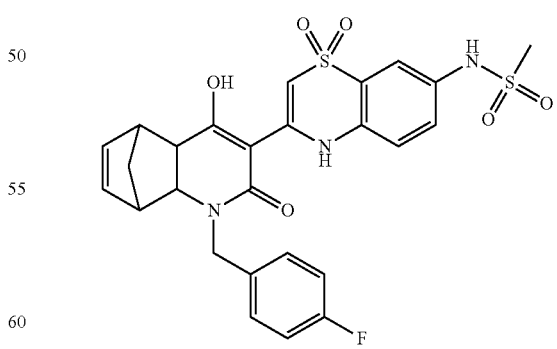

The crude (rac-di-exo)-3-{(4-fluoro-benzyl)-[2-(7-methanesulfonylamino-1,1-dioxo-1,4-dihydro-1λ$^6$-benzo[1,4]thiazin-3-yl)-acetyl]-amino}-bicyclo[2.2.1]hept-5-ene-2-carboxylic acid methyl ester was dissolved in ethanol. To this solution was added a 21 wt. % solution of sodium ethoxide in ethanol (0.399 g, 1.23 mmol) and the reaction mixture was stirred at 25° C. for 2.5 h. A 1.0 M aqueous hydrochloric acid solution (10 mL) was added and, after stirring for another 30 min, additional 1.0 M aqueous hydrochloric acid solution (5 mL) was added upon which the product precipitated. The solid was collected by vacuum filtration, washed with 1.0 M aqueous hydrochloric acid solution (5 mL), and then dried in vacuo, to afford the desired product, (rac-di-exo)-N-{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide (44 mg, 0.079 mmol, 19.3% over two steps), as a tan solid. $^1$H NMR (400 MHz, CDCl$_3$) δ: 0.83-0.93 (1H, m), 1.26-1.29 (2H, m), 1.51 (1H, d, J=8.4 Hz), 1.69 (1H, d, J=9.5 Hz), 2.59 (1H, d, J=8.3 Hz), 3.05 (3H, s), 3.09 (1H, s), 3.26 (1H, s), 3.35 (1H, d, J=7.7 Hz), 4.36 (1H, d, J=15.1 Hz), 5.24 (1H, d, J=15.6 Hz), 6.12 (1H, s), 6.33 (1H, s), 7.00-7.04 (2H, m), 7.19-7.26 (3H, m), 7.56 (1H, d, J=6.8 Hz), 7.68 (1H, s). LC-MS calcd for C$_{26}$H$_{24}$FN$_3$O$_6$S$_2$ 557.11, found 558.1 [M+H$^+$].

Example 38

(rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide

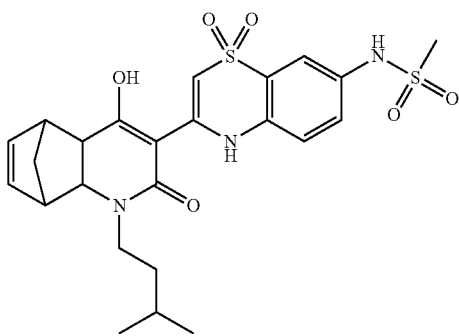 [SMILES: CC(C)CCN1C(=O)C(C2=CS(=O)(=O)c3cc(NS(C)(=O)=O)ccc3N2)=C(O)C2C3C=CC(C3)C21]

a) (rac-di-exo)-3-[[2-(7-Methanesulfonylamino-1,1-dioxo-1,4-dihydro-1$\lambda^6$-benzo[1,4]thiazin-3-yl)-acetyl]-(3-methyl-butyl)-amino]-bicyclo[2.2.1]hept-5-ene-2-carboxylic acid methyl ester

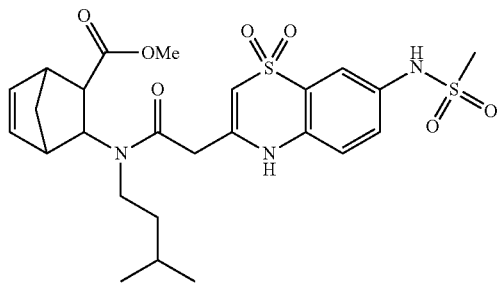

To a stirred solution of (rac-di-exo)-3-(3-methyl-butylamino)-bicyclo[2.2.1]hept-5-ene-2-carboxylic acid methyl ester (prepared as described in Example 31b, 97.2 mg, 0.410 mmol) in anhydrous N,N-dimethylformamide (3 mL) under a nitrogen atmosphere, (7-methanesulfonylamino-1,1-dioxo-1,4-dihydro-1$\lambda^6$-benzo[1,4]thiazin-3-yl)-acetic acid (prepared as described in Example 29a, 136 mg, 0.410 mmol), N-methylmorpholine (87.1 mg, 0.861 mmol) and 1-(3-dimethylaminopropyl)-3-ethylcarbodiimide hydrochloride (82.3 mg, 0.431 mmol) were added sequentially. After stirring at 25° C. for 90 min, 1.0 M aqueous hydrochloric acid solution (10 mL) and saturated aqueous brine solution (10 mL) were added to the reaction mixture. The mixture was extracted with ethyl acetate (3×10 mL) and the combined organic layers were dried over sodium sulfate, filtered, and concentrated in vacuo. The crude product, (rac-di-exo)-3-[[2-(7-methanesulfonylamino-1,1-dioxo-1,4-dihydro-1$\lambda^6$-benzo[1,4]thiazin-3-yl)-acetyl]-(3-methyl-butyl)-amino]-bicyclo[2.2.1]hept-5-ene-2-carboxylic acid methyl ester, was used in the next step without further purification. LC-MS calcd for C$_{25}$H$_{33}$N$_3$O$_7$S$_2$ 551.18, found 552.3 [M+H$^+$].

b) (rac-di-exo)-N-{3-[6-Hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide

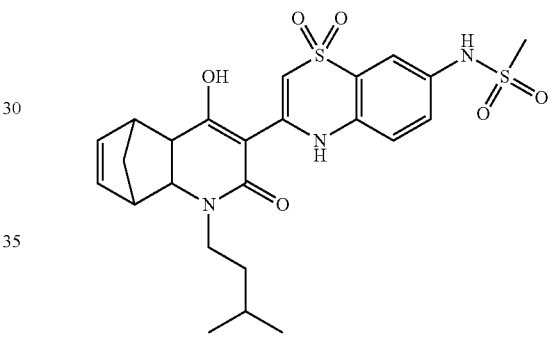

The crude (rac-di-exo)-3-[[2-(7-methanesulfonylamino-1,1-dioxo-1,4-dihydro-1$\lambda^6$-benzo[1,4]thiazin-3-yl)-acetyl]-(3-methyl-butyl)-amino]-bicyclo[2.2.1]hept-5-ene-2-carboxylic acid methyl ester was dissolved in ethanol (10 mL). To this solution was added a 21 wt. % solution of sodium ethoxide in ethanol (0.399 g, 1.23 mmol) and the reaction mixture was stirred at 25° C. for 2.5 h. A 1.0 M aqueous hydrochloric acid solution (10 mL) was added and, after stirring for another 30 min, additional 1.0 M aqueous hydrochloric acid solution (5 mL) was added upon which the product precipitated. The solid was collected by vacuum filtration, washed with 1.0 M aqueous hydrochloric acid solution (5 mL), and then dried in vacuo, to afford the desired product, (rac-di-exo)-N-{3-[6-hydroxy-3-(3-methyl-butyl)-4-oxo-3-aza-tricyclo[6.2.1.0$^{2,7}$]undeca-5,9-dien-5-yl]-1,1-dioxo-1,4-dihydro-1$\lambda^6$-benzo[1,4]thiazin-7-yl}-methanesulfonamide (48.6 mg, 0.094 mmol, 22.8% over two steps), as a tan solid. $^1$H NMR (400 MHz, CDCl$_3$) δ: 0.96-1.01 (6H, m), 1.26-1.29 (2H, m), 1.48-1.73 (5H, m), 2.58-2.63 (1H, m), 3.07 (3H, s), 3.08-3.17 (1H, m), 3.25 (1H, s), 3.37-3.40 (1H, m), 3.89-3.97 (1H, m), 4.90 (0.7H, d, J=17.3 Hz), 5.21 (0.3H, d, J=17.4 Hz), 5.28 (0.7H, d, J=16.7 Hz), 5.72 (0.3H, d, J=17.1 Hz), 6.17-6.22 (1H, m), 6.35-6.39 (1H, m), 7.23 (1H, d, J=8.5 Hz), 7.38

(1H, s), 7.56-7.62 (1H, m), 7.68-7.69 (1H, m). LC-MS calcd for $C_{24}H_{29}N_3O_6S_2$ 519.15, found 520.2 [M+H$^+$].

Example 39

(rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-N-methyl-methanesulfonamide

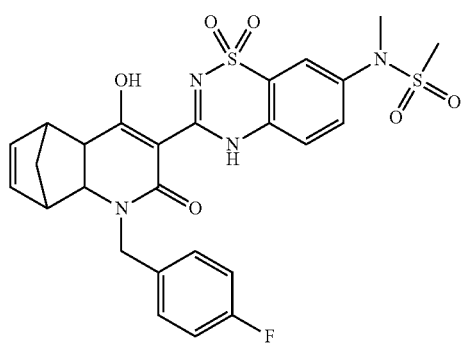 [SMILES: CN(c1ccc2c(c1)S(=O)(=O)N=C(C1=C(O)C3C4C=CC(C4)C3N(Cc3ccc(F)cc3)C1=O)N2)S(C)(=O)=O]

a) (rac-di-exo)-3-(4-Fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undeca-5,9-dien-4-one

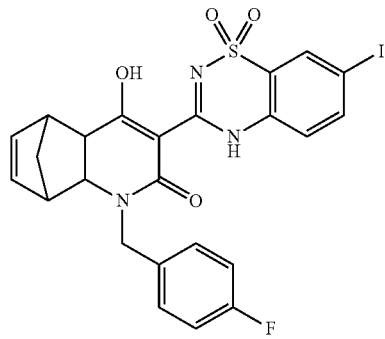 [SMILES: O=C1C(C2=NS(=O)(=O)c3cc(I)ccc3N2)=C(O)C2C3C=CC(C3)C2N1Cc1ccc(F)cc1]

To a stirred solution of (rac-di-exo)-3-(4-fluoro-benzylamino)-bicyclo[2.2.1]hept-5-ene-2-carboxylic acid methyl ester (prepared as described in Example 9b, 400 mg, 1.454 mmol) in anhydrous N,N-dimethylformamide (14 mL) under a nitrogen atmosphere, (7-iodo-1,1-dioxo-1,4-dihydro-1$\lambda^6$-benzo[1,2,4]thiadiazin-3-yl)-acetic acid (prepared as described in US patent application US 2008/0031852, 532.1 mg, 1.454 mmol), N-methylmorpholine (309 mg, 3.053 mmol) and 1-(3-dimethylaminopropyl)-3-ethylcarbodiimide hydrochloride (292 mg, 1.527 mmol) were added sequentially. After stirring at 25° C. for 4 h, triethylamine (441 mg, 4.362 mmol) was added, and the mixture was stirred at 50° C. for 2 h. The reaction mixture was allowed to cool to 25° C. and continued to stir for 16 h. Upon addition of a 1.0 M aqueous hydrochloric acid solution (10 mL), a white precipitate formed that was collected by vacuum filtration, washed with 1.0 M aqueous hydrochloric acid solution (5 mL), and dried in vacuo to afford the desired product, (rac-di-exo)-3-(4-fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undeca-5,9-dien-4-one (280.2 mg, 0.474 mmol, 32.6%), as a white solid. $^1$H NMR (400 MHz, DMSO-d$_6$) δ: 1.16-1.20 (2H, m), 1.38 (1H, d, J=9.4 Hz), 1.63 (1H, d, J=9.3 Hz), 2.86 (1H, bs), 3.21 (1H, bs), 3.41 (1H, d, J=9.2 Hz), 4.53 (1H, d, J=15.6 Hz), 5.05 (1H, d, J=15.6 Hz), 6.13-6.16 (1H, m), 6.35-6.37 (1H, m), 7.15 (2H, t, J=8.4 Hz), 7.33-7.38 (3H, m), 7.99-8.01 (1H, m), 8.09 (1H, s). LC-MS calcd for $C_{24}H_{19}FIN_3O_4S$ 591.01, found 592.4 [M+H$^+$].

b) (rac-di-exo)-N-{3-[3-(4-Fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-N-methyl-methanesulfonamide

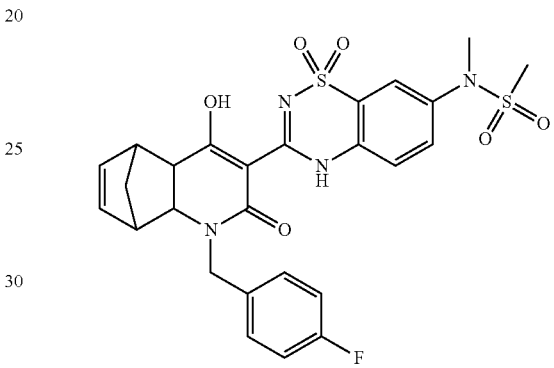

(rac-di-exo)-3-(4-Fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undeca-5,9-dien-4-one (0.100 g, 0.1692 mmol), potassium triphosphate (0.1075 g, 0.5076 mmol), sarcosine (N-methyl glycine) (0.0094 g, 0.1015 mmol), and copper (I) iodide (0.00128 g, 0.0677 mmol) were combined. Anhydrous N,N-dimethylformamide (3 mL) was added followed by N-methyl methanesulfonamide (0.09223 g, 0.8460 mmol). The solution was degassed and backfilled with nitrogen. The mixture was stirred at 100° C. for 16 h. Upon cooling, the mixture was diluted with ethyl acetate (200 mL), washed with 1.0 M aqueous hydrochloric acid solution (2×100 mL), dried over magnesium sulfate, filtered, and concentrated in vacuo to a solid. Purification by flash column chromatography (Teledyne Isco RediSep column; 0 to 100% ethyl acetate in hexanes) afforded the desired product, (rac-di-exo)-N-{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1$\lambda^6$-benzo[1,2,4]thiadiazin-7-yl}-N-methyl-methanesulfonamide (0.00105 g, 0.0184 mmol, 10.8%), as a pale yellow solid. $^1$H NMR (400 MHz, CDCl$_3$) δ: 1.27 (3H, s), 1.56 (1H, d, J=9.5 Hz), 1.66 (1H, d, J=9.2 Hz), 2.19 (1H, s), 2.64 (1H, s), 2.75 (1H, d, J=9.3 Hz), 3.19 (1H, bs), 3.39 (1H, d, J=9.4 Hz), 3.44 (1H, bs), 3.75 (1H, s), 4.32 (1H, d, J=15.4 Hz), 5.22 (1H, d, J=14.8 Hz), 6.11-6.13 (1H, m), 6.36-6.38 (1H, m), 6.97 (1H, d, J=8.6 Hz), 7.04 (2H, t, J=8.6 Hz), 7.20-7.24 (2H, m), 7.85 (1H, dd, J$_1$=8.6 Hz, J$_2$=2.2 Hz), 8.22 (1H, s). LC-MS calcd for $C_{26}H_{25}FN_4O_6S_2$ 572.12, found 573.3 [M+H$^+$].

Example 40

Cyclopropanesulfonic acid{3-(1R,2S,7R,8S)-[6-hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-amide

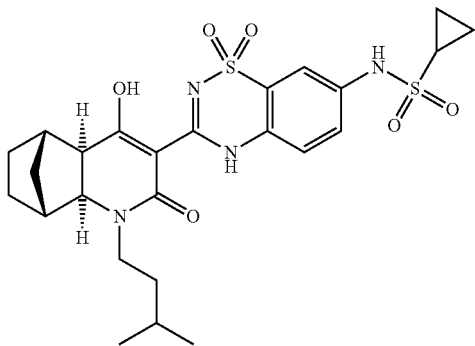

A reaction flask was charged with copper (I) iodide (20 mg, 0.11 mmol), sarcosine (N-methyl glycine) (14.7 mg, 0.17 mmol), cyclopropanesulfonamide (125 mg, 1.04 mmol), (1R,2S,7R,8S)-6-hydroxy-5-(7-iodo-1,1-dioxo-1,4-dihydro-1λ$^6$-benzo[1,2,4]thiadiazin-3-yl)-3-(3-methyl-butyl)-3-aza-tricyclo[6.2.1.0$^{2,7}$]undec-5-en-4-one (prepared as described in Example 34, 115 mg, 0.21 mmol) and potassium phosphate (176 mg, 0.83 mmol). The flask was degassed and backfilled with nitrogen, and then anhydrous N,N-dimethylformamide (5 mL) was added. The resulting suspension was vigorously stirred at 100° C. for 3 h, and then allowed to cool to 25° C. The mixture was passed through a plug of Celite and rinsed with 10% methanol/dichloromethane. The filtrate was concentrated in vacuo, and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, cyclopropanesulfonic acid{3-(1R,2S,7R,8S)-[6-hydroxy-3-(3-methyl-butyl)-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-amide (25 mg, 0.046 mmol, 22%), as a white solid. $^1$H NMR (400 MHz, DMSO-d$_6$) δ: 0.92-0.98 (10H, m), 1.20-1.64 (9H, m), 2.52 (1H, m), 2.62 (1H, s), 2.68 (1H, m), 3.00 (1H, d, J=9.6 Hz), 3.07 (1H, m), 3.61 (1H, d, J=10.4 Hz), 3.66 (1H, m), 7.50-7.59 (3H, m), 10.17 (1H, s). LC-MS (ESI) calcd for C$_{25}$H$_{32}$N$_4$O$_6$S$_2$ 548.18, found 549.4 [M+H$^+$].

Example 41

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-benzenesulfonamide

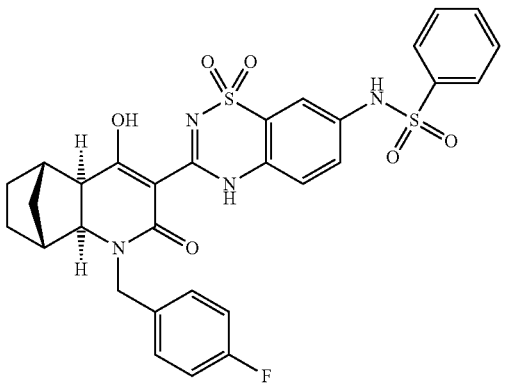

(1R,2S,7R,8S)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (prepared as described in Example 19, 0.10 g, 0.17 mmol), cyclopropane sulfonic acid amide (0.21 mg, 1.36 mmol), sarcosine (N-methyl glycine) (0.02 g, 0.26 mmol), copper (I) iodide (0.03 g, 0.17 mmol), and potassium phosphate (0.22 g, 1.02 mmol) were combined and dissolved in N,N-dimethylformamide (10 mL). The flask was degassed and backfilled with nitrogen (3×). The reaction was stirred at 100° C. for 4 h. The mixture was allowed to cool to 25° C., diluted with ethyl acetate (20 mL), and extracted with saturated aqueous sodium bicarbonate solution (2×20 mL). The combined organic layers were dried over magnesium sulfate, filtered and concentrated in vacuo. Purification by flash column chromatography (Teledyne Isco RediSep column; 0 to 8% methanol in dichloromethane) afforded the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-benzenesulfonamide (0.10 g, 0.16 mmol, 92%), as a white powder. $^1$H NMR (400 MHz, DMSO-d$_6$) δ: 1.16-1.19 (3H, m), 1.38-1.57 (5H, m), 2.98 (1H, d, J=8.4 Hz), 3.51 (1H, d, J=9.2 Hz), 4.40 (1H, d, J=15.6 Hz), 4.94 (1H, d, J=15.6 Hz), 7.11-7.15 (1H, m), 7.29-7.32 (2H, m), 7.39-7.47 (2H, m), 7.54-7.64 (4H, m), 7.74-7.82 (3H, m), 10.74 (1H, s). LC-MS (ESI) calcd for C$_{30}$H$_{27}$FN$_4$O$_6$S$_2$ 622.69, found 623.3 [M+H$^+$].

Example 42

(rac-di-exo)-Cyclopropanesulfonic acid{3-[6-hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-amide

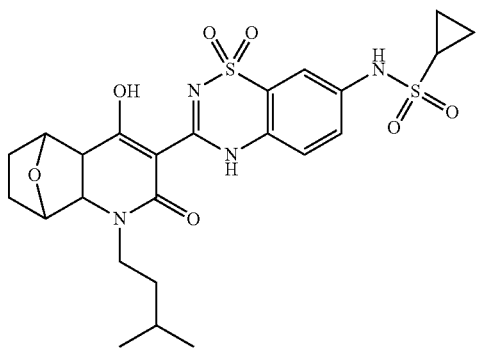 [SMILES: CC(C)CCN1C(=O)C(C2=NS(=O)(=O)c3cc(NS(=O)(=O)C4CC4)ccc3N2)=C(O)C2C3CCC(O3)C21]

A reaction flask was charged with copper (I) iodide (20 mg, 0.11 mmol), sarcosine (N-methyl glycine) (14.7 mg, 0.17 mmol), cyclopropanesulfonamide (125 mg, 1.04 mmol), (rac-di-exo)-6-hydroxy-5-(7-iodo-1,1-dioxo-1,4-dihydro-1λ$^6$-benzo[1,2,4]thiadiazin-3-yl)-3-(3-methyl-butyl)-11-oxa-3-aza-tricyclo[6.2.1.0$^{2,7}$]undec-5-en-4-one (prepared as described in Example 33, 115 mg, 0.21 mmol) and potassium phosphate (175 mg, 0.82 mmol). The flask was degassed and backfilled with nitrogen, and then anhydrous N,N-dimethylformamide (5 mL) was added. The resulting suspension was vigorously stirred at 100° C. for 5 h, and then allowed to cool to 25° C. The mixture was passed through a plug of Celite and rinsed with 10% methanol/dichloromethane. The filtrate was concentrated in vacuo, and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (rac-di-exo)-cyclopropanesulfonic acid{3-[6-hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-amide (17 mg, 0.031 mmol, 15%), as a white solid. $^1$H NMR (400 MHz, DMSO-d$_6$) δ: 0.91-0.96 (10H, m), 1.40-1.76 (7H, m), 2.69 (1H, m), 3.00 (1H, bs), 3.29 (1H, m), 3.84 (2H, m), 4.74 (2H, m), 7.51-7.59 (3H, m), 10.17 (1H, s). LC-MS (ESI) calcd for $C_{24}H_{30}N_4O_7S_2$ 550.16, found 551.4 [M+H$^+$].

Example 43

(rac-di-exo)-Cyclopropanesulfonic acid{3-[3-(3,3-dimethyl-butyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-amide

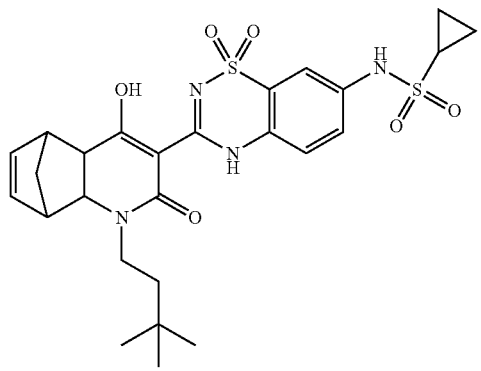 [SMILES: CC(C)(C)CCN1C(=O)C(C2=NS(=O)(=O)c3cc(NS(=O)(=O)C4CC4)ccc3N2)=C(O)C2C3C=CC(C3)C21]

a) (rac-di-exo)-3-{(3,3-Dimethyl-butyl)-[2-(7-iodo-1,1-dioxo-1,4-dihydro-1λ$^6$-benzo[1,2,4]thiadiazin-3-yl)-acetyl]-amino}-bicyclo[2.2.1]hept-5-ene-2-carboxylic acid methyl ester

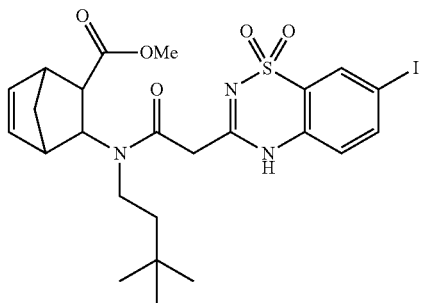 [SMILES: COC(=O)C1C2C=CC(C2)C1N(CCC(C)(C)C)C(=O)CC1=NS(=O)(=O)c2cc(I)ccc2N1]

To a solution of (rac-di-exo)-3-(3,3-dimethyl-butylamino)-bicyclo[2.2.1]hept-5-ene-2-carboxylic acid methyl ester (prepared as described in Example 32a, 227.8 mg, 0.907 mmol) in N,N-dimethylformamide (3 mL) was added (7-iodo-1,1-dioxo-1,4-dihydro-1λ$^6$-benzo[1,2,4]thiadiazin-3-yl)-acetic acid (prepared as described in US patent application US 2008/0031852, 398.2 mg, 1.088 mmol) and the mixture was vortexed until all material had completely dissolved. A 1.0 M solution of N,N-dicyclohexylcarbodiimide in dichloromethane (1.179 mL, 1.179 mmol) was added to the above solution and the mixture was stirred at 25° C. for 18 h under a nitrogen atmosphere. The precipitated N,N-dicyclohexylurea was removed by filtration over Celite, the filter cake was washed with dichloromethane (3×5 mL), and the solvent was removed in vacuo. The residue was dissolved in a 1:1 mixture of ethyl acetate and hexanes (20 mL), washed with saturated aqueous brine solution, saturated aqueous sodium bicarbonate solution and water. The layers were separated and the aqueous layers were back-extracted with a 1:1 mixture of ethyl acetate and hexanes (20 mL). The combined organic layers were dried over sodium sulfate, filtered, and concentrated in vacuo to afford the crude product, (rac-di-exo)-3-{(3,3-dimethyl-butyl)-[2-(7-iodo-1,1-dioxo-1,4-dihydro-1λ$^6$-benzo[1,2,4]thiadiazin-3-yl)-acetyl]-amino}-bicyclo[2.2.1]hept-5-ene-2-carboxylic acid methyl ester, as a yellow oil, which was used in the next step without any further purification. LC-MS calcd for $C_{24}H_{30}IN_3O_5S$ 599.10, found 600.3 [M+H$^+$].

b) (rac-di-exo)-3-(3,3-Dimethyl-butyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undeca-5,9-dien-4-one

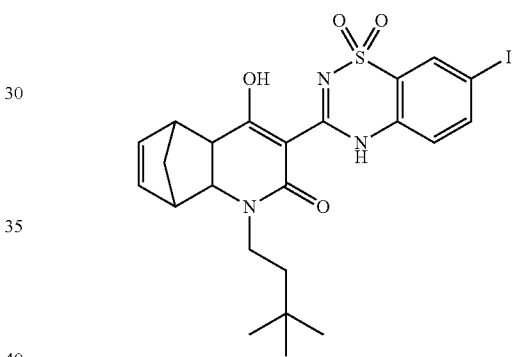

The crude (rac-di-exo)-3-{(3,3-dimethyl-butyl)-[2-(7-iodo-1,1-dioxo-1,4-dihydro-1λ$^6$-benzo[1,2,4]thiadiazin-3-yl)-acetyl]-amino}-bicyclo[2.2.1]hept-5-ene-2-carboxylic acid methyl ester (877.2 mg, 0.907 mmol) was dissolved in ethanol (20 mL). To this solution was added a 21 wt. % solution of sodium ethoxide in ethanol (1.176 g, 3.628 mmol) and the reaction mixture was stirred at 25° C. for 2 h. A 1.0 M aqueous hydrochloric acid solution (20 mL) was added upon which the product began to precipitate. The reaction mixture was stirred for another 30 min before the precipitate was collected by vacuum filtration. The solid was washed with 1.0 M aqueous hydrochloric acid solution followed by water and was then dried in vacuo. The resulting solid was then triturated with methanol, filtered and dried in vacuo. Further purification by flash column chromatography (Teledyne Isco RediSep column; 0 to 50% ethyl acetate in hexanes) afforded the desired product, (rac-di-exo)-3-(3,3-dimethyl-butyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undeca-5,9-dien-4-one (154.1 mg, 0.272 mmol, 30%), as a white solid. $^1$H NMR (400 MHz, CDCl$_3$) δ: 1.01 (9H, s), 1.32-2.00 (4H, m), 2.19 (1H, d, J=2.2 Hz), 2.75 (1H, d, J=9.5 Hz), 3.10-3.52 (4H, m), 3.78-3.88 (1H, m), 6.17-6.20 (1H, m), 6.40-6.46 (1H, m), 7.01 (1H, d, J=8.6 Hz), 7.84 (1H, dd, J$_1$=8.5 Hz, J$_2$=1.5 Hz), 8.22 (1H, s). LC-MS calcd for $C_{23}H_{26}IN_3O_4S$ 567.07, found 568.3 [M+H$^+$].

c) (rac-di-exo)-Cyclopropanesulfonic acid{3-[3-(3,3-dimethyl-butyl)-6-hydroxy-4-oxo-3-aza-tricyclo[6.2.1.0²,⁷]undeca-5,9-dien-5-yl]-1,1-dioxo-1,4-dihydro-1λ⁶-benzo[1,2,4]thiadiazin-7-yl}-amide

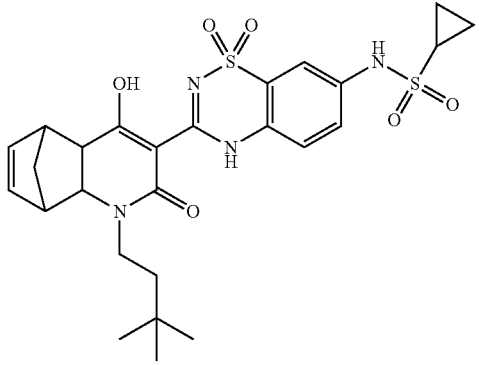 [SMILES: CC(C)(C)CCN1C(=O)C(C2=NS(=O)(=O)c3cc(NS(=O)(=O)C4CC4)ccc3N2)=C(O)C2C3C=CC(C3)C21]

(rac-di-exo)-3-(3,3-Dimethyl-butyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undeca-5,9-dien-4-one (0.155 g, 0.255 mmol), potassium triphosphate (0.271 g, 1.275 mmol), sarcosine (N-methyl glycine) (0.027 g, 0.306 mmol), and copper (I) iodide (0.024 g, 0.128 mmol) were combined. Anhydrous N,N-dimethylformamide (7 mL) was added followed by cyclopropanesulfonic acid amide (0.155 g, 1.275 mmol). The solution was degassed and backfilled with nitrogen. The mixture was stirred at 100° C. for 16 h. Upon cooling, the mixture was diluted with ethyl acetate (200 mL), washed with 1.0 M aqueous hydrochloric acid solution (2×100 mL), dried over magnesium sulfate, filtered, and concentrated in vacuo to a solid. Purification by flash column chromatography (Teledyne Isco RediSep column; 0 to 100% ethyl acetate in hexanes) afforded the desired product, (rac-di-exo)-cyclopropanesulfonic acid{3-[3-(3,3-dimethyl-butyl)-6-hydroxy-4-oxo-3-aza-tricyclo[6.2.1.0²,⁷]undeca-5,9-dien-5-yl]-1,1-dioxo-1,4-dihydro-1λ⁶-benzo[1,2,4]thiadiazin-7-yl}-amide (0.089 g, 0.159 mmol, 62.5%), as a pale yellow solid. ¹H NMR (400 MHz, CDCl₃) δ: 1.00 (9H, s), 1.14-1.21 (2H, m), 1.24-1.37 (2H, m), 1.51-1.63 (2H, m), 2.49-2.61 (1H, m), 2.73-2.76 (1H, m), 3.09-3.16 (1H, m), 3.19-3.25 (1H, m), 3.38-3.46 (2H, m), 3.79-3.88 (1H, m), 6.17-6.19 (1H, m), 6.38-6.40 (1H, m), 7.18-7.25 (1H, m), 7.57 (1H, s), 7.63-7.66 (1H, m), 7.73-7.79 (1H, m). LC-MS (ESI) calcd for C₂₆H₃₂N₄O₆S₂ 560.18, found 561.6 [M+H⁺].

Example 44

N-[3-(1R,2S,7R,8S)-3-Cyclopentyl-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl]-methanesulfonamide

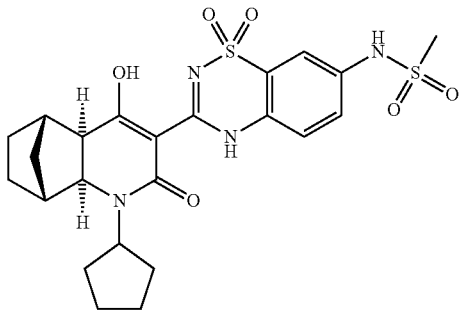

a) (1S,2R,3S,4R)-3-Cyclopentylamino-bicyclo[2.2.1]heptane-2-carboxylic acid ethyl ester

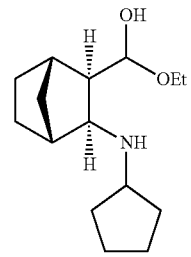 [SMILES: CCOC(O)[C@@H]1[C@H]2CC[C@H](C2)[C@@H]1NC1CCCC1]

Cyclopentanone (0.12 mL, 1.38 mmol) was added to a solution of (1S,2R,3S,4R)-3-amino-bicyclo[2.2.1]heptane-2-carboxylic acid ethyl ester (prepared as described in Example 6k, 230 mg, 1.26 mmol) in anhydrous methanol (10 mL) at 25° C. under a nitrogen atmosphere. After stirring for 10 min, glacial acetic acid (0.5 mL) and sodium cyanoborohydride (260 mg, 3.15 mmol) were added sequentially, and the resulting mixture was stirred at 50° C. for 30 min. The reaction mixture was poured into saturated aqueous sodium bicarbonate solution and extracted with ethyl acetate. The combined organic layers were washed with saturated aqueous brine solution, dried over sodium sulfate and filtered. The filtrate was concentrated in vacuo to afford the desired product, (1S,2R,3S,4R)-3-cyclopentylamino-bicyclo[2.2.1]heptane-2-carboxylic acid ethyl ester (237 mg, 0.94 mmol, 75%), as a yellow oil. LC-MS (ESI) calcd for C₁₅H₂₅NO₂ 251.19, found 252.0 [M+H⁺].

b) N-[3-(1R,2S,7R,8S)-3-Cyclopentyl-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl]-methanesulfonamide

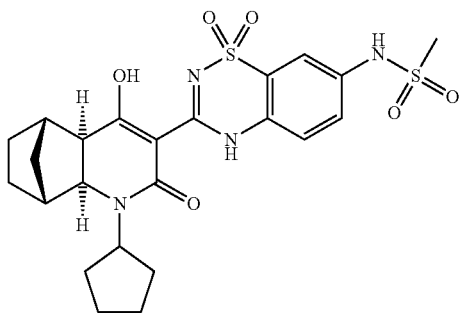

To a stirred solution of (1S,2R,3S,4R)-3-cyclopentylamino-7-oxa-bicyclo[2.2.1]heptane-2-carboxylic acid methyl ester (150 mg, 0.60 mmol) and (7-methanesulfonylamino-1,1-dioxo-1,4-dihydro-1λ⁶-benzo[1,2,4]thiadiazin-3-yl)-acetic acid (prepared as described in Example 1g, 181 mg, 0.54 mmol) in anhydrous N,N-dimethylformamide (5 mL) under a nitrogen atmosphere, N-methylmorpholine (0.12 mL, 1.08 mmol) and 1-(3-dimethylaminopropyl)-3-ethylcarbodiimide hydrochloride (104 mg, 0.54 mmol) were added sequentially. The mixture was stirred at 25° C. for 45 min, triethylamine (0.25 mL, 1.76 mmol) was added and the resulting mixture was stirred at 50° C. for 60 h. The reaction mixture was allowed to cool to 25° C., diluted with ethyl acetate, washed with 1.0 M aqueous hydrochloric acid solution and saturated aqueous brine solution, dried over magnesium sulfate and filtered. The filtrate was concentrated in vacuo and the residue was purified by prep-HPLC [Column Luna 5μ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, N-[3-(1R,2S,7R,8S)-3-cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (80 mg, 0.15 mmol, 26%), as a yellow solid. $^1$H NMR (400 MHz, DMSO-d$_6$) δ: 1.20-1.65 (8H, m), 1.75-1.95 (6H, m), 2.42 (1H, s), 2.60 (1H, s), 2.99 (1H, d, J=9.2 Hz), 3.05 (3H, s), 3.60 (1H, d, J=9.2 Hz), 3.93 (1H, m), 7.48-7.58 (3H, m), 10.17 (1H, s). LC-MS (ESI) calcd for $C_{23}H_{28}N_4O_6S_2$ 520.15, found 521.4 [M+H$^+$].

Example 45

(rac-di-exo)-Cyclopropanesulfonic acid{3-[6-hydroxy-3-(3-methyl-butyl)-4-oxo-3-aza-tricyclo [6.2.1.0$^{2,7}$]undeca-5,9-dien-5-yl]-1,1-dioxo-1,4-dihydro-1λ$^6$-benzo[1,2,4]thiadiazin-7-yl}-amide

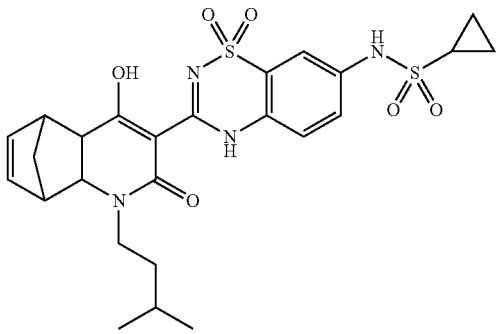 [SMILES: CC(C)CCN1C(=O)C(C2=NS(=O)(=O)c3cc(NS(=O)(=O)C4CC4)ccc3N2)=C(O)C2C3C=CC(C3)C21]

a) (rac-di-exo)-3-[[2-(7-Iodo-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester

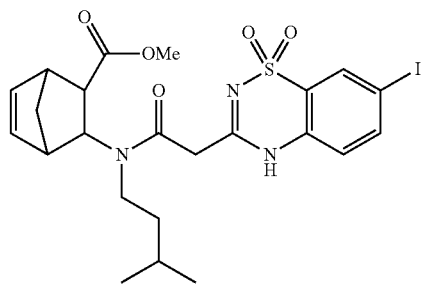 [SMILES: COC(=O)C1C2C=CC(C2)C1N(CCC(C)C)C(=O)CC1=NS(=O)(=O)c2cc(I)ccc2N1]

To a solution of (rac-di-exo)-3-(3-methyl-butylamino)-bicyclo[2.2.1]hept-5-ene-2-carboxylic acid methyl ester (prepared as described in Example 31b, 214.8 mg, 0.906 mmol) in N,N-dimethylformamide (3 mL) was added (7-iodo-1,1-dioxo-1,4-dihydro-1λ$^6$-benzo[1,2,4]thiadiazin-3-yl)-acetic acid (prepared as described in US patent application US 2008/0031852, 397.7 mg, 1.087 mmol) and the mixture was vortexed until all material had completely dissolved. A 1.0 M solution of N,N-dicyclohexylcarbodiimide in dichloromethane (1.178 mL, 1.178 mmol) was added to the above solution and the mixture was stirred at 25° C. for 18 h under a nitrogen atmosphere. The precipitated N,N-dicyclohexylurea was removed by filtration over Celite, the filter cake was washed with dichloromethane (3×5 mL), and the solvent was removed in vacuo. The residue was dissolved in a 1:1 mixture of ethyl acetate and hexanes (20 mL), washed with saturated aqueous brine solution, saturated aqueous sodium bicarbonate solution and water. The layers were separated and the aqueous layers were back-extracted with a 1:1 mixture of ethyl acetate and hexanes (20 mL). The combined organic layers were dried over sodium sulfate, filtered, and concentrated in vacuo to afford the crude product, (rac-di-exo)-3-[[2-(7-iodo-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester, as a yellow oil, which was used in the next step without any further purification. LC-MS calcd for $C_{23}H_{28}IN_3O_5S$ 585.08, found 586.3 [M+H$^+$].

b) (rac-di-exo)-6-Hydroxy-5-(7-iodo-1,1-dioxo-1,4-dihydro-1λ$^6$-benzo[1,2,4]thiadiazin-3-yl)-3-(3-methyl-butyl)-3-aza-tricyclo[6.2.1.0$^{2,7}$]undeca-5,9-dien-4-one

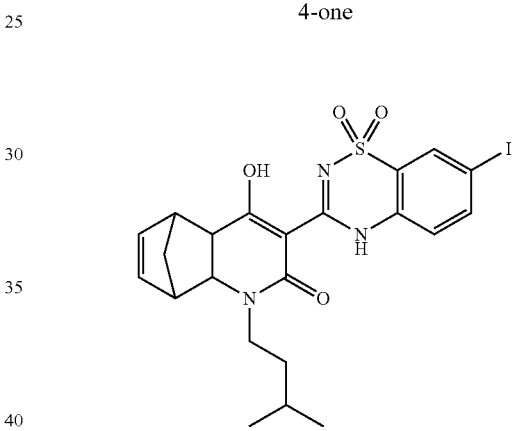

The crude (rac-di-exo)-3-[[2-(7-iodo-1,1-dioxo-1,4-dihydro-1λ$^6$-benzo[1,2,4]thiadiazin-3-yl)-acetyl]-(3-methyl-butyl)-amino]-bicyclo[2.2.1]hept-5-ene-2-carboxylic acid methyl ester was dissolved in ethanol (20 mL). To this solution was added a 21 wt. % solution of sodium ethoxide in ethanol (1.174 g, 3.624 mmol) and the reaction mixture was stirred at 25° C. for 2 h. A 1.0 M aqueous hydrochloric acid solution (20 mL) was added upon which the product began to precipitate. The reaction mixture was stirred for another 30 min before the precipitate was collected by vacuum filtration. The solid was washed with 1.0 M aqueous hydrochloric acid solution followed by water and was then dried in vacuo. The resulting solid was then triturated with methanol, filtered and dried in vacuo. Further purification by flash column chromatography (Teledyne Isco RediSep column; 0 to 50% ethyl acetate in hexanes) afforded the desired product, (rac-di-exo)-6-hydroxy-5-(7-iodo-1,1-dioxo-1,4-dihydro-1λ$^6$-benzo[1,2,4]thiadiazin-3-yl)-3-(3-methyl-butyl)-3-aza-tricyclo[6.2.1.0$^{2,7}$]undeca-5,9-dien-4-one (28.7 mg, 0.0519 mmol, 5.7% over two steps), as an off-white solid. $^1$H NMR (400 MHz, CDCl$_3$) δ: 0.98 (3H, d, J=3.3 Hz), 0.99 (3H, d, J=2.9 Hz), 1.47-1.68 (6H, m), 2.75 (1H, d, J=9.3 Hz), 3.08-3.32 (2H, m), 3.39-3.44 (2H, m), 3.82-3.89 (1H, m), 6.18-6.20 (1H, m), 6.39-6.41 (1H, m), 6.99 (1H, d, J=8.6 Hz), 7.84 (1H, d, J=10.8 Hz), 8.21 (1H, s). LC-MS calcd for $C_{22}H_{24}IN_3O_4S$ 553.05, found 554.1 [M+H$^+$].

c) (rac-di-exo)-Cyclopropanesulfonic acid{3-[6-hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-amide

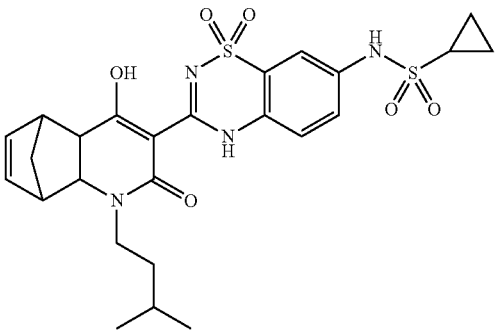 [SMILES: CC(C)CCN1C(=O)C(C2=NS(=O)(=O)c3cc(NS(=O)(=O)C4CC4)ccc3N2)=C(O)C2C3C=CC(C3)C21]

(rac-di-exo)-6-Hydroxy-5-(7-iodo-1,1-dioxo-1,4-dihydro-1λ$^6$-benzo[1,2,4]thiadiazin-3-yl)-3-(3-methyl-butyl)-3-aza-tricyclo[6.2.1.0$^{2,7}$]undeca-5,9-dien-4-one (0.029 g, 0.052 mmol), potassium triphosphate (0.055 g, 0.259 mmol), sarcosine (N-methyl glycine) (0.006 g, 0.062 mmol), and copper (I) iodide (0.005 g, 0.026 mmol) were combined. Anhydrous N,N-dimethylformamide (7 mL) was added followed by cyclopropanesulfonic acid amide (0.031 g, 0.259 mmol). The solution was degassed and backfilled with nitrogen. The mixture was stirred at 100° C. for 16 h. Upon cooling, the mixture was diluted with ethyl acetate (200 mL), washed with 1.0 M aqueous hydrochloric acid solution (2×100 mL), dried over magnesium sulfate, filtered, and concentrated in vacuo to a solid. Purification by flash column chromatography (Teledyne Isco RediSep column; 0 to 100% ethyl acetate in hexanes) afforded the desired product, (rac-di-exo)-cyclopropanesulfonic acid{3-[6-hydroxy-3-(3-methyl-butyl)-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-amide (0.009 g, 0.016 mmol, 31.6%), as a pale yellow solid. $^1$H NMR (400 MHz, CDCl$_3$) δ: 0.98-1.08 (6H, m), 1.17-1.26 (3H, m), 1.52-1.73 (4H, m), 2.48-2.62 (2H, m), 2.75-2.77 (1H, m), 3.08-3.15 (1H, m), 3.39-3.44 (2H, m), 3.83-3.91 (1H, m), 6.19 (1H, dd, J$_1$=5.5 Hz, J$_2$=3.1 Hz), 6.40 (1H, dd, J$_1$=5.4 Hz, J$_2$=4.0 Hz), 7.01 (1H, s), 7.24 (1H, t, J=7.1 Hz), 7.63-7.65 (1H, m), 7.70-7.73 (1H, m). LC-MS (ESI) calcd for C$_{25}$H$_{30}$N$_4$O$_6$S$_2$ 546.16, found 547.4 [M+H$^+$].

Example 46

(rac-di-exo)-Cyclopropanesulfonic acid{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-amide

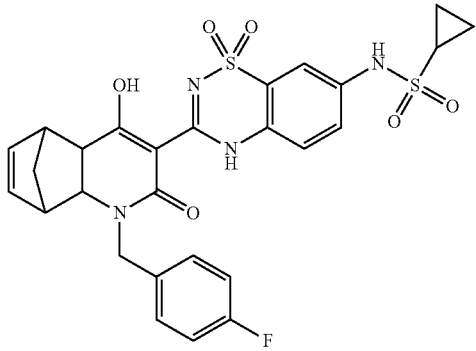 [SMILES: O=C1C(C2=NS(=O)(=O)c3cc(NS(=O)(=O)C4CC4)ccc3N2)=C(O)C2C3C=CC(C3)C2N1Cc1ccc(F)cc1]

(rac-di-exo)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undeca-5,9-dien-4-one (prepared as described in Example 39a, 0.169 g, 0.285 mmol), potassium triphosphate (0.303 g, 1.426 mmol), sarcosine (N-methyl glycine) (0.031 g, 0.342 mmol), and copper (I) iodide (0.027 g, 0.146 mmol) were combined. Anhydrous N,N-dimethylformamide (7 mL) was added followed by cyclopropanesulfonic acid amide (0.173 g, 1.426 mmol). The solution was degassed and backfilled with nitrogen. The mixture was stirred at 100° C. for 16 h. Upon cooling, the mixture was diluted with ethyl acetate (200 mL), washed with 1.0 M aqueous hydrochloric acid solution (2×100 mL), dried over magnesium sulfate, filtered, and concentrated in vacuo to a solid. Purification by flash column chromatography (Teledyne Isco RediSep column; 0 to 100% ethyl acetate in hexanes) afforded the desired product, (rac-di-exo)-cyclopropanesulfonic acid{3-[3-(4-fluoro-benzyl)-6-hydroxy-4-oxo-3-aza-tricyclo[6.2.1.0$^{2,7}$]undeca-5,9-dien-5-yl]-1,1-dioxo-1,4-dihydro-1λ$^6$-benzo[1,2,4]thiadiazin-7-yl}-amide (0.093 g, 0.159 mmol, 55.8%), as a pale yellow solid. $^1$H NMR (400 MHz, CDCl$_3$) δ: 0.97-1.04 (2H, m), 1.14-1.20 (2H, m), 1.53 (1H, d, J=9.4 Hz), 1.66 (1H, d, J=9.5 Hz), 2.48-2.61 (2H, m), 2.74 (1H, d, J=9.4 Hz), 3.37-3.41 (2H, m), 4.32 (1H, d, J=15.3 Hz), 5.19 (1H, d, J=14.8 Hz), 6.09-6.11 (1H, m), 6.33-6.36 (1H, m), 7.02 (2H, t, J=8.6 Hz), 7.16-7.23 (3H, m), 7.63 (1H, dd, J$_1$=9.3 Hz, J$_2$=2.3 Hz), 7.77 (1H, d, J=2.3 Hz), 8.04 (1H, s). LC-MS (ESI) calcd for C$_{27}$H$_{25}$FN$_4$O$_6$S$_2$ 584.12, found 585.2 [M+H$^+$].

Example 47

N-[3-(1R,2S,7R,8S)-(3-Cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide-N-isopropyl carbamate

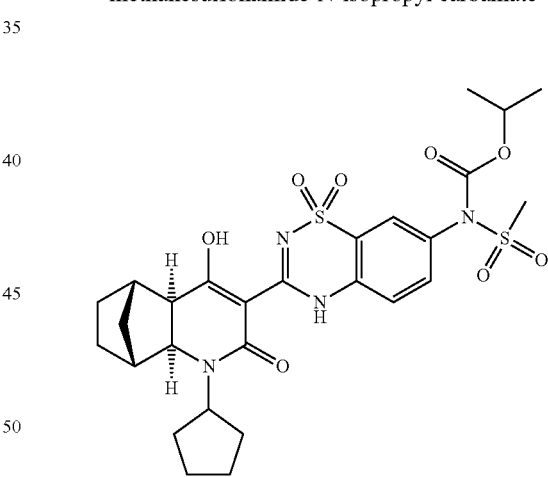

N-[3-(1R,2S,7R,8S)-3-cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (prepared as described in Example 44, 48.5 mg, 0.093 mmol) was dissolved in anhydrous pyridine (2 mL) under a nitrogen atmosphere, a 1.0 M solution of isopropyl chloroformate in toluene (0.46 mL, 0.46 mmol) was added slowly. The resulting mixture was stirred at 25° C. for 15 min, LC-MS showed the completion of the reaction. The reaction was quenched with methanol (1 mL) and the resulting mixture was concentrated in vacuo. The residue was purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, N-[3-(1R,2S,7R,8S)-(3-cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide-N-isopropyl carbamate (15 mg, 0.025 mmol, 27%), as a yellow solid. $^1$H NMR (400 MHz, DMSO-d$_6$) δ: 1.19 (6H, d, J=6.0 Hz), 1.30-1.65 (8H, m), 1.75-1.95 (6H, m), 2.43 (1H, m), 2.61 (1H, m), 3.00 (1H, m), 3.55 (1H, m), 3.62 (3H, s), 3.95 (1H, m), 4.94 (1H, m), 7.57 (1H, d, J=9.2 Hz), 7.64 (1H, dd, J=8.8, 1.6 Hz), 7.97 (1H, s). LC-MS (ESI) calcd for $C_{27}H_{34}N_4O_8S_2$ 606.16, found 607.3 [M+H$^+$].

Example 48

(rac-di-exo)-N-[3-(3-Cyclopentyl-6-hydroxy-4-oxo-11-oxa-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

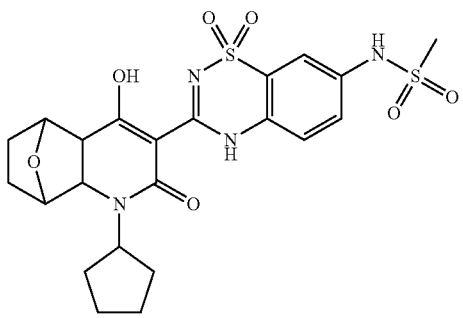 [SMILES: CS(=O)(=O)Nc1ccc2c(c1)S(=O)(=O)N=C(C1=C(O)C3C4CCC(O4)C3N(C3CCCC3)C1=O)N2]

a) (rac-di-exo)-3-Cyclopentylamino-7-oxa-bicyclo[2.2.1]heptane-2-carboxylic acid methyl ester

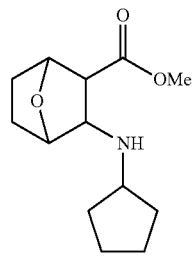 [SMILES: COC(=O)C1C2CCC(O2)C1NC1CCCC1]

Cyclopentanone (0.56 mL, 6.37 mmol) was added to a solution of (rac-di-exo)-3-amino-7-oxa-bicyclo[2.2.1]heptane-2-carboxylic acid methyl ester (prepared as described in Example 8a, 1.10 g, 6.37 mmol) in anhydrous methanol (15 mL) at 25° C. under a nitrogen atmosphere. After stirring for 20 min, glacial acetic acid (0.75 mL) and sodium cyanoborohydride (1.0 g, 15.92 mmol) were added sequentially, and the resulting mixture was stirred at 50° C. for 1 h. The reaction mixture was poured into saturated aqueous sodium bicarbonate solution and extracted with ethyl acetate. The combined organic layers were washed with saturated aqueous brine solution, dried over sodium sulfate and filtered. The filtrate was concentrated in vacuo to afford the desired product, (rac-di-exo)-3-cyclopentylamino-7-oxa-bicyclo[2.2.1]heptane-2-carboxylic acid methyl ester (1.06 g, 4.43 mmol, 70%), as a yellow oil. LC-MS (ESI) calcd for $C_{13}H_{21}NO_3$ 239.15, found 240.2 [M+H$^+$].

b) (rac-di-exo)-N-[3-(3-Cyclopentyl-6-hydroxy-4-oxo-11-oxa-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

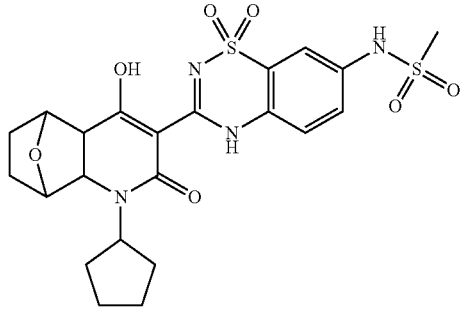 [SMILES: CS(=O)(=O)Nc1ccc2c(c1)S(=O)(=O)N=C(C1=C(O)C3C4CCC(O4)C3N(C3CCCC3)C1=O)N2]

To a stirred solution of (rac-di-exo)-3-cyclopentylamino-7-oxa-bicyclo[2.2.1]heptane-2-carboxylic acid methyl ester (170 mg, 0.71 mmol) and (7-methanesulfonylamino-1,1-dioxo-1,4-dihydro-1λ$^6$-benzo[1,2,4]thiadiazin-3-yl)-acetic acid (prepared as described in Example 1g, 197 mg, 0.60 mmol) in anhydrous N,N-dimethylformamide (5 mL) under a nitrogen atmosphere, N-methylmorpholine (0.132 mL, 1.20 mmol) and 1-(3-dimethylaminopropyl)-3-ethylcarbodiimide hydrochloride (115 mg, 0.60 mmol) were added sequentially. The mixture was stirred at 25° C. for 1 h, triethylamine (0.34 mL, 2.4 mmol) was added and the resulting mixture was stirred at 50° C. for 1 h. The reaction mixture was allowed to cool to 25° C., diluted with ethyl acetate, washed with 1.0 M aqueous hydrochloric acid solution and saturated aqueous brine solution, dried over magnesium sulfate and filtered. The filtrate was concentrated in vacuo and the residue was purified by prep-HPLC [Column Luna 5μ C18 (2) 100 Å AXIA 150× 21.2 mm, 5 micron, 30%-95% in 7 min @ 30 mL/min flow rate, 0.05% trifluoroacetic acid in acetonitrile/0.05% trifluoroacetic acid in water] to afford the desired product, (rac-di-exo)-N-[3-(3-cyclopentyl-6-hydroxy-4-oxo-11-oxa-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (120 mg, 0.23 mmol, 38%), as an off-white solid. $^1$H NMR (400 MHz, DMSO-d$_6$) δ: 1.48-1.96 (12H, m), 3.05 (3H, s), 3.30 (1H, d, J=8.0 Hz), 3.89 (1H, d, J=9.2 Hz), 4.13 (1H, m), 4.57 (1H, s), 4.74 (1H, s), 7.49-7.58 (3H, m), 10.17 (1H, s). LC-MS (ESI) calcd for $C_{22}H_{26}N_4O_7S_2$ 522.12, found 523.4 [M+H$^+$].

Example 49

N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

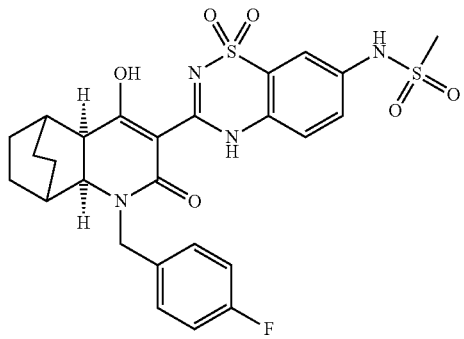

a) 4-Oxa-tricyclo[5.2.2.0$^{2,6}$]undecane-3,5-dione

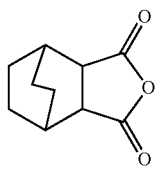

4-Oxa-tricyclo[5.2.2.0$^{2,6}$]undec-8-ene-3,5-dione (4.00 g, 22.45 mmol) was dissolved in ethyl acetate (100 mL). 10% Palladium on carbon (400 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. Purification by flash column chromatography (Teledyne Isco RediSep column; 0 to 30% ethyl acetate in hexanes) afforded the desired product, 4-oxa-tricyclo[5.2.2.0$^{2,6}$]undecane-3,5-dione (2.92 g, 16.20 mmol, 72%), as a white powder. $^1$H NMR (400 MHz, DMSO-d$_6$) δ: 1.55-1.64 (6H, m), 1.76 (2H, d, J=9.2 Hz), 2.25 (2H, s), 3.11 (2H, s). LC-MS (ESI) calcd for C$_{10}$H$_{12}$O$_3$ 180.20, found 181.0 [M+H$^+$].

b) (2S,3R)-Bicyclo[2.2.2]octane-2,3-dicarboxylic acid monomethyl ester

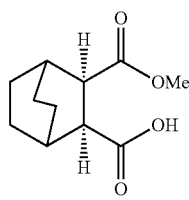

4-Oxa-tricyclo[5.2.2.0$^{2,6}$]undec-3,5-dione (0.90 g, 4.99 mmol) was dissolved in toluene (50 mL) and carbon tetrachloride (50 mL). Quinine (1.78 g, 5.49 mmol) was added and the mixture was cooled to −55° C. Methanol (0.61 mL, 14.97 mmol) was added dropwise to the above mixture. The reaction was stirred at −55° C. for 18 h. The reaction was warmed to 25° C. and concentrated in vacuo. The crude material was dissolved in ethyl acetate (50 mL) and washed with 1.0 M aqueous hydrochloric acid solution (2×40 mL). The organic layer was further washed with saturated aqueous brine solution (20 mL), dried over magnesium sulfate, filtered, and concentrated in vacuo to afford a clear oil. Purification by flash column chromatography (Teledyne Isco RediSep column; 0 to 50% ethyl acetate in hexanes) afforded the desired product, (2S,3R)-bicyclo[2.2.2]octane-2,3-dicarboxylic acid monomethyl ester (1.10 g, 5.18 mmol, 92%), as a clear oil. $^1$H NMR (400 MHz, DMSO-d$_6$) δ: 1.31 (2H, dd, J$_1$=20.0 Hz, J$_2$=12.4 Hz), 1.52-1.54 (4H, m), 1.63 (1H, t, J=10.4 Hz), 1.75 (1H, t, J=9.6 Hz), 1.87 (2H, bs), 2.84 (2H, dd, J$_1$=29.6 Hz, J$_2$=10.8 Hz), 3.52 (3H, s), 12.01 (1H, s). LC-MS (ESI) calcd for C$_{11}$H$_{16}$O$_4$ 212.24, found 213.1 [M+H$^+$].

c) (2R,3S)-3-Benzyloxycarbonylamino-bicyclo[2.2.2]octane-2-carboxylic acid methyl ester

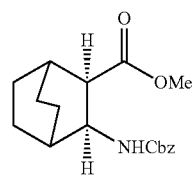 [SMILES: COC(=O)[C@@H]1C2CCC(CC2)[C@@H]1NC(=O)OCc1ccccc1]

(2S,3R)-Bicyclo[2.2.2]octane-2,3-dicarboxylic acid monomethyl ester (1.01 g, 4.76 mmol) was dissolved in anhydrous tetrahydrofuran (20 mL). The flask was degassed and backfilled with nitrogen and the mixture was cooled to 0° C. Triethylamine (1.99 mL, 14.28 mmol) was added followed by the dropwise addition of ethyl chloroformate (0.91 mL, 9.52 mmol) with vigorous stirring. The mixture was stirred at 0° C. for 1 h. Sodium azide (0.93 g, 14.28 mmol) was dissolved in water (5 mL) and added to the reaction mixture at 0° C. The mixture was stirred at 0° C. for 5 min. The ice bath was removed. The mixture was warmed to 25° C. and was stirred for 2 h. The mixture was poured into water (50 mL) and the product extracted into ethyl acetate (50 mL). The organic layer was further washed with half-saturated aqueous sodium bicarbonate solution (2×20 mL), saturated aqueous brine solution (20 mL), dried over magnesium sulfate, filtered, and concentrated in vacuo to afford a clear oil. The oil was dissolved in anhydrous benzene (10 mL) and refluxed while stirring under nitrogen for 2 h. Upon cooling to 25° C. the solution was concentrated in vacuo to afford a slightly yellow oil. The oil was dissolved in dichloromethane (10 mL) and benzyl alcohol (0.54 mL, 5.24 mmol) was added followed by triethylamine (1.33 mL, 9.52 mmol). The mixture was refluxed under nitrogen for 16 h. Upon cooling to 25° C. the solution was concentrated in vacuo to afford a golden oil. Purification by flash column chromatography (Teledyne Isco RediSep column; 0 to 20% ethyl acetate in hexanes) afforded the desired product, (2R,3S)-3-benzyloxycarbonylamino-bicyclo[2.2.2]octane-2-carboxylic acid methyl ester (0.58 g, 1.83 mmol, 38%), as a clear oil. $^1$H NMR (400 MHz, CDCl$_3$) δ: 1.18-1.28 (2H, m), 1.42-1.50 (5H, m), 1.73-1.96 (3H, m), 2.88 (1H, d, J$_1$=5.6 Hz), 3.27 (1H, s), 3.42 (3H, s), 4.00-4.04 (1H, m), 4.97 (2H, dd, J$_1$=46.4 Hz, J$_2$=12.8 Hz), 7.06 (1H, d, J=9.6 Hz), 7.24-7.34 (4H, m). LC-MS (ESI) calcd for C$_{18}$H$_{23}$NO$_4$ 317.38, found 317.9 [M+H$^+$].

d) (2R,3S)-3-Amino-bicyclo[2.2.2]octane-2-carboxylic acid methyl ester hydrochloride

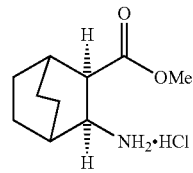

(2R,3S)-3-Benzyloxycarbonylamino-bicyclo[2.2.2]octane-2-carboxylic acid methyl ester (0.57 g, 1.79 mmol) was dissolved in ethyl acetate (20 mL). 10% Palladium on carbon (60 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (6 mL) and added dropwise with vigorous stirring to a mixture of 4.0 M solution of hydrochloric acid in 1,4-dioxane (1.02 mL) and diethyl ether (10 mL). The desired product began to precipitate as a white solid. The mixture was stirred for 20 min. The precipitate was collected by vacuum filtration, washed with additional diethyl ether (5 mL). The solid was further dried in vacuo for 1 h to afford the desired product, (2R,3S)-3-aminobicyclo[2,2,2]octane-2-carboxylic acid methyl ester hydrochloride (0.33 g, 1.50 mmol, 84%), as a white powder. $^1$H NMR (400 MHz, DMSO-$d_6$) δ: 1.38 (2H, dd, $J_1$=21.2 Hz, $J_2$=13.6 Hz), 1.55-1.63 (5H, m), 1.76-1.89 (3H, m), 3.02 (1H, dd, $J_1$=10.0 Hz, $J_2$=2.4 Hz), 3.47 (1H, bs), 3.65 (3H, s), 7.97 (3H, s). LC-MS (ESI) calcd for $C_{10}H_{17}NO_2$ (free amine) 183.25, found 184.2 [M+H$^+$].

e) (2R,3S)-3-(4-Fluoro-benzylamino)-bicyclo[2.2.2]octane-2-carboxylic acid methyl ester

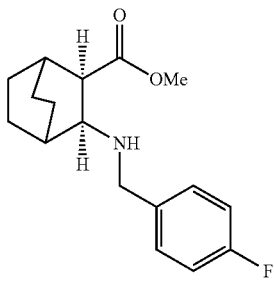 [SMILES: COC(=O)[C@@H]1C2CCC(CC2)[C@@H]1NCc1ccc(F)cc1]

(2R,3S)-3-Amino-bicyclo[2,2,2]octane-2-carboxylic acid methyl ester hydrochloride (0.34 g, 1.54 mmol) was dissolved in methanol (10 mL). Sodium acetate (0.25 g, 3.08 mmol) was added followed by 4 Å powdered molecular sieves (0.34 g) and 4-fluoro-benzaldehyde (0.16 mL, 1.54 mmol). Sodium cyanoborohydride (0.19 g, 3.08 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, (2R,3S)-3-(4-fluoro-benzylamino)-bicyclo[2,2,2]octane-2-carboxylic acid methyl ester (0.32 g, 1.11 mmol, 72%), as a clear oil. LC-MS (ESI) calcd for $C_{17}H_{22}FNO_2$ 291.36, found 292.2 [M+H$^+$].

f) N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

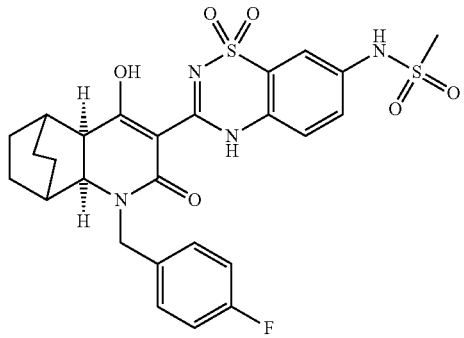

(2R,3S)-3-(4-Fluoro-benzylamino)-bicyclo[2,2,2]octane-2-carboxylic acid methyl ester (93 mg, 0.32 mmol) was dissolved in anhydrous N,N-dimethylformamide (4 mL). (7-Methanesulfonylamino-1,1-dioxo-1,4-dihydro-1λ$^6$-benzo[1,2,4]thiadiazin-3-yl)-acetic acid (prepared as described in Example 1g, 107 mg, 0.32 mmol) was added followed by N-methylmorpholine (74 µL, 0.67 mmol). The mixture was stirred until everything dissolved, approximately 5 min. 1-(3-Dimethylaminopropyl)-3-ethylcarbodiimide hydrochloride (65 mg, 0.34 mmol) was added and the mixture was stirred at 25° C. for 16 h. The reaction was quenched via addition of saturated aqueous sodium bicarbonate solution (20 mL). The mixture was extracted with ethyl acetate (3×30 mL). The combined organic layers were washed with saturated aqueous brine solution (20 mL), dried over magnesium sulfate, filtered, and concentrated in vacuo to afford a golden oil. The oil was dissolved in ethanol (5 mL). A 21 wt. % solution of sodium ethoxide in ethanol (0.36 mL, 0.96 mmol) was added. The reaction was refluxed for 16 h. The reaction was quenched via the addition of 1.0 M aqueous hydrochloric acid solution (10 mL). The mixture was extracted with ethyl acetate (3×20 mL). The organic layer was further washed with saturated sodium bicarbonate solution (2×20 mL), saturated aqueous brine solution (20 mL), dried over magnesium sulfate, filtered, and concentrated in vacuo to afford a clear oil. Purification by flash column chromatography (Teledyne Isco RediSep column; 0 to 20% ethyl acetate in dichloromethane) afforded the desired product, N-{3-[(2S,7R)-3-(4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide (0.11 g, 0.19 mmol, 59%), as a white powder. $^1$H NMR (400 MHz, DMSO-$d_6$) δ: 1.39 (2H, d, J=8.0 Hz), 1.54-1.59 (8H, m), 1.91 (1H, s), 2.14 (1H, s), 3.06 (3H, s), 3.75 (1H, d, J=11.6 Hz), 4.28 (1H, d, J=15.2 Hz), 5.03 (1H, d, J=15.6 Hz), 7.13-7.17 (2H, m), 7.34-7.37 (2H, m), 7.50-7.60 (3H, m), 10.18 (1H, s). LC-MS (ESI) calcd for $C_{26}H_{27}FN_4O_6S_2$ 574.64, found 575.1 [M+H$^+$]. m.p.: 203.8-205.7° C. ee=94.4% [HPLC-analysis: Chiralpak AS-RH 4.6×250 mm, 5 micron, 0.8 mL/min, 310 nm].

Example 50 cis-N-{3-[3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

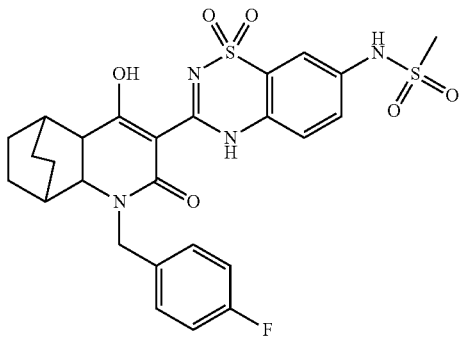 [SMILES: CS(=O)(=O)Nc1ccc2c(c1)S(=O)(=O)N=C(C1=C(O)C3C4CCC(CC4)C3N(Cc3ccc(F)cc3)C1=O)N2]

a) cis-Bicyclo[2.2.2]octane-2,3-dicarboxylic acid monomethyl ester

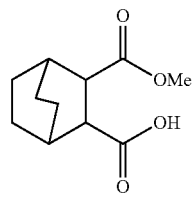 [SMILES: COC(=O)C1C2CCC(CC2)C1C(=O)O]

4-Oxa-tricyclo[5.2.2.0$^{2,6}$]undec-8-ene-3,5-dione (1.00 g, 5.61 mmol) was dissolved in methanol (20 mL). 10% Palladium on carbon (100 mg) was added. The flask was degassed and backfilled with hydrogen gas via balloon. The mixture was stirred at 25° C. for 16 h. The mixture was passed through a plug of Celite and the filtrate was left to stand at 25° C. for 72 h. The solution was then concentrated in vacuo to afford a clear oil. Purification by flash column chromatography (Teledyne Isco RediSep column; 0 to 60% ethyl acetate in hexanes) afforded the desired product, cis-bicyclo[2.2.2]octane-2,3-dicarboxylic acid monomethyl ester (1.10 g, 5.18 mmol, 92%), as a clear oil. $^1$H NMR (400 MHz, DMSO-d$_6$) δ: 1.31 (2H, dd, J$_1$=20.0 Hz, J$_2$=12.4 Hz), 1.52-1.54 (4H, m), 1.63 (1H, t, J=10.4 Hz), 1.75 (1H, t, J=9.6 Hz), 1.87 (2H, bs), 2.84 (2H, dd, J$_1$=29.6 Hz, J$_2$=10.8 Hz), 3.52 (3H, s), 12.01 (1H, s). LC-MS (ESI) calcd for C$_{11}$H$_{16}$O$_4$ 212.24, found 213.2 [M+H$^+$].

b) cis-3-Benzyloxycarbonylamino-bicyclo[2.2.2]octane-2-carboxylic acid methyl ester

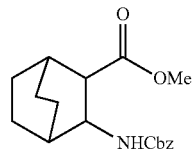 [SMILES: COC(=O)C1C2CCC(CC2)C1NC(=O)OCc1ccccc1]

cis-Bicyclo[2.2.2]octane-2,3-dicarboxylic acid monomethyl ester (1.09 g, 5.14 mmol) was dissolved in anhydrous tetrahydrofuran (20 mL). The flask was degassed and backfilled with nitrogen and the mixture was cooled to 0° C. Triethylamine (2.15 mL, 15.42 mmol) was added followed by the dropwise addition of ethyl chloroformate (0.98 mL, 10.28 mmol) with vigorous stirring. The mixture was stirred at 0° C. for 1 h. Sodium azide (1.00 g, 15.42 mmol) was dissolved in water (7 mL) and added to the reaction mixture at 0° C. The mixture was stirred at 0° C. for 5 min. The ice bath was removed. The mixture was warmed to 25° C. and was stirred for 2 h. The mixture was poured into water (70 mL) and the product extracted into ethyl acetate (70 mL). The organic layer was further washed with half-saturated aqueous sodium bicarbonate solution (2×30 mL), saturated aqueous brine solution (30 mL), dried over magnesium sulfate, filtered, and concentrated in vacuo to afford a clear oil. The oil was dissolved in anhydrous benzene (10 mL) and refluxed while stirring under nitrogen for 2 h. Upon cooling to 25° C. the solution was concentrated in vacuo to afford a slightly yellow oil. The oil was dissolved in dichloromethane (7 mL) and benzyl alcohol (0.58 mL, 5.65 mmol) was added followed by triethylamine (1.43 mL, 10.28 mmol). The mixture was refluxed under nitrogen for 16 h. Upon cooling to 25° C. the solution was concentrated in vacuo to afford a golden oil. Purification by flash column chromatography (Teledyne Isco RediSep column; 0 to 20% ethyl acetate in hexanes) afforded the desired product, cis-3-benzyloxycarbonylamino-bicyclo[2.2.2]octane-2-carboxylic acid methyl ester (1.32 g, 4.16 mmol, 81%), as a clear oil. $^1$H NMR (400 MHz, CDCl$_3$) δ: 1.18-1.28 (2H, m), 1.42-1.50 (5H, m), 1.73-1.96 (3H, m), 2.88 (1H, d, J$_1$=5.6 Hz), 3.27 (1H, s), 3.42 (3H, s), 4.00-4.04 (1H, m), 4.97 (2H, dd, J$_1$=46.4 Hz, J$_2$=12.8 Hz), 7.06 (1H, d, J=9.6 Hz), 7.24-7.34 (4H, m). LC-MS (ESI) calcd for C$_{18}$H$_{23}$NO$_4$ 317.38, found 317.92 [M+H$^+$].

c) cis-3-Amino-bicyclo[2.2.2]octane-2-carboxylic acid methyl ester hydrochloride

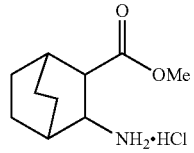

cis-3-Benzyloxycarbonylamino-bicyclo[2.2.2]octane-2-carboxylic acid methyl ester (0.67 g, 2.11 mmol) was dissolved in ethyl acetate (10 mL). 5% Palladium on carbon (97 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (6.7 mL) and added dropwise, with vigorous stirring, to a mixture of 4.0 M solution of hydrochloric acid in 1,4-dioxane (1.2 mL) in diethyl ether (12 mL). The desired product began to precipitate as a white solid. The mixture was stirred for 20 min. The precipitate was collected by vacuum filtration, washed with additional diethyl ether (5 mL). The solid was further dried in vacuo for 1 h to afford the desired product, cis-3-amino-bicyclo[2,2,2]octane-2-carboxylic acid methyl ester hydrochloride (0.35 g, 1.59 mmol, 75%), as a white powder. $^1$H NMR (400 MHz, DMSO-d$_6$) δ: 1.38 (2H, dd, J$_1$=21.2 Hz, J$_2$=13.6 Hz), 1.55-1.63 (5H, m), 1.76-1.89 (3H, m), 3.02 (1H, dd, J$_1$=10.0 Hz, J$_2$=2.4 Hz), 3.47 (1H, bs), 3.65 (3H, s), 7.97

(3H, s). LC-MS (ESI) calcd for $C_{10}H_{17}NO_2$ (free amine) 183.25, found 184.05 [M+H$^+$].

d) cis-3-(4-Fluoro-benzylamino)-bicyclo[2.2.2]octane-2-carboxylic acid methyl ester

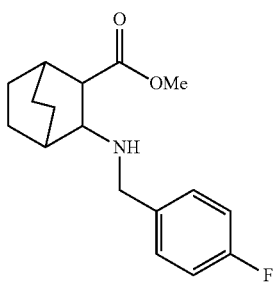 [SMILES: COC(=O)C1C2CCC(CC2)C1NCc1ccc(F)cc1]

cis-3-Amino-bicyclo[2,2,2]octane-2-carboxylic acid methyl ester hydrochloride (0.34 g, 1.55 mmol) was dissolved in methanol (10 mL). Sodium acetate (0.25 g, 3.10 mmol) was added followed by 4 Å powdered molecular sieves (0.34 g) and 4-fluoro-benzaldehyde (0.17 mL, 1.55 mmol). Sodium cyanoborohydride (0.20 g, 3.10 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, cis-3-(4-fluoro-benzylamino)-bicyclo[2,2,2]octane-2-carboxylic acid methyl ester (0.34 g, 1.17 mmol, 75%), as a clear oil. LC-MS (ESI) calcd for $C_{17}H_{22}FNO_2$ 291.36, found 292.18 [M+H$^+$].

d) cis-N-{3-[3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

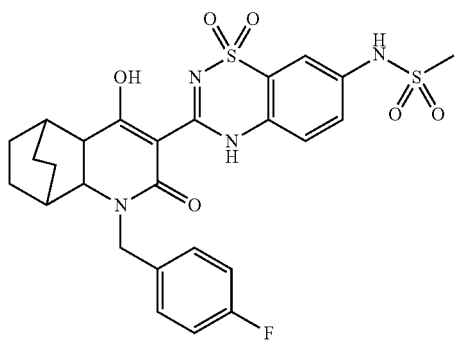 [SMILES: CS(=O)(=O)Nc1ccc2c(c1)S(=O)(=O)N=C(C1=C(O)C3C4CCC(CC4)C3N(Cc3ccc(F)cc3)C1=O)N2]

cis-3-(4-Fluoro-benzylamino)-bicyclo[2,2,2]octane-2-carboxylic acid methyl ester (0.20 g, 0.69 mmol) was dissolved in anhydrous N,N-dimethylformamide (8 mL). (7-Methanesulfonylamino-1,1-dioxo-1,4-dihydro-1λ$^6$-benzo[1,2,4]thiadiazin-3-yl)-acetic acid (prepared as described in Example 1g, 0.23 g, 0.69 mmol) was added followed by N-methylmorpholine (0.16 mL, 1.45 mmol). The mixture was stirred until everything dissolved, approximately 5 min. 1-(3-Dimethylaminopropyl)-3-ethylcarbodiimide hydrochloride (0.14 g, 0.72 mmol) was added and the mixture was stirred at 25° C. for 4 h. Triethylamine (0.29 mL, 2.07 mmol) was added and the mixture was stirred at 50° C. for 16 h. Upon cooling to 25° C., the solution was diluted with ethyl acetate (50 mL) and washed with 1.0 M aqueous hydrochloric acid solution (2×50 mL), saturated aqueous brine solution (20 mL), dried over magnesium sulfate, filtered, and concentrated in vacuo to afford a golden oil. Purification by flash column chromatography (Teledyne Isco RediSep column; 0 to 20% ethyl acetate in dichloromethane) afforded the desired product, cis-N-{3-[3-(4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide (0.30 g, 0.52 mmol, 76%), as a white powder. $^1$H NMR (400 MHz, DMSO-d$_6$) δ: 1.39 (2H, d, J=8.0 Hz), 1.54-1.59 (8H, m), 1.91 (1H, s), 2.14 (1H, s), 3.06 (3H, s), 3.75 (1H, d, J=11.6 Hz), 4.28 (1H, d, J=15.2 Hz), 5.03 (1H, d, J=15.6 Hz), 7.13-7.17 (2H, m), 7.34-7.37 (2H, m), 7.50-7.60 (3H, m), 10.18 (1H, s). LC-MS (ESI) calcd for $C_{26}H_{27}FN_4O_6S_2$ 574.64, found 575.4 [M+H$^+$]. m.p.: 203.8-205.7° C. Anal. calcd for $C_{26}H_{27}FN_4O_6S_2 \cdot 0.4$PhMe: C, 56.57; H, 4.98; N, 9.16. found C, 57.09; H, 5.08; N, 9.38.

Example 51 rac-N-{3-[(1R,2R,7S,8S,9S,11R)-3-[(4-Fluorophenyl)methyl]-6-hydroxy-4-oxo-3-azatetracyclo[6.3.2.0$^{2,7}$.0$^{9,11}$]tridec-5-en-5-yl]-1,1-dioxo-4H-1λ$^6$,2,4-benzothiadiazin-7-yl}methanesulfonamide

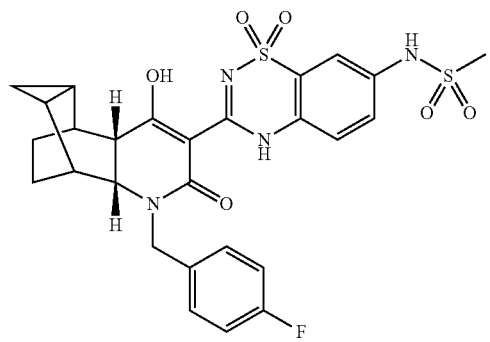 [SMILES: CS(=O)(=O)Nc1ccc2c(c1)S(=O)(=O)N=C(C1=C(O)[C@H]3C4CCC(C5CC54)[C@H]3N(Cc3ccc(F)cc3)C1=O)N2]

a) rac-(1R,2R,6S,7S,8S,10R)-4-Oxatetracyclo[5.3.2.0$^{2,6}$.0$^{8,10}$]dodec-11-ene-3,5-dione and rac-(1R,2S,6R,7S,8S,10R)-4-Oxatetracyclo[5.3.2.0$^{2,6}$.0$^{8,10}$]dodec-11-ene-3,5-dione

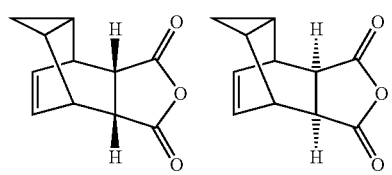

Furan-2,5-dione (5.32 g, 54.26 mmol) was partially dissolved in xylene (100 mL). Cyclohepta-1,3,5-triene (5 g, 54.26 mmol) was added. The reaction was stirred at 144° C.

for 5 h. The mixture was allowed to cool to 25° C. and concentrated in vacuo. Purification by flash column chromatography (Teledyne Isco RediSep column; 0 to 20% ethyl acetate in hexanes) afforded the desired products, rac-(1R,2R,6S,7S,8S,10R)-4-Oxatetracyclo[5.3.2.0$^{2,6}$.0$^{8,10}$]dodec-11-ene-3,5-dione (7.46 g, 39.22 mmol, 72%) and rac-(1R,2S,6R,7S,8S,10R)-4-Oxatetracyclo[5.3.2.0$^{2,6}$.0$^{8,10}$]dodec-11-ene-3,5-dione (0.88 g, 4.63 mmol, 8%), as white solids. $^1$H NMR (400 MHz, CDCl$_3$) δ: exo: 0.27-0.42 (2H, m), 1.11-1.15 (2H, m), 3.25 (2H, t, J=1.6 Hz), 3.46-3.50 (2H, m), 5.89 (2H, dd, J$_1$=4.8 Hz, J$_2$=3.2 Hz); endo: 0.14-0.26 (2H, m), 1.12-1.16 (2H, m), 3.09 (2H, s), 3.40-3.44 (2H, m), 5.94 (2H, dd, J$_1$=4.8 Hz, J$_2$=3.2 Hz). LC-MS (ESI) calcd for C$_{11}$H$_{10}$O$_3$ 190.20, found exo 191.0; endo 191.3 [M+H$^+$].

b) rac-(1S,2S,4R,5R,6R,7S)-7-(Methoxycarbonyl)tricyclo[3.2.2.0$^{2,4}$]non-8-ene-6-carboxylic acid

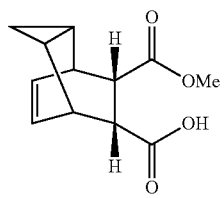 [SMILES: COC(=O)[C@H]1C2C=CC(C3CC32)[C@H]1C(=O)O]

rac-(1R,2R,6S,7S,8S,10R)-4-Oxatetracyclo[5.3.2.0$^{2,6}$.0$^{8,10}$]dodec-11-ene-3,5-dione (1.00 g, 5.26 mmol) was dissolved in methanol (20 mL). The reaction was stirred at 25° C. for 72 h. The mixture was concentrated in vacuo to afford a clear oil. Purification by flash column chromatography (Teledyne Isco RediSep column; 0 to 60% ethyl acetate in hexanes) afforded the desired product, rac-(1S,2S,4R,5R,6R,7S)-7-(Methoxycarbonyl)tricyclo[3.2.2.0$^{2,4}$]non-8-ene-6-carboxylic acid (1.11 g, 5.00 mmol, 95%), as a white solid. $^1$H NMR (400 MHz, DMSO-d$_6$) δ: 0.01-0.10 (2H, m), 0.93-1.02 (2H, m), 2.98-3.05 (4H, m), 3.45 (3H, s), 5.68-5.77 (2H, m), 11.94 (1H, s). LC-MS (ESI) calcd for C$_{12}$H$_{14}$O$_4$ 222.24, found 223.2 [M+H$^+$].

c) rac-Methyl (1R,2R,4S,5S,6S,7R)-7-{[(benzyloxy)carbonyl]amino}tricyclo[3.2.2.0$^{2,4}$]non-8-ene-6-carboxylate

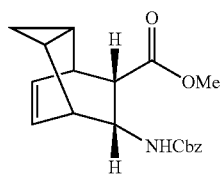 [SMILES: COC(=O)[C@H]1C2C=CC(C3CC32)[C@H]1NC(=O)OCc1ccccc1]

rac-(1S,2S,4R,5R,6R,7S)-7-(Methoxycarbonyl)tricyclo[3.2.2.0$^{2,4}$]non-8-ene-6-carboxylic acid (0.78 g, 3.53 mmol) was dissolved in anhydrous tetrahydrofuran (20 mL). The flask was degassed and backfilled with nitrogen and the mixture was cooled to 0° C. Triethylamine (1.48 mL, 10.59 mmol) was added followed by the dropwise addition of ethyl chloroformate (0.67 mL, 7.06 mmol) with vigorous stirring. The mixture was stirred at 0° C. for 1 h. Sodium azide (0.69 g, 10.59 mmol) was dissolved in water (5 mL) and added to the reaction mixture at 0° C. The mixture was stirred at 0° C. for 5 min. The ice bath was removed. The mixture was warmed to 25° C. and was stirred for 2 h. The mixture was poured into water (70 mL) and the product extracted into ethyl acetate (70 mL). The organic layer was further washed with half-saturated aqueous sodium bicarbonate solution (2×30 mL), saturated aqueous brine solution (30 mL), dried over magnesium sulfate, filtered, and concentrated in vacuo to afford a clear oil. The oil was dissolved in anhydrous benzene (10 mL) and refluxed while stirring under nitrogen for 2 h. Upon cooling to 25° C. the solution was concentrated in vacuo to afford a slightly yellow oil. The oil was dissolved in dichloromethane (10 mL) and benzyl alcohol (0.40 mL, 3.88 mmol) was added followed by triethylamine (0.98 mL, 7.06 mmol). The mixture was refluxed under nitrogen for 16 h. Upon cooling to 25° C. the solution was concentrated in vacuo to afford a golden oil. Purification by flash column chromatography (Teledyne Isco RediSep column; 0 to 20% ethyl acetate in hexanes) afforded the desired product, rac-Methyl (1R,2R,4S,5S,6S,7R)-7-{[(benzyloxy)carbonyl]amino}tricyclo[3.2.2.0$^{2,4}$]non-8-ene-6-carboxylate (0.62 g, 1.89 mmol, 54%) as a clear oil. $^1$H NMR (400 MHz, CDCl$_3$) δ: 0.17-0.22 (2H, m), 0.90-1.05 (2H, m), 2.98-3.14 (3H, m), 3.48 (3H, s), 4.38-4.43 (1H, m), 5.00-5.12 (2H, m), 5.77 (1H, t, J=7.2 Hz), 6.05 (1H, t, J=7.2 Hz), 7.29-7.37 (5H, m). LC-MS (ESI) calcd for C$_{19}$H$_{21}$NO$_4$ 327.37, found 328.3 [M+H$^+$].

d) rac-Methyl (1R,2R,4S,5S,6S,7R)-7-aminotricyclo[3.2.2.0$^{2,4}$]nonane-6-carboxylate hydrochloride

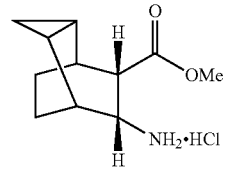

rac-Methyl (1R,2R,4S,5S,6S,7R)-7-{[(benzyloxy)carbonyl]amino}tricyclo[3.2.2.0$^{2,4}$]non-8-ene-6-carboxylate (0.61 g, 1.85 mmol) was dissolved in ethyl acetate (10 mL). 5% Palladium on carbon (0.10 g) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (6 mL) and added dropwise, with vigorous stirring, to a mixture of a 4.0 M solution of hydrochloric acid in 1,4-dioxane (0.93 mL) in diethyl ether (11 mL). The mixture was concentrated and dried in vacuo to afford the desired product, rac-Methyl (1R,2R,4S,5S,6S,7R)-7-aminotricyclo[3.2.2.0$^{2,4}$]nonane-6-carboxylate hydrochloride (0.43 g, 1.85 mmol, 100%), as a sticky gum. LC-MS (ESI) calcd for C$_{11}$H$_{17}$NO$_2$ (free amine) 195.26, found 196.5 [M+H$^+$].

e) rac-Methyl (1R,2R,4S,5S,6S,7R)-7-{[(4-fluorophenyl)methyl]amino}tricyclo[3.2.2.0$^{2,4}$]nonane-6-carboxylate

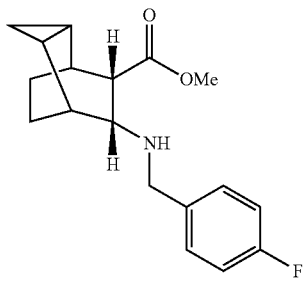 [SMILES: COC(=O)[C@H]1C2CCC(C3CC32)[C@H]1NCc1ccc(F)cc1]

rac-Methyl (1R,2R,4S,5S,6S,7R)-7-aminotricyclo[3.2.2.0²,⁴]nonane-6-carboxylate hydrochloride (0.43 g, 1.85 mmol) was dissolved in methanol (10 mL). Sodium acetate (0.30 g, 3.70 mmol) was added followed by 4 Å powdered molecular sieves (0.40 g) and 4-fluoro-benzaldehyde (0.20 mL, 1.85 mmol). Sodium cyanoborohydride (0.23 g, 3.70 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, rac-Methyl (1R,2R,4S,5S,6S,7R)-7-{[(4-fluorophenyl)methyl]amino}tricyclo[3.2.2.0²,⁴]nonane-6-carboxylate as a clear oil. LC-MS (ESI) calcd for $C_{17}H_{22}FNO_2$ 291.36, found 292.2 [M+H⁺].

f) rac-N-{3-[(1R,2R,7S,8S,9S,11R)-3-[(4-Fluorophenyl)methyl]-6-hydroxy-4-oxo-3-azatetracyclo[6.3.2.0²,⁷.0⁹,¹¹]tridec-5-en-5-yl]-1,1-dioxo-4H-1λ⁶,2,4-benzothiadiazin-7-yl}methanesulfonamide

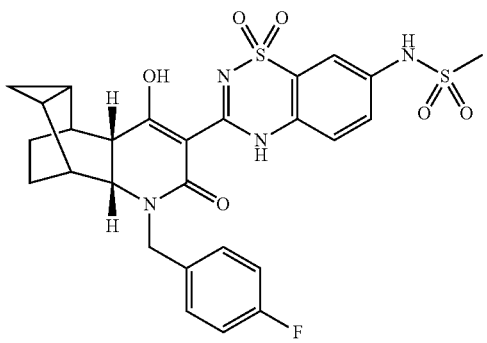 [SMILES: CS(=O)(=O)Nc1ccc2c(c1)S(=O)(=O)N=C(C1=C(O)[C@H]3C4CCC(C5CC54)[C@H]3N(Cc3ccc(F)cc3)C1=O)N2]

rac-Methyl (1R,2R,4S,5S,6S,7R)-7-{[(4-fluorophenyl)methyl]amino}tricyclo[3.2.2.0²,⁴]nonane-6-carboxylate (0.15 g, 0.49 mmol) was dissolved in anhydrous N,N-dimethylformamide (8 mL). (7-Methanesulfonylamino-1,1-dioxo-1,4-dihydro-1λ⁶-benzo[1,2,4]thiadiazin-3-yl)-acetic acid (prepared as described in Example 1g, 0.16 g, 0.49 mmol) was added followed by N-methylmorpholine (0.11 mL, 1.03 mmol). The mixture was stirred until everything dissolved, approximately 5 min. 1-(3-Dimethylaminopropyl)-3-ethylcarbodiimide hydrochloride (0.10 g, 0.51 mmol) was added and the mixture was stirred at 25° C. for 4 h. Triethylamine (0.20 mL, 1.47 mmol) was added and the mixture was stirred at 50° C. for 16 h. Upon cooling to 25° C., the solution was diluted with ethyl acetate (50 mL) and washed with 1.0 M aqueous hydrochloric acid solution (2×50 mL), saturated aqueous brine solution (20 mL), dried over magnesium sulfate, filtered, and concentrated in vacuo to afford a golden oil. Purification by flash column chromatography (Teledyne Isco RediSep column; 0 to 20% ethyl acetate in dichloromethane) afforded the desired product, rac-N-{3-[(1R,2R,7S,8S,9S,11R)-3-[(4-Fluorophenyl)methyl]-6-hydroxy-4-oxo-3-azatetracyclo[6.3.2.0²,⁷.0⁹,¹¹]tridec-5-en-5-yl]-1,1-dioxo-4H-1λ⁶,2,4-benzothiadiazin-7-yl}methanesulfonamide (0.23 g, 0.40 mmol, 82%), as a white powder. ¹H NMR (400 MHz, DMSO-d₆) δ: 0.44-1.28 (10H, m), 2.29 (1H, bs), 3.06 (3H, s), 3.82 (1H, d, J=11.6 Hz), 4.40 (1H, d, J=14.0 Hz), 4.98 (1H, d, J=15.6 Hz), 7.12-7.60 (7H, m), 10.19 (1H, s). LC-MS (ESI) calcd for $C_{27}H_{27}FN_4O_6S_2$ 586.65, found 587.5 [M+H⁺].

Example 52 rac-N-{3-[(1R,2S,7R,8S,9S,11R)-3-[(4-Fluorophenyl)methyl]-6-hydroxy-4-oxo-3-azatetracyclo[6.3.2.0²,⁷.0⁹,¹¹]trideca-5,12-dien-5-yl]-1,1-dioxo-4H-1λ⁶,2,4-benzothiadiazin-7-yl}methanesulfonamide

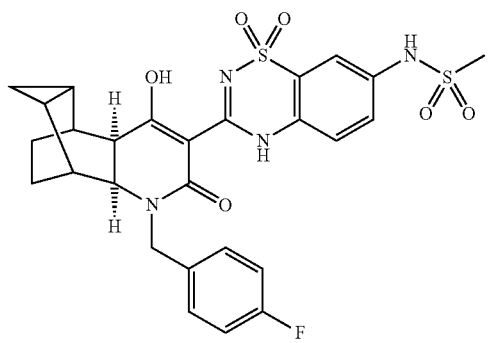

a) rac-(1S,2S,4R,5R,6S,7R)-7-(Methoxycarbonyl)tricyclo[3.2.2.0²,⁴]non-8-ene-6-carboxylic acid

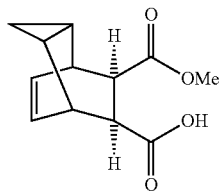

rac-(1R,2S,6R,7S,8S,10R)-4-Oxatetracyclo[5.3.2.0²,⁶.0⁸,¹⁰]dodec-11-ene-3,5-dione (prepared as described in Example 51a, 0.86 g, 4.50 mmol) was dissolved in methanol (20 mL). The reaction was stirred at 25° C. for 72 h. The mixture was concentrated to afford a clear oil. Purification by flash column chromatography (Teledyne Isco RediSep column; 0 to 60% ethyl acetate in hexanes) afforded the desired product, rac-(1S,2S,4R,5R,6S,7R)-7-(Methoxycarbonyl)tricyclo[3.2.2.0²,⁴]non-8-ene-6-carboxylic acid (0.94 g, 4.23 mmol, 94%) as a white solid. ¹H NMR (400 MHz, CDCl₃) δ: 0.06-0.17 (2H, m), 1.26-1.38 (2H, m), 2.74-2.85 (2H, m), 3.15-3.19 (2H, m), 3.67 (3H, s), 5.85-5.86 (2H, m). LC-MS (ESI) calcd for $C_{12}H_{14}O_4$ 222.24, found 223.5 [M+H⁺].

b) rac-Methyl (1R,2R,4S,5S,6R,7S)-7-{[(benzyloxy)carbonyl]amino}tricyclo[3.2.2.0²,⁴]non-8-ene-6-carboxylate

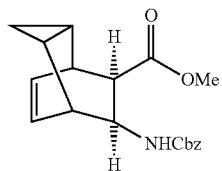

rac-(1S,2S,4R,5R,6S,7R)-7-(Methoxycarbonyl)tricyclo[3.2.2.0²,⁴]non-8-ene-6-carboxylic acid (0.68 g, 3.07 mmol) was dissolved in anhydrous tetrahydrofuran (20 mL). The flask was degassed and backfilled with nitrogen and the mixture was cooled to 0° C. Triethylamine (1.28 mL, 9.21 mmol) was added followed by the dropwise addition of ethyl chloroformate (0.58 mL, 6.14 mmol) with vigorous stirring. The mixture was stirred at 0° C. for 1 h. Sodium azide (0.60 g, 9.21 mmol) was dissolved in water (5 mL) and added to the reaction mixture at 0° C. The mixture was stirred at 0° C. for 5 min. The ice bath was removed. The mixture was warmed to 25° C. and was stirred for 2 h. The mixture was poured into water (70 mL) and the product extracted into ethyl acetate (70 mL). The organic layer was further washed with half-saturated aqueous sodium bicarbonate solution (2×30 mL), saturated aqueous brine solution (30 mL), dried over magnesium sulfate, filtered, and concentrated in vacuo to afford a clear oil. The oil was dissolved in anhydrous benzene (10 mL) and refluxed while stirring under nitrogen for 2 h. Upon cooling to 25° C. the solution was concentrated in vacuo to afford a slightly yellow oil. The oil was dissolved in dichloromethane (10 mL) and benzyl alcohol (0.35 mL, 3.38 mmol) was added followed by triethylamine (0.86 mL, 6.14 mmol). The mixture was refluxed under nitrogen for 16 h. Upon cooling to 25° C. the solution was concentrated in vacuo to afford a golden oil. Purification by flash column chromatography (Teledyne Isco RediSep column; 0 to 20% ethyl acetate in hexanes) afforded the desired product, rac-Methyl (1R,2R,4S,5S,6R,7S)-7-{[(benzyloxy)carbonyl]amino}tricyclo[3.2.2.0²,⁴]non-8-ene-6-carboxylate (0.36 g, 1.10 mmol, 36%) as a clear oil. ¹H NMR (400 MHz, CDCl₃) δ: 0.11-0.19 (2H, m), 0.13-1.34 (2H, m), 2.77-3.03 (3H, m), 3.62 (3H, s), 4.01-4.07 (1H, m), 5.07-5.14 (2H, m), 5.79-5.85 (2H, m), 7.30-7.38 (5H, m). LC-MS (ESI) calcd for $C_{19}H_{21}NO_4$ 327.37, found 328.3 [M+H⁺].

c) rac-Methyl (1R,2R,4S,5S,6R,7S)-7-aminotricyclo[3.2.2.0²,⁴]nonane-6-carboxylate

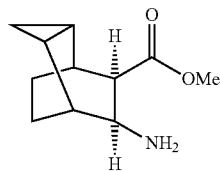

rac-Methyl (1R,2R,4S,5S,6R,7S)-7-{[(benzyloxy)carbonyl]amino}tricyclo[3.2.2.0²,⁴]non-8-ene-6-carboxylate (0.35 g, 1.07 mmol) was dissolved in ethyl acetate (10 mL). 5% Palladium on carbon (0.04 g) was added. The flask was degassed and backfilled with hydrogen gas via balloon. The mixture was stirred at 25° C. for 16 h. The mixture was passed through a plug of Celite and the filtrate was concentrated in vacuo to afford the crude product, rac-Methyl (1R,2R,4S,5S,6R,7S)-7-aminotricyclo[3.2.2.0²,⁴]nonane-6-carboxylate, as a thick clear oil, which was used in the next step without further purification. LC-MS (ESI) calcd for $C_{11}H_{17}NO_2$ (free amine) 195.26, found 196.3 [M+H⁺].

d) rac-Methyl (1R,2R,4S,5S,6R,7S)-7-{[(4-fluorophenyl)methyl]amino}tricyclo[3.2.2.0²,⁴]nonane-6-carboxylate

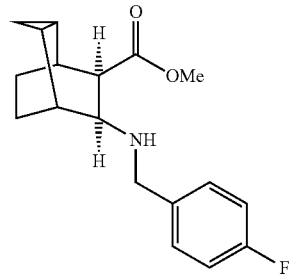

The crude rac-Methyl (1R,2R,4S,5S,6R,7S)-7-aminotricyclo[3.2.2.0²,⁴]nonane-6-carboxylate was dissolved in methanol (10 mL). Acetic acid (0.12 mL, 2.14 mmol) was added followed by 4-fluoro-benzaldehyde (0.12 mL, 1.07 mmol). Sodium cyanoborohydride (0.14 g, 2.14 mmol) was added and the mixture was stirred at 60° C. for 16 h. The mixture was cooled to 25° C. and poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, rac-Methyl (1R,2R,4S,5S,6R,7S)-7-{[(4-fluorophenyl)methyl]amino}tricyclo[3.2.2.0²,⁴]nonane-6-carboxylate, as a clear oil, which was used in the next step without further purification. LC-MS (ESI) calcd for $C_{17}H_{22}FNO_2$ 291.36, found 292.0 [M+H⁺].

e) rac-N-{3-[(1R,2S,7R,8S,9S,11R)-3-[(4-Fluorophenyl)methyl]-6-hydroxy-4-oxo-3-azatetracyclo[6.3.2.0²,⁷.0⁹,¹¹]trideca-5-en-5-yl]-1,1-dioxo-4H-1λ⁶,2,4-benzothiadiazin-7-yl}methanesulfonamide

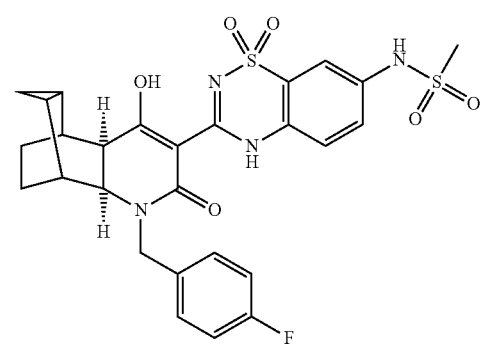

The crude rac-Methyl (1R,2R,4S,5S,6R,7S)-7-{[(4-fluorophenyl)methyl]amino}tricyclo[3.2.2.0²,⁴]nonane-6-carboxylate was dissolved in anhydrous N,N-dimethylformamide (8 mL). (7-Methanesulfonylamino-1,1-dioxo-1,4-dihydro-1λ⁶-benzo[1,2,4]thiadiazin-3-yl)-acetic acid (prepared as described in Example 1g, 0.22 g, 0.66 mmol)

was added followed by N-methylmorpholine (0.15 mL, 1.39 mmol). The mixture was stirred until everything dissolved, approximately 5 min. 1-(3-Dimethylaminopropyl)-3-ethylcarbodiimide hydrochloride (0.13 g, 0.69 mmol) was added and the mixture was stirred at 25° C. for 4 h. Triethylamine (0.28 mL, 1.98 mmol) was added and the mixture was stirred at 50° C. for 16 h. Upon cooling to 25° C., the solution was diluted with ethyl acetate (50 mL) and washed with 1.0 M aqueous hydrochloric acid solution (2×50 mL), saturated aqueous brine solution (20 mL), dried over magnesium sulfate, filtered, and concentrated in vacuo to afford a golden oil. Purification by flash column chromatography (Teledyne Isco RediSep column; 0 to 20% ethyl acetate in dichloromethane) afforded the desired product, rac-N-{3-[(1R,2S,7R,8S,9S,11R)-3-[(4-Fluorophenyl)methyl]-6-hydroxy-4-oxo-3-azatetracyclo[6.3.2.0$^{2,7}$.0$^{9,11}$]trideca-5-en-5-yl]-1,1-dioxo-4H-1$\lambda^6$,2,4-benzothiadiazin-7-yl}methanesulfonamide (0.50 g, 0.86 mmol, 80% over three steps), as a white powder. $^1$H NMR (400 MHz, DMSO-d$_6$) δ: 0.33-1.34 (10H, m), 2.30 (1H, bs), 3.06 (3H, s), 3.81 (1H, d, J=11.2 Hz), 4.48 (1H, d, J=15.6 Hz), 4.98 (1H, d, J=14.8 Hz), 7.13-7.60 (7H, m), 10.19 (1H, s). LC-MS (ESI) calcd for $C_{27}H_{27}FN_4O_6S_2$ 586.65, found 587.3 [M+H$^+$].

Example 53

(1R,2S,7R,8S)-5-(1,1-Dioxo-7-pyrrolidin-1-yl-1,4-dihydro-1$\lambda^6$-benzo[1,2,4]thiadiazin-3-yl)-6-hydroxy-3-(3-methyl-butyl)-3-aza-tricyclo[6.2.1.0$^{2,7}$]undec-5-en-4-one

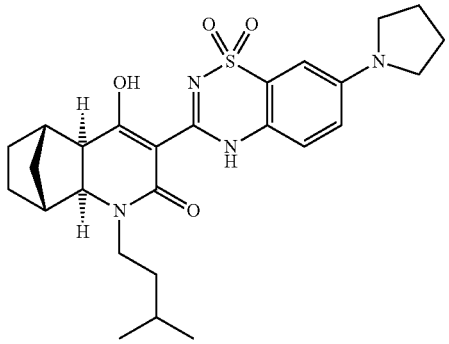

Pyrrolidine (15 mL, 0.180 mmol), sarcosine (N-methyl glycine) (3.2 mg, 0.018 mmol), copper (I) iodide (3.4 mg, 0.018 mmol), and potassium phosphate (57.3 mg, 0.270 mmol) were placed in a flask under a nitrogen atmosphere. (1R,2S,7R,8S)-6-Hydroxy-5-(7-iodo-1,1-dioxo-1,4-dihydro-1$\lambda^6$-benzo[1,2,4]thiadiazin-3-yl)-3-(3-methyl-butyl)-3-aza-tricyclo[6.2.1.0$^{2,7}$]undec-5-en-4-one (prepared as described in Example 34, 50 mg, 0.090 mmol) was dissolved in N,N-dimethylformamide (1 mL) and added to the above mixture. The mixture was stirred at 80° C. for 26 h. Additional pyrrolidine (50 µL, 0.60 mmol), sarcosine (N-methyl glycine) (10 mg, 0.056 mmol), and copper (I) iodide (15 mg, 0.079 mmol) were added and the mixture was stirred at 80° C. for another 16 h until LC-MS analysis indicated completion of the reaction. The reaction was repeated at the same scale as described above and after stirring at 80° C. for 24 h, additional pyrrolidine (50 µL, 0.60 mmol), sarcosine (N-methyl glycine) (10 mg, 0.056 mmol), and copper (I) iodide (15 mg, 0.079 mmol) were added and the mixture was stirred at 80° C. for another 18 h until LC-MS analysis indicated completion of the reaction. Both batches were combined and filtered through a plug of Celite. The filter cake was washed with 10% methanol in dichloromethane (2×2 mL) and N,N-dimethylformamide (2 mL). The filtrate was concentrated in vacuo and the residue was purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (1R,2S,7R,8S)-5-(1,1-dioxo-7-pyrrolidin-1-yl-1,4-dihydro-1$\lambda^6$-benzo[1,2,4]thiadiazin-3-yl)-6-hydroxy-3-(3-methyl-butyl)-3-aza-tricyclo[6.2.1.0$^{2,7}$]undec-5-en-4-one (36.7 mg, 0.074 mmol, 40.9%), as a yellow solid. $^1$H NMR (400 MHz, DMSO-d$_6$) δ: 0.92 (6H, d, J=5.5 Hz), 1.21-1.60 (9H, m), 1.96-1.99 (4H, m), 2.52-2.52 (1H, m), 2.62-2.65 (1H, m), 2.94-2.98 (1H, m), 3.03-3.10 (1H, m), 3.27-3.30 (4H, m), 3.60-3.71 (2H, m), 6.71 (1H, d, J=2.3 Hz), 6.90 (1H, dd, J$_1$=9.2 Hz, J$_2$=2.7 Hz), 7.41 (1H, d, J=9.5 Hz). LC-MS (ESI) calcd for $C_{26}H_{34}N_4O_4S$ 498.23, found 499.4 [M+H$^+$]. Anal. calcd for $C_{26}H_{34}N_4O_4S \cdot 0.5H_2O$: C, 61.51; H, 6.95; N, 11.04. found: C, 61.45, H, 6.74, N, 10.91.

Example 54

Pyridine-3-sulfonic acid{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide

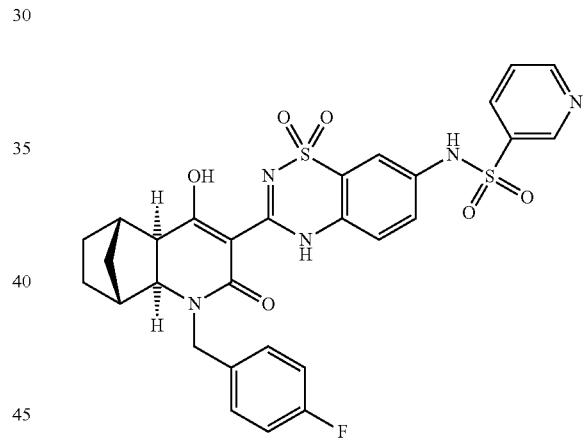

(1R,2S,7R,8S)-3-(4-Fluoro-benzyl)-6-hydroxy-5-(7-iodo-1,1-dioxo-1,4-dihydro-1$\lambda^6$-benzo[1,2,4]thiadiazin-3-yl)-3-aza-tricyclo[6.2.1.0$^{2,7}$]undec-5-en-4-one (prepared as described in Example 19, 100 mg, 0.17 mmol), pyridine-3-sulfonic acid amide (81 mg, 0.51 mmol), sarcosine (N-methyl glycine) (23 mg, 0.26 mmol), copper (I) iodide (33 mg, 0.17 mmol), and potassium phosphate (216 mg, 1.02 mmol) were combined and dissolved in N,N-dimethylformamide (10 mL). The flask was degassed and backfilled with nitrogen (3×). The reaction was stirred at 100° C. for 4 h. The mixture was cooled to 25° C., diluted with ethyl acetate (20 mL), and extracted with saturated aqueous sodium bicarbonate solution (2×20 mL). The combined organic layers were dried over magnesium sulfate, filtered, and concentrated in vacuo. Purification by flash column chromatography (Teledyne Isco RediSep column; 0 to 8% methanol in dichloromethane) afforded the desired product, pyridine-3-sulfonic acid{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-amide (56 mg, 0.09 mmol, 54%), as a white powder. ¹H NMR (400 MHz, DMSO-d₆) δ: 1.38-1.58 (6H, m), 2.61 (1H, s), 3.00 (1H, d, J=7.6 Hz), 3.52 (1H, d, J=8.4 Hz), 4.40 (1H, d, J=15.6 Hz), 4.94 (1H, d, J=15.2 Hz), 7.13 (2H, t, J=8.4 Hz), 7.29-7.32 (2H, m), 7.42-7.50 (3H, m), 7.60-7.63 (1H, m), 8.11 (1H, d, J=7.6 Hz), 8.79 (1H, d, J=4.4 Hz), 8.87 (1H, s), 10.94 (1H, s), 13.99 (1H, s). LC-MS (ESI) calcd for $C_{29}H_{26}FN_5O_6S_2$ 623.68, found 624.2 [M+H⁺].

Example 55

(1R,2S,7R,8S)-N-{3-[3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamide

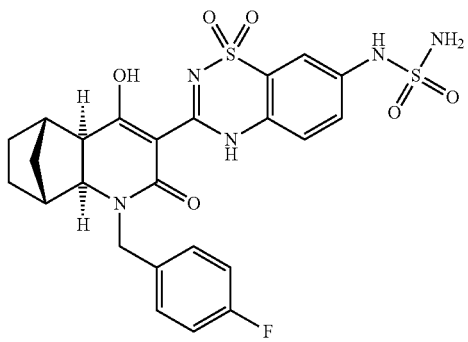

a) Benzyl [N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamoyl]carbamate

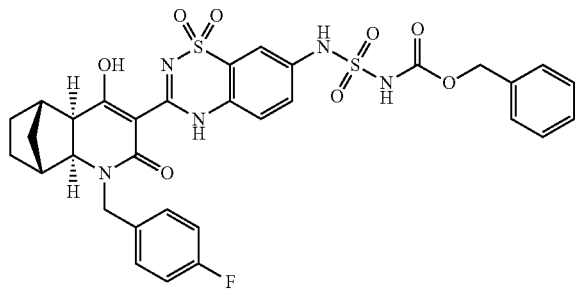 [SMILES: O=C(NS(=O)(=O)Nc1ccc2c(c1)S(=O)(=O)N=C(C1=C(O)[C@@H]3[C@H]4CC[C@H](C4)[C@@H]3N(Cc3ccc(F)cc3)C1=O)N2)OCc1ccccc1]

Benzyl alcohol (35 µL, 0.338 mmol) was dissolved in dichloromethane (3 mL) and cooled to 0° C. Chlorosulfonyl isocyanate (29.4 µL, 0.338 mmol) was added and the mixture was stirred at 0° C. for 2.5 h. Triethylamine (47 µL, 0.34 mmol) followed by a solution of (1R,2S,7R,8S)-5-(7-amino-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (prepared as described in Example 30, 81.4 mg, 0.169 mmol) in dichloromethane (2 mL) were added at 0° C. and the mixture was stirred at 25° C. for 17 h. The mixture was extracted with water (2×2 mL) and saturated aqueous brine solution (2 mL). The organic layer was concentrated in vacuo and further dried for 16 h under high vacuum to afford the crude product, benzyl [N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamoyl]carbamate, which was used in the next step without any further purification. LC-MS (ESI) calcd for $C_{32}H_{30}FN_5O_8S_2$ 695.15, found 696.6 [M+H⁺].

b) (1R,2S,7R,8S)-N-{3-[3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamide

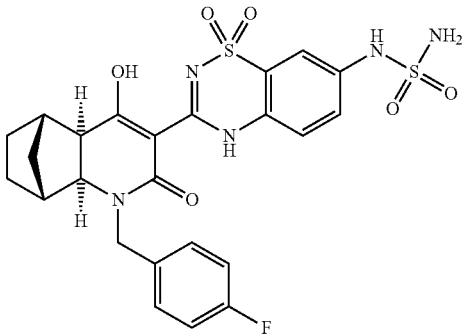

The crude benzyl [N-{3-[(1R,2S,7R,8S)-3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamoyl]carbamate was dissolved in methanol (5 mL) and the mixture was degassed and backfilled with nitrogen (3×). Palladium on carbon (10% dry, 180 mg) was added and the mixture was degassed and backfilled with hydrogen gas via balloon. The mixture was stirred at 25° C. for 16 h. The mixture was passed through a plug of Celite and the filtrate was concentrated in vacuo to afford the crude product, which was further purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, (1R,2S,7R,8S)-N-{3-[3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-sulfamide (55.7 mg, 0.099 mmol, 58.7% over two steps), as a white solid. ¹H NMR (400 MHz, DMSO-d₆) δ: 1.19-1.24 (2H, m), 1.40-1.60 (4H, m), 2.51-2.54 (1H, m), 2.64-2.65 (1H, m), 3.04 (1H, d, J=9.3 Hz), 3.53 (1H, d, J=9.3 Hz), 4.42 (1H, d, J=15.7 Hz), 4.96 (1H, d, J=15.6 Hz), 7.15 (2H, m), 7.31-7.34 (H, m), 7.43 (1H, dd, J₁=9.4 Hz, J₂=2.3 Hz), 7.51-7.55 (2H, m), 9.96 (1H, s). LC-MS (ESI) calcd for $C_{24}H_{24}FN_5O_6S$ 561.12, found 562.5 [M+H⁺]. Anal. calcd for $C_{24}H_{24}FN_5O_6S \cdot 0.5H_2O$: C, 50.51; H, 4.42; N, 12.27. found: C, 50.42, H, 4.35, N, 11.90.

Example 56

(1R,2S,7R,8S)-N-[3-(3-Benzyl-6-hydroxy-4-oxo-3-aza-tricyclo[6.2.1.0²,⁷]undec-5-en-5-yl)-1,1-dioxo-1,4-dihydro-1λ⁶-benzo[1,2,4]thiadiazin-7-yl]-methanesulfonamide

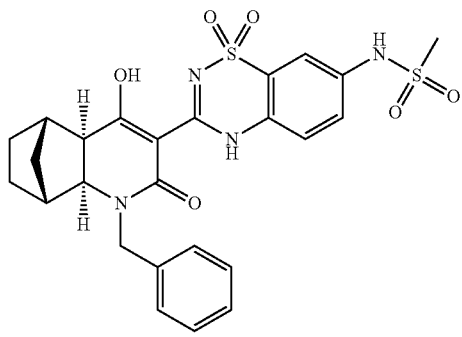 [SMILES: CS(=O)(=O)Nc1ccc2c(c1)S(=O)(=O)N=C(C1=C(O)[C@@H]3[C@H]4CC[C@H](C4)[C@@H]3N(Cc3ccccc3)C1=O)N2]

a) (1S,2R,3S,4R)-3-Benzylamino-bicyclo[2.2.1]heptane-2-carboxylic acid ethyl ester

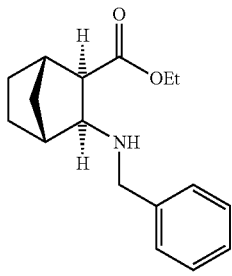

Benzaldehyde (0.454 mL, 4.47 mmol) and 10 drops glacial acetic acid were added sequentially to a solution of (1S,2R,3S,4R)-3-amino-bicyclo[2.2.1]heptane-2-carboxylic acid ethyl ester (prepared as described in Example 6k, 0.82 g, 4.47 mmol) in methanol (15 mL) at 25° C. Sodium cyanoborohydride (0.703 g, 11.2 mmol) was added, and the reaction mixture was stirred at 25° C. for 2 h, and then was partitioned between half-saturated aqueous sodium bicarbonate solution (150 mL) and ethyl acetate (2×150 mL). The organic layers were dried over sodium sulfate, filtered and concentrated in vacuo. The residue was purified by flash column chromatography (Teledyne Isco RediSep column; 0 to 35% ethyl acetate in hexanes) to afford the desired product, (1S,2R,3S,4R)-3-benzylamino-bicyclo[2.2.1]heptane-2-carboxylic acid ethyl ester (0.875 g, 3.22 mmol, 72%), as a clear oil. $^1$H NMR (400 MHz, CDCl$_3$) δ: 1.06-1.16 (2H, m), 1.20-1.23 (2H, m), 1.28 (3H, t, J=7.0 Hz), 1.46-1.61 (2H, m), 1.93-1.97 (1H, m), 2.33-2.34 (1H, m), 2.43-2.44 (1H, m), 2.59-2.62 (1H, m), 2.98-3.00 (1H, m), 3.71 (1H, d, J=14.0 Hz), 3.85 (1H, d, J=13.3 Hz), 4.14 (2H, q, J=7.3 Hz), 7.20-7.24 (1H, m), 7.27-7.33 (4H, m).

b) (1R,2S,7R,8S)-N-[3-(3-Benzyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

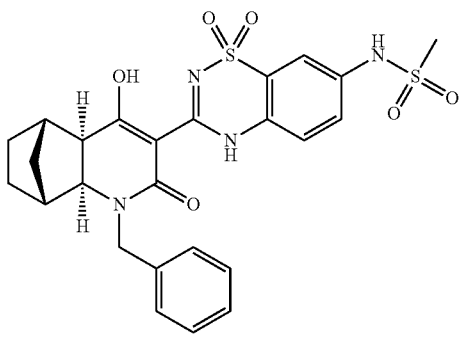 [SMILES: CS(=O)(=O)Nc1ccc2c(c1)S(=O)(=O)N=C(C1=C(O)[C@@H]3[C@H]4CC[C@H](C4)[C@@H]3N(Cc3ccccc3)C1=O)N2]

(7-Methanesulfonylamino-1,1-dioxo-1,4-dihydro-1λ$^6$-benzo[1,2,4]thiadiazin-3-yl)-acetic acid (prepared as described in Example 1g, 0.200 g, 0.600 mmol), 1-(3-dimethylaminopropyl)-3-ethylcarbodiimide hydrochloride (0.121 g, 0.631 mmol) and N-methylmorpholine (0.139 mL, 1.26 mmol) were added sequentially to a solution of (1S,2R,3S,4R)-3-benzylamino-bicyclo[2.2.1]heptane-2-carboxylic acid ethyl ester (0.164 g, 0.600 mmol) in N,N-dimethylformamide (5 mL) at 25° C. The reaction mixture was stirred at 25° C. for 2 h, and then was partitioned between 1.0 M aqueous hydrochloric acid solution (100 mL) and ethyl acetate (2×100 mL). The organic layers were dried over sodium sulfate, filtered and concentrated in vacuo. The residue was dissolved in ethanol (15 mL) at 25° C. A 21 wt. % solution of sodium ethoxide in ethanol (0.972 mL, 3.00 mmol) was added and the reaction mixture was heated at 60° C. for 1 h. After cooling to 25° C., the reaction mixture was partitioned between a 1.0 M aqueous hydrochloric acid solution (100 mL) and ethyl acetate (2×100 mL). The organic layers were dried over sodium sulfate, filtered and concentrated in vacuo. The residue was purified by flash column chromatography (Teledyne Isco RediSep column; 40 to 100% ethyl acetate in hexanes) to afford the desired product, (1R,2S,7R,8S)-N-[3-(3-benzyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (0.120 g, 0.222 mmol, 37%), as a white solid. $^1$H NMR (400 MHz, DMSO-d$_6$) δ: 1.15-1.21 (2H, m), 1.39-1.61 (4H, m), 2.52 (1H, bs), 2.64 (1H, bs), 3.05 (3H, s), 3.30 (2H, bs), 3.54 (1H, d, J=9.5 Hz), 4.43 (1H, d, J=16.4 Hz), 4.99 (1H, d, J=15.5 Hz), 7.23-7.28 (2H, m), 7.33 (2H, m), 7.48-7.51 (2H, m), 7.55-7.57 (2H, m), 10.17 (1H, s). LC-MS (ESI) calcd for C$_{25}$H$_{26}$N$_4$O$_6$S$_2$ 542.13, found 543.2 [M+H$^+$].

Example 57

(1R,2S,7R,8S)-N-[3-(6-Hydroxy-3-isobutyl-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

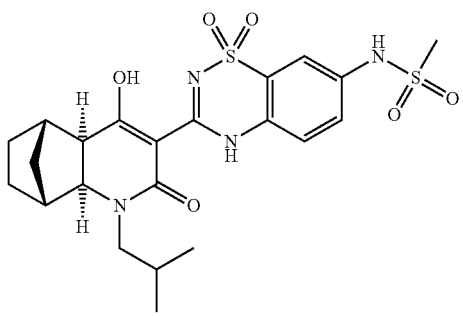

a) (1S,2R,3S,4R)-3-Isobutylamino-bicyclo[2.2.1]heptane-2-carboxylic acid ethyl ester

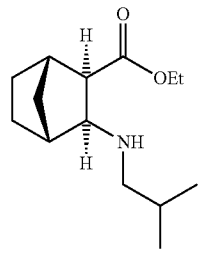

Isovaleraldehyde (0.374 mL, 4.10 mmol) and 10 drops glacial acetic acid were added sequentially to a solution of (1S,2R,3S,4R)-3-amino-bicyclo[2.2.1]heptane-2-carboxylic acid ethyl ester (prepared as described in Example 6k, 0.750 g, 4.09 mmol) in methanol (12 mL) at 25° C. Sodium cyanoborohydride (0.643 g, 10.2 mmol) was added, and the reaction mixture was stirred at 25° C. for 2 h, and then was partitioned between half-saturated aqueous sodium bicarbonate solution (150 mL) and ethyl acetate (2×150 mL). The organic layers were dried over sodium sulfate, filtered and concentrated in vacuo to afford the desired product, (1S,2R,3S,4R)-3-isobutylamino-bicyclo[2.2.1]heptane-2-carboxylic acid ethyl ester, as a clear oil, which was used in the next step without any further purification.

b) (1R,2S,7R,8S)-N-[3-(6-Hydroxy-3-isobutyl-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

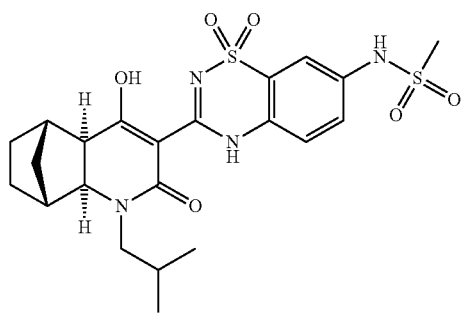

(7-Methanesulfonylamino-1,1-dioxo-1,4-dihydro-1λ$^6$-benzo[1,2,4]thiadiazin-3-yl)-acetic acid (prepared as described in Example 1g, 0.317 g, 0.951 mmol), 1-(3-dimethylaminopropyl)-3-ethylcarbodiimide hydrochloride (0.192 g, 1.00 mmol) and N-methylmorpholine (0.220 mL, 2.00 mmol) were added sequentially to a solution of crude (1S,2R,3S,4R)-3-isobutylamino-bicyclo[2.2.1]heptane-2-carboxylic acid ethyl ester (0.228 g, 0.952 mmol) in N,N-dimethylformamide (4 mL) at 25° C. The reaction mixture was stirred at 25° C. for 2 h, and then was partitioned between 1.0 M aqueous hydrochloric acid solution (100 mL) and ethyl acetate (2×100 mL). The organic layers were dried over sodium sulfate, filtered and concentrated in vacuo. The residue was dissolved in ethanol (15 mL) at 25° C. A 21 wt. % solution of sodium ethoxide in ethanol (1.23 mL, 3.80 mmol) was added and the reaction mixture was heated at 60° C. for 1.5 h. After cooling to 25° C., the reaction mixture was partitioned between 1.0 M aqueous hydrochloric acid solution (150 mL) and ethyl acetate (2×150 mL). The organic layers were dried over sodium sulfate, filtered and concentrated in vacuo. The residue was purified by flash column chromatography (Teledyne Isco RediSep column; 40 to 100% ethyl acetate in hexanes) to afford the desired product, (1R,2S,7R,8S)-N-[3-(6-hydroxy-3-isobutyl-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (0.096 g, 0.190 mmol, 20%), as a white solid. $^1$H NMR (400 MHz, DMSO-d$_6$) δ: 0.83 (3H, d, J=7.2 Hz), 0.93 (3H, d, J=7.1 Hz), 1.19-1.21 (1H, m), 1.28-1.32 (1H, m), 1.43-1.63 (3H, m), 2.09-2.15 (1H, m), 2.54 (1H, bs), 2.61-2.61 (1H, m), 2.74-2.79 (1H, m), 3.05 (3H, s), 3.30 (1H, bs), 3.60 (1H, d, J=9.2 Hz), 3.73-3.79 (1H, m), 7.49-7.52 (1H, m), 7.56-7.58 (2H, m), 10.17 (1H, s). LC-MS (ESI) calcd for C$_{22}$H$_{28}$N$_4$O$_6$S$_2$ 508.15, found 509.4 [M+H$^+$].

Example 58

(1R,2S,7R,8S)-N-{3-[3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

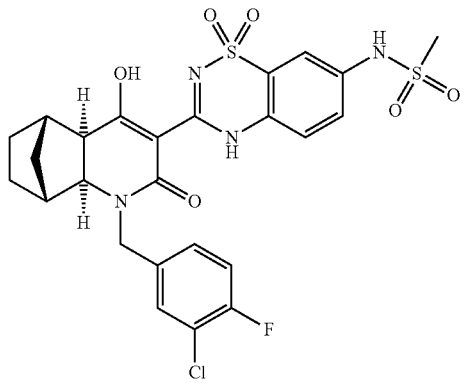

a) (1S,2R,3S,4R)-3-(3-Chloro-4-fluoro-benzylamino)-bicyclo[2.2.1]heptane-2-carboxylic acid ethyl ester

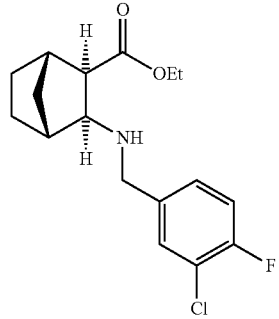

3-Chloro-4-fluoro-benzaldehyde (0.710 mL, 4.48 mmol) and 10 drops glacial acetic acid were added sequentially to a solution of (1S,2R,3S,4R)-3-amino-bicyclo[2.2.1]heptane-2-carboxylic acid ethyl ester (prepared as described in Example 6k, 0.82 g, 4.47 mmol) in methanol (15 mL) at 25° C. Sodium cyanoborohydride (0.709 g, 11.3 mmol) was added, and the reaction mixture was stirred at 25° C. for 2 h, and then was partitioned between half-saturated aqueous sodium bicarbonate solution (150 mL) and ethyl acetate (2×150 mL). The organic layers were dried over sodium sulfate, filtered and concentrated in vacuo. The residue was purified by flash column chromatography (Teledyne Isco RediSep column; 0 to 35% ethyl acetate in hexanes) to afford the desired product, (1S,2R,3S,4R)-3-(3-chloro-4-fluoro-benzylamino)-bicyclo[2.2.1]heptane-2-carboxylic acid ethyl ester (1.12 g, 3.44 mmol, 77%), as a clear oil. $^1$H NMR (400 MHz, CDCl$_3$) δ: 1.04-1.16 (2H, m), 1.18-1.24 (2H, m), 1.29 (3H, t, J=7.4 Hz), 1.44-1.61 (2H, m), 1.91-1.94 (1H, m), 2.27-2.28 (1H, m), 2.42-2.43 (1H, m), 2.60 (1H, d, J=7.7 Hz), 2.91 (1H, d, J=8.8 Hz), 3.64 (1H, d, J=13.9 Hz), 3.79 (1H, d, J=14.2 Hz), 4.14 (2H, q, J=7.0 Hz), 7.02-7.06 (1H, m), 7.13-7.17 (1H, m), 7.36-7.38 (1H, m).

b) (1R,2S,7R,8S)-N-{3-[3-(3-Chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

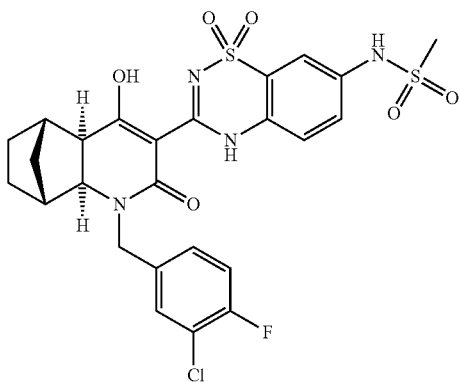

(7-Methanesulfonylamino-1,1-dioxo-1,4-dihydro-1λ$^6$-benzo[1,2,4]thiadiazin-3-yl)-acetic acid (prepared as described in Example 1g, 0.258 g, 0.774 mmol), 1-(3-dimethylaminopropyl)-3-ethylcarbodiimide hydrochloride (0.156 g, 0.814 mmol) and N-methylmorpholine (0.170 mL, 1.55 mmol) were added sequentially to a solution of (1S,2R,3S,4R)-3-(3-chloro-4-fluoro-benzylamino)-bicyclo[2.2.1]heptane-2-carboxylic acid ethyl ester (0.252 g, 0.773 mmol) in N,N-dimethylformamide (4 mL) at 25° C. The reaction mixture was stirred at 25° C. for 2 h, and then was partitioned between 1.0 M aqueous hydrochloric acid solution (100 mL) and ethyl acetate (2×100 mL). The organic layers were dried over sodium sulfate, filtered and concentrated in vacuo. The residue was dissolved in ethanol (20 mL) at 25° C. A 21 wt. % solution of sodium ethoxide in ethanol (1.00 mL, 3.09 mmol) was added and the reaction mixture was heated at 60° C. for 1 h. After cooling to 25° C., the reaction mixture was partitioned between 1.0 M aqueous hydrochloric acid solution (100 mL) and ethyl acetate (2×100 mL). The organic layers were dried over sodium sulfate, filtered and concentrated in vacuo. The residue was purified by flash column chromatography (Teledyne Isco RediSep column; 40 to 100% ethyl acetate in hexanes) to afford the desired product, (1R,2S,7R,8S)-N-{3-[3-(3-chloro-4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.196 g, 0.332 mmol, 43%), as a white solid. $^1$H NMR (400 MHz, DMSO-d$_6$) δ: 1.04-1.21 (4H, m), 1.40-1.60 (3H, m), 2.54-2.63 (1H, m), 3.05 (3H, s), 3.31-3.40 (2H, m), 3.55-3.58 (1H, m), 4.45 (1H, d, J=16.1 Hz), 4.91 (1H, d, J=14.7 Hz), 7.31-7.35 (2H, m), 7.51-7.57 (4H, m), 10.17 (1H, s), 13.96 (1H, s). LC-MS (ESI) calcd for C$_{25}$H$_{24}$ClFN$_4$O$_6$S$_2$ 594.08, found 595.3 [M+H$^+$].

Example 59

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide

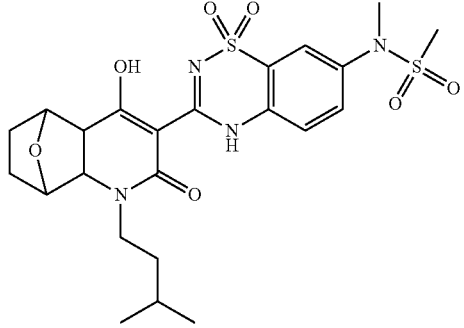

(rac-di-exo)-N-{3-[6-Hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 25, 67 mg, 0.128 mmol) was dissolved in N,N-dimethylformamide (2 mL). Potassium carbonate (35 mg, 0.25 mmol) and iodomethane (0.008 mL, 0.128 mmol) were added sequentially. The reaction was stirred at 25° C. for 2 h. The reaction was quenched via the addition of 1.0 M aqueous hydrochloric acid solution (20 mL). The mixture was extracted with ethyl acetate (2×100 mL). The combined organic layers were washed with saturated aqueous brine solution (50 mL), dried over sodium sulfate, filtered, and concentrated in vacuo to afford an oil. Purification by flash column chromatography (Teledyne Isco RediSep column; 0 to 100% ethyl acetate in hexanes) afforded the desired product, (rac-di-exo)-N-{3-[6-hydroxy-3-(3-methyl-butyl)-4-oxo-11-oxa-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-N-methyl-methanesulfonamide (36 mg, 0.067 mmol, 52%), as a white solid. $^1$H NMR (400 MHz, DMSO-d$_6$) δ: 0.92 (6H, d, J=6.2 Hz), 1.16-1.65 (7H, m), 2.79-2.93 (2H, m), 2.96 (3H, s), 3.26 (3H, s), 3.62-3.69 (1H, m), 3.76-3.83 (1H, m), 4.60 (2H, d, J=21.8 Hz), 7.27 (1H, d, J=7.3 Hz), 7.55 (1H, d, J=8.5 Hz), 7.65 (1H, s). LC-MS (ESI) calcd for C$_{23}$H$_{30}$N$_4$O$_7$S$_2$ 538.16, found 539.4 [M+H$^+$].

Example 60

N-{3-[(1R,2S,7R,8S)-3-(3-Fluoro-4-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

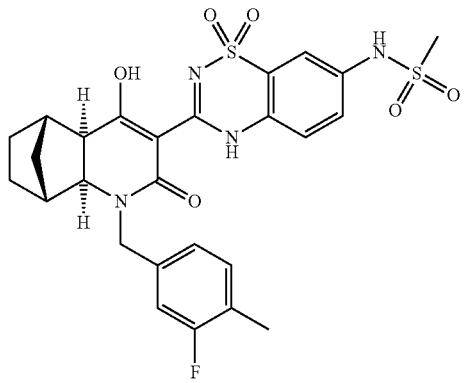

a) (1S,2R,3S,4R)-3-(3-Fluoro-4-methyl-benzylamino)-bicyclo[2.2.1]heptane-2-carboxylic acid ethyl ester

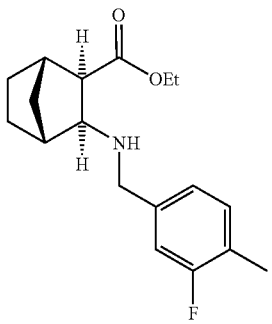

(1S,2R,3S,4R)-3-Amino-bicyclo[2.2.1]heptane-2-carboxylic acid ethyl ester (prepared as described in Example 6k, 300 mg, 1.637 mmol) was suspended in ethanol (5 mL). 3-Fluoro-4-methyl-benzaldehyde (0.2 mL, 1.637 mmol) was added followed by glacial acetic acid (0.1 mL, 3.724 mmol) and 4 Å powdered molecular sieves (0.6 g). Sodium cyanoborohydride (0.593 g, 9.406 mmol) was added and the mixture was stirred under nitrogen at 50° C. for 18 h. Upon cooling, the mixture was filtered through Celite. The filtrate was diluted with half-saturated aqueous sodium bicarbonate solution (50 mL) and extracted with ethyl acetate (2×75 mL). The layers were separated and the organic layer was washed with saturated aqueous brine solution, dried over sodium sulfate, filtered, and concentrated in vacuo. Further purification by flash column chromatography (Teledyne Isco RediSep column; 1$^{st}$ column: 0 to 25% ethyl acetate in hexanes; 2$^{nd}$ column: 0 to 20% ethyl acetate in hexanes) afforded the desired product, (1S,2R,3S,4R)-3-(3-fluoro-4-methyl-benzylamino)-bicyclo[2.2.1]heptane-2-carboxylic acid ethyl ester (221 mg, 0.724 mmol, 44%), as a clear thick oil. $^1$H NMR (400 MHz, CDCl$_3$) δ: 1.04-1.15 (2H, m), 1.21 (1H, d, J=10.1 Hz), 1.29 (3H, t, J=7.1 Hz), 1.42-1.63 (4H, m), 1.94 (1H, dt, J$_1$=10.2 Hz, J$_2$=2.0 Hz), 2.25 (3H, s), 2.43 (1H, d, J=3.5 Hz), 2.59 (1H, dd, J$_1$=8.6 Hz, J$_2$=1.6 Hz), 2.93 (1H, dd, J$_1$=8.6 Hz, J$_2$=1.6 Hz), 3.65 (1H, d, J=13.4 Hz), 3.79 (1H, d, J=14.2 Hz), 4.15 (2H, q, J=7.1 Hz), 6.94 (1H, d, J=7.9 Hz), 6.98 (1H, d, J=10.9 Hz), 7.08 (1H, t, J=7.8 Hz). LC-MS (ESI) calcd for C$_{18}$H$_{24}$FNO$_2$ 305.18, found 305.9 [M+H$^+$].

b) (1S,2R,3S,4R)-3-{(3-Fluoro-4-methyl-benzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester

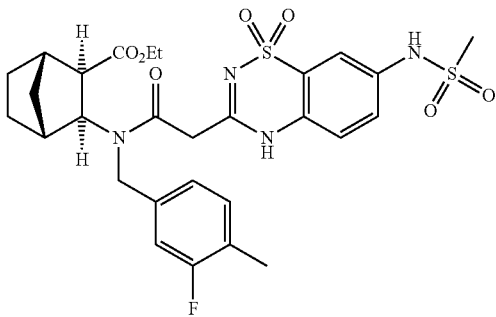

To a solution of (1S,2R,3S,4R)-3-(3-fluoro-4-methyl-benzylamino)-bicyclo[2.2.1]heptane-2-carboxylic acid ethyl ester (92 mg, 0.30 mmol), (7-methanesulfonylamino-1,1-dioxo-1,4-dihydro-1λ$^6$-benzo[1,2,4]thiadiazin-3-yl)-acetic acid (prepared as described in Example 1g, 100 mg, 0.30 mmol) and 1-[3-(dimethylamino)propyl]-3-ethylcarbodiimide hydrochloride (60 mg, 0.315 mmol) in N,N-dimethylformamide (4.0 mL) was added N-methylmorpholine (0.07 mL, 0.63 mmol). After stirring at 25° C. for 3 h, the mixture was poured into a 1.0 M aqueous hydrochloric acid solution and extracted with ethyl acetate (2×100 mL). The combined organic layers were washed with saturated aqueous brine solution, dried over sodium sulfate, filtered, and concentrated in vacuo to afford the crude product, (1S,2R,3S,4R)-3-{(3-fluoro-4-methyl-benzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester, as an orange oil. The crude product was used in the next step without further purification. LC-MS (ESI) calcd for C$_{28}$H$_{33}$FN$_4$O$_7$S$_2$ 620.18, found 621.4 [M+H$^+$].

c) N-{3-[(1R,2S,7R,8S)-3-(3-Fluoro-4-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

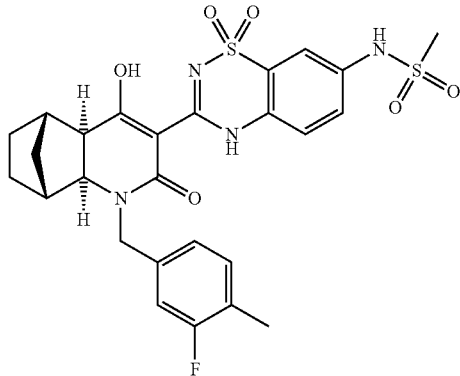

The crude (1S,2R,3S,4R)-3-{(3-fluoro-4-methyl-benzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester was dissolved in ethanol (5 mL) at 25° C. A 21 wt. % solution of sodium ethoxide in ethanol (0.224 mL, 0.60 mmol) was added and the reaction mixture was heated at 60° C. for 90 min. After cooling to 25° C., the reaction mixture stirred for 18 h at 25° C. The mixture was partitioned between a 1.0 M aqueous hydrochloric acid solution (100 mL) and ethyl acetate (2×100 mL). The organic layers were washed with saturated aqueous brine solution, dried over sodium sulfate, filtered and concentrated in vacuo. The residue was purified by flash column chromatography (Teledyne Isco RediSep column; 1$^{st}$ column: 0 to 10% ethyl acetate in hexanes; 2$^{nd}$ column: 30 to 80% ethyl acetate in hexanes) to afford the desired product, N-{3-[(1R,2S,7R,8S)-3-(3-fluoro-4-methyl-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (53 mg, 0.092 mmol, 31% over two steps), as a white solid. $^1$H NMR (400 MHz, DMSO-d$_6$) δ: 1.12-1.21 (2H, m), 1.39-1.64 (4H, m), 2.20 (3H, s), 2.63 (1H, bs), 3.02 (1H, d, J=9.9 Hz), 3.06 (3H, s), 3.54 (1H, d, J=9.3 Hz), 4.42

(1H, d, J=15.5 Hz), 4.92 (1H, d, J=15.5 Hz), 7.01-7.07 (2H, m), 7.23 (1H, t, J=8.1 Hz), 7.49-7.58 (3H, m), 10.17 (1H, s). LC-MS (ESI) calcd for $C_{26}H_{27}FN_4O_6S_2$ 574.14, found 575.4 [M+H$^+$].

Example 61

(1R,2S,7R,8S)-5-(7-Bromo-1,1-dioxo-1,4-dihydro-1λ$^6$-pyrido[2,3-e][1,2,4]thiadiazin-3-yl)-3-(4-fluoro-benzyl-6-hydroxy-3-aza-tricyclo[6.2.1.0$^{2,7}$]undec-5-en-4-one

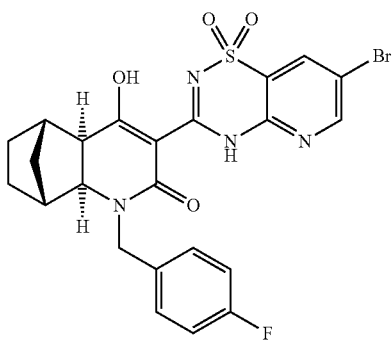

a) 2-Amino-5-bromo-pyridine-3-sulfonic acid amide

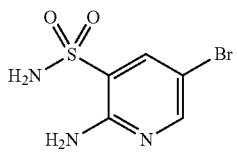 [SMILES: Nc1ncc(Br)cc1S(N)(=O)=O]

5-Bromo-pyridin-2-ylamine (10 g, 57.8 mmol) was added to chlorosulfonic acid (40 mL, 602 mmol) while stirring at 25° C. The mixture was heated at 160° C. while stirring for 3 h. Upon cooling to 25° C., the brown solution was carefully poured over ice (~500 g). The resulting precipitate was collected by vacuum filtration and rinsed with water to afford the intermediate, 2-amino-5-bromo-pyridine-3-sulfonyl chloride, as a beige solid. The solid was suspended in a 15% aqueous ammonium hydroxide solution. The reaction mixture stirred for 45 min. Everything was completely dissolved at this point. The mixture was cooled to 0° C. and the pH was adjusted to ~8 by the careful addition of 12.0 M aqueous hydrochloric acid solution. A solid precipitated and was collected by vacuum filtration, rinsed with water (2×50 mL) and dried in vacuo to afford the desired product, 2-amino-5-bromo-pyridine-3-sulfonic acid amide (7.48 g, 29.7 mmol, 51%), as a light beige solid. $^1$H NMR (400 MHz, DMSO-d$_6$) δ: 6.69 (2H, bs), 7.54 (2H, bs), 7.91 (1H, d, J=2.5 Hz), 8.22 (1H, d, J=2.3 Hz).

b) N-(5-Bromo-3-sulfamoyl-pyridin-2-yl)-malonamic acid ethyl ester

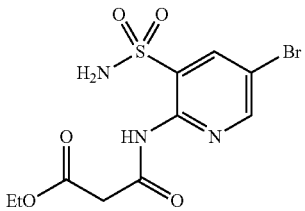 [SMILES: CCOC(=O)CC(=O)Nc1ncc(Br)cc1S(N)(=O)=O]

2-Amino-5-bromo-pyridine-3-sulfonic acid amide (2.5 g, 9.9 mmol) was dissolved in 1,4-dioxane (50 mL). Chlorocarbonyl-acetic acid ethyl ester (1.9 mL, 14.85 mmol) was added and the mixture was heated at 90° C. while stirring for 2 h. Upon cooling to 25° C., the mixture was poured into half-saturated aqueous sodium bicarbonate solution (250 mL). A solid precipitated and was collected by vacuum filtration, rinsed with water (50 mL) and dried in vacuo to afford the desired product, N-(5-bromo-3-sulfamoyl-pyridin-2-yl)-malonamic acid ethyl ester (2.5 g, 6.82 mmol, 69%), as a light beige solid. $^1$H NMR (400 MHz, DMSO-d$_6$) δ: 1.19 (3H, t, J=7.0 Hz), 3.67 (2H, s), 4.10 (2H, q, J=7.3 Hz), 7.78 (2H, bs), 8.33 (1H, d, J=2.3 Hz), 8.70 (1H, d, J=2.4 Hz), 9.85 (1H, bs).

c) (7-Bromo-1,1-dioxo-1,4-dihydro-1λ$^6$-pyrido[2,3-e][1,2,4]thiadiazin-3-yl)-acetic acid ethyl ester

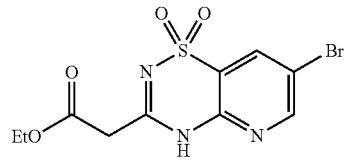 [SMILES: CCOC(=O)CC1=NS(=O)(=O)c2cc(Br)cnc2N1]

In a sealed tube, N-(5-Bromo-3-sulfamoyl-pyridin-2-yl)-malonamic acid ethyl ester (2.2 g, 6.0 mmol) was suspended in toluene (44 mL) and triethylamine (11 mL, 78.9 mmol) was added. The mixture was heated at 110° C. while stirring for 30 min. The solid was completely dissolved, yet an immiscible, oily residue was observed along the bottom of the flask. Upon cooling to 25° C., ethyl acetate (~50 mL) was added. Everything became miscible. The solution was concentrated in vacuo to afford a golden oil. The oil was dissolved in methanol (~50 mL) and concentrated in vacuo to afford the crude product, (7-bromo-1,1-dioxo-1,4-dihydro-1λ$^6$-pyrido[2,3-e][1,2,4]thiadiazin-3-yl)-acetic acid ethyl ester (2.18 g, >6.0 mmol, 100%, still contained some solvent), as a golden oil. LC-MS (ESI) calcd for $C_{10}H_{10}BrN_3O_4S$ 346.96, found 348.1 (100%), 349.2 (10%), 350.2 (99%) [M+H$^+$].

d) Sodium-(7-bromo-1,1-dioxo-1,4-dihydro-1λ$^6$-pyrido[2,3-e][1,2,4]thiadiazin-3-yl)-acetate

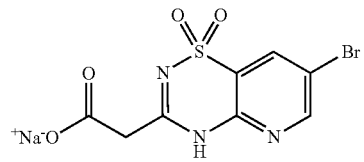

The crude (7-bromo-1,1-dioxo-1,4-dihydro-1λ⁶-pyrido[2,3-e][1,2,4]thiadiazin-3-yl)-acetic acid ethyl ester (1.14 g, 3.27 mmol) was dissolved in methanol (20 mL). Solid sodium hydroxide (0.392 g, 9.8 mmol) was added followed by water (10 mL). Everything was completely dissolved within ~5 minutes. After ~20 minutes, a solid began to precipitate. The mixture continued to stir for 10 min. The product was collected by vacuum filtration, rinsed with methanol (~5 mL) and dried under vacuum to afford the desired product, sodium-(7-bromo-1,1-dioxo-1,4-dihydro-1λ⁶-pyrido[2,3-e][1,2,4]thiadiazin-3-yl)-acetate (0.48 g, 1.5 mmol, 46%), as a white solid. $^1$H NMR (400 MHz, D$_2$O) δ: 3.30 (2H, s), 8.31 (1H, d, J=2.2 Hz), 8.57 (1H, d, J=1.6 Hz). Note: Successive NMR acquisitions of the product in DMSO-d$_6$ indicated decarboxylation over a period of ~30 min to afford 7-bromo-3-methyl-4H-pyrido[2,3-e][1,2,4]thiadiazine 1,1-dioxide. However, the product appears to be stable as the solid sodium salt form.

e) (1R,2S,7R,8S)-5-(7-Bromo-1,1-dioxo-1,4-dihydro-1λ⁶-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one

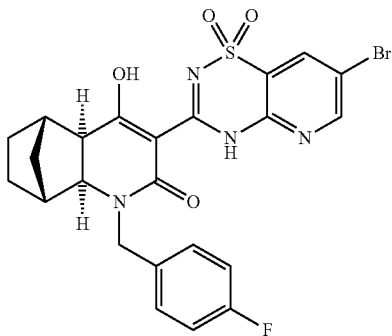

(1S,2R,3S,4R)-3-(4-Fluoro-benzylamino)-bicyclo[2.2.1]heptane-2-carboxylic acid ethyl ester (prepared as described in Example 61, 0.213 g, 0.73 mmol), sodium-(7-bromo-1,1-dioxo-1,4-dihydro-1λ⁶-pyrido[2,3-e][1,2,4]thiadiazin-3-yl)-acetate (0.25 g, 0.73 mmol) and O-(7-azabenzotriazol-1-yl)-1,1,3,3-tetramethyluronium hexafluorophosphate (0.305 g, 0.803 mmol) were combined and dissolved in N,N-dimethylformamide (1.5 mL). The mixture was shaken vigorously for about 1 min until everything dissolved. The solution continued to stir for 1 h. Triethylamine (0.5 mL, 3.65 mmol) was added and the mixture was stirred at 50° C. for 16 h. The mixture was concentrated in vacuo to a volume of ~5 mL. Water (~20 mL) was added and the product precipitated. The solid was collected by vacuum filtration and purified by flash column chromatography (Merck silical gel 60, 40-63 μm; 35% ethyl acetate in hexanes) to afford the desired product, (0.24 g, 0.44 mmol, 60%) as a white, brittle foam. A portion of the product (0.07 g, 0.128 mmol) was recrystallized from n-propanol (0.5 mL) to afford the pure desired product, 5-(7-bromo-1,1-dioxo-1,4-dihydro-1λ⁶-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one (0.044 g, 0.081 mmol, 63%), as a yellow powder. $^1$H NMR (400 MHz, DMSO-d$_6$) δ: 1.13-1.23 (2H, m), 1.38-1.60 (4H, m), 2.51 (1H, s), 2.63 (1H, s), 3.00 (1H, d, J=8.4 Hz), 3.55 (1H, d, J=9.4 Hz), 4.41 (1H, d, J=14.7 Hz), 4.95 (1H, d, J=15.4 Hz), 7.14 (2H, t, J=9.0 Hz), 7.33 (2H, dd, J$_1$=8.6 Hz, J$_2$=5.5 Hz), 8.66 (1H, s), 8.82 (1H, s). LC-MS (ESI) calcd for C$_{23}$H$_{20}$BrFN$_4$O$_4$S 546.04, found 547.2 [M+H$^+$].

Example 62

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ⁶-pyrido[2,3-e][1,2,4]thiadiazin-7-yl}-methanesulfonamide

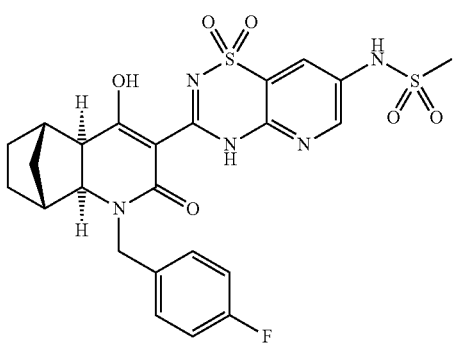

Methane sulfonamide (0.348 g, 3.66 mmol), potassium phosphate (0.078 g, 0.366 mmol), L-proline (0.021 g, 0.183 mmol) and copper iodide (0.035 g, 0.183 mmol) were combined and suspended in dimethylsulfoxide (0.5 mL). The flask was degassed and backfilled with argon. The mixture was heated, while stirring, at 110° C. for 5 min. 5-(7-Bromo-1,1-dioxo-1,4-dihydro-1λ⁶-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one (prepared as described in Example 62, 0.1 g, 0.183 mmol) was dissolved in dimethylsulfoxide (0.5 mL) and transferred to the reaction mixture. The mixture was stirred at 110° C. for 16 h. Upon cooling, the mixture was poured into ethyl acetate (150 mL) and saturated aqueous ammonium chloride solution (100 mL). The mixture was shaken and everything was passed through a plug of Celite. The organic layer was separated from the filtrate, washed with saturated aqueous ammonium chloride solution (50 mL), saturated aqueous brine solution (50 mL), dried over magnesium sulfate, filtered and concentrated in vacuo to a brown waxy solid. Flash column chromatography (Merck silica gel 60, 40-63 μm; 0 to 50% ethyl acetate in dichloromethane) afforded the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ⁶-pyrido[2,3-e][1,2,4]thiadiazin-7-yl}-methanesulfonamide (0.018 g, 0.032 mmol, 17.5%), as a beige solid. $^1$H NMR (400 MHz, DMSO-d$_6$) δ: 1.04-1.52 (6H, m), 2.37-2.41 (1H, m), 2.53-2.56 (1H, m), 3.05 (3H, s), 3.25-3.34 (2H, m), 4.25 (1H, d, J=15.1 Hz), 4.93 (1H, d, J=15.0 Hz), 7.11 (2H, t, J=9.1 Hz), 7.27 (2H, dd, J$_1$=8.7 Hz, J$_2$=5.4 Hz), 7.81 (1H, s), 8.36 (1H, s), 10.01 (1H, bs). LC-MS (ESI) calcd for C$_{24}$H$_{24}$FN$_5$O$_6$S$_2$ 561.12, found 562.4 [M+H$^+$].

Example 63

(1R,2S,7R,8S)-5-(1,1-Dioxo-1,4-dihydro-1λ$^6$-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one

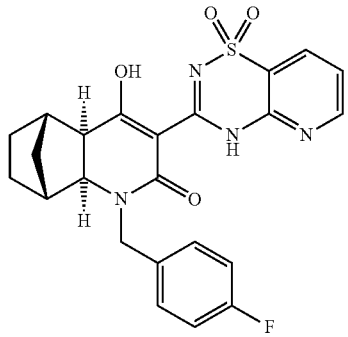

5-(7-Bromo-1,1-dioxo-1,4-dihydro-1λ$^6$-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one (prepared as described in Example 62, 0.07 g, 0.128 mmol) was dissolved in methanol (8 mL). Ammonium formate (0.2 g, 3.17 mmol) followed by 10% palladium on carbon (wet, 0.1 g) were added. The mixture stirred at 50° C. for 3 h. The mixture was filtered through Celite and the filtrate was concentrated in vacuo. The residue was dissolved in water (5 mL) and ethyl acetate (50 mL). The mixture was shaken and the layers were separated. The organic layer was dried over magnesium sulfate, filtered and concentrated in vacuo to a clear oil. Flash column chromatography (Merck silica gel 60, 40-63 μm; 20 to 40% ethyl acetate in hexanes) afforded the desired product, (1R,2S,7R,8S)-5-(1,1-dioxo-1,4-dihydro-1λ$^6$-pyrido[2,3-e][1,2,4]thiadiazin-3-yl)-3-(4-fluoro-benzyl)-6-hydroxy-3-aza-tricyclo[6.2.1.0$^{2,7}$]undec-5-en-4-one (0.0441 g, 0.094 mmol, 74%), as a white, brittle foam. $^1$H NMR (400 MHz, DMSO-d$_6$) δ: 1.11-1.61 (6H, m), 2.51 (1H, s), 2.63 (1H, s), 2.99 (1H, d, J=9.4 Hz), 3.54 (1H, d, J=9.4 Hz), 4.41 (1H, d, J=15.7 Hz), 4.95 (1H, d, J=15.4 Hz), 7.14 (2H, t, J=8.6 Hz), 7.33 (2H, dd, J$_1$=8.6 Hz, J$_2$=5.4 Hz), 7.51 (1H, dd, J$_1$=7.8 Hz, J$_2$=4.5 Hz), 8.34 (1H, d, J=7.6 Hz), 8.68 (1H, dd, J$_1$=4.6 Hz, J$_2$=1.7 Hz). LC-MS (ESI) calcd for C$_{23}$H$_{21}$FN$_4$O$_4$S 468.13, found 469.4 [M+H$^+$].

Example 64

(1R,2S,7R,8S)-5-(1,1-Dioxo-1,4-dihydro-1λ$^6$-pyrido[4,3-e][1,2,4]thiadiazin-3-yl)-3-(4-fluoro-benzyl)-6-hydroxy-3-aza-tricyclo[6.2.1.0$^{2,7}$]undec-5-en-4-one

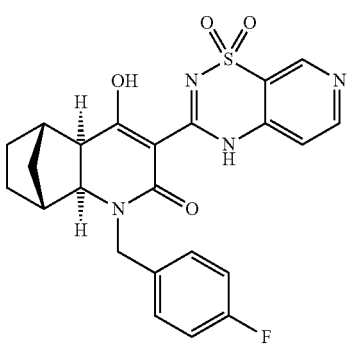

a) 4-Azido-pyridine-3-sulfonic acid amide

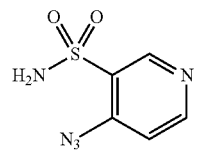

4-Chloro-pyridine-3-sulfonic acid amide (4 g, 20.77 mmol) and sodium azide (13.7 g, 210 mmol) were combined. Anhydrous N,N-dimethylformamide (80 mL) and water (30 mL) were added. The mixture was stirred at 90° C. for 2 h. Upon cooling, the mixture was diluted with saturated aqueous ammonium chloride solution (200 mL). The product was extracted into ethyl acetate (6×200 mL). The combined organic layers were dried over magnesium sulfate, filtered and concentrated in vacuo to afford the desired product, 4-azido-pyridine-3-sulfonic acid amide (3.75 g, 18.83 mmol, 91%), as a pale yellow solid. $^1$H NMR (400 MHz, DMSO-d$_6$) δ: 7.54 (2H, bs), 7.57 (1H, d, J=5.4 Hz), 8.68 (1H, d, J=5.5 Hz), 8.81 (1H, s).

b) 4-Amino-pyridine-3-sulfonic acid amide

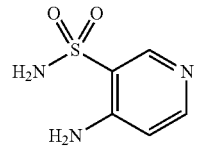

4-Azido-pyridine-3-sulfonic acid amide (3.75 g, 18.83 mmol) was dissolved in methanol (80 mL). Sodium borohydride (0.712 g, 18.83 mmol) was carefully added portionwise. Vigorous effervescence was observed. The mixture continued to stir at 25° C. for 25 min. The mixture was concentrated in vacuo to a thick yellow sludge. The residue was dissolved in a mixture of ethyl acetate (200 mL) and saturated aqueous ammonium chloride solution (200 mL). The aqueous layer was back extracted with ethyl acetate (6×200 mL). The combined organic layers were dried over magnesium sulfate, filtered and concentrated in vacuo to afford the desired product, 4-amino-pyridine-3-sulfonic acid amide (1.8 g, 10.4 mmol, 55%), as a pale yellow solid. $^1$H NMR (400 MHz, DMSO-d$_6$) δ: 6.63 (2H, bs), 6.68 (1H, d, J=5.4 Hz), 7.40 (2H, bs), 8.06 (1H, d, J=5.5 Hz), 8.43 (1H, s).

c) (1,1-Dioxo-1,4-dihydro-1λ$^6$-pyrido[4,3-e][1,2,4]thiadiazin-3-yl)-acetic acid methyl ester

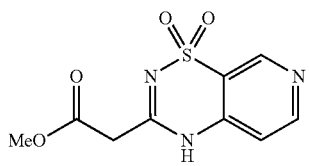 [SMILES: COC(=O)CC1=NS(=O)(=O)c2cnccc2N1]

4-amino-pyridine-3-sulfonic acid amide (0.25 g, 1.44 mmol) was suspended in malonic acid dimethyl ester (5 mL, 43.75 mmol). The flask was purged with nitrogen and the mixture was stirred at 180° C. for 60 min. Upon cooling, the mixture was diluted with ethyl acetate (5 mL) causing immediate precipitation of an undesired side product. The solid was removed by vacuum filtration and rinsed with ethyl acetate (2 mL). The filtrate was passed through a plug of silica gel, eluting with ethyl acetate followed by 5% methanol in ethyl acetate. The fractions containing the 5% methanol in ethyl acetate were combined and concentrated in vacuo to afford the desired product, (1,1-dioxo-1,4-dihydro-1$\lambda^6$-pyrido[4,3-e][1,2,4]thiadiazin-3-yl)-acetic acid methyl ester (0.135 g, 0.529 mmol, 37%) as a yellow oil. LC-MS (ESI) calculated for $C_9H_9N_3O_4S$ 255.03, found 256.0 [M+H$^+$].

d) Sodium-(1,1-dioxo-1,4-dihydro-1$\lambda^6$-pyrido[4,3-e][1,2,4]thiadiazin-3-yl)-acetate

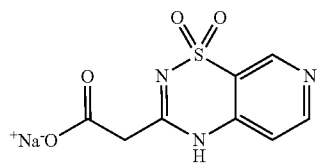

(1,1-Dioxo-1,4-dihydro-1$\lambda^6$-pyrido[4,3-e][1,2,4]thiadiazin-3-yl)-acetic acid methyl ester (0.13 g, 0.51 mmol) was dissolved in methanol (3 mL). Sodium hydroxide (0.08 g, 2.0 mmol) was dissolved in water (1.5 mL). The solutions were combined and were stirred at 25° C. for 3 h. The mixture was concentrated in vacuo to afford the desired product, sodium-(1,1-dioxo-1,4-dihydro-1$\lambda^6$-pyrido[4,3-e][1,2,4]thiadiazin-3-yl)-acetate, as a yellow oil. LC-MS (ESI) calculated for $C_8H_7N_3O_4S$ (free acid) 241.02, found 242.2 [M+H$^+$].

e) (1R,2S,7R,8S)-5-(1,1-Dioxo-1,4-dihydro-1$\lambda^6$-pyrido[4,3-e][1,2,4]thiadiazin-3-yl)-3-(4-fluoro-benzyl)-6-hydroxy-3-aza-tricyclo[6.2.1.0$^{2,7}$]undec-5-en-4-one

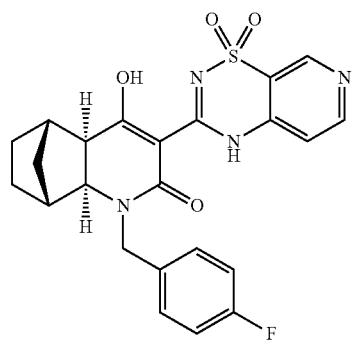 [SMILES: O=C1C(C2=NS(=O)(=O)c3cnccc3N2)=C(O)[C@@H]2[C@H]3CC[C@H](C3)[C@@H]2N1Cc1ccc(F)cc1]

The crude sodium-(1,1-dioxo-1,4-dihydro-1$\lambda^6$-pyrido[4,3-e][1,2,4]thiadiazin-3-yl)-acetate, (1S,2R,3S,4R)-3-(4-fluoro-benzylamino)-bicyclo[2.2.1]heptane-2-carboxylic acid ethyl ester (prepared as described in Example 61, 0.149 g, 0.51 mmol) and O-(7-azabenzotriazol-1-yl)-N,N,N',N'-tetramethyluronium hexafluorophosphate (0.194 g, 0.51 mmol) were combined and dissolved in anhydrous N,N-dimethylformamide (1 mL). The mixture was stirred at 25° C. for 1 h. Triethylamine (0.35 mL, 2.6 mmol) was added and the mixture was stirred at 50° C. for 16 h. Upon cooling, the mixture was diluted with ethyl acetate (100 mL), washed with saturated aqueous ammonium chloride solution (2×25 mL) and saturated aqueous brine solution (25 mL). The organic layer was dried over magnesium sulfate, filtered and concentrated in vacuo. Purification by flash column chromatography (Merck silica gel 60, 40-63 µm, 75% to 100% ethyl acetate in hexanes) followed trituration of the resulting oil with a 1:1 mixture of hexanes and diethyl ether (2 mL) afforded the desired product, (1R,2S,7R,8S)-5-(1,1-dioxo-1,4-dihydro-1$\lambda^6$-pyrido[4,3-e][1,2,4]thiadiazin-3-yl)-3-(4-fluoro-benzyl)-6-hydroxy-3-aza-tricyclo[6.2.1.0$^{2,7}$]undec-5-en-4-one (0.0184 g, 0.039 mmol, 7.7% over two steps), as a pale yellow powder. LC-MS (ESI) calculated for $C_{23}H_{21}FN_4O_4S$ 468.13, found 469.2 [M+H$^+$]. $^1$H NMR (400 MHz, DMSO-d$_6$) δ: 1.01-1.54 (6H, m), 2.35 (1H, d, J=3.7 Hz), 2.46 (1H, s), 2.53 (1H, s), 3.26 (1H, d, J=9.5 Hz), 4.23 (1H, d, J=15.8 Hz), 4.94 (1H, d, J=15.0 Hz), 7.08-7.13 (3H, m), 7.24-7.28 (2H, m), 8.44 (1H, d, J=4.8 Hz), 8.67 (1H, s).

Example 65

(1R,2S,7R,8S)-5-(1,1-Dioxo-1,4-dihydro-1$\lambda^6$-pyrido[3,2-e][1,2,4]thiadiazin-3-yl)-3-(4-fluoro-benzyl)-6-hydroxy-3-aza-tricyclo[6.2.1.0$^{2,7}$]undec-5-en-4-one

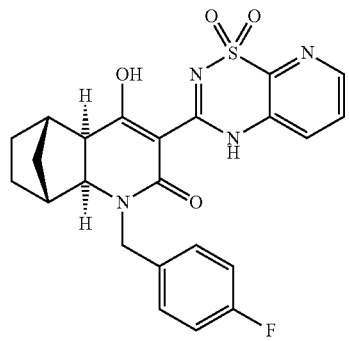

a) 2-Benzylsulfanyl-3-nitro-pyridine

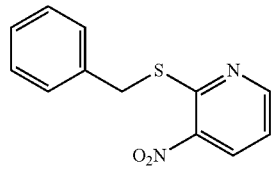 [SMILES: O=[N+]([O-])c1cccnc1SCc1ccccc1]

Ethanol (150 mL) was added to a mixture of 2-chloro-3-nitro-pyridine (5 g, 31.54 mmol) and potassium carbonate (4.8 g, 34.7 mmol). Benzyl mercaptan (4.09 mL, 34.7 mmol) was added followed by water (30 mL). The mixture stirred at 25° C. for 4 h. Water (350 mL) was added and the product precipitated. The solid was collected by vacuum filtration, rinsed with water (100 mL) and dried in vacuo for 4 h to afford the desired product, 2-benzylsulfanyl-3-nitro-pyridine (6.6 g, 26.8 mmol, 85%), as a yellow powder. $^1$H NMR (400 MHz, DMSO-d$_6$) δ: 4.47 (2H, s), 7.21-7.31 (3H, m), 7.40-7.45 (3H, m), 8.58 (1H, dd, J$_1$=8.6 Hz, J$_2$=1.7 Hz), 8.83 (1H, dd, J$_1$=4.7 Hz, J$_2$=1.7 Hz).

b) 3-Nitro-pyridine-2-sulfonyl chloride

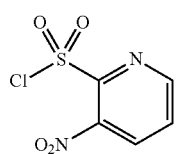

2-Benzylsulfanyl-3-nitro-pyridine (6 g, 24.39 mmol) was dissolved in dichloromethane (84 mL). Acetic acid (12 mL) and water (24 mL) were added. The mixture was chilled to 0° C. With vigorous stirring, 1,3-dichloro-5,5-dimethyl-imidazolidine-2,4-dione (14.4 g, 73.17 mmol) was added portionwise as a suspension in dichloromethane (48 mL). The mixture was allowed to slowly warm to 25° C. and continued to stir for 16 h. The mixture was poured into 5% aqueous sodium metabisulfite solution (100 mL) and shaken well. Dichloromethane (200 mL) and 20% aqueous dibasic potassium phosphate solution (100 mL) were added and the mixture was shaken well. The layers were separated. The crude desired product, 3-nitro-pyridine-2-sulfonyl chloride, dissolved in the organic layer was used directly in the next step without further isolation or characterization.

c) 3-Nitro-pyridine-2-sulfonic acid amide

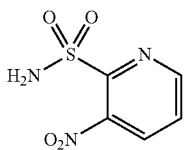 [SMILES: NS(=O)(=O)c1ncccc1[N+](=O)[O-]]

The organic layer was chilled to 0° C. and concentrated aqueous ammonium hydroxide solution (25 mL) was added. The mixture was stirred for 10 min. The mixture was washed with 10% aqueous citric acid solution (added until pH<7, ~200 mL). The organic layer was dried over magnesium sulfate, filtered and concentrated in vacuo. The resulting solid was triturated with a 1:1 mixture of hexanes and ethyl acetate (~15 mL), collected by vacuum filtration and dried in vacuo for 16 h to afford the desired product, 3-nitro-pyridine-2-sulfonic acid amide (3.1 g, 15.26 mmol, 63%), as a beige solid. $^1$H NMR (400 MHz, DMSO-d$_6$) δ: 7.89 (1H, d, J=4.7 Hz), 7.95 (2H, s), 8.48 (1H, dd, J$_1$=8.6 Hz, J$_2$=1.6 Hz), 8.92 (1H, d, J=4.7 Hz).

d) 3-Amino-pyridine-2-sulfonic acid amide

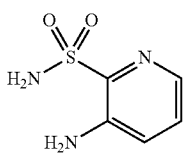

3-Nitro-pyridine-2-sulfonic acid amide (3 g, 14.77 mmol) and iron powder (5 g, <10 micron) were suspended in ethanol (100 mL). Saturated aqueous ammonium chloride solution (60 mL) was added and the mixture stirred at 105° C. for 1.5 h. Upon cooling to 25° C., ethyl acetate (200 mL) was added and the mixture was shaken vigorously. The entire mixture was filtered through a plug of Celite. The resulting filtrate was diluted with ethyl acetate (100 mL) and the layers were separated. The aqueous layer was back-extracted with ethyl acetate (3×200 mL). The organic layers were combined, dried over magnesium sulfate, filtered and concentrated in vacuo to dryness. The resulting solid was triturated with a 3:1 mixture of hexanes and ethyl acetate (~10 mL). The solid was collected by vacuum filtration and dried in vacuo for 16 h to afford the desired product, 3-amino-pyridine-2-sulfonic acid amide (1.95 g, 11.27 mmol, 76%), as an off-white powder. $^1$H NMR (400 MHz, DMSO-d$_6$) δ: 5.98 (2H, bs), 7.19-7.21 (1H, m), 7.32 (2H, bs), 7.79-7.80 (1H, m), 7.90-7.91 (1H, m).

e) (1,1-Dioxo-1,4-dihydro-1λ$^6$-thia-2,4,8-triaza-naphthalen-3-yl)-acetic acid ethyl ester

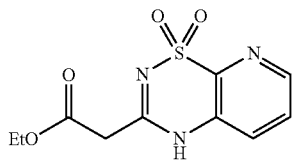 [SMILES: CCOC(=O)CC1=NS(=O)(=O)c2ncccc2N1]

3-Amino-pyridine-2-sulfonic acid amide (1.8 g, 10.4 mmol) was dissolved in 1,4-dioxane (45 mL). Chlorocarbonyl-acetic acid ethyl ester (1.57 mL, 12.48 mmol) was added. The mixture was stirred at 90° C. for 1.5 h. Upon cooling, the mixture was diluted with ethyl acetate (300 mL) and washed with half-saturated aqueous sodium bicarbonate solution (100 mL) followed by saturated aqueous brine solution (100 mL). The organic layer was dried over magnesium sulfate, filtered and concentrated in vacuo. The resulting oily residue was treated with toluene (36 mL) and triethylamine (9 mL). The mixture was stirred at 110° C. in a sealed tube for 1.5 h. The residue never completely dissolved. Upon cooling, the mixture was concentrated in vacuo to afford a thick oil. Trituration with a minimal amount of ethyl acetate (~5 mL) solidified the product. The solids were collected by vacuum filtration and dried in vacuo for 16 h to afford the desired product, (1,1-dioxo-1,4-dihydro-1λ$^6$-thia-2,4,8-triaza-naphthalen-3-yl)-acetic acid ethyl ester (0.3 g, 1.11 mmol, 11%), as a white solid. $^1$H NMR (400 MHz, DMSO-d$_6$) δ: 1.21 (3H, t, J=7.0 Hz), 3.71 (2H, s), 4.16 (2H, quartet, J=7.1 Hz), 7.70-7.76 (2H, m), 8.62 (1H, dd, J$_1$=4.0 Hz, J$_2$=1.5 Hz), 12.29 (1H, bs). LC-MS (ESI) calcd for C$_{10}$H$_{11}$N$_3$O$_4$S 269.05, found 270.1 [M+H$^+$].

f) (1,1-Dioxo-1,4-dihydro-1λ$^6$-thia-2,4,8-triaza-naphthalen-3-yl)-acetic acid sodium salt

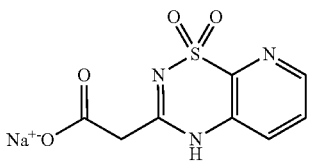

(1,1-Dioxo-1,4-dihydro-1λ⁶-thia-2,4,8-triaza-naphthalen-3-yl)-acetic acid ethyl ester (0.25 g, 0.928 mmol) was dissolved in methanol (5 mL) at approximately 60° C. Sodium hydroxide (0.111 g, 2.79 mmol) was dissolved in water (2.5 mL). Upon cooling to 25° C., the solutions were combined. The mixture was stirred at 25° C. for 3 h. The mixture was stored at −40° C. for 16 h. The mixture was concentrated in vacuo to afford the crude product, (1,1-dioxo-1,4-dihydro-1λ⁶-thia-2,4,8-triaza-naphthalen-3-yl)-acetic acid sodium salt (~0.928 mmol), as a yellow film, which was used in the next step without further purification.

g) (1R,2S,7R,8S)-5-(1,1-Dioxo-1,4-dihydro-1λ⁶-thia-2,4,8-triaza-naphthalen-3-yl)-3-(4-fluoro-benzyl)-6-hydroxy-3-aza-tricyclo[6.2.1.0²,⁷]undec-5-en-4-one

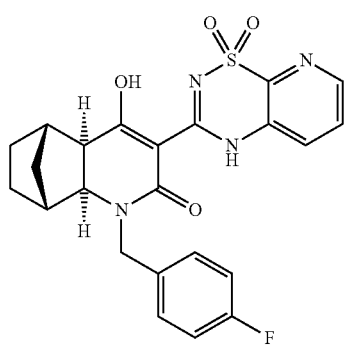

The crude (1,1-dioxo-1,4-dihydro-1λ⁶-thia-2,4,8-triaza-naphthalen-3-yl)-acetic acid sodium salt (~0.928 mmol), (1S,2R,3S,4R)-3-(4-fluoro-benzylamino)-bicyclo[2.2.1]heptane-2-carboxylic acid ethyl ester (0.27 g, 0.928 mmol) and 047-azabenzotriazol-1-yl)-1,1,3,3-tetramethyluronium hexafluorophosphate (0.494 g, 1.3 mmol) were combined and dissolved in anhydrous N,N-dimethylformamide (2 mL). The mixture was stirred at 25° C. for 1.5 h. Triethylamine (0.697 mL, 5 mmol) was added and the mixture was stirred at 50° C. for 16 h. Upon cooling, the mixture was diluted with ethyl acetate (100 mL), washed with saturated aqueous ammonium chloride solution (2×25 mL) and saturated aqueous brine solution (25 mL). The organic layer was dried over magnesium sulfate, filtered and concentrated in vacuo. The resulting solid was triturated with ethyl acetate (~15 mL) and the product solidified. The solid was collected by vacuum filtration and dried in vacuo for 16 h to afford the desired product, (1R,2S,7R,8S)-5-(1,1-dioxo-1,4-dihydro-1λ⁶-thia-2,4,8-triaza-naphthalen-3-yl)-3-(4-fluoro-benzyl)-6-hydroxy-3-aza-tricyclo[6.2.1.0²,⁷]undec-5-en-4-one (0.03 g, 0.064 mmol, 6.9%), as a white powder. ¹H NMR (400 MHz, DMSO-d₆) δ: 0.92-1.05 (2H, m), 1.18-1.46 (4H, m), 2.26 (1H, d, J=3.1 Hz), 2.36 (1H, d, J=9.5 Hz), 2.45 (1H, d, J=3.0 Hz), 3.15 (1H, d, J=9.4 Hz), 4.13 (1H, d, J=15.6 Hz), 4.86 (1H, d, J=15.6 Hz), 7.01-7.05 (2H, m), 7.16-7.20 (2H, m), 7.39-7.42 (1H, m), 7.50 (1H, dd, J₁=8.6 Hz, J₂=1.6 Hz), 8.26 (1H, dd, J₁=4.6 Hz, J₂=1.5 Hz). LC-MS (ESI) calcd for C₂₃H₂₁FN₄O₄S 468.13, found 469.2 [M+H⁺].

Example 66

N-{3-[(1R,2S,7R,8S)-3-(2-Cyclopropyl-ethyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

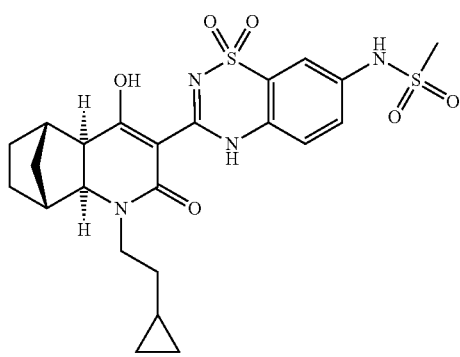

a) (1S,2R,3S,4R)-3-(2-Cyclopropyl-ethylamino)-bicyclo[2.2.1]heptane-2-carboxylic acid ethyl ester

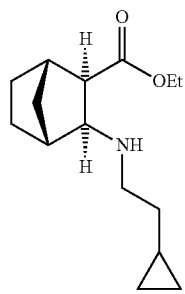

A 1.4 M solution of cyclopropylacetaldehyde in dichloromethane (prepared as described in Example 23a, 3.4 mL, 4.76 mmol) was added to a solution of (1S,2R,3S,4R)-3-amino-bicyclo[2.2.1]heptane-2-carboxylic acid ethyl ester (prepared as described in Example 6k, 580 mg, 3.17 mmol) in anhydrous methanol (15 mL) at 25° C. under a nitrogen atmosphere. After stirring for 20 min, glacial acetic acid (0.6 mL) was added. The solution was cooled to 0° C., sodium triacetoxyborohydride (1.7 g, 7.93 mmol) was added, and the resulting mixture was stirred at 25° C. for 20 h. The reaction mixture was quenched with saturated aqueous sodium bicarbonate solution (25 mL) and was extracted with ethyl acetate (3×60 mL). The combined organic layers were washed with saturated aqueous brine solution, dried over sodium sulfate and filtered. The filtrate was concentrated in vacuo to afford the desired product, (1S,2R,3S,4R)-3-(2-cyclopropyl-ethylamino)-bicyclo[2.2.1]heptane-2-carboxylic acid ethyl ester (676.4 mg, 2.69 mmol, 84.9%), as a yellow oil. LC-MS (ESI) calcd for C₁₅H₂₅NO₂ 251.19, found 252.0 [M+H⁺].

b) (1S,2R,3S,4R)-3-{(2-Cyclopropyl-ethyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester

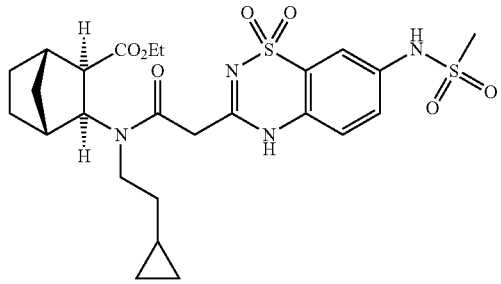

To a stirred solution of (1S,2R,3S,4R)-3-(2-cyclopropyl-ethylamino)-bicyclo[2.2.1]heptane-2-carboxylic acid ethyl ester (338.2 mg, 1.35 mmol) in anhydrous N,N-dimethylformamide (10 mL) under a nitrogen atmosphere, (7-methanesulfonylamino-1,1-dioxo-1,4-dihydro-1λ$^6$-benzo[1,2,4]thiadiazin-3-yl)-acetic acid (prepared as described in Example 1g, 493 mg, 1.48 mmol), N-methylmorpholine (0.33 mL, 2.96 mmol) and 1-(3-dimethylaminopropyl)-3-ethylcarbodiimide hydrochloride (284 mg, 1.48 mmol) were added sequentially. After shaking at 25° C. for 21 h, additional (7-methanesulfonylamino-1,1-dioxo-1,4-dihydro-1λ$^6$-benzo[1,2,4]thiadiazin-3-yl)-acetic acid (prepared as described in Example 1g, 150 mg, 0.45 mmol) and 1-(3-dimethylaminopropyl)-3-ethylcarbodiimide hydrochloride (85 mg, 0.44 mmol) were added. After another 26 h, a 1.0 M aqueous hydrochloric acid solution (12 mL) was added and the mixture was extracted with ethyl acetate (3×60 mL). The combined organic layers were washed with saturated aqueous brine solution (15 mL), dried over sodium sulfate, filtered, and concentrated in vacuo to afford the crude product, (1S,2R,3S,4R)-3-{(2-cyclopropyl-ethyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester, as a red oil, which was used in the next step without any further purification. LC-MS (ESI) calcd for $C_{25}H_{34}N_4O_7S_2$ 566.19, found 567.4 [M+H$^+$].

c) N-{3-[(1R,2S,7R,8S)-3-(2-Cyclopropyl-ethyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

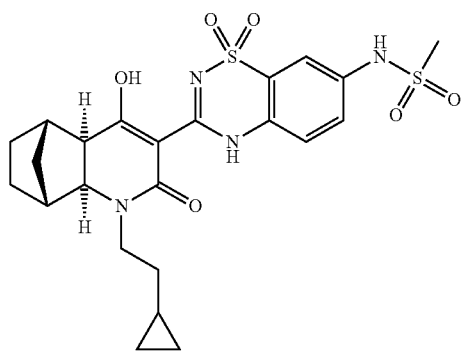

To a solution of the crude (1S,2R,3S,4R)-3-{(2-cyclopropyl-ethyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester in absolute ethanol (11 mL) was added a 21 wt. % solution of sodium ethoxide in ethanol (2.4 mL, 7.41 mmol). After shaking at 25° C. for 23 h, additional 21 wt. % solution of sodium ethoxide in ethanol (1.0 mL, 3.09 mmol) was added. After shaking at 25° C. for 6 h, additional 21 wt. % solution of sodium ethoxide in ethanol (1.0 mL, 3.09 mmol) was added and the mixture was shaken for another 24 h. The mixture was then acidified with 1.0 M aqueous hydrochloric acid solution (22 mL) and was extracted with ethyl acetate (3×60 mL). The combined organic layers were dried over sodium sulfate, filtered, and concentrated in vacuo. The crude mixture was purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, N-{3-[(1R,2S,7R,8S)-3-(2-cyclopropyl-ethyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (160.7 mg, 0.309 mmol, 22.9% over two steps), as a solid. $^1$H NMR (400 MHz, CDCl$_3$) δ: 0.09-0.15 (2H, m), 0.49-0.54 (2H, m), 0.64-0.73 (1H, m), 1.27-1.31 (2H, m), 1.48-1.78 (6H, m), 2.55-2.56 (1H, m), 2.74-2.80 (1H, m), 2.85 (1H, d, J=9.2 Hz), 3.06 (3H, s), 3.10-3.17 (1H, m), 3.57 (1H, d, J=9.2 Hz), 3.80-3.87 (1H, m), 6.99 (1H, s), 7.22-7.25 (1H, m), 7.62-7.68 (2H, m). LC-MS (ESI) calcd for $C_{23}H_{28}N_4O_6S_2$ 520.15, found 521.4 [M+H$^+$].

Example 67

N-{3-[(1R,2S,7R,8S)-3-(4-Fluoro-benzyl)-6,9-dihydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

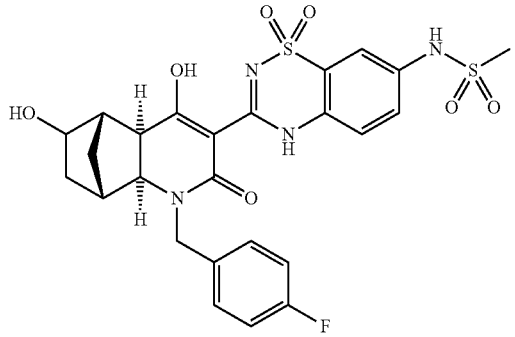

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 6, 168 mg, 0.299 mmol) was dissolved in dimethyl sulfoxide (15 mL). Reaction buffer was prepared by combining anhydrous D-glucose (3.3 g), GDH-102 (375 mg), and NADP$^+$ (570 mg) in a 100 mM aqueous potassium phosphate (pH 8.0) solution (700 mL). Lyophilized MCYP-P1C11 (1800 mg, 1500 nmol, 0.84 nmol P450/mg, Codexis, Inc.) was dissolved in a 50 mM aqueous potassium phosphate (pH 8.0) solution (29 mL). The following components were added in order to a 2.8 L baffled Fernbach flask: the reaction buffer, followed by the MCYP-P1C11 stock solution, then the N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide solution. The vial used to make the N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide stock solution was washed with 0.1 M aqueous potassium phosphate (pH 8.0) solution (6 mL) and this solution was then added to the flask, bringing the total volume of the reaction to 750 mL. The mixture was then incubated for 24 h at 30° C. with gentle shaking, followed by freezing at −80° C. Methanol (1.5 L) was added to the thawed reaction mixture resulting in the formation of a precipitate. The solids were removed as a pellet by centrifugation for 45 min at 10,000 rpm. The supernatant was concentrated in vacuo and the residue was purified by prep-HPLC to afford the desired product, N-{3-[(1R,2S,7R,8S)-3-(4-fluoro-benzyl)-6,9-dihydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (49.5 mg, 0.086 mmol, 29%), as a white solid. $^1$H NMR (500 MHz, DMSO-d$_6$) δ: 1.21 (1H, dd, J$_1$=14.7 Hz, J$_2$=4.8 Hz), 1.46-1.59 (3H, m), 2.44 (1H, s), 2.53 (1H, s), 2.87 (1H, d, J=8.7 Hz), 3.07 (3H, s), 3.39 (1H, d, J=8.5 Hz), 3.80 (1H, d, J=6.0 Hz), 4.42 (1H, d, J=15.5 Hz), 4.96 (1H, d, J=15.7 Hz), 7.16 (2H, t, J=8.7 Hz), 7.32-7.34 (2H, m), 7.52 (1H, dd, J$_1$=9.0 Hz, J$_2$=2.3 Hz), 7.59-7.60 (2H, m), 10.23 (1H, s), 14.08 (1H, s), 15.03 (1H, bs). LC-MS (ESI) calcd for C$_{25}$H$_{25}$FN$_4$O$_7$S$_2$ 576.11, found 577.5 [M+H$^+$].

Example 68

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, L-arginine salt

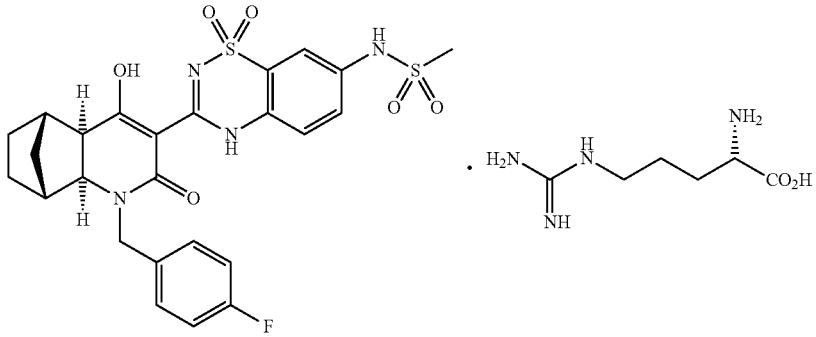

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 6, 0.280 g, 0.499 mmol) was dissolved in acetonitrile (5.0 mL). A 0.1 M aqueous L-arginine solution (3.0 mL, 0.3 mmol) was added, which was followed by addition of a 0.1 M solution of L-arginine in 1-propanol (2.0 mL, 0.2 mmol). After stirring for 6 h at 23° C., the flask was opened to the atmosphere and the suspension was stirred for 16 h. The solid was collected by filtration and further dried in vacuo at 23° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, L-arginine salt, monohydrate (0.257 g, 0.341 mmol, 68%), as a crystalline solid. $^1$H NMR (300 MHz, DMSO-d$_6$) δ: 0.96-1.17 (2H, m), 1.28 (1H, app t, J=10.0 Hz), 1.35-1.82 (7H, m), 2.33 (1H, app d, J=3.0 Hz), 2.43 (1H, d, J=9.3 Hz), 2.97 (3H, s), 3.00-3.17 (2H, m), 3.23 (1H, d, J=9.3 Hz), 4.21 (1H, d, J=15.3 Hz), 4.94 (1H, d, J=15.3 Hz), 7.04-7.15 (3H, m), 7.27 (2H, dd, J=5.7, 8.7 Hz), 7.35 (1H, dd, J=2.5, 8.9 Hz), 7.35-7.51 (4H, m), 8.82 (1H, br s), 15.29 (1H, br s). Anal. calcd for C$_{31}$H$_{39}$FN$_8$O$_8$S$_2$.H$_2$O: C, 49.46; H, 5.49; N, 14.88; O, 19.13; S, 8.52; F, 2.52. found: C, 49.49; H, 5.23; N, 14.96; O, 18.69; S, 8.82; F, 2.81. m.p.=216° C. (DSC).

Example 69

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, L-lysine salt

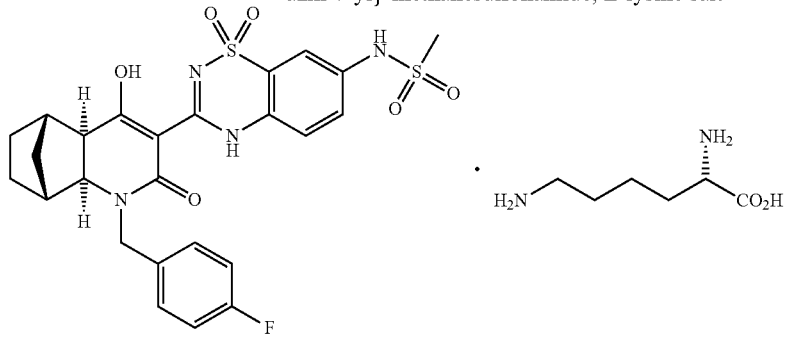

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 6, 0.090 g, 0.160 mmol) was dissolved in acetonitrile (2.5 mL). An aqueous solution of L-lysine (0.469 mL of a 50 mg/mL solution in water, 0.160 mmol) was added. The solvent was allowed to evaporate under a flow of nitrogen and ethanol (0.5 mL) was added. The mixture was stirred at 35° C. for 2 d, and was then immersed in an ultrasonic bath. Water (0.5 mL) was added, and the mixture was stirred at 23° C. for 3 d. The solid was collected by filtration and further dried in vacuo at 23° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, L-lysine salt, monohydrate (0.070 g, 0.096 mmol, 60%), as a crystalline solid. $^1$H NMR (300 MHz, DMSO-d$_6$) δ: 0.96-1.15 (2H, m), 1.22-1.76 (10H, m), 2.34 (1H, app d, J=2.7 Hz), 2.43 (1H, d, J=9.3 Hz), 2.74-2.78 (2H, m), 2.97 (3H, s), 3.18-3.29 (1H, m), 4.21 (1H, d, J=15.3 Hz), 4.95 (1H, d, J=15.6 Hz), 7.07-7.18 (3H, m), 7.27 (2H, dd, J=5.7, 8.7 Hz), 7.36 (1H, dd, J=2.4, 8.7 Hz), 7.44 (1H, d, J=2.4 Hz), 15.31 (1H, br s). Anal. calcd for $C_{31}H_{39}FN_6O_8S_2 \cdot H_2O$: C, 51.37; H, 5.70; N, 11.59; O, 19.87; S, 8.85; F, 2.62. found: C, 51.13; H, 5.52; N, 11.63; O, 20.07; S, 9.20; F, 2.71. m.p.=200° C. (DSC).

Example 70

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, hemi magnesium salt

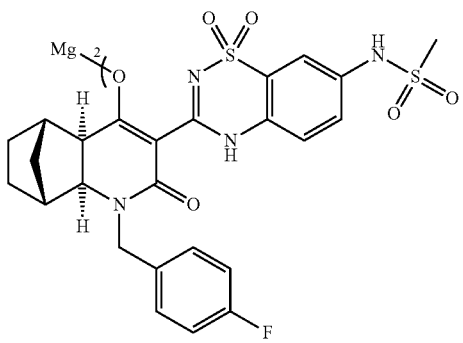

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 6, 0.465 g, 0.829 mmol) was dissolved in acetone (9.0 mL). A 7-8 wt. % solution of magnesium methoxide in methanol (0.593 mL, 0.414 mmol) was added. The solvent was evaporated, and the residue was then diluted with water (0.9 mL) and acetone (1.8 mL). The resulting mixture was stirred at 23° C. for 16 h. The solid was collected by filtration and further dried in vacuo at 23° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, hemi magnesium salt, trihydrate (0.377 g, 0.602 mmol, 73%), as a crystalline solid. $^1$H NMR (300 MHz, DMSO-d$_6$) δ: 0.96-1.17 (2H, m), 1.22-1.58 (4H, m), 2.33 (1H, br s), 2.44 (1H, d, J=9.6 Hz), 2.98 (3H, s), 3.23 (1H, d, J=9.3 Hz), 4.21 (1H, d, J=14.7 Hz), 4.94 (1H, d, J=15.3 Hz), 7.03-7.19 (3H, m), 7.21-7.48 (4H, m), 9.81 (1H, br s), 15.35 (1H, br s). Anal. calcd for $C_{25}H_{24}N_4O_6FS_2 \cdot 0.5Mg \cdot 3H_2O$: C, 47.98; H, 4.83; N, 8.95; O, 23.01; S, 10.25; F, 3.04; Mg, 1.94. found: C, 47.66; H, 4.89; N, 8.98; O, 23.00; S, 11.36; F, 3.09; Mg, 1.82. m.p.=184° C. (DSC).

Example 71

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, sodium salt

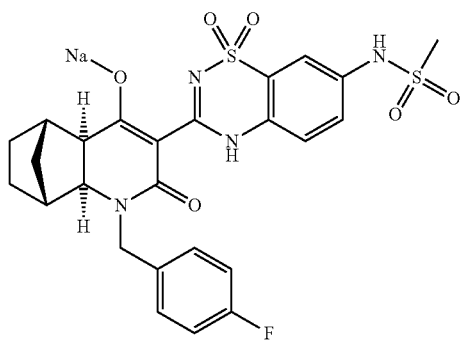

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (prepared as described in Example 6, 0.407 g, 0.726 mmol) was suspended in ethanol (11.0 mL). A 1.0 M aqueous sodium hydroxide solution (0.726 mL, 0.726 mmol) and water (1.0 mL) were added. The mixture was seeded with a crystal of N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, sodium salt (produced from a separate batch), and the mixture was then stirred at 23° C. for 1 d. The solid was collected by filtration and further dried in vacuo at 23° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, sodium salt, hydrate (2.25 molar equiv. water) (0.235 g, 0.377 mmol, 52%), as a crystalline solid. $^1$H NMR (300 MHz, DMSO-d$_6$) δ: 0.99-1.11 (2H, m), 1.28 (1H, app t, J=10.2 Hz), 1.36-1.53 (3H, m), 2.33 (1H, app d, J=2.7 Hz), 2.42 (1H, d, J=9.3 Hz), 2.97 (3H, s), 3.22 (1H, d, J=9.3 Hz), 4.20 (1H, d, J=15.3 Hz), 4.95 (1H, d, J=15.3 Hz), 7.09-7.16 (3H, m), 7.25-7.36 (3H, m), 7.42 (1H, d, J=2.4 Hz), 9.79 (1H, s), 15.32 (1H, s). Anal. calcd for $C_{25}H_{24}FN_4NaO_6S_2 \cdot 2.25H_2O$: C, 48.19; H, 4.61; N, 8.99; O, 21.18; S, 10.29; F, 3.05; Na, 3.69. found: C, 48.14; H, 4.67; N, 8.97; O, 21.07; S, 10.25; F, 3.13; Na, 3.87. m.p.=182-188° C. (DSC).

Example 72

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, potassium salt

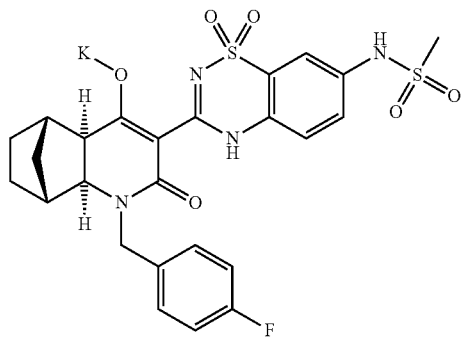

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (prepared as described in Example 6, 0.281 g, 0.501 mmol) was dissolved in methyl ethyl ketone (8.0 mL). A 0.5 M aqueous potassium hydroxide solution (1.0 mL, 0.500 mmol) was added. The solution was seeded with crystalline N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, potassium salt (produced from a separate batch), and the resulting mixture was then stirred at 23° C. for 3 h. The solid was collected by filtration and further dried in vacuo at 23° C. to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide, potassium salt, hydrate (0.75 molar equiv. water) (0.127 g, 0.207 mmol, 41%), as a crystalline solid. $^1$H NMR (300 MHz, DMSO-d$_6$) δ: 0.99-1.11 (2H, m), 1.27 (1H, app t, J=10.3 Hz), 1.36-1.54 (3H, m), 2.33 (1H, br s), 2.42 (1H, d, J=9.0 Hz), 2.95 (3H, s), 3.22 (1H, d, J=9.3 Hz), 4.20 (1H, d, J=15.3 Hz), 4.96 (1H, d, J=15.6 Hz), 7.09-7.15 (3H, m), 7.25-7.34 (3H, m), 7.41 (1H, d, J=2.7 Hz), 9.84 (1H, br s), 15.30 (1H, s). Anal. calcd for C$_{25}$H$_{24}$FKN$_4$O$_6$S$_2$.0.75H$_2$O: C, 49.05; H, 4.20; N, 9.15; O, 17.64; S, 10.48; F, 3.10; K, 6.39. found: C, 48.82; H, 4.11; N, 9.06; O, 17.35; S, 10.37; F, 3.18; K, 6.75. m.p.=278° C. (DSC).

Biological Testing

The ability of compounds of Formula I to inhibit HCV replication can be demonstrated in the following in vitro assays.

Compounds were tested for HCV polymerase inhibition. Assays were performed in a 96-well streptavidin-coated FlashPlate using 20 nM enzyme, 0.5 µCi of [α-$^{33}$P]GTP, 0.6 µM GTP, and 250 nM 5'biotinylated oligo (rG$_{13}$)/poly rC in 20 mM Tris-HCl, pH 7.5, 5 mM MgCl$_2$, 5 mM dithiothreitol, 0.1 g/L bovine serum albumin, and 100 U/mL RNAse inhibitor. The reaction was stopped by aspiration after 75 min at 28° C. and the plate was washed several times. After washing and drying the plate, incorporated radioactivity was counted using a Microbeta scintillation counter. IC$_{50}$ values were calculated relative to the uninhibited control and inhibition data were fitted to a 4-parameter IC$_{50}$ equation. For very potent inhibitors, the data were fitted to a tight binding quadratic equation to obtain IC$_{50}$ values.

Test results (IC$_{50}$ values) for compounds of Formula I are summarized in Table 1, wherein ++++ means NS5B polymerase inhibition with IC$_{50}$ values less than 0.02 µM, +++ means IC$_{50}$ values between 0.02 µM and 0.1 µM, ++ means IC$_{50}$ values between 0.1 µM and 1 µM, and + means IC$_{50}$ values between 1 µM and 100 µM. Test results for Example numbers 64 and 65 in Table 1 are EC$_{50}$ values, wherein ** means HCV replicon inhibition with EC$_{50}$ values less than 0.02 µM, * means EC$_{50}$ values between 0.02 µM and 0.1 µM, ** means EC$_{50}$ values between 0.1 µM and 1 µM, and * means EC$_{50}$ values between 1 µM and 100 µM

TABLE 1

| Example # | IC$_{50}$ |
|---|---|
| 1 | ++++ |
| 2 | ++++ |
| 3 | ++ |
| 4 | ++++ |
| 5 | ++ |
| 6 | ++++ |
| 7 | ++ |
| 8 | ++++ |
| 9 | +++ |
| 10 | +++ |
| 11 | ++++ |
| 12 | ++++ |
| 13 | +++ |
| 14 | ++++ |
| 15 | ++++ |
| 16 | ++++ |
| 17 | +++ |
| 18 | +++ |
| 19 | + |
| 20 | ++ |
| 21 | +++ |
| 22 | +++ |
| 23 | ++++ |
| 24 | ++ |
| 25 | ++++ |
| 26 | ++ |
| 27 | + |
| 28 | ++ |
| 29 | ++++ |
| 30 | ++ |
| 31 | +++ |
| 32 | +++ |
| 33 | + |
| 34 | + |
| 35 | +++ |
| 36 | +++ |
| 37 | ++++ |
| 38 | +++ |
| 39 | + |
| 40 | +++ |
| 41 | +++ |
| 42 | +++ |
| 43 | +++ |
| 44 | ++ |
| 45 | +++ |
| 46 | ++++ |
| 47 | + |
| 48 | +++ |
| 49 | ++++ |
| 50 | ++++ |
| 51 | +++ |
| 52 | +++ |
| 53 | + |
| 54 | ++ |

TABLE 1-continued

| Example # | IC$_{50}$ |
|---|---|
| 55 | ++++ |
| 56 | ++++ |
| 57 | +++ |
| 58 | ++++ |
| 59 | ++ |
| 60 | +++ |
| 61 | + |
| 62 | +++ |
| 63 | ++ |
| 64 | ** |
| 65 | ** |
| 66 | +++ |
| 67 | ++++ |

HCV Replicon Assay (Replicon EC$_{50}$ (μM))

The cell culture component of the assay is performed essentially as described by Bartenschlager et al., Hepatology 2002, 35, 694-703, wherein exponentially growing HCV Huh-7/C24 replicon cells are seeded at 4.5×10³ cells/well in 96 well plates and 24 hours later are treated with six point half-log concentration of compound. After 72 hours exposure the media is discarded from the compound assay plate and the cell monolayers are lysed by addition of 150 □L lysis mixture (Genospectra) with incubation at 53° C. for 45 minutes. Following incubation, each lysate is thoroughly mixed and 5 □l (NS3 probe) or 10 □L (GAPDH probe) of each lysate is then transferred to the capture plate and analyzed by bDNA assay.

Branched DNA (bDNA) Assay

Based on provided sequences for NS3 [AJ242652], Genospectra (Fremont, Calif., USA) designed and synthesized probes to these analytes (together with GAPDH). Cellular bDNA analysis is carried out essentially as described in the Genospectra protocol (details in Shyamala, V. et al., Anal. Biochem. 1999, 266, 140-7), wherein target specific capture extenders, label extenders and blocking probes are added to the capture plate after the addition of 5 or 10 μL cell lysate. After annealing overnight, during which the target RNA is captured to the plate via interaction with the capture extenders, the plate is washed, and then amplifier (which binds via the label extenders) and label probe are sequentially added.

After subsequent addition of the chemilumigenic substrate (dioxetan), each plate is read by luminometer (Wallac 1420 Multilabel HTS Counter Victor 2). The luminescence signal is proportional to the amount of mRNA present in each lysate. In addition to the samples, cell lysate only (no probe) background controls are also included on each bDNA assay plate and the average signal from these control wells is subtracted from the sample reading prior to analysis. Percent of no drug control is determined for both the NS3 and GAPDH signals for each compound also. Percent inhibition is determined for each compound concentration in relation to the no drug control to calculate the EC$_{50}$.

Luciferase-Based HCV Replicon Assay Protocol

Exponentially growing HCV Huh-luc/neo-ET replicon cells were seeded at 6×10³ cells/well in 96 well assay plate. 24 hours later the cells were treated with various concentrations of compound in triplicate. After 72 hours exposure to the compound the luciferase activity in the wells was determined using Bright-Glo reagent (Promega, Madison, Wis.) with a luminometer (Wallac 1420 Multilabel HTS Counter Victor 2). The background control was replicon cells treated with 100 nM BILN-2061, an inhibitor of the HCV protease. % Inhibition was determined for each compound concentration in relation to the negative (no compound) control to calculate the EC$_{50}$.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention.

What is claimed is:

1. A compound of Formula I

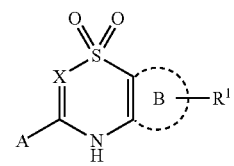

I wherein
X is CR³,
A is

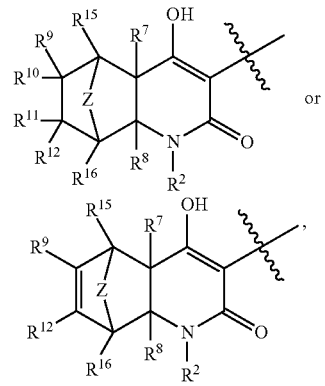

or

Ring B is 6-membered aryl, optionally substituted by 1-3 R¹ moieties, wherein is R¹ is H, halo, nitro, —CHR⁴— S(O)₂R⁵, —C(S(O)₂R⁵)=CHR⁴—, —NR⁵R⁶, —NR⁴S (O)₂R⁵, or —NR⁴S(O)₂NR⁵R⁶, wherein R⁴, R⁵, and R⁶ are independently H, C$_1$-C$_6$ alkyl, C$_3$-C$_8$ cycloalkyl, C(O)O—(C$_1$-C$_6$ alkyl), aryl, or heterocyclyl, or R⁴ and R⁵ or R⁵ and R⁶ combine with the atom(s) to which they are attached to form a 5- or 6-membered heterocyclyl ring, R² is H, C$_1$-C$_6$ alkyl, C$_3$-C$_8$ cycloalkyl, —C$_1$-C$_6$ alkylene (C$_3$-C$_8$ cycloalkyl), —C$_1$-C$_6$ alkylene(aryl), —C$_1$-C$_6$ alkylene(heterocyclyl), aryl, or heterocyclyl, R³ is H, halo, or C$_1$-C$_6$ alkyl, Z is —(CR¹³R¹⁴)$_n$—, or O, n is 1 or 2, R⁷ and R⁸ are independently H or C$_1$-C$_6$ alkyl, R⁹, R¹⁰, R¹¹, R¹², R¹³, R¹⁴, R¹⁵, and R¹⁶ are independently H, C$_1$-C$_6$ alkyl, hydroxy, or halo, wherein the above alkyl, alkylene, aryl, cycloalkyl, or heterocyclyl moieties provided in R¹, R², R³, R⁴, R⁵, R⁶, R⁷, R⁸, R⁹, R¹⁰, R¹¹, R¹², R¹³, R¹⁴, R¹⁵, and R¹⁶ are each optionally and independently substituted by 1-3 substituents selected from alkylamine,
amino,
aryl, cycloalkyl, heterocyclyl,
C$_1$-C$_6$ alkyl, C$_1$-C$_6$ haloalkyl, C$_1$-C$_6$ hydroxyalkyl, C$_1$-C$_6$ alkoxy, C$_1$-C$_6$ alkylamine, C$_1$-C$_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, keto, nitro, —C(O)OH, —C(O)NH$_2$, —C(O)($C_1$-$C_6$ alkylamine), —C(O)($C_1$-$C_6$ dialkylamine), —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt or stereoisomer thereof.

2. The compound according to claim 1 wherein $R^1$ is H, halo, nitro, —CHR$^4$—S(O)$_2$R$^5$, —C(S(O)$_2$R$^5$)=CHR$^4$—, —NR$^5$R$^6$, —NR$^4$S(O)$_2$R$^5$, or —NR$^4$S(O)$_2$NR$^5$R$^6$.

3. The compound according to claim 2 wherein $R^1$ is —NR$^4$S(O)$_2$R$^5$, and R$^4$ and R$^5$ are independently H, $C_1$-$C_6$ alkyl, or $C_3$-$C_8$ cycloalkyl.

4. The compound according to claim 3 wherein $R^1$ is selected from

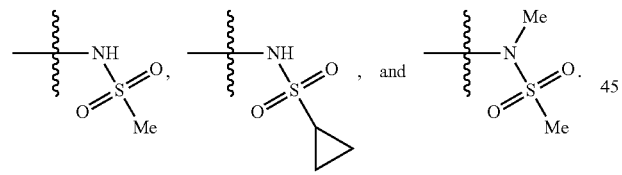

5. The compound according to claim 1 wherein $R^2$ is selected from

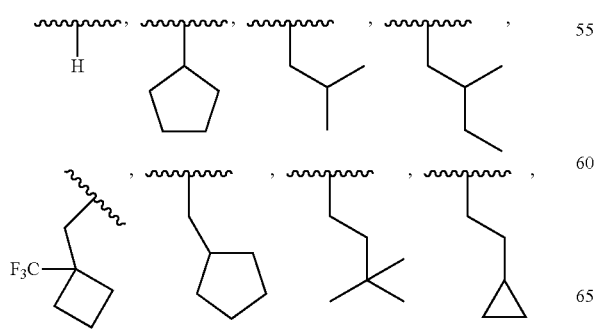

6. The compound according to claim 5 wherein $R^2$ is selected from

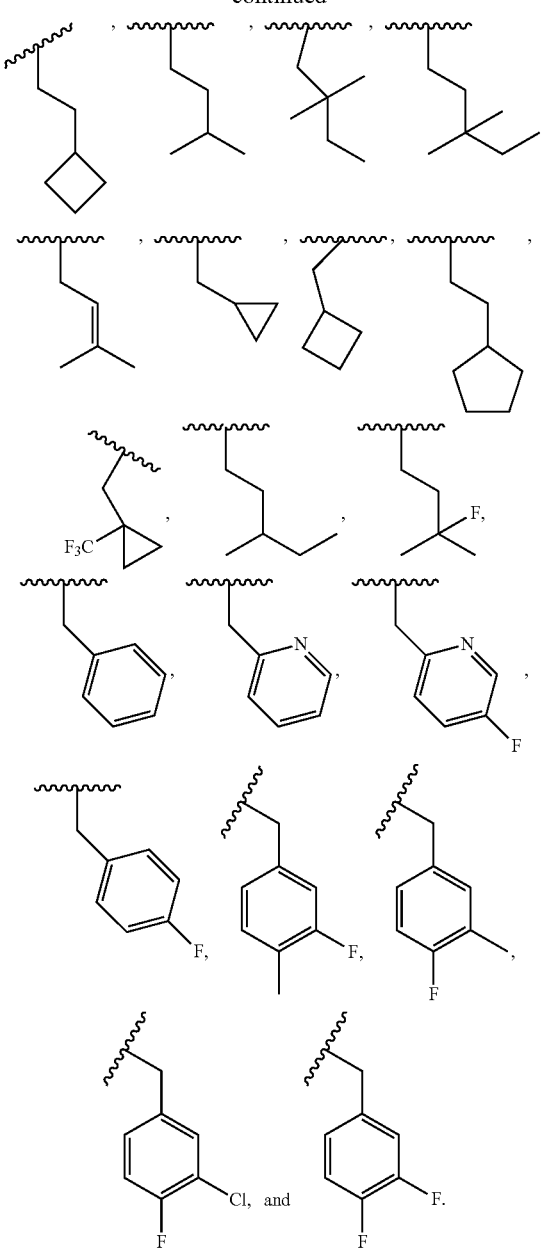

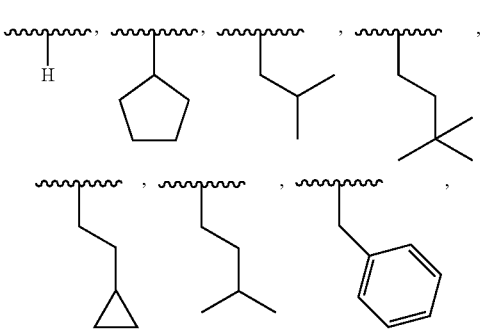

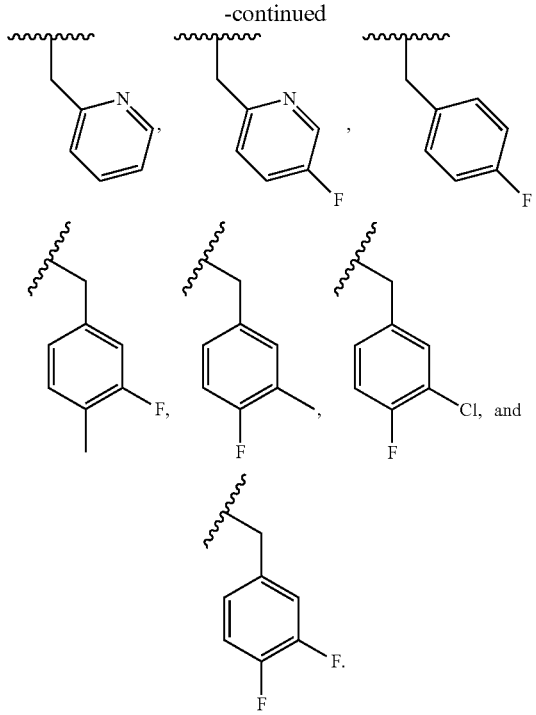

7. The compound according to claim 6 wherein R² is selected from

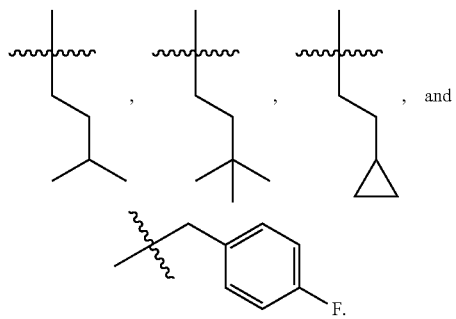

8. The compound according to claim 1 wherein R³ is selected from hydrogen or C₁-C₆ alkyl.

9. The compound according to claim 8 wherein R³ is selected from

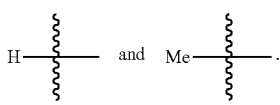

10. The compound according to claim 1 wherein R⁷ and R⁸ are H.

11. The compound according to claim 1 wherein R⁹, R¹⁰, R¹¹, R¹², R¹³, R¹⁴, R¹⁵, and R¹⁶ are independently selected from

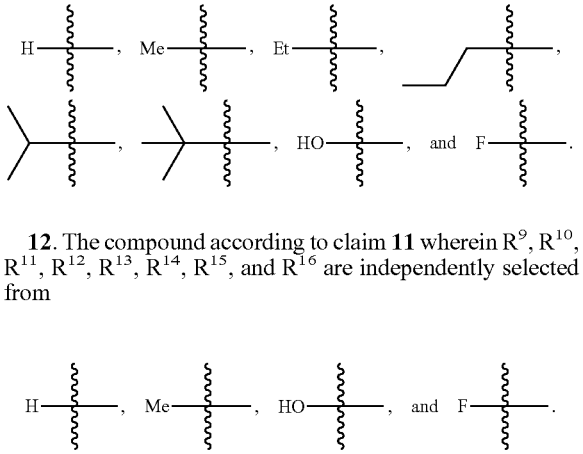

12. The compound according to claim 11 wherein R⁹, R¹⁰, R¹¹, R¹², R¹³, R¹⁴, R¹⁵, and R¹⁶ are independently selected from

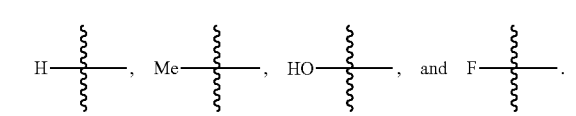

13. The compound according to claim 12 wherein R⁹, R¹⁰, R¹¹, R¹², R¹³, R¹⁴, R¹⁵, and R¹⁶ are H or hydroxy.

14. The compound according to claim 13 wherein R⁹, R¹⁰, R¹¹, R¹², R¹³, R¹⁴, R¹⁵, and R¹⁶ are H.

15. The compound according to claim 1 wherein n is 1.

16. A compound selected from
N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,4]thiazin-7-yl}-methanesulfonamide,
(rac-di-exo)-N-{3-[3-(3,3-Dimethyl-butyl)-6-hydroxy-4-oxo-3-aza-tricyclo[6.2.1.0²,⁷]undeca-5,9-dien-5-yl]-1,1-dioxo-1,4-dihydro-1λ⁶-benzo[1,4]thiazin-7-yl}-methanesulfonamide,
(rac-di-exo)-N-{3-[3-(4-Fluoro-benzyl)-6-hydroxy-4-oxo-3-aza-tricyclo[6.2.1.0²,⁷]undeca-5,9-dien-5-yl]-1,1-dioxo-1,4-dihydro-1λ⁶-benzo[1,4]thiazin-7-yl}-methanesulfonamide, and
(rac-di-exo)-N-{3-[6-Hydroxy-3-(3-methyl-butyl)-4-oxo-3-aza-tricyclo[6.2.1.0²,⁷]undeca-5,9-dien-5-yl]-1,1-dioxo-1,4-dihydro-1λ⁶-benzo[1,4]thiazin-7-yl-}-methanesulfonamide,
or a pharmaceutically acceptable salt thereof.

17. A pharmaceutically acceptable composition comprising a compound of claim 1 and a pharmaceutically acceptable carrier.

18. A method for treating hepatitis C virus infection in a mammal in need thereof, comprising administering to the mammal a therapeutically effective amount of a compound of claim 1, or a pharmaceutically acceptable salt thereof.

19. The method of claim 18 wherein the mammal is a human.

20. The method of claim 18 further comprising administering one or more additional therapeutic agents to the mammal.

21. The method of claim 20 wherein the additional therapeutic agent is selected from the group consisting of an antibiotic, an antiemetic agent, an antidepressant, an antifungal agent, an antiviral agent, an anti-inflammatory agent, an anti-cancer agent, an immunomodulatory agent, an α-interferon, a β-interferon, a ribavirin, an alkylating agent, a hormone, a cytokine and a toll receptor-like modulator.

22. The method of claim 21 wherein the additional therapeutic agent is ITMN-191, or a pharmaceutically acceptable salt thereof.

* * * * *